United States Patent
Quanz

(10) Patent No.: US 8,975,064 B2
(45) Date of Patent: Mar. 10, 2015

(54) METHODS AND MEANS FOR PRODUCING HYALURONAN

(75) Inventor: Martin Quanz, Berlin (DE)

(73) Assignee: Bayer Cropscience AG, Monheim am Rhein (DE)

( * ) Notice: Subject to any disclaimer, the term of this patent is extended or adjusted under 35 U.S.C. 154(b) by 1727 days.

(21) Appl. No.: 11/817,000

(22) PCT Filed: Feb. 22, 2006

(86) PCT No.: PCT/EP2006/002913
§ 371 (c)(1),
(2), (4) Date: Jun. 17, 2008

(87) PCT Pub. No.: WO2006/089808
PCT Pub. Date: Aug. 31, 2006

(65) Prior Publication Data
US 2009/0170807 A1 Jul. 2, 2009

Related U.S. Application Data

(60) Provisional application No. 60/657,107, filed on Feb. 28, 2005.

(30) Foreign Application Priority Data

Feb. 23, 2005 (EP) ...................... 05090042

(51) Int. Cl.
 *C12N 1/14* (2006.01)
 *C12N 15/74* (2006.01)
 *C12P 19/04* (2006.01)
 *C12P 19/26* (2006.01)
 *C12N 9/10* (2006.01)
 *C12N 15/80* (2006.01)

(52) U.S. Cl.
 CPC .............. *C12P 19/26* (2013.01); *C12N 9/1051* (2013.01); *C12N 9/1077* (2013.01); *C12N 15/80* (2013.01)
 USPC .................. 435/254.1; 435/471; 435/101

(58) Field of Classification Search
 None
 See application file for complete search history.

(56) References Cited

FOREIGN PATENT DOCUMENTS

| EP | 0 584 809 B1 | 8/1993 |
|---|---|---|
| EP | 0 881 294 A | 5/1998 |
| WO | WO 97/40174 | 10/1997 |
| WO | WO 03/054163 A | 7/2003 |
| WO | WO 03/060063 | 7/2003 |

OTHER PUBLICATIONS

Noel et al. (Mycoscience 1995, 36, pp. 127-133).*
P.L. Deangelis, et al., "Yeast-derived Recombinant DG42 Protein of *Xenopus* Can Synthesize Hyaluronan in Vitro," *Journal of Biological Chemistry*, 271(39):23657-23660 (1996).
V.L. Tlapak-Simmons, et al. "The Active Streptococcoccal Hyaluronan Synthases (HASs) Contain a Single HAS Monomer and Multiple Cardiolipin Molecules," *Journal of Biological Chemistry*, 273(40):26100-269109 (1998).
J. Brinck and P. Heldin, "Expression of Recombinant Hyaluronan Synthase (HAS) Isoforms in CHO Cells Reduces Cell Migration and Cell Surface CD44," *Experimental Cell Research* 252(2):342-351 (1999).
A. Regina, et al., "High-amylose wheat generated by RNA interference improves indices of large-bowel health in rats," *Journal of Biological Chemistry* 10(10): 3546-3551 (2006).
A. Evans and D.B. Thompson, "Resistance to α-Amylase Digestion in Four Native High-Amylose Maize Starches," *Cereal Chemistry*, 81(1): 31-37 (2004).
Japanese Office Action in Japanese Patent Application No. 2007-556574, mailed Jul. 5, 2011.
Hashida et al. (2003) *Bioscience and Industry* 61(9):611-614.

* cited by examiner

*Primary Examiner* — Tekchand Saidha
*Assistant Examiner* — Md. Younus Meah
(74) *Attorney, Agent, or Firm* — Hunton & Williams LLP

(57) ABSTRACT

The present invention relates to fungal cells and fungi which synthesize hyaluronan and to methods for preparing such fungi, and also to methods for preparing hyaluronan with the aid of these fungal cells or fungi. Furthermore, the present invention relates to the use of fungi for preparing hyaluronan and to food or feed which comprises hyaluronan.

19 Claims, 2 Drawing Sheets

SEQUENCE LISTING

```
<160> NUMBER OF SEQ ID NOS: 65

<210> SEQ ID NO 1
<211> LENGTH: 1707
<212> TYPE: DNA
<213> ORGANISM: Paramecium bursaria Chlorella Virus 1
<220> FEATURE:
<221> NAME/KEY: CDS
<222> LOCATION: (1)..(1707)
<223> OTHER INFORMATION: Hyaluronan synthase
<300> PUBLICATION INFORMATION:
<308> DATABASE ACCESSION NUMBER: PB42580
<309> DATABASE ENTRY DATE: 1995-12-24
<313> RELEVANT RESIDUES IN SEQ ID NO: (50903)..(52609)

<400> SEQUENCE: 1 atg ggt aaa aat ata atc ata atg gtt tcg tgg tac acc ata act       48
Met Gly Lys Asn Ile Ile Ile Met Val Ser Trp Tyr Thr Ile Thr
1               5                  10                  15 tca aat cta atc gcg gtt gga gga gcc tct cta atc ttg gct ccg gca   96
Ser Asn Leu Ile Ala Val Gly Gly Ala Ser Leu Ile Leu Ala Pro Ala
                20                  25                  30 att act ggg tat gtt cta cat tgg aat att gct ctc tcg aca atc tgg  144
Ile Thr Gly Tyr Val Leu His Trp Asn Ile Ala Leu Ser Thr Ile Trp
            35                  40                  45 gga gta tca gct tat ggt att ttc gtt ttt ggg ttt ttc ctt gca caa  192
Gly Val Ser Ala Tyr Gly Ile Phe Val Phe Gly Phe Phe Leu Ala Gln
        50                  55                  60 gtt tta ttt tca gaa ctg aac agg aaa cgt ctt cgc aag tgg att tct  240
Val Leu Phe Ser Glu Leu Asn Arg Lys Arg Leu Arg Lys Trp Ile Ser
65                  70                  75                  80 ctc aga cct aag ggt tgg aat gat gtt cgt ttg gct gtg atc att gct  288
Leu Arg Pro Lys Gly Trp Asn Asp Val Arg Leu Ala Val Ile Ile Ala
                85                  90                  95 gga tat cgc gag gat cct tat atg ttc cag aag tgc ctc gag tct gta  336
Gly Tyr Arg Glu Asp Pro Tyr Met Phe Gln Lys Cys Leu Glu Ser Val
            100                 105                 110 cgt gac tct gat tat ggc aac gtt gcc cgt ctg att tgt gtg att gac  384
Arg Asp Ser Asp Tyr Gly Asn Val Ala Arg Leu Ile Cys Val Ile Asp
        115                 120                 125 ggt gat gag gac gat gat atg agg atg gct gcc gtt tac aag gcg atc  432
Gly Asp Glu Asp Asp Asp Met Arg Met Ala Ala Val Tyr Lys Ala Ile
    130                 135                 140 tac aat gat aat atc aag aag ccc gag ttt gtt ctg tgt gag tca gac  480
Tyr Asn Asp Asn Ile Lys Lys Pro Glu Phe Val Leu Cys Glu Ser Asp
145                 150                 155                 160 gac aag gaa ggt gaa cgc atc gac tct gat ttc tct cgc gac att tgt  528
Asp Lys Glu Gly Glu Arg Ile Asp Ser Asp Phe Ser Arg Asp Ile Cys
                165                 170                 175 gtc ctc cag cct cat cgt gga aaa cgg gag tgt ctt tat act ggg ttt  576
```

```
Val Leu Gln Pro His Arg Gly Lys Arg Glu Cys Leu Tyr Thr Gly Phe
            180                 185                 190 caa ctt gca aag atg gac ccc agt gtc aat gct gtc gtt ctg att gac    624
Gln Leu Ala Lys Met Asp Pro Ser Val Asn Ala Val Val Leu Ile Asp
            195                 200                 205 agc gat acc gtt ctc gag aag gat gct att ctg gaa gtt gta tac cca    672
Ser Asp Thr Val Leu Glu Lys Asp Ala Ile Leu Glu Val Val Tyr Pro
210                 215                 220 ctt gca tgc gat ccc gag atc caa gcc gtt gca ggt gag tgt aag att    720
Leu Ala Cys Asp Pro Glu Ile Gln Ala Val Ala Gly Glu Cys Lys Ile
225                 230                 235                 240 tgg aac aca gac act ctt ttg agt ctt ctc gtc gct tgg cgg tac tat    768
Trp Asn Thr Asp Thr Leu Leu Ser Leu Leu Val Ala Trp Arg Tyr Tyr
                245                 250                 255 tct gcg ttt tgt gtg gag agg agt gcc cag tct ttt ttc agg act gtt    816
Ser Ala Phe Cys Val Glu Arg Ser Ala Gln Ser Phe Phe Arg Thr Val
                260                 265                 270 cag tgc gtt ggg ggg cca ctg ggt gcc tac aag att gat atc att aag    864
Gln Cys Val Gly Gly Pro Leu Gly Ala Tyr Lys Ile Asp Ile Ile Lys
            275                 280                 285 gag att aag gac ccc tgg att tcc cag cgc ttt ctt ggt cag aag tgt    912
Glu Ile Lys Asp Pro Trp Ile Ser Gln Arg Phe Leu Gly Gln Lys Cys
290                 295                 300 act tac ggt gac gac cgc cgg cta acc aac gag atc ttg atg cgt ggt    960
Thr Tyr Gly Asp Asp Arg Arg Leu Thr Asn Glu Ile Leu Met Arg Gly
305                 310                 315                 320 aaa aag gtt gtg ttc act cca ttt gct gtt ggt tgg tct gac agt ccg   1008
Lys Lys Val Val Phe Thr Pro Phe Ala Val Gly Trp Ser Asp Ser Pro
                325                 330                 335 acc aat gtg ttt cgg tac atc gtt cag cag acc cgc tgg agt aag tcg   1056
Thr Asn Val Phe Arg Tyr Ile Val Gln Gln Thr Arg Trp Ser Lys Ser
                340                 345                 350 tgg tgc cgc gaa att tgg tac acc ctc ttc gcc gcg tgg aag cac ggt   1104
Trp Cys Arg Glu Ile Trp Tyr Thr Leu Phe Ala Ala Trp Lys His Gly
            355                 360                 365 ttg tct gga att tgg ctg gcc ttt gaa tgt ttg tat caa att aca tac   1152
Leu Ser Gly Ile Trp Leu Ala Phe Glu Cys Leu Tyr Gln Ile Thr Tyr
370                 375                 380 ttc ttc ctc gtg att tac ctc ttt tct cgc cta gcc gtt gag gcc gac   1200
Phe Phe Leu Val Ile Tyr Leu Phe Ser Arg Leu Ala Val Glu Ala Asp
385                 390                 395                 400 cct cgc gcc cag aca gcc acg gtg att gtg agc acc acg gtt gca ttg   1248
Pro Arg Ala Gln Thr Ala Thr Val Ile Val Ser Thr Thr Val Ala Leu
                405                 410                 415 att aag tgt ggg tat ttt tca ttc cga gcc aag gat att cgg gcg ttt   1296
Ile Lys Cys Gly Tyr Phe Ser Phe Arg Ala Lys Asp Ile Arg Ala Phe
            420                 425                 430 tac ttt gtg ctt tat aca ttt gtt tac ttt ttc tgt atg att ccg gcc   1344
Tyr Phe Val Leu Tyr Thr Phe Val Tyr Phe Phe Cys Met Ile Pro Ala
            435                 440                 445 agg att act gca atg atg acg ctt tgg gac att ggc tgg ggt act cgc   1392
Arg Ile Thr Ala Met Met Thr Leu Trp Asp Ile Gly Trp Gly Thr Arg
450                 455                 460 ggt gga aac gag aag cct tcc gtt ggc acc cgg gtc gct ctg tgg gca   1440
Gly Gly Asn Glu Lys Pro Ser Val Gly Thr Arg Val Ala Leu Trp Ala
465                 470                 475                 480 aag caa tat ctc att gca tat atg tgg tgg gcc gcg gtt gtt ggc gct   1488
Lys Gln Tyr Leu Ile Ala Tyr Met Trp Trp Ala Ala Val Val Gly Ala
                485                 490                 495
```

```
gga gtt tac agc atc gtc cat aac tgg atg ttc gat tgg aat tct ctt    1536
Gly Val Tyr Ser Ile Val His Asn Trp Met Phe Asp Trp Asn Ser Leu
            500                 505                 510 tct tat cgt ttt gct ttg gtt ggt att tgt tct tac att gtt ttt att    1584
Ser Tyr Arg Phe Ala Leu Val Gly Ile Cys Ser Tyr Ile Val Phe Ile
            515                 520                 525 gtt att gtg ctg gtg gtt tat ttc acc ggc aaa att acg act tgg aat    1632
Val Ile Val Leu Val Val Tyr Phe Thr Gly Lys Ile Thr Thr Trp Asn
            530                 535                 540 ttc acg aag ctt cag aag gag cta atc gag gat cgc gtt ctg tac gat    1680
Phe Thr Lys Leu Gln Lys Glu Leu Ile Glu Asp Arg Val Leu Tyr Asp
545                 550                 555                 560 gca act acc aat gct cag tct gtg tga                                1707
Ala Thr Thr Asn Ala Gln Ser Val
            565
```

<210> SEQ ID NO 2
<211> LENGTH: 568
<212> TYPE: PRT
<213> ORGANISM: Paramecium bursaria Chlorella Virus 1

<400> SEQUENCE: 2

```
Met Gly Lys Asn Ile Ile Ile Met Val Ser Trp Tyr Thr Ile Ile Thr
1               5                   10                  15

Ser Asn Leu Ile Ala Val Gly Gly Ala Ser Leu Ile Leu Ala Pro Ala
            20                  25                  30

Ile Thr Gly Tyr Val Leu His Trp Asn Ile Ala Leu Ser Thr Ile Trp
        35                  40                  45

Gly Val Ser Ala Tyr Gly Ile Phe Val Phe Gly Phe Phe Leu Ala Gln
    50                  55                  60

Val Leu Phe Ser Glu Leu Asn Arg Lys Arg Leu Arg Lys Trp Ile Ser
65                  70                  75                  80

Leu Arg Pro Lys Gly Trp Asn Asp Val Arg Leu Ala Val Ile Ile Ala
                85                  90                  95

Gly Tyr Arg Glu Asp Pro Tyr Met Phe Gln Lys Cys Leu Glu Ser Val
            100                 105                 110

Arg Asp Ser Asp Tyr Gly Asn Val Ala Arg Leu Ile Cys Val Ile Asp
        115                 120                 125

Gly Asp Glu Asp Asp Met Arg Met Ala Ala Val Tyr Lys Ala Ile
    130                 135                 140

Tyr Asn Asp Asn Ile Lys Lys Pro Glu Phe Val Leu Cys Glu Ser Asp
145                 150                 155                 160

Asp Lys Glu Gly Glu Arg Ile Asp Ser Asp Phe Ser Arg Asp Ile Cys
                165                 170                 175

Val Leu Gln Pro His Arg Gly Lys Arg Glu Cys Leu Tyr Thr Gly Phe
            180                 185                 190

Gln Leu Ala Lys Met Asp Pro Ser Val Asn Ala Val Leu Ile Asp
        195                 200                 205

Ser Asp Thr Val Leu Glu Lys Asp Ala Ile Leu Glu Val Val Tyr Pro
210                 215                 220

Leu Ala Cys Asp Pro Glu Ile Gln Ala Val Ala Gly Glu Cys Lys Ile
225                 230                 235                 240

Trp Asn Thr Asp Thr Leu Leu Ser Leu Leu Val Ala Trp Arg Tyr Tyr
                245                 250                 255

Ser Ala Phe Cys Val Glu Arg Ser Ala Gln Ser Phe Pro Arg Thr Val
            260                 265                 270
```

```
Gln Cys Val Gly Gly Pro Leu Gly Ala Tyr Lys Ile Asp Ile Ile Lys
            275                 280                 285

Glu Ile Lys Asp Pro Trp Ile Ser Gln Arg Phe Leu Gly Gln Lys Cys
    290                 295                 300

Thr Tyr Gly Asp Asp Arg Arg Leu Thr Asn Glu Ile Leu Met Arg Gly
305                 310                 315                 320

Lys Lys Val Val Phe Thr Pro Phe Ala Val Gly Trp Ser Asp Ser Pro
                325                 330                 335

Thr Asn Val Phe Arg Tyr Ile Val Gln Gln Thr Arg Trp Ser Lys Ser
            340                 345                 350

Trp Cys Arg Glu Ile Trp Tyr Thr Leu Phe Ala Ala Trp Lys His Gly
        355                 360                 365

Leu Ser Gly Ile Trp Leu Ala Phe Glu Cys Leu Tyr Gln Ile Thr Tyr
    370                 375                 380

Phe Phe Leu Val Ile Tyr Leu Phe Ser Arg Leu Ala Val Glu Ala Asp
385                 390                 395                 400

Pro Arg Ala Gln Thr Ala Thr Val Ile Val Ser Thr Thr Val Ala Leu
                405                 410                 415

Ile Lys Cys Gly Tyr Phe Ser Phe Arg Ala Lys Asp Ile Arg Ala Phe
            420                 425                 430

Tyr Phe Val Leu Tyr Thr Phe Val Tyr Phe Cys Met Ile Pro Ala
        435                 440                 445

Arg Ile Thr Ala Met Met Thr Leu Trp Asp Ile Gly Trp Gly Thr Arg
    450                 455                 460

Gly Gly Asn Glu Lys Pro Ser Val Gly Thr Arg Val Ala Leu Trp Ala
465                 470                 475                 480

Lys Gln Tyr Leu Ile Ala Tyr Met Trp Trp Ala Ala Val Val Gly Ala
                485                 490                 495

Gly Val Tyr Ser Ile Val His Asn Trp Met Phe Asp Trp Asn Ser Leu
            500                 505                 510

Ser Tyr Arg Phe Ala Leu Val Gly Ile Cys Ser Tyr Ile Val Phe Ile
        515                 520                 525

Val Ile Val Leu Val Val Tyr Phe Thr Gly Lys Ile Thr Thr Trp Asn
    530                 535                 540

Phe Thr Lys Leu Gln Lys Glu Leu Ile Glu Asp Arg Val Leu Tyr Asp
545                 550                 555                 560

Ala Thr Thr Asn Ala Gln Ser Val
                565

<210> SEQ ID NO 3
<211> LENGTH: 1707
<212> TYPE: DNA
<213> ORGANISM: Artificial sequence
<220> FEATURE:
<221> NAME/KEY: CDS
<222> LOCATION: (1)..(1707)
<223> OTHER INFORMATION: Synthetic sequence encoding Paramecium bursaria
      Chlorella Virus 1 Hyaluronan synthase protein

<400> SEQUENCE: 3 atg ggt aag aac att atc att atg gtg tcc tgg tac aca att att aca      48
Met Gly Lys Asn Ile Ile Ile Met Val Ser Trp Tyr Thr Ile Ile Thr
1               5                   10                  15 agt aat ctc atc gca gtt ggt ggt gca tct ctt att ctc gct cca gct      96
Ser Asn Leu Ile Ala Val Gly Gly Ala Ser Leu Ile Leu Ala Pro Ala
            20                  25                  30 atc act gga tat gtt ctt cac tgg aac atc gcc ctc tca act att tgg     144
```

|     |     |     |     |     |     |     |     |     |     |     |     |     |     |     |
| --- | --- | --- | --- | --- | --- | --- | --- | --- | --- | --- | --- | --- | --- | --- |
| Ile | Thr | Gly | Tyr | Val | Leu | His | Trp | Asn | Ile | Ala | Leu | Ser | Thr | Ile | Trp |
|     |     | 35  |     |     |     |     | 40  |     |     |     |     | 45  |     |     |     |

| gga | gtt | tcc | gca | tat | ggt | att | ttt | gtt | ttc | ggg | ttc | ttt | ttg | gct | cag | 192 |
| --- | --- | --- | --- | --- | --- | --- | --- | --- | --- | --- | --- | --- | --- | --- | --- | --- |
| Gly | Val | Ser | Ala | Tyr | Gly | Ile | Phe | Val | Phe | Gly | Phe | Phe | Leu | Ala | Gln |     |
|     | 50  |     |     |     |     | 55  |     |     |     |     | 60  |     |     |     |     |     |

| gtt | ctg | ttc | tca | gag | ctc | aat | cgt | aag | aga | ctc | agg | aag | tgg | att | agc | 240 |
| --- | --- | --- | --- | --- | --- | --- | --- | --- | --- | --- | --- | --- | --- | --- | --- | --- |
| Val | Leu | Phe | Ser | Glu | Leu | Asn | Arg | Lys | Arg | Leu | Arg | Lys | Trp | Ile | Ser |     |
| 65  |     |     |     |     | 70  |     |     |     |     | 75  |     |     |     |     | 80  |     |

| ctt | aga | cca | aag | ggg | tgg | aat | gac | gtt | cgt | ctc | gct | gtc | att | atc | gct | 288 |
| --- | --- | --- | --- | --- | --- | --- | --- | --- | --- | --- | --- | --- | --- | --- | --- | --- |
| Leu | Arg | Pro | Lys | Gly | Trp | Asn | Asp | Val | Arg | Leu | Ala | Val | Ile | Ile | Ala |     |
|     |     |     |     | 85  |     |     |     |     | 90  |     |     |     |     | 95  |     |     |

| ggc | tac | cgt | gaa | gat | cct | tac | atg | ttt | caa | aag | tgc | ttg | gaa | tca | gtt | 336 |
| --- | --- | --- | --- | --- | --- | --- | --- | --- | --- | --- | --- | --- | --- | --- | --- | --- |
| Gly | Tyr | Arg | Glu | Asp | Pro | Tyr | Met | Phe | Gln | Lys | Cys | Leu | Glu | Ser | Val |     |
|     |     |     | 100 |     |     |     |     | 105 |     |     |     |     | 110 |     |     |     |

| agg | gat | agt | gat | tat | ggc | aac | gtc | gct | aga | ctg | atc | tgt | gtg | att | gat | 384 |
| --- | --- | --- | --- | --- | --- | --- | --- | --- | --- | --- | --- | --- | --- | --- | --- | --- |
| Arg | Asp | Ser | Asp | Tyr | Gly | Asn | Val | Ala | Arg | Leu | Ile | Cys | Val | Ile | Asp |     |
|     |     | 115 |     |     |     |     | 120 |     |     |     |     | 125 |     |     |     |     |

| gga | gat | gag | gac | gac | gat | atg | agg | atg | gca | gct | gtt | tat | aag | gct | atc | 432 |
| --- | --- | --- | --- | --- | --- | --- | --- | --- | --- | --- | --- | --- | --- | --- | --- | --- |
| Gly | Asp | Glu | Asp | Asp | Asp | Met | Arg | Met | Ala | Ala | Val | Tyr | Lys | Ala | Ile |     |
|     | 130 |     |     |     |     | 135 |     |     |     |     | 140 |     |     |     |     |     |

| tat | aat | gat | aac | att | aag | aag | cct | gaa | ttt | gtt | ctt | tgc | gag | tct | gat | 480 |
| --- | --- | --- | --- | --- | --- | --- | --- | --- | --- | --- | --- | --- | --- | --- | --- | --- |
| Tyr | Asn | Asp | Asn | Ile | Lys | Lys | Pro | Glu | Phe | Val | Leu | Cys | Glu | Ser | Asp |     |
| 145 |     |     |     |     | 150 |     |     |     |     | 155 |     |     |     |     | 160 |     |

| gac | aag | gaa | gga | gaa | cgg | att | gat | tca | gat | ttc | tca | cgt | gat | atc | tgc | 528 |
| --- | --- | --- | --- | --- | --- | --- | --- | --- | --- | --- | --- | --- | --- | --- | --- | --- |
| Asp | Lys | Glu | Gly | Glu | Arg | Ile | Asp | Ser | Asp | Phe | Ser | Arg | Asp | Ile | Cys |     |
|     |     |     |     | 165 |     |     |     |     | 170 |     |     |     |     | 175 |     |     |

| gtt | ctc | caa | cct | cat | cgt | ggg | aag | cgt | gaa | tgt | ctt | tat | aca | ggt | ttc | 576 |
| --- | --- | --- | --- | --- | --- | --- | --- | --- | --- | --- | --- | --- | --- | --- | --- | --- |
| Val | Leu | Gln | Pro | His | Arg | Gly | Lys | Arg | Glu | Cys | Leu | Tyr | Thr | Gly | Phe |     |
|     |     |     | 180 |     |     |     |     | 185 |     |     |     |     | 190 |     |     |     |

| caa | ctc | gcc | aaa | atg | gac | cca | tca | gtg | aac | gct | gtg | gtt | ctt | atc | gat | 624 |
| --- | --- | --- | --- | --- | --- | --- | --- | --- | --- | --- | --- | --- | --- | --- | --- | --- |
| Gln | Leu | Ala | Lys | Met | Asp | Pro | Ser | Val | Asn | Ala | Val | Val | Leu | Ile | Asp |     |
|     |     | 195 |     |     |     |     | 200 |     |     |     |     | 205 |     |     |     |     |

| agt | gat | act | gtg | ctg | gag | aaa | gat | gct | atc | ttg | gag | gtt | gtt | tac | cct | 672 |
| --- | --- | --- | --- | --- | --- | --- | --- | --- | --- | --- | --- | --- | --- | --- | --- | --- |
| Ser | Asp | Thr | Val | Leu | Glu | Lys | Asp | Ala | Ile | Leu | Glu | Val | Val | Tyr | Pro |     |
|     | 210 |     |     |     |     | 215 |     |     |     |     | 220 |     |     |     |     |     |

| ctt | gcc | tgt | gat | cct | gaa | att | caa | gct | gtg | gct | gga | gag | tgc | aag | atc | 720 |
| --- | --- | --- | --- | --- | --- | --- | --- | --- | --- | --- | --- | --- | --- | --- | --- | --- |
| Leu | Ala | Cys | Asp | Pro | Glu | Ile | Gln | Ala | Val | Ala | Gly | Glu | Cys | Lys | Ile |     |
| 225 |     |     |     |     | 230 |     |     |     |     | 235 |     |     |     |     | 240 |     |

| tgg | aac | aca | gat | act | ctt | ctt | tct | ctg | ctt | gtc | gca | tgg | aga | tat | tac | 768 |
| --- | --- | --- | --- | --- | --- | --- | --- | --- | --- | --- | --- | --- | --- | --- | --- | --- |
| Trp | Asn | Thr | Asp | Thr | Leu | Leu | Ser | Leu | Leu | Val | Ala | Trp | Arg | Tyr | Tyr |     |
|     |     |     |     | 245 |     |     |     |     | 250 |     |     |     |     | 255 |     |     |

| tcc | gca | ttc | tgt | gtg | gag | agg | agc | gct | caa | tcc | ttt | ttc | cgt | acc | gtt | 816 |
| --- | --- | --- | --- | --- | --- | --- | --- | --- | --- | --- | --- | --- | --- | --- | --- | --- |
| Ser | Ala | Phe | Cys | Val | Glu | Arg | Ser | Ala | Gln | Ser | Phe | Phe | Arg | Thr | Val |     |
|     |     |     | 260 |     |     |     |     | 265 |     |     |     |     | 270 |     |     |     |

| caa | tgc | gtt | ggt | ggt | cct | ttg | gga | gct | tac | aaa | att | gat | atc | atc | aag | 864 |
| --- | --- | --- | --- | --- | --- | --- | --- | --- | --- | --- | --- | --- | --- | --- | --- | --- |
| Gln | Cys | Val | Gly | Gly | Pro | Leu | Gly | Ala | Tyr | Lys | Ile | Asp | Ile | Ile | Lys |     |
|     |     | 275 |     |     |     |     | 280 |     |     |     |     | 285 |     |     |     |     |

| gag | att | aag | gac | cca | tgg | att | agt | caa | agg | ttt | ctt | ggt | cag | aag | tgc | 912 |
| --- | --- | --- | --- | --- | --- | --- | --- | --- | --- | --- | --- | --- | --- | --- | --- | --- |
| Glu | Ile | Lys | Asp | Pro | Trp | Ile | Ser | Gln | Arg | Phe | Leu | Gly | Gln | Lys | Cys |     |
|     | 290 |     |     |     |     | 295 |     |     |     |     | 300 |     |     |     |     |     |

| act | tat | ggc | gat | gat | cgt | aga | ttg | act | aac | gaa | atc | ctt | atg | agg | ggc | 960 |
| --- | --- | --- | --- | --- | --- | --- | --- | --- | --- | --- | --- | --- | --- | --- | --- | --- |
| Thr | Tyr | Gly | Asp | Asp | Arg | Arg | Leu | Thr | Asn | Glu | Ile | Leu | Met | Arg | Gly |     |
| 305 |     |     |     |     | 310 |     |     |     |     | 315 |     |     |     |     | 320 |     |

| aag | aaa | gtc | gtt | ttt | act | cca | ttt | gct | gtc | gga | tgg | tct | gat | tca | cct | 1008 |
| --- | --- | --- | --- | --- | --- | --- | --- | --- | --- | --- | --- | --- | --- | --- | --- | --- |
| Lys | Lys | Val | Val | Phe | Thr | Pro | Phe | Ala | Val | Gly | Trp | Ser | Asp | Ser | Pro |     |
|     |     |     |     | 325 |     |     |     |     | 330 |     |     |     |     | 335 |     |     |

| aca | aat | gtt | ttc | cgt | tat | att | gtg | caa | caa | aca | cgt | tgg | agt | aag | agc | 1056 |
| --- | --- | --- | --- | --- | --- | --- | --- | --- | --- | --- | --- | --- | --- | --- | --- | --- |
| Thr | Asn | Val | Phe | Arg | Tyr | Ile | Val | Gln | Gln | Thr | Arg | Trp | Ser | Lys | Ser |     |
|     |     │     | 340 |     |     |     |     | 345 |     |     |     |     | 350 |     |     |     |

```
tgg tgt agg gag atc tgg tac act ttg ttc gct gct tgg aag cac ggg    1104
Trp Cys Arg Glu Ile Trp Tyr Thr Leu Phe Ala Ala Trp Lys His Gly
        355                 360                 365 ctt agc gga att tgg ctt gct ttt gaa tgc ctt tac cag att aca tac    1152
Leu Ser Gly Ile Trp Leu Ala Phe Glu Cys Leu Tyr Gln Ile Thr Tyr
    370                 375                 380 ttt ttc ttg gtg atc tat ttg ttt tca cgt ctt gcc gtc gag gct gac    1200
Phe Phe Leu Val Ile Tyr Leu Phe Ser Arg Leu Ala Val Glu Ala Asp
385                 390                 395                 400 cct aga gca cag act gca act gtg att gtt tct act aca gtc gca ctt    1248
Pro Arg Ala Gln Thr Ala Thr Val Ile Val Ser Thr Thr Val Ala Leu
                405                 410                 415 att aag tgt ggc tat ttc agt ttt aga gca aaa gat att aga gcc ttc    1296
Ile Lys Cys Gly Tyr Phe Ser Phe Arg Ala Lys Asp Ile Arg Ala Phe
            420                 425                 430 tat ttt gtt ttg tac aca ttt gtt tat ttc ttt tgc atg att cca gct    1344
Tyr Phe Val Leu Tyr Thr Phe Val Tyr Phe Phe Cys Met Ile Pro Ala
        435                 440                 445 cgt att acc gct atg atg acc ttg tgg gac atc gga tgg gga act aga    1392
Arg Ile Thr Ala Met Met Thr Leu Trp Asp Ile Gly Trp Gly Thr Arg
450                 455                 460 ggt ggt aac gaa aag cct tct gtg gga aca agg gtg gcc ctt tgg gca    1440
Gly Gly Asn Glu Lys Pro Ser Val Gly Thr Arg Val Ala Leu Trp Ala
465                 470                 475                 480 aaa caa tat ctc atc gcc tac atg tgg tgg gcc gct gtc gtt ggt gcc    1488
Lys Gln Tyr Leu Ile Ala Tyr Met Trp Trp Ala Ala Val Val Gly Ala
                485                 490                 495 gga gtg tac tca atc gtt cat aac tgg atg ttt gac tgg aac tct ttg    1536
Gly Val Tyr Ser Ile Val His Asn Trp Met Phe Asp Trp Asn Ser Leu
            500                 505                 510 agc tat cgt ttc gct ctt gtg ggt att tgt tct tac att gtt ttc atc    1584
Ser Tyr Arg Phe Ala Leu Val Gly Ile Cys Ser Tyr Ile Val Phe Ile
        515                 520                 525 gtg att gtg ctc gtt gtg tat ttc act ggt aaa atc aca acc tgg aat    1632
Val Ile Val Leu Val Val Tyr Phe Thr Gly Lys Ile Thr Thr Trp Asn
530                 535                 540 ttc act aaa ctt caa aag gaa ttg att gaa gac agg gtt ctg tat gat    1680
Phe Thr Lys Leu Gln Lys Glu Leu Ile Glu Asp Arg Val Leu Tyr Asp
545                 550                 555                 560 gct act acc aac gcc cag tca gtt taa                                1707
Ala Thr Thr Asn Ala Gln Ser Val
                565

<210> SEQ ID NO 4
<211> LENGTH: 568
<212> TYPE: PRT
<213> ORGANISM: Artificial sequence
<220> FEATURE:
<223> OTHER INFORMATION: Synthetic sequence encoding Paramecium bursaria
      Chlorella Virus 1 Hyaluronan synthase protein

<400> SEQUENCE: 4

Met Gly Lys Asn Ile Ile Ile Met Val Ser Trp Tyr Thr Ile Ile Thr
1               5                   10                  15

Ser Asn Leu Ile Ala Val Gly Gly Ala Ser Leu Ile Leu Ala Pro Ala
            20                  25                  30

Ile Thr Gly Tyr Val Leu His Trp Asn Ile Ala Leu Ser Thr Ile Trp
        35                  40                  45

Gly Val Ser Ala Tyr Gly Ile Phe Val Phe Gly Phe Phe Leu Ala Gln
    50                  55                  60
```

```
Val Leu Phe Ser Glu Leu Asn Arg Lys Arg Leu Arg Lys Trp Ile Ser
 65                  70                  75                  80

Leu Arg Pro Lys Gly Trp Asn Asp Val Arg Leu Ala Val Ile Ile Ala
                 85                  90                  95

Gly Tyr Arg Glu Asp Pro Tyr Met Phe Gln Lys Cys Leu Glu Ser Val
            100                 105                 110

Arg Asp Ser Asp Tyr Gly Asn Val Ala Arg Leu Ile Cys Val Ile Asp
        115                 120                 125

Gly Asp Glu Asp Asp Met Arg Met Ala Ala Val Tyr Lys Ala Ile
130                 135                 140

Tyr Asn Asp Asn Ile Lys Lys Pro Glu Phe Val Leu Cys Glu Ser Asp
145                 150                 155                 160

Asp Lys Glu Gly Glu Arg Ile Asp Ser Asp Phe Ser Arg Asp Ile Cys
                165                 170                 175

Val Leu Gln Pro His Arg Gly Lys Arg Glu Cys Leu Tyr Thr Gly Phe
            180                 185                 190

Gln Leu Ala Lys Met Asp Pro Ser Val Asn Ala Val Leu Ile Asp
        195                 200                 205

Ser Asp Thr Val Leu Glu Lys Asp Ala Ile Leu Glu Val Val Tyr Pro
210                 215                 220

Leu Ala Cys Asp Pro Glu Ile Gln Ala Val Ala Gly Glu Cys Lys Ile
225                 230                 235                 240

Trp Asn Thr Asp Thr Leu Leu Ser Leu Leu Val Ala Trp Arg Tyr Tyr
                245                 250                 255

Ser Ala Phe Cys Val Glu Arg Ser Ala Gln Ser Phe Phe Arg Thr Val
            260                 265                 270

Gln Cys Val Gly Gly Pro Leu Gly Ala Tyr Lys Ile Asp Ile Ile Lys
        275                 280                 285

Glu Ile Lys Asp Pro Trp Ile Ser Gln Arg Phe Leu Gly Gln Lys Cys
290                 295                 300

Thr Tyr Gly Asp Asp Arg Arg Leu Thr Asn Glu Ile Leu Met Arg Gly
305                 310                 315                 320

Lys Lys Val Val Phe Thr Pro Phe Ala Val Gly Trp Ser Asp Ser Pro
                325                 330                 335

Thr Asn Val Phe Arg Tyr Ile Val Gln Gln Thr Arg Trp Ser Lys Ser
            340                 345                 350

Trp Cys Arg Glu Ile Trp Tyr Thr Leu Phe Ala Ala Trp Lys His Gly
        355                 360                 365

Leu Ser Gly Ile Trp Leu Ala Phe Glu Cys Leu Tyr Gln Ile Thr Tyr
370                 375                 380

Phe Phe Leu Val Ile Tyr Leu Phe Ser Arg Leu Ala Val Glu Ala Asp
385                 390                 395                 400

Pro Arg Ala Gln Thr Ala Thr Val Ile Val Ser Thr Val Ala Leu
                405                 410                 415

Ile Lys Cys Gly Tyr Phe Ser Phe Arg Ala Lys Asp Ile Arg Ala Phe
            420                 425                 430

Tyr Phe Val Leu Tyr Thr Phe Val Tyr Phe Cys Met Ile Pro Ala
        435                 440                 445

Arg Ile Thr Ala Met Met Thr Leu Trp Asp Ile Gly Trp Gly Thr Arg
450                 455                 460

Gly Gly Asn Glu Lys Pro Ser Val Gly Thr Arg Val Ala Leu Trp Ala
465                 470                 475                 480

Lys Gln Tyr Leu Ile Ala Tyr Met Trp Trp Ala Ala Val Val Gly Ala
```

```
                485                 490                 495
Gly Val Tyr Ser Ile Val His Asn Trp Met Phe Asp Trp Asn Ser Leu
            500                 505                 510

Ser Tyr Arg Phe Ala Leu Val Gly Ile Cys Ser Tyr Ile Val Phe Ile
        515                 520                 525

Val Ile Val Leu Val Val Tyr Phe Thr Gly Lys Ile Thr Thr Trp Asn
530                 535                 540

Phe Thr Lys Leu Gln Lys Glu Leu Ile Glu Asp Arg Val Leu Tyr Asp
545                 550                 555                 560

Ala Thr Thr Asn Ala Gln Ser Val
                565

<210> SEQ ID NO 5
<211> LENGTH: 1662
<212> TYPE: DNA
<213> ORGANISM: Homo sapiens
<220> FEATURE:
<221> NAME/KEY: CDS
<222> LOCATION: (1)..(1662)
<223> OTHER INFORMATION: Hyaluronan synthase 3

<400> SEQUENCE: 5 atg ccg gtg cag ctg acg aca gcc ctg cgt gtg gtg ggc acc agc ctg      48
Met Pro Val Gln Leu Thr Thr Ala Leu Arg Val Val Gly Thr Ser Leu
1               5                   10                  15 ttt gcc ctg gca gtg ctg ggt ggc atc ctg gca gcc tat gtg acg ggc      96
Phe Ala Leu Ala Val Leu Gly Gly Ile Leu Ala Ala Tyr Val Thr Gly
            20                  25                  30 tac cag ttc atc cac acg gaa aag cac tac ctg tcc ttc ggc ctg tac     144
Tyr Gln Phe Ile His Thr Glu Lys His Tyr Leu Ser Phe Gly Leu Tyr
        35                  40                  45 ggc gcc atc ctg ggc ctg cac ctg ctc att cag agc ctt ttt gcc ttc     192
Gly Ala Ile Leu Gly Leu His Leu Leu Ile Gln Ser Leu Phe Ala Phe
    50                  55                  60 ctg gag cac cgg cgc atg caa cgt gcc ggc cag gcc ctg aag ctg ccc     240
Leu Glu His Arg Arg Met Gln Arg Ala Gly Gln Ala Leu Lys Leu Pro
65                  70                  75                  80 tcc ccg cgg cgg ggc tcg gtg gca ctg tgc att gcc gca tac cag gag     288
Ser Pro Arg Arg Gly Ser Val Ala Leu Cys Ile Ala Ala Tyr Gln Glu
                85                  90                  95 gac cct gac tac ttg cgc aag tgc ctg cgc tcg gcc cag cgc atc tcc     336
Asp Pro Asp Tyr Leu Arg Lys Cys Leu Arg Ser Ala Gln Arg Ile Ser
            100                 105                 110 ttc cct gac ctc aag gtg gtc atg gtg gtg gat ggc aac cgc cag gag     384
Phe Pro Asp Leu Lys Val Val Met Val Val Asp Gly Asn Arg Gln Glu
        115                 120                 125 gac gcc tac atg ctg gac atc ttc cac gag gtg ctg ggc ggc acc gag     432
Asp Ala Tyr Met Leu Asp Ile Phe His Glu Val Leu Gly Gly Thr Glu
    130                 135                 140 cag gcc ggc ttc ttt gtg tgg cgc agc aac ttc cat gag gca ggc gag     480
Gln Ala Gly Phe Phe Val Trp Arg Ser Asn Phe His Glu Ala Gly Glu
145                 150                 155                 160 ggt gag acg gag gcc agc ctg cag gag ggc atg gac cgt gtg cgg gat     528
Gly Glu Thr Glu Ala Ser Leu Gln Glu Gly Met Asp Arg Val Arg Asp
                165                 170                 175 gtg gtg cgg gcc agc acc ttc tcg tgc atc atg cag aag tgg gga ggc     576
Val Val Arg Ala Ser Thr Phe Ser Cys Ile Met Gln Lys Trp Gly Gly
            180                 185                 190 aag cgc gag gtc atg tac acg gcc ttc aag gcc ctc ggc gat tcg gtg     624
Lys Arg Glu Val Met Tyr Thr Ala Phe Lys Ala Leu Gly Asp Ser Val
```

-continued

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     |     | 195 |     |     |     | 200 |     |     |     | 205 |     |     |     |     |      |
| gac | tac | atc | cag | gtg | tgc | gac | tct | gac | act | gtg | ctg | gat | cca | gcc | tgc | 672  |
| Asp | Tyr | Ile | Gln | Val | Cys | Asp | Ser | Asp | Thr | Val | Leu | Asp | Pro | Ala | Cys |      |
|     |     | 210 |     |     |     |     | 215 |     |     |     |     | 220 |     |     |     |      |
| acc | atc | gag | atg | ctt | cga | gtc | ctg | gag | gag | gat | ccc | caa | gta | ggg | gga | 720  |
| Thr | Ile | Glu | Met | Leu | Arg | Val | Leu | Glu | Glu | Asp | Pro | Gln | Val | Gly | Gly |      |
| 225 |     |     |     |     | 230 |     |     |     |     | 235 |     |     |     |     | 240 |      |
| gtc | ggg | gga | gat | gtc | cag | atc | ctc | aac | aag | tac | gac | tca | tgg | att | tcc | 768  |
| Val | Gly | Gly | Asp | Val | Gln | Ile | Leu | Asn | Lys | Tyr | Asp | Ser | Trp | Ile | Ser |      |
|     |     |     |     | 245 |     |     |     |     | 250 |     |     |     |     | 255 |     |      |
| ttc | ctg | agc | agc | gtg | cgg | tac | tgg | atg | gcc | ttc | aac | gtg | gag | cgg | gcc | 816  |
| Phe | Leu | Ser | Ser | Val | Arg | Tyr | Trp | Met | Ala | Phe | Asn | Val | Glu | Arg | Ala |      |
|     |     |     | 260 |     |     |     |     | 265 |     |     |     |     | 270 |     |     |      |
| tgc | cag | tcc | tac | ttt | ggc | tgt | gtg | cag | tgt | att | agt | ggg | ccc | ttg | ggc | 864  |
| Cys | Gln | Ser | Tyr | Phe | Gly | Cys | Val | Gln | Cys | Ile | Ser | Gly | Pro | Leu | Gly |      |
|     |     | 275 |     |     |     |     | 280 |     |     |     |     | 285 |     |     |     |      |
| atg | tac | cgc | aac | agc | ctc | ctc | cag | cag | ttc | ctg | gag | gac | tgg | tac | cat | 912  |
| Met | Tyr | Arg | Asn | Ser | Leu | Leu | Gln | Gln | Phe | Leu | Glu | Asp | Trp | Tyr | His |      |
|     |     | 290 |     |     |     |     | 295 |     |     |     |     | 300 |     |     |     |      |
| cag | aag | ttc | cta | ggc | agc | aag | tgc | agc | ttc | ggg | gat | gac | cgg | cac | ctc | 960  |
| Gln | Lys | Phe | Leu | Gly | Ser | Lys | Cys | Ser | Phe | Gly | Asp | Asp | Arg | His | Leu |      |
| 305 |     |     |     |     | 310 |     |     |     |     | 315 |     |     |     |     | 320 |      |
| acc | aac | cga | gtc | ctg | agc | ctt | ggc | tac | cga | act | aag | tat | acc | gcg | cgc | 1008 |
| Thr | Asn | Arg | Val | Leu | Ser | Leu | Gly | Tyr | Arg | Thr | Lys | Tyr | Thr | Ala | Arg |      |
|     |     |     |     | 325 |     |     |     |     | 330 |     |     |     |     | 335 |     |      |
| tcc | aag | tgc | ctc | aca | gag | acc | ccc | act | aag | tac | ctc | cgg | tgg | ctc | aac | 1056 |
| Ser | Lys | Cys | Leu | Thr | Glu | Thr | Pro | Thr | Lys | Tyr | Leu | Arg | Trp | Leu | Asn |      |
|     |     |     | 340 |     |     |     |     | 345 |     |     |     |     | 350 |     |     |      |
| cag | caa | acc | cgc | tgg | agc | aag | tct | tac | ttc | cgg | gag | tgg | ctc | tac | aac | 1104 |
| Gln | Gln | Thr | Arg | Trp | Ser | Lys | Ser | Tyr | Phe | Arg | Glu | Trp | Leu | Tyr | Asn |      |
|     |     | 355 |     |     |     |     | 360 |     |     |     |     | 365 |     |     |     |      |
| tct | ctg | tgg | ttc | cat | aag | cac | cac | ctc | tgg | atg | acc | tac | gag | tca | gtg | 1152 |
| Ser | Leu | Trp | Phe | His | Lys | His | His | Leu | Trp | Met | Thr | Tyr | Glu | Ser | Val |      |
|     | 370 |     |     |     |     | 375 |     |     |     |     | 380 |     |     |     |     |      |
| gtc | acg | ggt | ttc | ttc | ccc | ttc | ttc | ctc | att | gcc | acg | gtt | ata | cag | ctt | 1200 |
| Val | Thr | Gly | Phe | Phe | Pro | Phe | Phe | Leu | Ile | Ala | Thr | Val | Ile | Gln | Leu |      |
| 385 |     |     |     |     | 390 |     |     |     |     | 395 |     |     |     |     | 400 |      |
| ttc | tac | cgg | ggc | cgc | atc | tgg | aac | att | ctc | ctc | ttc | ctg | ctg | acg | gtg | 1248 |
| Phe | Tyr | Arg | Gly | Arg | Ile | Trp | Asn | Ile | Leu | Leu | Phe | Leu | Leu | Thr | Val |      |
|     |     |     |     | 405 |     |     |     |     | 410 |     |     |     |     | 415 |     |      |
| cag | ctg | gtg | ggc | att | atc | aag | gcc | acc | tac | gcc | tgc | ttc | ctt | cgg | ggc | 1296 |
| Gln | Leu | Val | Gly | Ile | Ile | Lys | Ala | Thr | Tyr | Ala | Cys | Phe | Leu | Arg | Gly |      |
|     |     |     | 420 |     |     |     |     | 425 |     |     |     |     | 430 |     |     |      |
| aat | gca | gag | atg | atc | ttc | atg | tcc | ctc | tac | tcc | ctc | ctc | tat | atg | tcc | 1344 |
| Asn | Ala | Glu | Met | Ile | Phe | Met | Ser | Leu | Tyr | Ser | Leu | Leu | Tyr | Met | Ser |      |
|     |     | 435 |     |     |     |     | 440 |     |     |     |     | 445 |     |     |     |      |
| agc | ctt | ctg | ccg | gcc | aag | atc | ttt | gcc | att | gct | acc | atc | aac | aaa | tct | 1392 |
| Ser | Leu | Leu | Pro | Ala | Lys | Ile | Phe | Ala | Ile | Ala | Thr | Ile | Asn | Lys | Ser |      |
| 450 |     |     |     |     | 455 |     |     |     |     | 460 |     |     |     |     |     |      |
| ggc | tgg | ggc | acc | tct | ggc | cga | aaa | acc | att | gtg | gtg | aac | ttc | att | ggc | 1440 |
| Gly | Trp | Gly | Thr | Ser | Gly | Arg | Lys | Thr | Ile | Val | Val | Asn | Phe | Ile | Gly |      |
| 465 |     |     |     |     | 470 |     |     |     |     | 475 |     |     |     |     | 480 |      |
| ctc | att | cct | gtg | tcc | atc | tgg | gtg | gca | gtt | ctc | ctg | gga | ggg | ctg | gcc | 1488 |
| Leu | Ile | Pro | Val | Ser | Ile | Trp | Val | Ala | Val | Leu | Leu | Gly | Gly | Leu | Ala |      |
|     |     |     |     | 485 |     |     |     |     | 490 |     |     |     |     | 495 |     |      |
| tac | aca | gct | tat | tgc | cag | gac | ctg | ttc | agt | gag | aca | gag | cta | gcc | ttc | 1536 |
| Tyr | Thr | Ala | Tyr | Cys | Gln | Asp | Leu | Phe | Ser | Glu | Thr | Glu | Leu | Ala | Phe |      |
|     |     |     | 500 |     |     |     |     | 505 |     |     |     |     | 510 |     |     |      |
| ctt | gtc | tct | ggg | gct | ata | ctg | tat | ggc | tgc | tac | tgg | gtg | gcc | ctc | ctc | 1584 |

```
Leu Val Ser Gly Ala Ile Leu Tyr Gly Cys Tyr Trp Val Ala Leu Leu
            515                 520                 525 atg cta tat ctg gcc atc atc gcc cgg cga tgt ggg aag aag ccg gag      1632
Met Leu Tyr Leu Ala Ile Ile Ala Arg Arg Cys Gly Lys Lys Pro Glu
530                 535                 540 cag tca agc ttg gct ttt gct gag gtg tga                              1662
Gln Ser Ser Leu Ala Phe Ala Glu Val
545                 550
```

<210> SEQ ID NO 6
<211> LENGTH: 553
<212> TYPE: PRT
<213> ORGANISM: Homo sapiens

<400> SEQUENCE: 6

```
Met Pro Val Gln Leu Thr Thr Ala Leu Arg Val Gly Thr Ser Leu
1               5                   10                  15

Phe Ala Leu Ala Val Leu Gly Gly Ile Leu Ala Ala Tyr Val Thr Gly
                20                  25                  30

Tyr Gln Phe Ile His Thr Glu Lys His Tyr Leu Ser Phe Gly Leu Tyr
                35                  40                  45

Gly Ala Ile Leu Gly Leu His Leu Leu Ile Gln Ser Leu Phe Ala Phe
            50                  55                  60

Leu Glu His Arg Arg Met Gln Arg Ala Gly Gln Ala Leu Lys Leu Pro
65                  70                  75                  80

Ser Pro Arg Arg Gly Ser Val Ala Leu Cys Ile Ala Ala Tyr Gln Glu
                    85                  90                  95

Asp Pro Asp Tyr Leu Arg Lys Cys Leu Arg Ser Ala Gln Arg Ile Ser
                100                 105                 110

Phe Pro Asp Leu Lys Val Val Met Val Val Asp Gly Asn Arg Gln Glu
            115                 120                 125

Asp Ala Tyr Met Leu Asp Ile Phe His Glu Val Leu Gly Gly Thr Glu
130                 135                 140

Gln Ala Gly Phe Phe Val Trp Arg Ser Asn Phe His Glu Ala Gly Glu
145                 150                 155                 160

Gly Glu Thr Glu Ala Ser Leu Gln Glu Gly Met Asp Arg Val Arg Asp
                165                 170                 175

Val Val Arg Ala Ser Thr Phe Ser Cys Ile Met Gln Lys Trp Gly Gly
                180                 185                 190

Lys Arg Glu Val Met Tyr Thr Ala Phe Lys Ala Leu Gly Asp Ser Val
            195                 200                 205

Asp Tyr Ile Gln Val Cys Asp Ser Asp Thr Val Leu Asp Pro Ala Cys
210                 215                 220

Thr Ile Glu Met Leu Arg Val Leu Glu Glu Asp Pro Gln Val Gly Gly
225                 230                 235                 240

Val Gly Gly Asp Val Gln Ile Leu Asn Lys Tyr Asp Ser Trp Ile Ser
                245                 250                 255

Phe Leu Ser Ser Val Arg Tyr Trp Met Ala Phe Asn Val Glu Arg Ala
                260                 265                 270

Cys Gln Ser Tyr Phe Gly Cys Val Gln Cys Ile Ser Gly Pro Leu Gly
            275                 280                 285

Met Tyr Arg Asn Ser Leu Leu Gln Gln Phe Leu Glu Asp Trp Tyr His
290                 295                 300

Gln Lys Phe Leu Gly Ser Lys Cys Ser Phe Gly Asp Asp Arg His Leu
305                 310                 315                 320
```

```
Thr Asn Arg Val Leu Ser Leu Gly Tyr Arg Thr Lys Tyr Thr Ala Arg
            325                 330                 335

Ser Lys Cys Leu Thr Glu Thr Pro Thr Lys Tyr Leu Arg Trp Leu Asn
            340                 345                 350

Gln Gln Thr Arg Trp Ser Lys Ser Tyr Phe Arg Glu Trp Leu Tyr Asn
            355                 360                 365

Ser Leu Trp Phe His Lys His His Leu Trp Met Thr Tyr Glu Ser Val
            370                 375                 380

Val Thr Gly Phe Phe Pro Phe Phe Leu Ile Ala Thr Val Ile Gln Leu
385                 390                 395                 400

Phe Tyr Arg Gly Arg Ile Trp Asn Ile Leu Leu Phe Leu Leu Thr Val
                405                 410                 415

Gln Leu Val Gly Ile Ile Lys Ala Thr Tyr Ala Cys Phe Leu Arg Gly
            420                 425                 430

Asn Ala Glu Met Ile Phe Met Ser Leu Tyr Ser Leu Leu Tyr Met Ser
            435                 440                 445

Ser Leu Leu Pro Ala Lys Ile Phe Ala Ile Ala Thr Ile Asn Lys Ser
            450                 455                 460

Gly Trp Gly Thr Ser Gly Arg Lys Thr Ile Val Val Asn Phe Ile Gly
465                 470                 475                 480

Leu Ile Pro Val Ser Ile Trp Val Ala Val Leu Leu Gly Gly Leu Ala
                485                 490                 495

Tyr Thr Ala Tyr Cys Gln Asp Leu Phe Ser Glu Thr Glu Leu Ala Phe
            500                 505                 510

Leu Val Ser Gly Ala Ile Leu Tyr Gly Cys Tyr Trp Val Ala Leu Leu
            515                 520                 525

Met Leu Tyr Leu Ala Ile Ile Ala Arg Arg Cys Gly Lys Lys Pro Glu
            530                 535                 540

Gln Ser Ser Leu Ala Phe Ala Glu Val
545                 550

<210> SEQ ID NO 7
<211> LENGTH: 1662
<212> TYPE: DNA
<213> ORGANISM: Artificial sequence
<220> FEATURE:
<221> NAME/KEY: CDS
<222> LOCATION: (1)..(1662)
<223> OTHER INFORMATION: Synthetic sequnce encoding Homo sapiens HAS-3
      Protein

<400> SEQUENCE: 7 atg cct gtt cag ctg act aca gca ctt aga gtc gta ggt aca agc ttg      48
Met Pro Val Gln Leu Thr Thr Ala Leu Arg Val Val Gly Thr Ser Leu
1               5                   10                  15 ttc gct ctg gca gtg ttg ggc ggt att cta gct gca tat gta act gga      96
Phe Ala Leu Ala Val Leu Gly Gly Ile Leu Ala Ala Tyr Val Thr Gly
                20                  25                  30 tat cag ttc att cat act gag aag cac tac cta tca ttc gga tta tac     144
Tyr Gln Phe Ile His Thr Glu Lys His Tyr Leu Ser Phe Gly Leu Tyr
            35                  40                  45 ggt gca att ttg ggt ttg cac ttg cta att caa tct ttg ttt gct ttt     192
Gly Ala Ile Leu Gly Leu His Leu Leu Ile Gln Ser Leu Phe Ala Phe
        50                  55                  60 ctt gag cat cgt aga atg caa aga gcc gga caa gct ttg aaa ctt cca     240
Leu Glu His Arg Arg Met Gln Arg Ala Gly Gln Ala Leu Lys Leu Pro
65                  70                  75                  80 tct cca agg aga ggg agt gtg gca tta tgc atc gct gcc tac caa gaa     288
```

```
Ser Pro Arg Arg Gly Ser Val Ala Leu Cys Ile Ala Ala Tyr Gln Glu
            85                  90                  95 gat cca gat tat ctt cgt aag tgt tta aga tca gca caa agg ata tct    336
Asp Pro Asp Tyr Leu Arg Lys Cys Leu Arg Ser Ala Gln Arg Ile Ser
            100                 105                 110 ttc cct gat cta aaa gtc gtt atg gtt gtg gat ggg aat aga caa gag    384
Phe Pro Asp Leu Lys Val Val Met Val Val Asp Gly Asn Arg Gln Glu
            115                 120                 125 gat gct tat atg ttg gat ata ttc cat gaa gtt tta ggt gga aca gaa    432
Asp Ala Tyr Met Leu Asp Ile Phe His Glu Val Leu Gly Gly Thr Glu
        130                 135                 140 cag gct ggt ttc ttt gtt tgg agg tct aac ttc cac gag gct ggc gag    480
Gln Ala Gly Phe Phe Val Trp Arg Ser Asn Phe His Glu Ala Gly Glu
145                 150                 155                 160 gga gaa act gag gct tct ttg cag gag ggg atg gat aga gtc agg gat    528
Gly Glu Thr Glu Ala Ser Leu Gln Glu Gly Met Asp Arg Val Arg Asp
                165                 170                 175 gtg gtt cga gcc agt acc ttt tca tgc att atg caa aaa tgg ggt gga    576
Val Val Arg Ala Ser Thr Phe Ser Cys Ile Met Gln Lys Trp Gly Gly
            180                 185                 190 aaa agg gaa gtg atg tac act gct ttt aag gct ttg ggt gac tcc gtt    624
Lys Arg Glu Val Met Tyr Thr Ala Phe Lys Ala Leu Gly Asp Ser Val
        195                 200                 205 gat tat atc cag gta tgc gac tca gac act gtt ttg gac cca gca tgt    672
Asp Tyr Ile Gln Val Cys Asp Ser Asp Thr Val Leu Asp Pro Ala Cys
210                 215                 220 acc att gaa atg ctc cgt gtt ctt gag gaa gat cca cag gtg ggg ggt    720
Thr Ile Glu Met Leu Arg Val Leu Glu Glu Asp Pro Gln Val Gly Gly
225                 230                 235                 240 gta gga ggt gat gta cag ata ctc aac aaa tat gac agt tgg atc tca    768
Val Gly Gly Asp Val Gln Ile Leu Asn Lys Tyr Asp Ser Trp Ile Ser
                245                 250                 255 ttc ctt tcc tct gtc agg tac tgg atg gca ttt aat gtt gaa aga gcc    816
Phe Leu Ser Ser Val Arg Tyr Trp Met Ala Phe Asn Val Glu Arg Ala
            260                 265                 270 tgc caa tct tat ttt ggc tgt gtt caa tgt att tct gga cct ttg ggt    864
Cys Gln Ser Tyr Phe Gly Cys Val Gln Cys Ile Ser Gly Pro Leu Gly
        275                 280                 285 atg tac aga aat agt tta ctt caa cag ttc ctg gaa gat tgg tat cac    912
Met Tyr Arg Asn Ser Leu Leu Gln Gln Phe Leu Glu Asp Trp Tyr His
290                 295                 300 caa aaa ttt cta ggg agt aag tgt tct ttt gga gac gat aga cat cta    960
Gln Lys Phe Leu Gly Ser Lys Cys Ser Phe Gly Asp Asp Arg His Leu
305                 310                 315                 320 aca aat cgt gtc ctc agt ctt ggc tac agg act aag tat acc gct aga   1008
Thr Asn Arg Val Leu Ser Leu Gly Tyr Arg Thr Lys Tyr Thr Ala Arg
                325                 330                 335 agt aaa tgc ctg act gaa act cct aca aag tat ctg aga tgg tta aat   1056
Ser Lys Cys Leu Thr Glu Thr Pro Thr Lys Tyr Leu Arg Trp Leu Asn
            340                 345                 350 cag caa act aga tgg tca aag tct tac ttc agg gaa tgg ttg tac aat   1104
Gln Gln Thr Arg Trp Ser Lys Ser Tyr Phe Arg Glu Trp Leu Tyr Asn
        355                 360                 365 tca tta tgg ttt cat aaa cat cat ctg tgg atg aca tac gaa tcc gtt   1152
Ser Leu Trp Phe His Lys His His Leu Trp Met Thr Tyr Glu Ser Val
370                 375                 380 gtc aca ggt ttt ttc cca ttt ttc tta att gca aca gtt att cag ctt   1200
Val Thr Gly Phe Phe Pro Phe Phe Leu Ile Ala Thr Val Ile Gln Leu
385                 390                 395                 400
```

```
ttt tat aga gga agg atc tgg aac att ctt ttg ttt ctc ctt aca gtt    1248
Phe Tyr Arg Gly Arg Ile Trp Asn Ile Leu Leu Phe Leu Leu Thr Val
                405                 410                 415 caa ttg gtg ggc att ata aag gct aca tat gca tgt ttt ctc agg gga    1296
Gln Leu Val Gly Ile Ile Lys Ala Thr Tyr Ala Cys Phe Leu Arg Gly
            420                 425                 430 aac gca gaa atg att ttc atg tca ctt tac agc ctg tta tat atg tcc    1344
Asn Ala Glu Met Ile Phe Met Ser Leu Tyr Ser Leu Leu Tyr Met Ser
        435                 440                 445 tca ctt tta ccc gca aag atc ttt gct att gct acc ata aat aag tct    1392
Ser Leu Leu Pro Ala Lys Ile Phe Ala Ile Ala Thr Ile Asn Lys Ser
    450                 455                 460 ggg tgg gga act tct gga cga aag aca atc gtt gtg aat ttt att ggc    1440
Gly Trp Gly Thr Ser Gly Arg Lys Thr Ile Val Val Asn Phe Ile Gly
465                 470                 475                 480 ttg ata ccc gtt tca att tgg gta gct gtt ctt ctc ggt gga ctt gca    1488
Leu Ile Pro Val Ser Ile Trp Val Ala Val Leu Leu Gly Gly Leu Ala
                485                 490                 495 tat act gct tac tgt caa gat ctt ttt tca gag act gaa ctt gcc ttt    1536
Tyr Thr Ala Tyr Cys Gln Asp Leu Phe Ser Glu Thr Glu Leu Ala Phe
            500                 505                 510 ctc gtt agt gga gct att ttg tat gga tgt tat tgg gtg gct ctt cta    1584
Leu Val Ser Gly Ala Ile Leu Tyr Gly Cys Tyr Trp Val Ala Leu Leu
        515                 520                 525 atg ctt tat ctt gca atc ata gcc cgt cga tgt ggt aaa aaa cct gaa    1632
Met Leu Tyr Leu Ala Ile Ile Ala Arg Arg Cys Gly Lys Lys Pro Glu
    530                 535                 540 caa agc tcc ctc gct ttt gct gag gtg taa                            1662
Gln Ser Ser Leu Ala Phe Ala Glu Val
545                 550

<210> SEQ ID NO 8
<211> LENGTH: 553
<212> TYPE: PRT
<213> ORGANISM: Artificial sequence
<220> FEATURE:
<223> OTHER INFORMATION: Synthetic sequnce encoding Homo sapiens HAS-3
      Protein

<400> SEQUENCE: 8

Met Pro Val Gln Leu Thr Thr Ala Leu Arg Val Val Gly Thr Ser Leu
1               5                   10                  15

Phe Ala Leu Ala Val Leu Gly Gly Ile Leu Ala Ala Tyr Val Thr Gly
                20                  25                  30

Tyr Gln Phe Ile His Thr Glu Lys His Tyr Leu Ser Phe Gly Leu Tyr
            35                  40                  45

Gly Ala Ile Leu Gly Leu His Leu Leu Ile Gln Ser Leu Phe Ala Phe
        50                  55                  60

Leu Glu His Arg Arg Met Gln Arg Ala Gly Gln Ala Leu Lys Leu Pro
65                  70                  75                  80

Ser Pro Arg Arg Gly Ser Val Ala Leu Cys Ile Ala Ala Tyr Gln Glu
                85                  90                  95

Asp Pro Asp Tyr Leu Arg Lys Cys Leu Arg Ser Ala Gln Arg Ile Ser
            100                 105                 110

Phe Pro Asp Leu Lys Val Val Met Val Val Asp Gly Asn Arg Gln Glu
        115                 120                 125

Asp Ala Tyr Met Leu Asp Ile Phe His Glu Val Leu Gly Gly Thr Glu
    130                 135                 140

Gln Ala Gly Phe Phe Val Trp Arg Ser Asn Phe His Glu Ala Gly Glu
```

```
            145                 150                 155                 160
        Gly Glu Thr Glu Ala Ser Leu Gln Glu Gly Met Asp Arg Val Arg Asp
                        165                 170                 175

Val Val Arg Ala Ser Thr Phe Ser Cys Ile Met Gln Lys Trp Gly Gly
                        180                 185                 190

Lys Arg Glu Val Met Tyr Thr Ala Phe Lys Ala Leu Gly Asp Ser Val
                        195                 200                 205

Asp Tyr Ile Gln Val Cys Asp Ser Asp Thr Val Leu Asp Pro Ala Cys
                        210                 215                 220

Thr Ile Glu Met Leu Arg Val Leu Glu Glu Asp Pro Gln Val Gly Gly
        225                 230                 235                 240

Val Gly Gly Asp Val Gln Ile Leu Asn Lys Tyr Asp Ser Trp Ile Ser
                        245                 250                 255

Phe Leu Ser Ser Val Arg Tyr Trp Met Ala Phe Asn Val Glu Arg Ala
                        260                 265                 270

Cys Gln Ser Tyr Phe Gly Cys Val Gln Cys Ile Ser Gly Pro Leu Gly
                        275                 280                 285

Met Tyr Arg Asn Ser Leu Leu Gln Gln Phe Leu Glu Asp Trp Tyr His
                        290                 295                 300

Gln Lys Phe Leu Gly Ser Lys Cys Ser Phe Gly Asp Asp Arg His Leu
        305                 310                 315                 320

Thr Asn Arg Val Leu Ser Leu Gly Tyr Arg Thr Lys Tyr Thr Ala Arg
                        325                 330                 335

Ser Lys Cys Leu Thr Glu Thr Pro Thr Lys Tyr Leu Arg Trp Leu Asn
                        340                 345                 350

Gln Gln Thr Arg Trp Ser Lys Ser Tyr Phe Arg Glu Trp Leu Tyr Asn
                        355                 360                 365

Ser Leu Trp Phe His Lys His His Leu Trp Met Thr Tyr Glu Ser Val
                        370                 375                 380

Val Thr Gly Phe Phe Pro Phe Phe Leu Ile Ala Thr Val Ile Gln Leu
        385                 390                 395                 400

Phe Tyr Arg Gly Arg Ile Trp Asn Ile Leu Leu Phe Leu Leu Thr Val
                        405                 410                 415

Gln Leu Val Gly Ile Ile Lys Ala Thr Tyr Ala Cys Phe Leu Arg Gly
                        420                 425                 430

Asn Ala Glu Met Ile Phe Met Ser Leu Tyr Ser Leu Leu Tyr Met Ser
                        435                 440                 445

Ser Leu Leu Pro Ala Lys Ile Phe Ala Ile Ala Thr Ile Asn Lys Ser
        450                 455                 460

Gly Trp Gly Thr Ser Gly Arg Lys Thr Ile Val Val Asn Phe Ile Gly
        465                 470                 475                 480

Leu Ile Pro Val Ser Ile Trp Val Ala Val Leu Leu Gly Gly Leu Ala
                        485                 490                 495

Tyr Thr Ala Tyr Cys Gln Asp Leu Phe Ser Glu Thr Glu Leu Ala Phe
                        500                 505                 510

Leu Val Ser Gly Ala Ile Leu Tyr Gly Cys Tyr Trp Val Ala Leu Leu
                        515                 520                 525

Met Leu Tyr Leu Ala Ile Ile Ala Arg Arg Cys Gly Lys Lys Pro Glu
                        530                 535                 540

Gln Ser Ser Leu Ala Phe Ala Glu Val
        545                 550

<210> SEQ ID NO 9
```

```
<211> LENGTH: 1632
<212> TYPE: DNA
<213> ORGANISM: Homo sapiens
<220> FEATURE:
<221> NAME/KEY: CDS
<222> LOCATION: (1)..(1632)
<223> OTHER INFORMATION: Hyaluronan synthase 1
<300> PUBLICATION INFORMATION:
<308> DATABASE ACCESSION NUMBER: D84424.1
<309> DATABASE ENTRY DATE: 1996-07-02
<313> RELEVANT RESIDUES IN SEQ ID NO: (149)..(1780)

<400> SEQUENCE: 9 atg acc tgg gcc tac gcc gcc ggg gtg ccg ctg gcc tcc gat cgc tac       48
Met Thr Trp Ala Tyr Ala Ala Gly Val Pro Leu Ala Ser Asp Arg Tyr
1               5                   10                  15 ggc ctc ctg gcc ttc ggc ctc tac ggg gcc ttc ctt tca gcg cac ctg       96
Gly Leu Leu Ala Phe Gly Leu Tyr Gly Ala Phe Leu Ser Ala His Leu
            20                  25                  30 gtg gcg cag agc ctc ttc gcg tac ctg gag cac cgg cgg gtg gcg gcg      144
Val Ala Gln Ser Leu Phe Ala Tyr Leu Glu His Arg Arg Val Ala Ala
35                  40                  45 gcg gcg cgg ggg ccg ctg gat gca gcc acc gcg cgc agt gtg gcg ctg      192
Ala Ala Arg Gly Pro Leu Asp Ala Ala Thr Ala Arg Ser Val Ala Leu
50                  55                  60 acc atc tcc gcc tac cag gag gac ccc gcg tac ctg cgc cag tgc ctg      240
Thr Ile Ser Ala Tyr Gln Glu Asp Pro Ala Tyr Leu Arg Gln Cys Leu
65                  70                  75                  80 gcg tcc gcc cgc gcc ctg ctc tac ccg cgc gcg cgc gtg cgc gtc ctc      288
Ala Ser Ala Arg Ala Leu Leu Tyr Pro Arg Ala Arg Val Arg Val Leu
                85                  90                  95 atg gtg gtg gat ggc aac cgc gcc gag gac ctc tac atg gtc gac atg      336
Met Val Val Asp Gly Asn Arg Ala Glu Asp Leu Tyr Met Val Asp Met
            100                 105                 110 ttc cgc gag gtc ttc gct gac gag gac ccc gcc acg tac gtg tgg gac      384
Phe Arg Glu Val Phe Ala Asp Glu Asp Pro Ala Thr Tyr Val Trp Asp
        115                 120                 125 ggc aac tac cac cag ccc tgg gaa ccc gcg gcg gcg ggc gcg gtg ggc      432
Gly Asn Tyr His Gln Pro Trp Glu Pro Ala Ala Ala Gly Ala Val Gly
    130                 135                 140 gcc gga gcc tat cgg gag gtg gag gcg gag gat cct ggg cgg ctg gca      480
Ala Gly Ala Tyr Arg Glu Val Glu Ala Glu Asp Pro Gly Arg Leu Ala
145                 150                 155                 160 gtg gag gcg ctg gtg agg act cgc agg tgc gtg tgc gtg gcg cag cgc      528
Val Glu Ala Leu Val Arg Thr Arg Arg Cys Val Cys Val Ala Gln Arg
                165                 170                 175 tgg ggc ggc aag cgc gag gtc atg tac aca gcc ttc aag gcg ctc gga      576
Trp Gly Gly Lys Arg Glu Val Met Tyr Thr Ala Phe Lys Ala Leu Gly
            180                 185                 190 gat tcg gtg gac tac gtg cag gtc tgt gac tcg gac aca agg ttg gac      624
Asp Ser Val Asp Tyr Val Gln Val Cys Asp Ser Asp Thr Arg Leu Asp
        195                 200                 205 ccc atg gca ctg ctg gag ctc gtg cgg gta ctg gac gag gac ccc cgg      672
Pro Met Ala Leu Leu Glu Leu Val Arg Val Leu Asp Glu Asp Pro Arg
    210                 215                 220 gta ggg gct gtt ggt ggg gat gtg cgg atc ctt aac cct ctg gac tcc      720
Val Gly Ala Val Gly Gly Asp Val Arg Ile Leu Asn Pro Leu Asp Ser
225                 230                 235                 240 tgg gtc agc ttc cta agc agc ctg cga tac tgg gta gcc ttc aat gtg      768
Trp Val Ser Phe Leu Ser Ser Leu Arg Tyr Trp Val Ala Phe Asn Val
                245                 250                 255 gag cgg gct tgt cag agc tac ttc cac tgt gta tcc tgc atc agc ggt      816
Glu Arg Ala Cys Gln Ser Tyr Phe His Cys Val Ser Cys Ile Ser Gly
```

```
                Glu Arg Ala Cys Gln Ser Tyr Phe His Cys Val Ser Cys Ile Ser Gly
                                260                 265                 270 cct cta ggc cta tat agg aat aac ctc ttg cag cag ttt ctt gag gcc        864
Pro Leu Gly Leu Tyr Arg Asn Asn Leu Leu Gln Gln Phe Leu Glu Ala
            275                 280                 285 tgg tac aac cag aag ttc ctg ggt acc cac tgt act ttt ggg gat gac        912
Trp Tyr Asn Gln Lys Phe Leu Gly Thr His Cys Thr Phe Gly Asp Asp
        290                 295                 300 cgg cac ctc acc aac cgc atg ctc agc atg ggt tat gct acc aag tac        960
Arg His Leu Thr Asn Arg Met Leu Ser Met Gly Tyr Ala Thr Lys Tyr
305                 310                 315                 320 acc tcc agg tcc cgc tgc tac tca gag acg ccc tcg tcc ttc ctg cgg       1008
Thr Ser Arg Ser Arg Cys Tyr Ser Glu Thr Pro Ser Ser Phe Leu Arg
                325                 330                 335 tgg ctg agc cag cag aca cgc tgg tcc aag tcg tac ttc cgt gag tgg       1056
Trp Leu Ser Gln Gln Thr Arg Trp Ser Lys Ser Tyr Phe Arg Glu Trp
            340                 345                 350 ctg tac aac gcg ctc tgg tgg cac cgg cac cat gcg tgg atg acc tac       1104
Leu Tyr Asn Ala Leu Trp Trp His Arg His His Ala Trp Met Thr Tyr
        355                 360                 365 gag gcg gtg gtc tcc ggc ctg ttc ccc ttc ttc gtg gcg gcc act gtg       1152
Glu Ala Val Val Ser Gly Leu Phe Pro Phe Phe Val Ala Ala Thr Val
370                 375                 380 ctg cgt ctg ttc tac gcg ggc cgc cct tgg gcg ctg ctg tgg gtg ctg       1200
Leu Arg Leu Phe Tyr Ala Gly Arg Pro Trp Ala Leu Leu Trp Val Leu
385                 390                 395                 400 ctg tgc gtg cag ggc gtg gca ctg gcc aag gcg gcc ttc gcg gcc tgg       1248
Leu Cys Val Gln Gly Val Ala Leu Ala Lys Ala Ala Phe Ala Ala Trp
                405                 410                 415 ctg cgg ggc tgc ctg cgc atg gtg ctt ctg tcg ctc tac gcg ccc ctc       1296
Leu Arg Gly Cys Leu Arg Met Val Leu Leu Ser Leu Tyr Ala Pro Leu
            420                 425                 430 tac atg tgt ggc ctc ctg cct gcc aag ttc ctg gcg cta gtc acc atg       1344
Tyr Met Cys Gly Leu Leu Pro Ala Lys Phe Leu Ala Leu Val Thr Met
        435                 440                 445 aac cag agt ggc tgg ggc acc tcg ggc cgg cgg aag ctg gcc gct aac       1392
Asn Gln Ser Gly Trp Gly Thr Ser Gly Arg Arg Lys Leu Ala Ala Asn
450                 455                 460 tac gtc cct ctg ctg ccc ctg gcg ctc tgg gcg ctg ctg ctt ggg           1440
Tyr Val Pro Leu Leu Pro Leu Ala Leu Trp Ala Leu Leu Leu Gly
465                 470                 475                 480 ggc ctg gtc cgc agc gta gca cac gag gcc agg gcc gac tgg agc ggc       1488
Gly Leu Val Arg Ser Val Ala His Glu Ala Arg Ala Asp Trp Ser Gly
                485                 490                 495 cct tcc cgc gca gcc gag gcc tac cac ttg gcc gcg ggg gcc ggc gcc       1536
Pro Ser Arg Ala Ala Glu Ala Tyr His Leu Ala Ala Gly Ala Gly Ala
            500                 505                 510 tac gtg ggc tac tgg gtg gcc atg ttg acg ctg tac tgg gtg ggc gtg       1584
Tyr Val Gly Tyr Trp Val Ala Met Leu Thr Leu Tyr Trp Val Gly Val
        515                 520                 525 cgg agg ctt tgc cgg cgg cgg acc ggg ggc tac cgc gtc cag gtg tga       1632
Arg Arg Leu Cys Arg Arg Arg Thr Gly Gly Tyr Arg Val Gln Val
530                 535                 540

<210> SEQ ID NO 10
<211> LENGTH: 543
<212> TYPE: PRT
<213> ORGANISM: Homo sapiens

<400> SEQUENCE: 10
```

```
Met Thr Trp Ala Tyr Ala Ala Gly Val Pro Leu Ala Ser Asp Arg Tyr
1               5                   10                  15

Gly Leu Leu Ala Phe Gly Leu Tyr Gly Ala Phe Leu Ser Ala His Leu
            20                  25                  30

Val Ala Gln Ser Leu Phe Ala Tyr Leu Glu His Arg Arg Val Ala Ala
            35                  40                  45

Ala Ala Arg Gly Pro Leu Asp Ala Ala Thr Ala Arg Ser Val Ala Leu
50                  55                  60

Thr Ile Ser Ala Tyr Gln Glu Asp Pro Ala Tyr Leu Arg Gln Cys Leu
65                  70                  75                  80

Ala Ser Ala Arg Ala Leu Leu Tyr Pro Arg Ala Arg Val Arg Val Leu
            85                  90                  95

Met Val Val Asp Gly Asn Arg Ala Glu Asp Leu Tyr Met Val Asp Met
            100                 105                 110

Phe Arg Glu Val Phe Ala Asp Glu Asp Pro Ala Thr Tyr Val Trp Asp
            115                 120                 125

Gly Asn Tyr His Gln Pro Trp Glu Pro Ala Ala Gly Ala Val Gly
            130                 135                 140

Ala Gly Ala Tyr Arg Glu Val Glu Ala Glu Asp Pro Gly Arg Leu Ala
145                 150                 155                 160

Val Glu Ala Leu Val Arg Thr Arg Arg Cys Val Cys Val Ala Gln Arg
            165                 170                 175

Trp Gly Gly Lys Arg Glu Val Met Tyr Thr Ala Phe Lys Ala Leu Gly
            180                 185                 190

Asp Ser Val Asp Tyr Val Gln Val Cys Asp Ser Asp Thr Arg Leu Asp
            195                 200                 205

Pro Met Ala Leu Leu Glu Leu Val Arg Val Leu Asp Glu Asp Pro Arg
            210                 215                 220

Val Gly Ala Val Gly Gly Asp Val Arg Ile Leu Asn Pro Leu Asp Ser
225                 230                 235                 240

Trp Val Ser Phe Leu Ser Ser Leu Arg Tyr Trp Val Ala Phe Asn Val
            245                 250                 255

Glu Arg Ala Cys Gln Ser Tyr Phe His Cys Val Ser Cys Ile Ser Gly
            260                 265                 270

Pro Leu Gly Leu Tyr Arg Asn Asn Leu Leu Gln Gln Phe Leu Glu Ala
            275                 280                 285

Trp Tyr Asn Gln Lys Phe Leu Gly Thr His Cys Thr Phe Gly Asp Asp
            290                 295                 300

Arg His Leu Thr Asn Arg Met Leu Ser Met Gly Tyr Ala Thr Lys Tyr
305                 310                 315                 320

Thr Ser Arg Ser Arg Cys Tyr Ser Glu Thr Pro Ser Ser Phe Leu Arg
            325                 330                 335

Trp Leu Ser Gln Gln Thr Arg Trp Ser Lys Ser Tyr Phe Arg Glu Trp
            340                 345                 350

Leu Tyr Asn Ala Leu Trp Trp His Arg His Ala Trp Met Thr Tyr
            355                 360                 365

Glu Ala Val Val Ser Gly Leu Phe Pro Phe Val Ala Ala Thr Val
370                 375                 380

Leu Arg Leu Phe Tyr Ala Gly Arg Pro Trp Ala Leu Leu Trp Val Leu
385                 390                 395                 400

Leu Cys Val Gln Gly Val Ala Leu Ala Lys Ala Ala Phe Ala Ala Trp
            405                 410                 415

Leu Arg Gly Cys Leu Arg Met Val Leu Leu Ser Leu Tyr Ala Pro Leu
```

```
                420                 425                 430
Tyr Met Cys Gly Leu Leu Pro Ala Lys Phe Leu Ala Leu Val Thr Met
            435                 440                 445

Asn Gln Ser Gly Trp Gly Thr Ser Gly Arg Arg Lys Leu Ala Ala Asn
        450                 455                 460

Tyr Val Pro Leu Leu Pro Leu Ala Leu Trp Ala Leu Leu Leu Leu Gly
465                 470                 475                 480

Gly Leu Val Arg Ser Val Ala His Glu Ala Arg Ala Asp Trp Ser Gly
                485                 490                 495

Pro Ser Arg Ala Ala Glu Ala Tyr His Leu Ala Ala Gly Ala Gly Ala
            500                 505                 510

Tyr Val Gly Tyr Trp Val Ala Met Leu Thr Leu Tyr Trp Val Gly Val
        515                 520                 525

Arg Arg Leu Cys Arg Arg Arg Thr Gly Gly Tyr Arg Val Gln Val
530                 535                 540

<210> SEQ ID NO 11
<211> LENGTH: 1659
<212> TYPE: DNA
<213> ORGANISM: Homo sapiens
<220> FEATURE:
<221> NAME/KEY: CDS
<222> LOCATION: (1)..(1659)
<223> OTHER INFORMATION: Hyaluronan synthase 2
<300> PUBLICATION INFORMATION:
<308> DATABASE ACCESSION NUMBER: U54804.1
<309> DATABASE ENTRY DATE: 1996-08-10
<313> RELEVANT RESIDUES IN SEQ ID NO: (536)..(2194)

<400> SEQUENCE: 11 atg cat tgt gag agg ttt cta tgt atc ctg aga ata att gga acc aca      48
Met His Cys Glu Arg Phe Leu Cys Ile Leu Arg Ile Ile Gly Thr Thr
1               5                   10                  15 ctc ttt gga gtc tct ctc ctc ctt gga atc aca gct gct tat att gtt      96
Leu Phe Gly Val Ser Leu Leu Leu Gly Ile Thr Ala Ala Tyr Ile Val
            20                  25                  30 ggc tac cag ttt atc caa acg gat aat tac tat ttc tct ttt gga ctg     144
Gly Tyr Gln Phe Ile Gln Thr Asp Asn Tyr Tyr Phe Ser Phe Gly Leu
        35                  40                  45 tat ggt gcc ttt ttg gca tca cac ctc atc atc caa agc ctg ttt gcc     192
Tyr Gly Ala Phe Leu Ala Ser His Leu Ile Ile Gln Ser Leu Phe Ala
    50                  55                  60 ttt ttg gag cac cga aaa atg aaa aaa tcc cta gaa acc ccc ata aag     240
Phe Leu Glu His Arg Lys Met Lys Lys Ser Leu Glu Thr Pro Ile Lys
65                  70                  75                  80 ttg aac aaa aca gtt gcc ctt tgc atc gct gcc tat caa gaa gat cca     288
Leu Asn Lys Thr Val Ala Leu Cys Ile Ala Ala Tyr Gln Glu Asp Pro
            85                  90                  95 gac tac tta agg aaa tgt ttg caa tct gtg aaa agg cta acc tac cct     336
Asp Tyr Leu Arg Lys Cys Leu Gln Ser Val Lys Arg Leu Thr Tyr Pro
        100                 105                 110 ggg att aaa gtt gtc atg gtc ata gat ggg aac tca gaa gat gac ctt     384
Gly Ile Lys Val Val Met Val Ile Asp Gly Asn Ser Glu Asp Asp Leu
    115                 120                 125 tac atg atg gac atc ttc agt gaa gtc atg ggc aga gac aaa tca gcc     432
Tyr Met Met Asp Ile Phe Ser Glu Val Met Gly Arg Asp Lys Ser Ala
130                 135                 140 act tat atc tgg aag aac aac ttc cac gaa aag ggt ccc ggt gag aca     480
Thr Tyr Ile Trp Lys Asn Asn Phe His Glu Lys Gly Pro Gly Glu Thr
            150                 155                 160
```

```
gat gag tca cat aaa gaa agc tcg caa cac gta acg caa ttg gtc ttg      528
Asp Glu Ser His Lys Glu Ser Ser Gln His Val Thr Gln Leu Val Leu
                165                 170                 175 tcc aac aaa agt atc tgc atc atg caa aaa tgg ggt gga aaa aga gaa      576
Ser Asn Lys Ser Ile Cys Ile Met Gln Lys Trp Gly Gly Lys Arg Glu
            180                 185                 190 gtc atg tac aca gcc ttc aga gca ctg gga cga agt gtg gat tat gta      624
Val Met Tyr Thr Ala Phe Arg Ala Leu Gly Arg Ser Val Asp Tyr Val
        195                 200                 205 cag gtt tgt gat tca gac act atg ctt gac cca gcc tca tct gtg gag      672
Gln Val Cys Asp Ser Asp Thr Met Leu Asp Pro Ala Ser Ser Val Glu
    210                 215                 220 atg gta aaa gtt tta gaa gaa gat ccc atg gtt gga ggt gtt ggg gga      720
Met Val Lys Val Leu Glu Glu Asp Pro Met Val Gly Gly Val Gly Gly
225                 230                 235                 240 gat gtc cag att tta aac aag tac gat tcc tgg atc tca ttc ctc agc      768
Asp Val Gln Ile Leu Asn Lys Tyr Asp Ser Trp Ile Ser Phe Leu Ser
                245                 250                 255 agt gta aga tat tgg atg gct ttt aat ata gaa agg gcc tgt cag tct      816
Ser Val Arg Tyr Trp Met Ala Phe Asn Ile Glu Arg Ala Cys Gln Ser
            260                 265                 270 tat ttt ggg tgt gtt cag tgc att agt gga cct ctg gga atg tac aga      864
Tyr Phe Gly Cys Val Gln Cys Ile Ser Gly Pro Leu Gly Met Tyr Arg
        275                 280                 285 aac tcc ttg ttg cat gag ttt gtg gaa gat tgg tac aat caa gaa ttt      912
Asn Ser Leu Leu His Glu Phe Val Glu Asp Trp Tyr Asn Gln Glu Phe
    290                 295                 300 atg ggc aac caa tgt agc ttt ggt gat gac agg cat ctc acg aac cgg      960
Met Gly Asn Gln Cys Ser Phe Gly Asp Asp Arg His Leu Thr Asn Arg
305                 310                 315                 320 gtg ctg agc ctg ggc tat gca aca aaa tac aca gct cga tct aag tgc     1008
Val Leu Ser Leu Gly Tyr Ala Thr Lys Tyr Thr Ala Arg Ser Lys Cys
                325                 330                 335 ctt act gaa aca cct ata gag tat ctc aga tgg cta aac cag cag acc     1056
Leu Thr Glu Thr Pro Ile Glu Tyr Leu Arg Trp Leu Asn Gln Gln Thr
            340                 345                 350 cgt tgg agc aag tcc tac ttc cga gaa tgg ctg tac aat gca atg tgg     1104
Arg Trp Ser Lys Ser Tyr Phe Arg Glu Trp Leu Tyr Asn Ala Met Trp
        355                 360                 365 ttt cac aaa cat cac ttg tgg atg acc tac gaa gcg att atc act gga     1152
Phe His Lys His His Leu Trp Met Thr Tyr Glu Ala Ile Ile Thr Gly
    370                 375                 380 ttc ttt cct ttc ttt ctc att gcc aca gta atc cag ctc ttc tac cgg     1200
Phe Phe Pro Phe Phe Leu Ile Ala Thr Val Ile Gln Leu Phe Tyr Arg
385                 390                 395                 400 ggt aaa att tgg aac att ctc ctc ttc ttg tta act gtc cag cta gta     1248
Gly Lys Ile Trp Asn Ile Leu Leu Phe Leu Leu Thr Val Gln Leu Val
                405                 410                 415 ggt ctc ata aaa tca tct ttt gcc agc tgc ctt aga gga aat atc gtc     1296
Gly Leu Ile Lys Ser Ser Phe Ala Ser Cys Leu Arg Gly Asn Ile Val
            420                 425                 430 atg gtc ttc atg tct ctc tac tca gtg tta tac atg tcg agt tta ctt     1344
Met Val Phe Met Ser Leu Tyr Ser Val Leu Tyr Met Ser Ser Leu Leu
        435                 440                 445 ccc gcc aag atg ttt gca att gca aca ata aac aaa gct ggg tgg ggc     1392
Pro Ala Lys Met Phe Ala Ile Ala Thr Ile Asn Lys Ala Gly Trp Gly
    450                 455                 460 aca tca gga agg aaa acc att gtt gtt aat ttc ata gga ctc att cca     1440
Thr Ser Gly Arg Lys Thr Ile Val Val Asn Phe Ile Gly Leu Ile Pro
465                 470                 475                 480
```

```
gta tca gtt tgg ttt aca atc ctc ctg ggt ggt gtg att ttc acc att    1488
Val Ser Val Trp Phe Thr Ile Leu Leu Gly Gly Val Ile Phe Thr Ile
            485                 490                 495 tat aag gag tct aaa agg cca ttt tca gaa tcc aaa cag aca gtt cta    1536
Tyr Lys Glu Ser Lys Arg Pro Phe Ser Glu Ser Lys Gln Thr Val Leu
            500                 505                 510 att gtt gga acg ttg ctc tat gca tgc tat tgg gtc atg ctt ttg acg    1584
Ile Val Gly Thr Leu Leu Tyr Ala Cys Tyr Trp Val Met Leu Leu Thr
            515                 520                 525 ctg tat gta gtt ctc atc aat aag tgt ggc agg cgg aag aag gga caa    1632
Leu Tyr Val Val Leu Ile Asn Lys Cys Gly Arg Arg Lys Lys Gly Gln
        530                 535                 540 caa tat gac atg gtg ctt gat gta tga                                1659
Gln Tyr Asp Met Val Leu Asp Val
545                 550

<210> SEQ ID NO 12
<211> LENGTH: 552
<212> TYPE: PRT
<213> ORGANISM: Homo sapiens

<400> SEQUENCE: 12

Met His Cys Glu Arg Phe Leu Cys Ile Leu Arg Ile Ile Gly Thr Thr
1               5                   10                  15

Leu Phe Gly Val Ser Leu Leu Gly Ile Thr Ala Ala Tyr Ile Val
            20                  25                  30

Gly Tyr Gln Phe Ile Gln Thr Asp Asn Tyr Tyr Phe Ser Phe Gly Leu
            35                  40                  45

Tyr Gly Ala Phe Leu Ala Ser His Leu Ile Ile Gln Ser Leu Phe Ala
    50                  55                  60

Phe Leu Glu His Arg Lys Met Lys Lys Ser Leu Glu Thr Pro Ile Lys
65                  70                  75                  80

Leu Asn Lys Thr Val Ala Leu Cys Ile Ala Ala Tyr Gln Glu Asp Pro
                85                  90                  95

Asp Tyr Leu Arg Lys Cys Leu Gln Ser Val Lys Arg Leu Thr Tyr Pro
            100                 105                 110

Gly Ile Lys Val Val Met Val Ile Asp Gly Asn Ser Glu Asp Asp Leu
        115                 120                 125

Tyr Met Met Asp Ile Phe Ser Glu Val Met Gly Arg Asp Lys Ser Ala
    130                 135                 140

Thr Tyr Ile Trp Lys Asn Asn Phe His Glu Lys Gly Pro Gly Glu Thr
145                 150                 155                 160

Asp Glu Ser His Lys Glu Ser Ser Gln His Val Thr Gln Leu Val Leu
                165                 170                 175

Ser Asn Lys Ser Ile Cys Ile Met Gln Lys Trp Gly Gly Lys Arg Glu
            180                 185                 190

Val Met Tyr Thr Ala Phe Arg Ala Leu Gly Arg Ser Val Asp Tyr Val
        195                 200                 205

Gln Val Cys Asp Ser Asp Thr Met Leu Asp Pro Ala Ser Ser Val Glu
    210                 215                 220

Met Val Lys Val Leu Glu Glu Asp Pro Met Val Gly Gly Val Gly Gly
225                 230                 235                 240

Asp Val Gln Ile Leu Asn Lys Tyr Asp Ser Trp Ile Ser Phe Leu Ser
                245                 250                 255

Ser Val Arg Tyr Trp Met Ala Phe Asn Ile Glu Arg Ala Cys Gln Ser
            260                 265                 270
```

```
Tyr Phe Gly Cys Val Gln Cys Ile Ser Gly Pro Leu Gly Met Tyr Arg
            275                 280                 285

Asn Ser Leu Leu His Glu Phe Val Glu Asp Trp Tyr Asn Gln Glu Phe
    290                 295                 300

Met Gly Asn Gln Cys Ser Phe Gly Asp Asp Arg His Leu Thr Asn Arg
305                 310                 315                 320

Val Leu Ser Leu Gly Tyr Ala Thr Lys Tyr Thr Ala Arg Ser Lys Cys
                325                 330                 335

Leu Thr Glu Thr Pro Ile Glu Tyr Leu Arg Trp Leu Asn Gln Gln Thr
            340                 345                 350

Arg Trp Ser Lys Ser Tyr Phe Arg Glu Trp Leu Tyr Asn Ala Met Trp
        355                 360                 365

Phe His Lys His His Leu Trp Met Thr Tyr Glu Ala Ile Ile Thr Gly
    370                 375                 380

Phe Phe Pro Phe Phe Leu Ile Ala Thr Val Ile Gln Leu Phe Tyr Arg
385                 390                 395                 400

Gly Lys Ile Trp Asn Ile Leu Phe Leu Leu Thr Val Gln Leu Val
                405                 410                 415

Gly Leu Ile Lys Ser Ser Phe Ala Ser Cys Leu Arg Gly Asn Ile Val
            420                 425                 430

Met Val Phe Met Ser Leu Tyr Ser Val Leu Tyr Met Ser Ser Leu Leu
        435                 440                 445

Pro Ala Lys Met Phe Ala Ile Ala Thr Ile Asn Lys Ala Gly Trp Gly
    450                 455                 460

Thr Ser Gly Arg Lys Thr Ile Val Val Asn Phe Ile Gly Leu Ile Pro
465                 470                 475                 480

Val Ser Val Trp Phe Thr Ile Leu Leu Gly Gly Val Ile Phe Thr Ile
                485                 490                 495

Tyr Lys Glu Ser Lys Arg Pro Phe Ser Glu Ser Lys Gln Thr Val Leu
            500                 505                 510

Ile Val Gly Thr Leu Leu Tyr Ala Cys Tyr Trp Val Met Leu Leu Thr
        515                 520                 525

Leu Tyr Val Val Leu Ile Asn Lys Cys Gly Arg Arg Lys Lys Gly Gln
    530                 535                 540

Gln Tyr Asp Met Val Leu Asp Val
545                 550

<210> SEQ ID NO 13
<211> LENGTH: 1752
<212> TYPE: DNA
<213> ORGANISM: Papio anubis
<220> FEATURE:
<221> NAME/KEY: CDS
<222> LOCATION: (1)..(1752)
<223> OTHER INFORMATION: Hyaluronan synthase 1
<300> PUBLICATION INFORMATION:
<308> DATABASE ACCESSION NUMBER: AY463695
<309> DATABASE ENTRY DATE: 2003-12-08
<313> RELEVANT RESIDUES IN SEQ ID NO: (36)..(1787)

<400> SEQUENCE: 13 atg aca cag cgg gac acg ccc aag ccc act cct gca gcc cgc cgc tgc     48
Met Thr Gln Arg Asp Thr Pro Lys Pro Thr Pro Ala Ala Arg Arg Cys
1               5                   10                  15 tcc ggc ctg gcc cgg agg gtg ctg acc atc gcc ttc gcc ctc ctc atc     96
Ser Gly Leu Ala Arg Arg Val Leu Thr Ile Ala Phe Ala Leu Leu Ile
            20                  25                  30
```

-continued

| | | |
|---|---|---|
| ctg ggc ctc atg acc tgg gcc tac gcc gcc ggg gtg ccg ctg gcc tcc<br>Leu Gly Leu Met Thr Trp Ala Tyr Ala Ala Gly Val Pro Leu Ala Ser<br>35                       40                     45 | 144 |
| gat cgc tac ggc ctc ctg gcc ttc ggc ctc tac ggg gcc ttc ctc tcg<br>Asp Arg Tyr Gly Leu Leu Ala Phe Gly Leu Tyr Gly Ala Phe Leu Ser<br>50                       55                     60 | 192 |
| gcg cac ctg ttg gcg cag agc ctc ttc gcg tac ctg gag cat cgg cgg<br>Ala His Leu Leu Ala Gln Ser Leu Phe Ala Tyr Leu Glu His Arg Arg<br>65                       70                     75                     80 | 240 |
| gtg gcg gcg gcg gcg cgg cgc gcg gca cgg ggg cgc ctg gat gca<br>Val Ala Ala Ala Ala Arg Arg Ala Ala Arg Gly Arg Leu Asp Ala<br>                   85                     90                     95 | 288 |
| gcc acg gcg cgc agc gtg gcg ctg acc att tcc gcc tac cag gag gac<br>Ala Thr Ala Arg Ser Val Ala Leu Thr Ile Ser Ala Tyr Gln Glu Asp<br>                 100                  105                 110 | 336 |
| ccc gcg tac ctg cgc cag tgc ctg gtg tcc gcc cgc gcc ctg ctg tac<br>Pro Ala Tyr Leu Arg Gln Cys Leu Val Ser Ala Arg Ala Leu Leu Tyr<br>                 115                  120                 125 | 384 |
| ccg cgc gcg cgg ctg cgc gtc ctc atg gtg gtg gac ggc aac cgc ccc<br>Pro Arg Ala Arg Leu Arg Val Leu Met Val Val Asp Gly Asn Arg Pro<br>130                       135                     140 | 432 |
| gag gac ctc tac atg gta gac atg ttc cgc gag gtc ttc gcc gac gag<br>Glu Asp Leu Tyr Met Val Asp Met Phe Arg Glu Val Phe Ala Asp Glu<br>145                       150                     155                 160 | 480 |
| gac ccc gcc acg tac gtg tgg gac ggc aac tac cac cag ccc tgg gaa<br>Asp Pro Ala Thr Tyr Val Trp Asp Gly Asn Tyr His Gln Pro Trp Glu<br>                 165                  170                 175 | 528 |
| ccc gcg gcg gtg ggc gcg gtg ggc gtc gga gcc tac cgg gag gtg gag<br>Pro Ala Ala Val Gly Ala Val Gly Val Gly Ala Tyr Arg Glu Val Glu<br>                   180                  185                 190 | 576 |
| gcg gag gat ccc ggg cgg ttg gcg gtg gag gcg ctg gtg agg act cgc<br>Ala Glu Asp Pro Gly Arg Leu Ala Val Glu Ala Leu Val Arg Thr Arg<br>                 195                  200                 205 | 624 |
| agg tgc gtg tgc gtg gcg cag cgc tgg ggc ggc aag cgc gag gtc atg<br>Arg Cys Val Cys Val Ala Gln Arg Trp Gly Gly Lys Arg Glu Val Met<br>210                       215                     220 | 672 |
| tac acc gcc ttc aag gcg ctc gga gac tcg gtg gac tac gtg cag gtc<br>Tyr Thr Ala Phe Lys Ala Leu Gly Asp Ser Val Asp Tyr Val Gln Val<br>225                       230                     235                 240 | 720 |
| tgt gac tcg gac aca agg ttg gac ccc atg gca ctg ctg gag ctc gtg<br>Cys Asp Ser Asp Thr Arg Leu Asp Pro Met Ala Leu Leu Glu Leu Val<br>                 245                  250                 255 | 768 |
| cag gtc ctg gat gag gac ccc cgg gta ggg gct gtt ggt ggg gac gtg<br>Gln Val Leu Asp Glu Asp Pro Arg Val Gly Ala Val Gly Gly Asp Val<br>                 260                  265                 270 | 816 |
| cgg atc ctt aac cct ctg gac tcc tgg gtc agc ttc cta agc agc ctg<br>Arg Ile Leu Asn Pro Leu Asp Ser Trp Val Ser Phe Leu Ser Ser Leu<br>                 275                  280                 285 | 864 |
| cga tac tgg gta gcc ttc aat gtg gag cgg gct tgt cag agc tac ttc<br>Arg Tyr Trp Val Ala Phe Asn Val Glu Arg Ala Cys Gln Ser Tyr Phe<br>290                       295                     300 | 912 |
| cac tgt gtg tcc tgc atc agt ggt cct cta ggc cta tat agg aac aac<br>His Cys Val Ser Cys Ile Ser Gly Pro Leu Gly Leu Tyr Arg Asn Asn<br>305                       310                     315                 320 | 960 |
| ctc ttg cag cag ttt ctt gag gcc tgg tac aac cag aag ttc ctg gga<br>Leu Leu Gln Gln Phe Leu Glu Ala Trp Tyr Asn Gln Lys Phe Leu Gly<br>                 325                  330                 335 | 1008 |
| acc cac tgt act ttt ggg gac gac cgg cac ctc acc aac cgc atg ctc<br>Thr His Cys Thr Phe Gly Asp Asp Arg His Leu Thr Asn Arg Met Leu<br>340                       345                     350 | 1056 |

```
agc atg ggt tat gct acc aag tac acc tcc agg tct cgt tgc tac tca    1104
Ser Met Gly Tyr Ala Thr Lys Tyr Thr Ser Arg Ser Arg Cys Tyr Ser
    355                 360                 365 gag aca ccc tcg tcc ttc ctg cgc tgg ctg agt cag cag act cgc tgg    1152
Glu Thr Pro Ser Ser Phe Leu Arg Trp Leu Ser Gln Gln Thr Arg Trp
370                 375                 380 tcc aag tcg tac ttc cgt gaa tgg ctg tac aac gcg ctc tgg tgg cac    1200
Ser Lys Ser Tyr Phe Arg Glu Trp Leu Tyr Asn Ala Leu Trp Trp His
385                 390                 395                 400 cgg cat cac gcc tgg atg acc tac gag gcg gtg gtc tcg ggc ctg ttc    1248
Arg His His Ala Trp Met Thr Tyr Glu Ala Val Val Ser Gly Leu Phe
                405                 410                 415 ccc ttc ttc gtg gcg gcc acg gtg ctg cgt ctg ttc tat gcg ggc cgc    1296
Pro Phe Phe Val Ala Ala Thr Val Leu Arg Leu Phe Tyr Ala Gly Arg
            420                 425                 430 ccg tgg gcg ctg ctg tgg gtg ctg cta tgc gtg cag ggc gtg gca ctg    1344
Pro Trp Ala Leu Leu Trp Val Leu Leu Cys Val Gln Gly Val Ala Leu
        435                 440                 445 gcc aag gcg gcc ttt gcg gcc tgg ctg cgg ggc tgc ctg cgt atg gtg    1392
Ala Lys Ala Ala Phe Ala Ala Trp Leu Arg Gly Cys Leu Arg Met Val
    450                 455                 460 ctg ctg tcg ctc tac gcg ccc ctc tac atg tgt ggc ctc ctg ccc gcc    1440
Leu Leu Ser Leu Tyr Ala Pro Leu Tyr Met Cys Gly Leu Leu Pro Ala
465                 470                 475                 480 aag ttc ctg gcg ctg gtc acc atg aac cag agt ggc tgg ggc acc tcg    1488
Lys Phe Leu Ala Leu Val Thr Met Asn Gln Ser Gly Trp Gly Thr Ser
                485                 490                 495 ggc cgg cgg aag ctg gcc gct aat tac gtc cct ctg ctg ccc ctg gcg    1536
Gly Arg Arg Lys Leu Ala Ala Asn Tyr Val Pro Leu Leu Pro Leu Ala
            500                 505                 510 ctc tgg gcg ctg ctg ctt ggg ggc ctg gtc cgc agt gtg gca cac        1584
Leu Trp Ala Leu Leu Leu Gly Gly Leu Val Arg Ser Val Ala His
        515                 520                 525 gag gcc agg gcc gac tgg agc ggc cct tcc cgc gca gcg gag gcc tac    1632
Glu Ala Arg Ala Asp Trp Ser Gly Pro Ser Arg Ala Ala Glu Ala Tyr
    530                 535                 540 cac tta gcc gcg ggg gcc ggc gcc tac gtg ggc tac tgg gtg gtc atg    1680
His Leu Ala Ala Gly Ala Gly Ala Tyr Val Gly Tyr Trp Val Val Met
545                 550                 555                 560 ttg acg ctg tac tgg gtg ggc gtg cgg agg ctt tgc cgg cgg cgg acc    1728
Leu Thr Leu Tyr Trp Val Gly Val Arg Arg Leu Cys Arg Arg Arg Thr
                565                 570                 575 ggg ggc tac cgt gtc cag gtg tga                                    1752
Gly Gly Tyr Arg Val Gln Val
            580

<210> SEQ ID NO 14
<211> LENGTH: 583
<212> TYPE: PRT
<213> ORGANISM: Papio anubis

<400> SEQUENCE: 14

Met Thr Gln Arg Asp Thr Pro Lys Pro Thr Pro Ala Ala Arg Arg Cys
1               5                   10                  15

Ser Gly Leu Ala Arg Arg Val Leu Thr Ile Ala Phe Ala Leu Leu Ile
            20                  25                  30

Leu Gly Leu Met Thr Trp Ala Tyr Ala Ala Gly Val Pro Leu Ala Ser
        35                  40                  45

Asp Arg Tyr Gly Leu Leu Ala Phe Gly Leu Tyr Gly Ala Phe Leu Ser
```

```
            50                  55                  60
Ala His Leu Leu Ala Gln Ser Leu Phe Ala Tyr Leu Glu His Arg Arg
 65                  70                  75                  80

Val Ala Ala Ala Arg Arg Ala Ala Arg Gly Arg Leu Asp Ala
             85                  90                  95

Ala Thr Ala Arg Ser Val Ala Leu Thr Ile Ser Ala Tyr Gln Glu Asp
                100                 105                 110

Pro Ala Tyr Leu Arg Gln Cys Leu Val Ser Ala Arg Ala Leu Leu Tyr
            115                 120                 125

Pro Arg Ala Arg Leu Arg Val Leu Met Val Val Asp Gly Asn Arg Pro
130                 135                 140

Glu Asp Leu Tyr Met Val Asp Met Phe Arg Glu Val Phe Ala Asp Glu
145                 150                 155                 160

Asp Pro Ala Thr Tyr Val Trp Asp Gly Asn Tyr His Gln Pro Trp Glu
                165                 170                 175

Pro Ala Ala Val Gly Ala Val Gly Val Gly Ala Tyr Arg Glu Val Glu
            180                 185                 190

Ala Glu Asp Pro Gly Arg Leu Ala Val Glu Ala Leu Val Arg Thr Arg
        195                 200                 205

Arg Cys Val Cys Val Ala Gln Arg Trp Gly Gly Lys Arg Glu Val Met
210                 215                 220

Tyr Thr Ala Phe Lys Ala Leu Gly Asp Ser Val Asp Tyr Val Gln Val
225                 230                 235                 240

Cys Asp Ser Asp Thr Arg Leu Asp Pro Met Ala Leu Leu Glu Leu Val
                245                 250                 255

Gln Val Leu Asp Glu Asp Pro Arg Val Gly Ala Val Gly Gly Asp Val
            260                 265                 270

Arg Ile Leu Asn Pro Leu Asp Ser Trp Val Ser Phe Leu Ser Ser Leu
        275                 280                 285

Arg Tyr Trp Val Ala Phe Asn Val Glu Arg Ala Cys Gln Ser Tyr Phe
290                 295                 300

His Cys Val Ser Cys Ile Ser Gly Pro Leu Gly Leu Tyr Arg Asn Asn
305                 310                 315                 320

Leu Leu Gln Gln Phe Leu Glu Ala Trp Tyr Asn Gln Lys Phe Leu Gly
                325                 330                 335

Thr His Cys Thr Phe Gly Asp Asp Arg His Leu Thr Asn Arg Met Leu
            340                 345                 350

Ser Met Gly Tyr Ala Thr Lys Tyr Thr Ser Arg Ser Arg Cys Tyr Ser
        355                 360                 365

Glu Thr Pro Ser Ser Phe Leu Arg Trp Leu Ser Gln Gln Thr Arg Trp
370                 375                 380

Ser Lys Ser Tyr Phe Arg Glu Trp Leu Tyr Asn Ala Leu Trp Trp His
385                 390                 395                 400

Arg His His Ala Trp Met Thr Tyr Glu Ala Val Val Ser Gly Leu Phe
                405                 410                 415

Pro Phe Phe Val Ala Ala Thr Val Leu Arg Leu Phe Tyr Ala Gly Arg
            420                 425                 430

Pro Trp Ala Leu Leu Trp Val Leu Leu Cys Val Gln Gly Val Ala Leu
        435                 440                 445

Ala Lys Ala Ala Phe Ala Ala Trp Leu Arg Gly Cys Leu Arg Met Val
450                 455                 460

Leu Leu Ser Leu Tyr Ala Pro Leu Tyr Met Cys Gly Leu Leu Pro Ala
465                 470                 475                 480
```

```
Lys Phe Leu Ala Leu Val Thr Met Asn Gln Ser Gly Trp Gly Thr Ser
            485                 490                 495

Gly Arg Arg Lys Leu Ala Ala Asn Tyr Val Pro Leu Leu Pro Leu Ala
                500                 505                 510

Leu Trp Ala Leu Leu Leu Gly Gly Leu Val Arg Ser Val Ala His
        515                 520                 525

Glu Ala Arg Ala Asp Trp Ser Gly Pro Ser Arg Ala Ala Glu Ala Tyr
            530                 535                 540

His Leu Ala Ala Gly Ala Gly Ala Tyr Val Gly Tyr Trp Val Val Met
545                 550                 555                 560

Leu Thr Leu Tyr Trp Val Gly Val Arg Arg Leu Cys Arg Arg Thr
                565                 570                 575

Gly Gly Tyr Arg Val Gln Val
            580
```

<210> SEQ ID NO 15
<211> LENGTH: 1752
<212> TYPE: DNA
<213> ORGANISM: Mus musculus
<220> FEATURE:
<221> NAME/KEY: CDS
<222> LOCATION: (1)..(1752)
<223> OTHER INFORMATION: Hyaluronan synthase 1
<300> PUBLICATION INFORMATION:
<308> DATABASE ACCESSION NUMBER: D82964.1
<309> DATABASE ENTRY DATE: 1996-05-31
<313> RELEVANT RESIDUES IN SEQ ID NO: (49)..(1800)

<400> SEQUENCE: 15

```
atg aga cag gac atg cca aag ccc tca gag gca gcg cgt tgc tgc tct      48
Met Arg Gln Asp Met Pro Lys Pro Ser Glu Ala Ala Arg Cys Cys Ser
1               5                   10                  15 ggc ctg gcc agg cga gca ctc acg atc atc ttt gcc ctg ctc atc ctg      96
Gly Leu Ala Arg Arg Ala Leu Thr Ile Ile Phe Ala Leu Leu Ile Leu
                20                  25                  30 ggc ctc atg acc tgg gcc tac gcc gca ggc gtt cct ctg gct tca gat     144
Gly Leu Met Thr Trp Ala Tyr Ala Ala Gly Val Pro Leu Ala Ser Asp
            35                  40                  45 cgc tat gga ctc ctg gcc ttt ggc ctc tat ggg gca ttc ctc agc gca     192
Arg Tyr Gly Leu Leu Ala Phe Gly Leu Tyr Gly Ala Phe Leu Ser Ala
        50                  55                  60 cac cta gtg gca cag agc ctc ttc gct tac ctg gag cac cga agg gtg     240
His Leu Val Ala Gln Ser Leu Phe Ala Tyr Leu Glu His Arg Arg Val
65                  70                  75                  80 gca gcg gct gcg cgg cgc tcc ttg gcg aag ggg ccc ctg gat gcg gcc     288
Ala Ala Ala Ala Arg Arg Ser Leu Ala Lys Gly Pro Leu Asp Ala Ala
                85                  90                  95 act gca cgc agc gtg gca ctc acc atc tca gcc tac caa gag gat ccc     336
Thr Ala Arg Ser Val Ala Leu Thr Ile Ser Ala Tyr Gln Glu Asp Pro
                100                 105                 110 gct tac ctg cgc cag tgc ttg acc tcc gcg cgc gcc ttg ctg tac ccg     384
Ala Tyr Leu Arg Gln Cys Leu Thr Ser Ala Arg Ala Leu Leu Tyr Pro
            115                 120                 125 cac acg agg tta cgc gtg ctc atg gtg gtg gac ggc aac cgc gct gag     432
His Thr Arg Leu Arg Val Leu Met Val Val Asp Gly Asn Arg Ala Glu
        130                 135                 140 gat ctg tac atg gtg gac atg ttc cga gaa gtc ttc gcc gat gag gac     480
Asp Leu Tyr Met Val Asp Met Phe Arg Glu Val Phe Ala Asp Glu Asp
145                 150                 155                 160 ccc gcc act tat gtg tgg gat ggc aac tac cat cag ccc tgg gaa cca     528
```

|     |     |     |     |     |     |     |     |     |     |     |     |      |
| --- | --- | --- | --- | --- | --- | --- | --- | --- | --- | --- | --- | ---- |
| Pro | Ala | Thr | Tyr | Val | Trp | Asp | Gly | Asn | Tyr | His | Gln | Pro  | Trp | Glu | Pro |
|     |     |     |     | 165 |     |     |     | 170 |     |     |     | 175  |

```
gcg gag gct acg ggc gct gtc ggt gaa ggt gcc tac cgg gag gtg gag    576
Ala Glu Ala Thr Gly Ala Val Gly Glu Gly Ala Tyr Arg Glu Val Glu
            180                 185                 190 gcg gag gac ccc ggg cgg ttg gcg gtg gag gcg ctg gtg aga aca cgc    624
Ala Glu Asp Pro Gly Arg Leu Ala Val Glu Ala Leu Val Arg Thr Arg
            195                 200                 205 agg tgc gtg tgc gtg gct cag cgt tgg ggc ggc aaa cgt gag gtc atg    672
Arg Cys Val Cys Val Ala Gln Arg Trp Gly Gly Lys Arg Glu Val Met
    210                 215                 220 tac aca gct ttc aag gca ctg ggc gac tcc gtg gac tac gtg cag gtc    720
Tyr Thr Ala Phe Lys Ala Leu Gly Asp Ser Val Asp Tyr Val Gln Val
225                 230                 235                 240 tgt gac tca gac aca aga cta gac ccc atg gca ctg ctg gag ctt gtg    768
Cys Asp Ser Asp Thr Arg Leu Asp Pro Met Ala Leu Leu Glu Leu Val
                245                 250                 255 cga gtg ttg gat gaa gac ccc cgg gta ggg gct gtt gga ggg gat gtg    816
Arg Val Leu Asp Glu Asp Pro Arg Val Gly Ala Val Gly Gly Asp Val
            260                 265                 270 agg atc ctt aac cct ctg gac tcc tgg gtc agc ttc ttg agc agt ctt    864
Arg Ile Leu Asn Pro Leu Asp Ser Trp Val Ser Phe Leu Ser Ser Leu
        275                 280                 285 cga tac tgg gta gcc ttc aat gtg gaa cga gct tgt cag agc tac ttc    912
Arg Tyr Trp Val Ala Phe Asn Val Glu Arg Ala Cys Gln Ser Tyr Phe
    290                 295                 300 cac tgt gtg tcc tgc atc agt ggt cct ctg ggt cta tac aga aac aat    960
His Cys Val Ser Cys Ile Ser Gly Pro Leu Gly Leu Tyr Arg Asn Asn
305                 310                 315                 320 ctc ctg cag cag ttc ttg gag gcc tgg tac aac caa aag ttc ctg ggc   1008
Leu Leu Gln Gln Phe Leu Glu Ala Trp Tyr Asn Gln Lys Phe Leu Gly
                325                 330                 335 acc cac tgc aca ttt ggg gat gac agg cac ctc acc aac cga atg ctt   1056
Thr His Cys Thr Phe Gly Asp Asp Arg His Leu Thr Asn Arg Met Leu
            340                 345                 350 agc atg ggc tat gct acc aag tat acc tcg cgc tcc aga tgc tac tcg   1104
Ser Met Gly Tyr Ala Thr Lys Tyr Thr Ser Arg Ser Arg Cys Tyr Ser
        355                 360                 365 gag acg ccc tcc tcc ttc ctt cgt tgg ttg agc caa cag acc cgc tgg   1152
Glu Thr Pro Ser Ser Phe Leu Arg Trp Leu Ser Gln Gln Thr Arg Trp
    370                 375                 380 tcc aaa tct tac ttc cga gag tgg cta tac aat gct ctg tgg tgg cat   1200
Ser Lys Ser Tyr Phe Arg Glu Trp Leu Tyr Asn Ala Leu Trp Trp His
385                 390                 395                 400 cgc cac cac gca tgg atg acc tat gaa gcg gtg gtc tcg ggc ctc ttc   1248
Arg His His Ala Trp Met Thr Tyr Glu Ala Val Val Ser Gly Leu Phe
                405                 410                 415 cct ttc ttc gtg gct gcc acg gtg ttg agg ctc ttc tat gca ggg cgc   1296
Pro Phe Phe Val Ala Ala Thr Val Leu Arg Leu Phe Tyr Ala Gly Arg
            420                 425                 430 ccg tgg gct ctg ctc tgg gtg ctg ctc tgt gtg cag ggc gta gca ctg   1344
Pro Trp Ala Leu Leu Trp Val Leu Leu Cys Val Gln Gly Val Ala Leu
        435                 440                 445 gca aag gca gcc ttt gca gcc tgg ctg cgt ggc tgc gtg cgc atg gtg   1392
Ala Lys Ala Ala Phe Ala Ala Trp Leu Arg Gly Cys Val Arg Met Val
    450                 455                 460 ctg ctg tca ctc tat gca cca ctc tac atg tgc ggc ctc ctg cct gcc   1440
Leu Leu Ser Leu Tyr Ala Pro Leu Tyr Met Cys Gly Leu Leu Pro Ala
465                 470                 475                 480
```

```
aaa ttc cta gcg ttg gtt acc atg aat caa agt ggt tgg ggt acc tcg      1488
Lys Phe Leu Ala Leu Val Thr Met Asn Gln Ser Gly Trp Gly Thr Ser
                485                 490                 495 ggc cgg aag aaa ctg gct gct aac tat gtc ccc gtg ttg ccc ctg gca      1536
Gly Arg Lys Lys Leu Ala Ala Asn Tyr Val Pro Val Leu Pro Leu Ala
        500                 505                 510 ctc tgg gct cta ctg ctg ctt gga ggc ctg gcc cgc agt gtg gcc cag      1584
Leu Trp Ala Leu Leu Leu Leu Gly Gly Leu Ala Arg Ser Val Ala Gln
            515                 520                 525 gag gcc aga gct gac tgg agt ggc cca tcc cga gca gct gaa gcc tac      1632
Glu Ala Arg Ala Asp Trp Ser Gly Pro Ser Arg Ala Ala Glu Ala Tyr
530                 535                 540 cac ctt gct gct ggg gct ggt gcc tat gtg gcc tac tgg gtg gta atg      1680
His Leu Ala Ala Gly Ala Gly Ala Tyr Val Ala Tyr Trp Val Val Met
545                 550                 555                 560 tta act atc tac tgg gta ggt gtg agg agg ctg tgc aga cgt cgg agc      1728
Leu Thr Ile Tyr Trp Val Gly Val Arg Arg Leu Cys Arg Arg Arg Ser
                565                 570                 575 ggt ggt tac cgt gtc caa gta tga                                      1752
Gly Gly Tyr Arg Val Gln Val
        580
```

<210> SEQ ID NO 16
<211> LENGTH: 583
<212> TYPE: PRT
<213> ORGANISM: Mus musculus

<400> SEQUENCE: 16

```
Met Arg Gln Asp Met Pro Lys Pro Ser Glu Ala Ala Arg Cys Cys Ser
1               5                   10                  15

Gly Leu Ala Arg Arg Ala Leu Thr Ile Ile Phe Ala Leu Leu Ile Leu
            20                  25                  30

Gly Leu Met Thr Trp Ala Tyr Ala Ala Gly Val Pro Leu Ala Ser Asp
        35                  40                  45

Arg Tyr Gly Leu Leu Ala Phe Gly Leu Tyr Gly Ala Phe Leu Ser Ala
    50                  55                  60

His Leu Val Ala Gln Ser Leu Phe Ala Tyr Leu Glu His Arg Arg Val
65                  70                  75                  80

Ala Ala Ala Ala Arg Arg Ser Leu Ala Lys Gly Pro Leu Asp Ala Ala
                85                  90                  95

Thr Ala Arg Ser Val Ala Leu Thr Ile Ser Ala Tyr Gln Glu Asp Pro
            100                 105                 110

Ala Tyr Leu Arg Gln Cys Leu Thr Ser Ala Arg Ala Leu Leu Tyr Pro
        115                 120                 125

His Thr Arg Leu Arg Val Leu Met Val Val Asp Gly Asn Arg Ala Glu
    130                 135                 140

Asp Leu Tyr Met Val Asp Met Phe Arg Glu Val Phe Ala Asp Glu Asp
145                 150                 155                 160

Pro Ala Thr Tyr Val Trp Asp Gly Asn Tyr His Gln Pro Trp Glu Pro
                165                 170                 175

Ala Glu Ala Thr Gly Ala Val Gly Glu Gly Ala Tyr Arg Glu Val Glu
            180                 185                 190

Ala Glu Asp Pro Gly Arg Leu Ala Val Glu Ala Leu Val Arg Thr Arg
        195                 200                 205

Arg Cys Val Cys Val Ala Gln Arg Trp Gly Gly Lys Arg Glu Val Met
    210                 215                 220

Tyr Thr Ala Phe Lys Ala Leu Gly Asp Ser Val Asp Tyr Val Gln Val
```

```
            225                 230                 235                 240

Cys Asp Ser Asp Thr Arg Leu Asp Pro Met Ala Leu Leu Glu Leu Val
                245                 250                 255

Arg Val Leu Asp Glu Asp Pro Arg Val Gly Ala Val Gly Gly Asp Val
                260                 265                 270

Arg Ile Leu Asn Pro Leu Asp Ser Trp Val Ser Phe Leu Ser Ser Leu
                275                 280                 285

Arg Tyr Trp Val Ala Phe Asn Val Glu Arg Ala Cys Gln Ser Tyr Phe
            290                 295                 300

His Cys Val Ser Cys Ile Ser Gly Pro Leu Gly Leu Tyr Arg Asn Asn
305                 310                 315                 320

Leu Leu Gln Gln Phe Leu Glu Ala Trp Tyr Asn Gln Lys Phe Leu Gly
                325                 330                 335

Thr His Cys Thr Phe Gly Asp Asp Arg His Leu Thr Asn Arg Met Leu
                340                 345                 350

Ser Met Gly Tyr Ala Thr Lys Tyr Thr Ser Arg Ser Arg Cys Tyr Ser
                355                 360                 365

Glu Thr Pro Ser Ser Phe Leu Arg Trp Leu Ser Gln Gln Thr Arg Trp
            370                 375                 380

Ser Lys Ser Tyr Phe Arg Glu Trp Leu Tyr Asn Ala Leu Trp Trp His
385                 390                 395                 400

Arg His His Ala Trp Met Thr Tyr Glu Ala Val Val Ser Gly Leu Phe
                405                 410                 415

Pro Phe Phe Val Ala Ala Thr Val Leu Arg Leu Phe Tyr Ala Gly Arg
                420                 425                 430

Pro Trp Ala Leu Leu Trp Val Leu Leu Cys Val Gln Gly Val Ala Leu
            435                 440                 445

Ala Lys Ala Ala Phe Ala Ala Trp Leu Arg Gly Cys Val Arg Met Val
                450                 455                 460

Leu Leu Ser Leu Tyr Ala Pro Leu Tyr Met Cys Gly Leu Leu Pro Ala
465                 470                 475                 480

Lys Phe Leu Ala Leu Val Thr Met Asn Gln Ser Gly Trp Gly Thr Ser
                485                 490                 495

Gly Arg Lys Lys Leu Ala Ala Asn Tyr Val Pro Val Leu Pro Leu Ala
            500                 505                 510

Leu Trp Ala Leu Leu Leu Gly Gly Leu Ala Arg Ser Val Ala Gln
            515                 520                 525

Glu Ala Arg Ala Asp Trp Ser Gly Pro Ser Arg Ala Ala Glu Ala Tyr
            530                 535                 540

His Leu Ala Ala Gly Ala Gly Ala Tyr Val Ala Tyr Trp Val Val Met
545                 550                 555                 560

Leu Thr Ile Tyr Trp Val Gly Val Arg Arg Leu Cys Arg Arg Ser
                565                 570                 575

Gly Gly Tyr Arg Val Gln Val
            580

<210> SEQ ID NO 17
<211> LENGTH: 1659
<212> TYPE: DNA
<213> ORGANISM: Mus musculus
<220> FEATURE:
<221> NAME/KEY: CDS
<222> LOCATION: (1)..(1659)
<223> OTHER INFORMATION: Hyaluronan synthase 2
<300> PUBLICATION INFORMATION:
<308> DATABASE ACCESSION NUMBER: U52524.2
```

<309> DATABASE ENTRY DATE: 1996-10-15
<313> RELEVANT RESIDUES IN SEQ ID NO: (508)..(2166)

<400> SEQUENCE: 17

```
atg cat tgt gag agg ttt cta tgt gtc ctg aga ata att gga act aca        48
Met His Cys Glu Arg Phe Leu Cys Val Leu Arg Ile Ile Gly Thr Thr
1               5                   10                  15 ctt ttt gga gtg tct ctc ctc ctc gga atc aca gct gct tat att gtt        96
Leu Phe Gly Val Ser Leu Leu Leu Gly Ile Thr Ala Ala Tyr Ile Val
            20                  25                  30 ggc tac cag ttt atc caa aca gat aat tac tac ttc tca ttt gga ctg       144
Gly Tyr Gln Phe Ile Gln Thr Asp Asn Tyr Tyr Phe Ser Phe Gly Leu
        35                  40                  45 tac ggt gcc ttt tta gcc tcg cat ctc atc atc caa agc ctc ttt gcc       192
Tyr Gly Ala Phe Leu Ala Ser His Leu Ile Ile Gln Ser Leu Phe Ala
    50                  55                  60 ttt ttg gaa cac cgg aaa atg aag aag tcc ctt gaa acc ccg att aaa       240
Phe Leu Glu His Arg Lys Met Lys Lys Ser Leu Glu Thr Pro Ile Lys
65                  70                  75                  80 ttg aac aaa acg gta gca ctc tgc atc gct gcg tac caa gag gac cct       288
Leu Asn Lys Thr Val Ala Leu Cys Ile Ala Ala Tyr Gln Glu Asp Pro
                85                  90                  95 gac tac tta cgg aaa tgt ttg caa tct gtg aaa agg ctg acc tac cct       336
Asp Tyr Leu Arg Lys Cys Leu Gln Ser Val Lys Arg Leu Thr Tyr Pro
            100                 105                 110 ggg att aaa gtc gtg atg gtc atc gat ggg aac tca gac gac gac ctt       384
Gly Ile Lys Val Val Met Val Ile Asp Gly Asn Ser Asp Asp Asp Leu
        115                 120                 125 tac atg atg gac ata ttc agc gaa gtt att ggc agg gac aaa tcg gcc       432
Tyr Met Met Asp Ile Phe Ser Glu Val Ile Gly Arg Asp Lys Ser Ala
    130                 135                 140 acg tac atc tgg aag aac aac ttt cat gaa aag gga cct ggt gag aca       480
Thr Tyr Ile Trp Lys Asn Asn Phe His Glu Lys Gly Pro Gly Glu Thr
145                 150                 155                 160 gaa gag tcc cat aaa gaa agt tca caa cat gtc acc caa ttg gtc ttg       528
Glu Glu Ser His Lys Glu Ser Ser Gln His Val Thr Gln Leu Val Leu
                165                 170                 175 tct aac aaa agt att tgc atc atg caa aaa tgg ggt gga aag aga gaa       576
Ser Asn Lys Ser Ile Cys Ile Met Gln Lys Trp Gly Gly Lys Arg Glu
            180                 185                 190 gtc atg tac aca gcc ttc aga gca ctg ggg cga agc gtg gat tat gta       624
Val Met Tyr Thr Ala Phe Arg Ala Leu Gly Arg Ser Val Asp Tyr Val
        195                 200                 205 cag gtg tgt gac tca gat act atg ctt gac cct gcc tca tct gtg gag       672
Gln Val Cys Asp Ser Asp Thr Met Leu Asp Pro Ala Ser Ser Val Glu
    210                 215                 220 atg gtg aag gtc tta gag gaa gac cct atg gtt gga ggt gtt gga gga       720
Met Val Lys Val Leu Glu Glu Asp Pro Met Val Gly Gly Val Gly Gly
225                 230                 235                 240 gat gtc cag att tta aac aag tat gat tcc tgg atc tcc ttc ctc agc       768
Asp Val Gln Ile Leu Asn Lys Tyr Asp Ser Trp Ile Ser Phe Leu Ser
                245                 250                 255 agc gtg aga tac tgg atg gct ttt aat ata gaa agg gcc tgc cag tct       816
Ser Val Arg Tyr Trp Met Ala Phe Asn Ile Glu Arg Ala Cys Gln Ser
            260                 265                 270 tat ttt ggc tgt gtc cag tgc ata agc ggt cct ctg gga atg tac aga       864
Tyr Phe Gly Cys Val Gln Cys Ile Ser Gly Pro Leu Gly Met Tyr Arg
        275                 280                 285 aac tcc ttg ctg cat gaa ttt gtg gaa gac tgg tac aat cag gaa ttc       912
Asn Ser Leu Leu His Glu Phe Val Glu Asp Trp Tyr Asn Gln Glu Phe
```

```
                    290                 295                 300
atg ggt aac caa tgc agt ttt ggt gac gac agg cac ctt acc aac agg      960
Met Gly Asn Gln Cys Ser Phe Gly Asp Asp Arg His Leu Thr Asn Arg
305                 310                 315                 320 gtg ttg agt ctg ggc tat gca act aaa tac acg gct cgg tcc aag tgc     1008
Val Leu Ser Leu Gly Tyr Ala Thr Lys Tyr Thr Ala Arg Ser Lys Cys
                325                 330                 335 ctt act gaa act ccc ata gaa tat ctg aga tgg ctg aac cag cag acc     1056
Leu Thr Glu Thr Pro Ile Glu Tyr Leu Arg Trp Leu Asn Gln Gln Thr
            340                 345                 350 cga tgg agc aag tcc tac ttc cga gag tgg ctg tac aat gcc atg tgg     1104
Arg Trp Ser Lys Ser Tyr Phe Arg Glu Trp Leu Tyr Asn Ala Met Trp
        355                 360                 365 ttt cac aag cat cac ctg tgg atg acc tat gaa gct gtt atc act gga     1152
Phe His Lys His His Leu Trp Met Thr Tyr Glu Ala Val Ile Thr Gly
370                 375                 380 ttc ttt cct ttc ttt ctc att gcc aca gtc atc cag ctc ttc tac agg     1200
Phe Phe Pro Phe Phe Leu Ile Ala Thr Val Ile Gln Leu Phe Tyr Arg
385                 390                 395                 400 ggt aaa atc tgg aac atc ctc ctc ttc ctg tta act gtc cag cta gtg     1248
Gly Lys Ile Trp Asn Ile Leu Leu Phe Leu Leu Thr Val Gln Leu Val
                405                 410                 415 ggt ctc atc aag tca tct ttt gcc agc tgc ctt aga gga aat atc gtc     1296
Gly Leu Ile Lys Ser Ser Phe Ala Ser Cys Leu Arg Gly Asn Ile Val
            420                 425                 430 atg gta ttc atg tct ctg tat tca gtg tta tac atg tca agt cta ctt     1344
Met Val Phe Met Ser Leu Tyr Ser Val Leu Tyr Met Ser Ser Leu Leu
        435                 440                 445 cct gcc aag atg ttt gca att gca acc ata aac aaa gct ggg tgg ggc     1392
Pro Ala Lys Met Phe Ala Ile Ala Thr Ile Asn Lys Ala Gly Trp Gly
450                 455                 460 aca tct gga agg aag acc att gtt gtt aat ttc ata gga ctt att cca     1440
Thr Ser Gly Arg Lys Thr Ile Val Val Asn Phe Ile Gly Leu Ile Pro
465                 470                 475                 480 gtg tcc gtg tgg ttt aca atc ctt cta ggt ggt gta att ttc acc att     1488
Val Ser Val Trp Phe Thr Ile Leu Leu Gly Gly Val Ile Phe Thr Ile
                485                 490                 495 tat aag gaa tct aaa aag cca ttt tcc gaa tcc aaa cag act gtt ctc     1536
Tyr Lys Glu Ser Lys Lys Pro Phe Ser Glu Ser Lys Gln Thr Val Leu
            500                 505                 510 atc gtg gga act ttg atc tat gca tgc tac tgg gtc atg ctt ttg act     1584
Ile Val Gly Thr Leu Ile Tyr Ala Cys Tyr Trp Val Met Leu Leu Thr
        515                 520                 525 ctc tat gtg gtt ctc atc aat aag tgt ggc agg cgg aag aag gga caa     1632
Leu Tyr Val Val Leu Ile Asn Lys Cys Gly Arg Arg Lys Lys Gly Gln
530                 535                 540 cag tat gac atg gtg ctt gat gta tga                                 1659
Gln Tyr Asp Met Val Leu Asp Val
545                 550

<210> SEQ ID NO 18
<211> LENGTH: 552
<212> TYPE: PRT
<213> ORGANISM: Mus musculus

<400> SEQUENCE: 18

Met His Cys Glu Arg Phe Leu Cys Val Leu Arg Ile Ile Gly Thr Thr
1               5                   10                  15

Leu Phe Gly Val Ser Leu Leu Leu Gly Ile Thr Ala Ala Tyr Ile Val
            20                  25                  30
```

```
Gly Tyr Gln Phe Ile Gln Thr Asp Asn Tyr Tyr Phe Ser Phe Gly Leu
        35                  40                  45

Tyr Gly Ala Phe Leu Ala Ser His Leu Ile Ile Gln Ser Leu Phe Ala
     50                  55                  60

Phe Leu Glu His Arg Lys Met Lys Lys Ser Leu Glu Thr Pro Ile Lys
 65                  70                  75                  80

Leu Asn Lys Thr Val Ala Leu Cys Ile Ala Ala Tyr Gln Glu Asp Pro
                 85                  90                  95

Asp Tyr Leu Arg Lys Cys Leu Gln Ser Val Lys Arg Leu Thr Tyr Pro
                100                 105                 110

Gly Ile Lys Val Val Met Val Ile Asp Gly Asn Ser Asp Asp Asp Leu
             115                 120                 125

Tyr Met Met Asp Ile Phe Ser Glu Val Ile Gly Arg Asp Lys Ser Ala
             130                 135                 140

Thr Tyr Ile Trp Lys Asn Asn Phe His Glu Lys Gly Pro Gly Glu Thr
145                 150                 155                 160

Glu Glu Ser His Lys Glu Ser Ser Gln His Val Thr Gln Leu Val Leu
                 165                 170                 175

Ser Asn Lys Ser Ile Cys Ile Met Gln Lys Trp Gly Gly Lys Arg Glu
             180                 185                 190

Val Met Tyr Thr Ala Phe Arg Ala Leu Gly Arg Ser Val Asp Tyr Val
             195                 200                 205

Gln Val Cys Asp Ser Asp Thr Met Leu Asp Pro Ala Ser Ser Val Glu
     210                 215                 220

Met Val Lys Val Leu Glu Asp Pro Met Val Gly Val Gly Val Gly Gly
225                 230                 235                 240

Asp Val Gln Ile Leu Asn Lys Tyr Asp Ser Trp Ile Ser Phe Leu Ser
                 245                 250                 255

Ser Val Arg Tyr Trp Met Ala Phe Asn Ile Glu Arg Ala Cys Gln Ser
             260                 265                 270

Tyr Phe Gly Cys Val Gln Cys Ile Ser Gly Pro Leu Gly Met Tyr Arg
             275                 280                 285

Asn Ser Leu Leu His Glu Phe Val Glu Asp Trp Tyr Asn Gln Glu Phe
             290                 295                 300

Met Gly Asn Gln Cys Ser Phe Gly Asp Asp Arg His Leu Thr Asn Arg
305                 310                 315                 320

Val Leu Ser Leu Gly Tyr Ala Thr Lys Tyr Thr Ala Arg Ser Lys Cys
                 325                 330                 335

Leu Thr Glu Thr Pro Ile Glu Tyr Leu Arg Trp Leu Asn Gln Gln Thr
             340                 345                 350

Arg Trp Ser Lys Ser Tyr Phe Arg Glu Trp Leu Tyr Asn Ala Met Trp
             355                 360                 365

Phe His Lys His His Leu Trp Met Thr Tyr Glu Ala Val Ile Thr Gly
             370                 375                 380

Phe Phe Pro Phe Phe Leu Ile Ala Thr Val Ile Gln Leu Phe Tyr Arg
385                 390                 395                 400

Gly Lys Ile Trp Asn Ile Leu Leu Phe Leu Leu Thr Val Gln Leu Val
                 405                 410                 415

Gly Leu Ile Lys Ser Ser Phe Ala Ser Cys Leu Arg Gly Asn Ile Val
             420                 425                 430

Met Val Phe Met Ser Leu Tyr Ser Val Leu Tyr Met Ser Ser Leu Leu
             435                 440                 445
```

-continued

```
Pro Ala Lys Met Phe Ala Ile Ala Thr Ile Asn Lys Ala Gly Trp Gly
    450                 455                 460
Thr Ser Gly Arg Lys Thr Ile Val Val Asn Phe Ile Gly Leu Ile Pro
465                 470                 475                 480
Val Ser Val Trp Phe Thr Ile Leu Leu Gly Gly Val Ile Phe Thr Ile
                485                 490                 495
Tyr Lys Glu Ser Lys Lys Pro Phe Ser Glu Ser Lys Gln Thr Val Leu
                500                 505                 510
Ile Val Gly Thr Leu Ile Tyr Ala Cys Tyr Trp Val Met Leu Leu Thr
            515                 520                 525
Leu Tyr Val Val Leu Ile Asn Lys Cys Gly Arg Arg Lys Lys Gly Gln
    530                 535                 540
Gln Tyr Asp Met Val Leu Asp Val
545                 550

<210> SEQ ID NO 19
<211> LENGTH: 1665
<212> TYPE: DNA
<213> ORGANISM: Mus musculus
<220> FEATURE:
<221> NAME/KEY: CDS
<222> LOCATION: (1)..(1665)
<223> OTHER INFORMATION: Hyaluronan synthase 3
<300> PUBLICATION INFORMATION:
<308> DATABASE ACCESSION NUMBER: U86408.2
<309> DATABASE ENTRY DATE: 1997-04-16
<313> RELEVANT RESIDUES IN SEQ ID NO: (175)..(1839)

<400> SEQUENCE: 19 atg ccg gtg cag ctg act aca gcc ctg cgt gtg gtg ggc acc agt ctg      48
Met Pro Val Gln Leu Thr Thr Ala Leu Arg Val Val Gly Thr Ser Leu
1               5                   10                  15 ttt gcc ctg gta gtg ctg gga ggc atc ctg gcg gcc tat gtg aca ggc      96
Phe Ala Leu Val Val Leu Gly Gly Ile Leu Ala Ala Tyr Val Thr Gly
            20                  25                  30 tac cag ttt atc cac aca gaa aag cac tac ctg tcc ttt ggc ctc tac     144
Tyr Gln Phe Ile His Thr Glu Lys His Tyr Leu Ser Phe Gly Leu Tyr
        35                  40                  45 ggt gcc atc ctg ggt cta cat ctg ctc atc cag agc ctg ttt gcc ttc     192
Gly Ala Ile Leu Gly Leu His Leu Leu Ile Gln Ser Leu Phe Ala Phe
    50                  55                  60 ctg gag cac cgt cga atg cgc agg gca ggg cgc ccc ctc aag ctg cac     240
Leu Glu His Arg Arg Met Arg Arg Ala Gly Arg Pro Leu Lys Leu His
65                  70                  75                  80 tgc tcc cag agg tcg cgt tca gtg gca ctc tgc att gct gcc tac caa     288
Cys Ser Gln Arg Ser Arg Ser Val Ala Leu Cys Ile Ala Ala Tyr Gln
                85                  90                  95 gag gac ccc gaa tac ctg cgc aag tgc ctt cgc tca gct cag cgc att     336
Glu Asp Pro Glu Tyr Leu Arg Lys Cys Leu Arg Ser Ala Gln Arg Ile
            100                 105                 110 gcc ttt cca aac ctc aag gtg gtc atg gta gtg gat ggc aat gcg cag     384
Ala Phe Pro Asn Leu Lys Val Val Met Val Val Asp Gly Asn Ala Gln
        115                 120                 125 gaa gat acc tac atg ttg gac atc ttc cat gag gtg ctg ggt ggc act     432
Glu Asp Thr Tyr Met Leu Asp Ile Phe His Glu Val Leu Gly Gly Thr
    130                 135                 140 gag caa gct ggc ttc ttt gtg tgg cgt agc aat ttc cat gag gcg ggt     480
Glu Gln Ala Gly Phe Phe Val Trp Arg Ser Asn Phe His Glu Ala Gly
145                 150                 155                 160 gaa gga gag aca gag gcc agc ctg cag gaa ggc atg gag cgt gtg cga     528
Glu Gly Glu Thr Glu Ala Ser Leu Gln Glu Gly Met Glu Arg Val Arg
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---  |
|     |     |     |     | 165 |     |     |     |     | 170 |     |     |     |     | 175 |     |      |
| gct | gtg | gtg | tgg | gcc | agc | acc | ttc | tca | tgc | atc | atg | cag | aag | tgg | ggg | 576  |
| Ala | Val | Val | Trp | Ala | Ser | Thr | Phe | Ser | Cys | Ile | Met | Gln | Lys | Trp | Gly |      |
|     |     |     | 180 |     |     |     |     | 185 |     |     |     |     | 190 |     |     |      |
| ggc | aag | cgt | gag | gtc | atg | tac | act | gcc | ttc | aag | gcc | ctt | ggc | aac | tca | 624  |
| Gly | Lys | Arg | Glu | Val | Met | Tyr | Thr | Ala | Phe | Lys | Ala | Leu | Gly | Asn | Ser |      |
|     |     | 195 |     |     |     |     | 200 |     |     |     |     | 205 |     |     |     |      |
| gtg | gac | tac | atc | cag | gtg | tgt | gac | tct | gac | act | gtg | ctg | gac | cca | gcc | 672  |
| Val | Asp | Tyr | Ile | Gln | Val | Cys | Asp | Ser | Asp | Thr | Val | Leu | Asp | Pro | Ala |      |
|     | 210 |     |     |     |     | 215 |     |     |     |     | 220 |     |     |     |     |      |
| tgc | acc | att | gag | atg | ctt | cga | gtc | ttg | gaa | gaa | gat | ccc | caa | gta | gga | 720  |
| Cys | Thr | Ile | Glu | Met | Leu | Arg | Val | Leu | Glu | Glu | Asp | Pro | Gln | Val | Gly |      |
| 225 |     |     |     |     | 230 |     |     |     |     | 235 |     |     |     |     | 240 |      |
| ggt | gtt | gga | gga | gat | gtc | caa | atc | ctc | aac | aag | tat | gat | tca | tgg | atc | 768  |
| Gly | Val | Gly | Gly | Asp | Val | Gln | Ile | Leu | Asn | Lys | Tyr | Asp | Ser | Trp | Ile |      |
|     |     |     |     | 245 |     |     |     |     | 250 |     |     |     |     | 255 |     |      |
| tcc | ttc | ctg | agc | agt | gtg | agg | tac | tgg | atg | gct | ttc | aac | gtg | gag | cgg | 816  |
| Ser | Phe | Leu | Ser | Ser | Val | Arg | Tyr | Trp | Met | Ala | Phe | Asn | Val | Glu | Arg |      |
|     |     |     | 260 |     |     |     |     | 265 |     |     |     |     | 270 |     |     |      |
| gcc | tgc | cag | tcc | tac | ttt | ggc | tgt | gtg | caa | tgt | att | agt | ggg | cct | ttg | 864  |
| Ala | Cys | Gln | Ser | Tyr | Phe | Gly | Cys | Val | Gln | Cys | Ile | Ser | Gly | Pro | Leu |      |
|     |     | 275 |     |     |     |     | 280 |     |     |     |     | 285 |     |     |     |      |
| ggc | atg | tac | cgc | aac | agc | ctc | ctt | cag | cag | ttc | ctg | gag | gat | tgg | tac | 912  |
| Gly | Met | Tyr | Arg | Asn | Ser | Leu | Leu | Gln | Gln | Phe | Leu | Glu | Asp | Trp | Tyr |      |
|     | 290 |     |     |     |     | 295 |     |     |     |     | 300 |     |     |     |     |      |
| cat | cag | aag | ttc | cta | ggc | agc | aag | tgc | agc | ttt | ggg | gat | gat | cgg | cac | 960  |
| His | Gln | Lys | Phe | Leu | Gly | Ser | Lys | Cys | Ser | Phe | Gly | Asp | Asp | Arg | His |      |
| 305 |     |     |     |     | 310 |     |     |     |     | 315 |     |     |     |     | 320 |      |
| ctt | acc | aac | cga | gtc | ctg | agt | ctt | ggc | tac | cgg | act | aag | tat | aca | gca | 1008 |
| Leu | Thr | Asn | Arg | Val | Leu | Ser | Leu | Gly | Tyr | Arg | Thr | Lys | Tyr | Thr | Ala |      |
|     |     |     |     | 325 |     |     |     |     | 330 |     |     |     |     | 335 |     |      |
| cgc | tct | aag | tgc | ctc | aca | gag | acc | ccc | act | agg | tac | ctt | cga | tgg | ctc | 1056 |
| Arg | Ser | Lys | Cys | Leu | Thr | Glu | Thr | Pro | Thr | Arg | Tyr | Leu | Arg | Trp | Leu |      |
|     |     |     | 340 |     |     |     |     | 345 |     |     |     |     | 350 |     |     |      |
| aat | cag | caa | acc | cgc | tgg | agc | aag | tct | tac | ttt | cgg | gaa | tgg | ctc | tac | 1104 |
| Asn | Gln | Gln | Thr | Arg | Trp | Ser | Lys | Ser | Tyr | Phe | Arg | Glu | Trp | Leu | Tyr |      |
|     |     | 355 |     |     |     |     | 360 |     |     |     |     | 365 |     |     |     |      |
| aat | tct | ctg | tgg | ttc | cat | aag | cac | cac | ctc | tgg | atg | acc | tat | gaa | tca | 1152 |
| Asn | Ser | Leu | Trp | Phe | His | Lys | His | His | Leu | Trp | Met | Thr | Tyr | Glu | Ser |      |
|     | 370 |     |     |     |     | 375 |     |     |     |     | 380 |     |     |     |     |      |
| gtg | gtc | aca | ggt | ttc | ttc | cca | ttc | ttc | ctc | att | gct | aca | gtc | ata | caa | 1200 |
| Val | Val | Thr | Gly | Phe | Phe | Pro | Phe | Phe | Leu | Ile | Ala | Thr | Val | Ile | Gln |      |
| 385 |     |     |     |     | 390 |     |     |     |     | 395 |     |     |     |     | 400 |      |
| ctt | ttc | tac | cgt | ggc | cgc | atc | tgg | aac | att | ctc | ctc | ttc | ctg | cta | aca | 1248 |
| Leu | Phe | Tyr | Arg | Gly | Arg | Ile | Trp | Asn | Ile | Leu | Leu | Phe | Leu | Leu | Thr |      |
|     |     |     |     | 405 |     |     |     |     | 410 |     |     |     |     | 415 |     |      |
| gtg | cag | ctg | gtg | ggc | att | atc | aag | gct | acc | tat | gcc | tgc | ttc | ctt | cga | 1296 |
| Val | Gln | Leu | Val | Gly | Ile | Ile | Lys | Ala | Thr | Tyr | Ala | Cys | Phe | Leu | Arg |      |
|     |     |     | 420 |     |     |     |     | 425 |     |     |     |     | 430 |     |     |      |
| ggc | aat | gca | gag | atg | atc | ttc | atg | tcc | ctc | tac | tcc | ctt | ctc | tat | atg | 1344 |
| Gly | Asn | Ala | Glu | Met | Ile | Phe | Met | Ser | Leu | Tyr | Ser | Leu | Leu | Tyr | Met |      |
|     |     | 435 |     |     |     |     | 440 |     |     |     |     | 445 |     |     |     |      |
| tcc | agc | ctc | ttg | cca | gcc | aag | atc | ttt | gct | att | gct | acc | atc | aac | aag | 1392 |
| Ser | Ser | Leu | Leu | Pro | Ala | Lys | Ile | Phe | Ala | Ile | Ala | Thr | Ile | Asn | Lys |      |
|     | 450 |     |     |     |     | 455 |     |     |     |     | 460 |     |     |     |     |      |
| tct | ggc | tgg | ggc | act | tct | ggc | agg | aaa | acc | att | gtc | gtg | aac | ttc | att | 1440 |
| Ser | Gly | Trp | Gly | Thr | Ser | Gly | Arg | Lys | Thr | Ile | Val | Val | Asn | Phe | Ile |      |
| 465 |     |     |     |     | 470 |     |     |     |     | 475 |     |     |     |     | 480 |      |
| ggc | cta | atc | ccc | gtg | tcc | atc | tgg | gtg | gca | gtt | ctt | cta | ggg | ggg | tta | 1488 |

```
Gly Leu Ile Pro Val Ser Ile Trp Val Ala Val Leu Leu Gly Gly Leu
                485                 490                 495 gcc tac aca gct tat tgc cag gac ctg ttc agt gag acc gag cta gcc      1536
Ala Tyr Thr Ala Tyr Cys Gln Asp Leu Phe Ser Glu Thr Glu Leu Ala
                500                 505                 510 ttc cta gtc tct ggg gcc atc ctg tat ggc tgc tac tgg gtg gcc ctc      1584
Phe Leu Val Ser Gly Ala Ile Leu Tyr Gly Cys Tyr Trp Val Ala Leu
                515                 520                 525 ctc atg ctg tat ctg gcc att att gcc cgg agg tgt ggg aag aag cca      1632
Leu Met Leu Tyr Leu Ala Ile Ile Ala Arg Arg Cys Gly Lys Lys Pro
            530                 535                 540 gaa cag tat agc ctg gct ttt gcg gag gtg tga                           1665
Glu Gln Tyr Ser Leu Ala Phe Ala Glu Val
545                 550

<210> SEQ ID NO 20
<211> LENGTH: 554
<212> TYPE: PRT
<213> ORGANISM: Mus musculus

<400> SEQUENCE: 20

Met Pro Val Gln Leu Thr Thr Ala Leu Arg Val Gly Thr Ser Leu
1               5                   10                  15

Phe Ala Leu Val Val Leu Gly Gly Ile Leu Ala Ala Tyr Val Thr Gly
                20                  25                  30

Tyr Gln Phe Ile His Thr Glu Lys His Tyr Leu Ser Phe Gly Leu Tyr
            35                  40                  45

Gly Ala Ile Leu Gly Leu His Leu Leu Ile Gln Ser Leu Phe Ala Phe
        50                  55                  60

Leu Glu His Arg Arg Met Arg Arg Ala Gly Arg Pro Leu Lys Leu His
65                  70                  75                  80

Cys Ser Gln Arg Ser Arg Ser Val Ala Leu Cys Ile Ala Ala Tyr Gln
                85                  90                  95

Glu Asp Pro Glu Tyr Leu Arg Lys Cys Leu Arg Ser Ala Gln Arg Ile
                100                 105                 110

Ala Phe Pro Asn Leu Lys Val Val Met Val Val Asp Gly Asn Arg Gln
            115                 120                 125

Glu Asp Thr Tyr Met Leu Asp Ile Phe His Glu Val Leu Gly Gly Thr
        130                 135                 140

Glu Gln Ala Gly Phe Phe Val Trp Arg Ser Asn Phe His Glu Ala Gly
145                 150                 155                 160

Glu Gly Glu Thr Glu Ala Ser Leu Gln Glu Gly Met Glu Arg Val Arg
                165                 170                 175

Ala Val Val Trp Ala Ser Thr Phe Ser Cys Ile Met Gln Lys Trp Gly
            180                 185                 190

Gly Lys Arg Glu Val Met Tyr Thr Ala Phe Lys Ala Leu Gly Asn Ser
        195                 200                 205

Val Asp Tyr Ile Gln Val Cys Asp Ser Asp Thr Val Leu Asp Pro Ala
    210                 215                 220

Cys Thr Ile Glu Met Leu Arg Val Leu Glu Glu Asp Pro Gln Val Gly
225                 230                 235                 240

Gly Val Gly Gly Asp Val Gln Ile Leu Asn Lys Tyr Asp Ser Trp Ile
                245                 250                 255

Ser Phe Leu Ser Ser Val Arg Tyr Trp Met Ala Phe Asn Val Glu Arg
            260                 265                 270

Ala Cys Gln Ser Tyr Phe Gly Cys Val Gln Cys Ile Ser Gly Pro Leu
```

```
                    275                 280                 285
        Gly Met Tyr Arg Asn Ser Leu Leu Gln Gln Phe Leu Glu Asp Trp Tyr
        290                 295                 300

His Gln Lys Phe Leu Gly Ser Lys Cys Ser Phe Gly Asp Asp Arg His
        305                 310                 315                 320

Leu Thr Asn Arg Val Leu Ser Leu Gly Tyr Arg Thr Lys Tyr Thr Ala
                        325                 330                 335

Arg Ser Lys Cys Leu Thr Glu Thr Pro Thr Arg Tyr Leu Arg Trp Leu
                        340                 345                 350

Asn Gln Gln Thr Arg Trp Ser Lys Ser Tyr Phe Arg Glu Trp Leu Tyr
                        355                 360                 365

Asn Ser Leu Trp Phe His Lys His Leu Trp Met Thr Tyr Glu Ser
                370                 375                 380

Val Val Thr Gly Phe Phe Pro Phe Phe Leu Ile Ala Thr Val Ile Gln
        385                 390                 395                 400

Leu Phe Tyr Arg Gly Arg Ile Trp Asn Ile Leu Leu Phe Leu Leu Thr
                        405                 410                 415

Val Gln Leu Val Gly Ile Ile Lys Ala Thr Tyr Ala Cys Phe Leu Arg
                        420                 425                 430

Gly Asn Ala Glu Met Ile Phe Met Ser Leu Tyr Ser Leu Leu Tyr Met
                        435                 440                 445

Ser Ser Leu Leu Pro Ala Lys Ile Phe Ala Ile Ala Thr Ile Asn Lys
        450                 455                 460

Ser Gly Trp Gly Thr Ser Gly Arg Lys Thr Ile Val Val Asn Phe Ile
        465                 470                 475                 480

Gly Leu Ile Pro Val Ser Ile Trp Val Ala Val Leu Gly Gly Leu
                        485                 490                 495

Ala Tyr Thr Ala Tyr Cys Gln Asp Leu Phe Ser Glu Thr Glu Leu Ala
                        500                 505                 510

Phe Leu Val Ser Gly Ala Ile Leu Tyr Gly Cys Tyr Trp Val Ala Leu
                        515                 520                 525

Leu Met Leu Tyr Leu Ala Ile Ile Ala Arg Arg Cys Gly Lys Lys Pro
        530                 535                 540

Glu Gln Tyr Ser Leu Ala Phe Ala Glu Val
        545                 550

<210> SEQ ID NO 21
<211> LENGTH: 1752
<212> TYPE: DNA
<213> ORGANISM: Rattus norvegicus
<220> FEATURE:
<221> NAME/KEY: CDS
<222> LOCATION: (1)..(1752)
<223> OTHER INFORMATION: Hyaluronan synthase 1
<300> PUBLICATION INFORMATION:
<308> DATABASE ACCESSION NUMBER: AB097568
<309> DATABASE ENTRY DATE: 2004-04-28

<400> SEQUENCE: 21 atg aga cag gac atg cca aag ccc tca gag gca gca cgt tgc tgc tcc      48
Met Arg Gln Asp Met Pro Lys Pro Ser Glu Ala Ala Arg Cys Cys Ser
1               5                   10                  15 ggt ctg gcc agg cgg gtg ctc acg atc acc ttc gcc ctc ctc atc ctg      96
Gly Leu Ala Arg Arg Val Leu Thr Ile Thr Phe Ala Leu Leu Ile Leu
            20                  25                  30 ggc ctc atg acc tgg gcc tac gca gca gga gta cct ctg gct tct gat     144
Gly Leu Met Thr Trp Ala Tyr Ala Ala Gly Val Pro Leu Ala Ser Asp
        35                  40                  45
```

| | | |
|---|---|---|
| ccc tat ggc ctc ctg gcc ttt ggg ctc tat ggg gcg ttc ctc agt gcg<br>Pro Tyr Gly Leu Leu Ala Phe Gly Leu Tyr Gly Ala Phe Leu Ser Ala<br>50                             55                          60 | 192 |
| cac cta gtg gca cag agc ctc ttc gct tac ctg gag cac cga agg gtg<br>His Leu Val Ala Gln Ser Leu Phe Ala Tyr Leu Glu His Arg Arg Val<br>65                     70                     75                  80 | 240 |
| acc gtg gct gcg cgg cgc gct ttt gcg aag gga ccc ctg gat gcg gcc<br>Thr Val Ala Ala Arg Arg Ala Phe Ala Lys Gly Pro Leu Asp Ala Ala<br>                  85                     90                     95 | 288 |
| act gcg cgc agc gtg gca ctc acc atc tca gcc tac cag gag gac ccc<br>Thr Ala Arg Ser Val Ala Leu Thr Ile Ser Ala Tyr Gln Glu Asp Pro<br>100                           105                     110 | 336 |
| act tac ctg cgc cag tgc ttg acc tcc gcg cgc gcc ttg ctg tac ccg<br>Thr Tyr Leu Arg Gln Cys Leu Thr Ser Ala Arg Ala Leu Leu Tyr Pro<br>                 115                     120                     125 | 384 |
| cgc acg cgg ctg cgc gtg ctt atg gtt gta gac ggc aat cgc gcg gag<br>Arg Thr Arg Leu Arg Val Leu Met Val Val Asp Gly Asn Arg Ala Glu<br>130                           135                     140 | 432 |
| gat ctg tac atg gtg gac atg ttc cga gaa gtc ttc gca gat gag gac<br>Asp Leu Tyr Met Val Asp Met Phe Arg Glu Val Phe Ala Asp Glu Asp<br>145                         150                     155                  160 | 480 |
| cct gcc act tat gtg tgg gat ggc aac tac cat cag cct tgg gag cca<br>Pro Ala Thr Tyr Val Trp Asp Gly Asn Tyr His Gln Pro Trp Glu Pro<br>                 165                     170                     175 | 528 |
| gct gag gcg gcg ggt gct gtg ggt gaa ggt gcc tac cgc gag gtg gag<br>Ala Glu Ala Ala Gly Ala Val Gly Glu Gly Ala Tyr Arg Glu Val Glu<br>                 180                     185                     190 | 576 |
| gct gag gac cct ggg cgg ctg gcg gta gag gcg ctg gtg agg acc cgc<br>Ala Glu Asp Pro Gly Arg Leu Ala Val Glu Ala Leu Val Arg Thr Arg<br>                 195                     200                     205 | 624 |
| agg tgc gtg tgc gtg gct cag cgc tgg ggt ggc aag cgc gaa gtc atg<br>Arg Cys Val Cys Val Ala Gln Arg Trp Gly Gly Lys Arg Glu Val Met<br>210                           215                     220 | 672 |
| tac acg gct ttc aag gca ctg ggt gac tcc gtg gac tac gtg cag gtc<br>Tyr Thr Ala Phe Lys Ala Leu Gly Asp Ser Val Asp Tyr Val Gln Val<br>225                         230                     235                  240 | 720 |
| tgt gac tca gac aca agg tta gac ccc atg gca ctg ctg gag ctt gtg<br>Cys Asp Ser Asp Thr Arg Leu Asp Pro Met Ala Leu Leu Glu Leu Val<br>                 245                     250                     255 | 768 |
| cga gtg ctg gat gaa gac ccc cgg gta ggt gct gtt gga gga gat gtg<br>Arg Val Leu Asp Glu Asp Pro Arg Val Gly Ala Val Gly Gly Asp Val<br>                 260                     265                     270 | 816 |
| aga atc ctt aac cct ctg gac tct tgg gtc agc ttc ttg agc agc ctt<br>Arg Ile Leu Asn Pro Leu Asp Ser Trp Val Ser Phe Leu Ser Ser Leu<br>                 275                     280                     285 | 864 |
| cga tac tgg gta gcc ttc aat gtg gag cga gct tgt cag agc tac ttt<br>Arg Tyr Trp Val Ala Phe Asn Val Glu Arg Ala Cys Gln Ser Tyr Phe<br>290                           295                     300 | 912 |
| cac tgt gtg tcc tgc atc agt ggt cct ctg ggt cta tac aga aac aat<br>His Cys Val Ser Cys Ile Ser Gly Pro Leu Gly Leu Tyr Arg Asn Asn<br>305                           310                     315                  320 | 960 |
| ctc ctg cag cag ttc ctg gag gcc tgg tac aac cag aag ttc ctg ggc<br>Leu Leu Gln Gln Phe Leu Glu Ala Trp Tyr Asn Gln Lys Phe Leu Gly<br>                 325                     330                     335 | 1008 |
| acc cac tgc aca ttt ggg gat gac agg cac ctc acc aac cgc atg ctt<br>Thr His Cys Thr Phe Gly Asp Asp Arg His Leu Thr Asn Arg Met Leu<br>                 340                     345                     350 | 1056 |
| agc atg ggc tac gct acc aag tat acc tcg cgc tcc aga tgc tat tca<br>Ser Met Gly Tyr Ala Thr Lys Tyr Thr Ser Arg Ser Arg Cys Tyr Ser | 1104 |

```
                    355                 360                 365
gag acg ccc tcc tct ttc ctt cgt tgg ctg agc cag cag acc cgc tgg    1152
Glu Thr Pro Ser Ser Phe Leu Arg Trp Leu Ser Gln Gln Thr Arg Trp
370                 375                 380 tcc aaa tct tat ttc cga gag tgg cta tac aac gcc ctg tgg tgg cac    1200
Ser Lys Ser Tyr Phe Arg Glu Trp Leu Tyr Asn Ala Leu Trp Trp His
385                 390                 395                 400 cgc cac cac gcg tgg atg acc tat gaa gcg gtg gtt tct ggc ctc ttc    1248
Arg His His Ala Trp Met Thr Tyr Glu Ala Val Val Ser Gly Leu Phe
                405                 410                 415 cct ttc ttt gtg gct gcc acg gtg ctg agg ctc ttc tat gca ggg cgc    1296
Pro Phe Phe Val Ala Ala Thr Val Leu Arg Leu Phe Tyr Ala Gly Arg
            420                 425                 430 cca tgg gct ctg ctc tgg gtg ctg ctc tgc gtg cag ggc gtg gca ctg    1344
Pro Trp Ala Leu Leu Trp Val Leu Leu Cys Val Gln Gly Val Ala Leu
        435                 440                 445 gca aag gca gcc ttt gca gcc tgg ctg cgt ggc tgc ctg cgc atg gtg    1392
Ala Lys Ala Ala Phe Ala Ala Trp Leu Arg Gly Cys Leu Arg Met Val
    450                 455                 460 ctg ctg tca ctc tat gca cca ctc tac atg tgc ggc ctg ctg cct gcc    1440
Leu Leu Ser Leu Tyr Ala Pro Leu Tyr Met Cys Gly Leu Leu Pro Ala
465                 470                 475                 480 aag ttc ctg gcg ttg gtt acc atg aat caa agt ggt tgg ggc acc tcg    1488
Lys Phe Leu Ala Leu Val Thr Met Asn Gln Ser Gly Trp Gly Thr Ser
                485                 490                 495 ggc cgg aag aaa ctg gct gct aac tat gta ccc gtg ttg ccc ctg gca    1536
Gly Arg Lys Lys Leu Ala Ala Asn Tyr Val Pro Val Leu Pro Leu Ala
            500                 505                 510 ctc tgg gct cta ctg ctg ctt gga ggc ctg atc cgc agt gtg gcc cag    1584
Leu Trp Ala Leu Leu Leu Leu Gly Gly Leu Ile Arg Ser Val Ala Gln
        515                 520                 525 gag gtc aga gct gac tgg agt ggc cca tca cga gca gct gaa gcc tac    1632
Glu Val Arg Ala Asp Trp Ser Gly Pro Ser Arg Ala Ala Glu Ala Tyr
    530                 535                 540 cac ctt gct gct ggg gcc agt gcc tat gtg gcc tac tgg gtg ata atg    1680
His Leu Ala Ala Gly Ala Ser Ala Tyr Val Ala Tyr Trp Val Ile Met
545                 550                 555                 560 ttg act atc tat tgg gta ggt gta agg aga ctg tgc aga cgt cgg agc    1728
Leu Thr Ile Tyr Trp Val Gly Val Arg Arg Leu Cys Arg Arg Arg Ser
                565                 570                 575 ggt ggc tac cgt gtc caa gta tga                                    1752
Gly Gly Tyr Arg Val Gln Val
            580

<210> SEQ ID NO 22
<211> LENGTH: 583
<212> TYPE: PRT
<213> ORGANISM: Rattus norvegicus

<400> SEQUENCE: 22

Met Arg Gln Asp Met Pro Lys Pro Ser Glu Ala Ala Arg Cys Cys Ser
1               5                   10                  15

Gly Leu Ala Arg Arg Val Leu Thr Ile Thr Phe Ala Leu Leu Ile Leu
            20                  25                  30

Gly Leu Met Thr Trp Ala Tyr Ala Gly Val Pro Leu Ala Ser Asp
        35                  40                  45

Pro Tyr Gly Leu Leu Ala Phe Gly Leu Tyr Gly Ala Phe Leu Ser Ala
    50                  55                  60

His Leu Val Ala Gln Ser Leu Phe Ala Tyr Leu Glu His Arg Arg Val
```

-continued

```
             65                  70                  75                  80
        Thr Val Ala Ala Arg Arg Ala Phe Ala Lys Gly Pro Leu Asp Ala Ala
                         85                  90                  95

Thr Ala Arg Ser Val Ala Leu Thr Ile Ser Ala Tyr Gln Glu Asp Pro
                        100                 105                 110

Thr Tyr Leu Arg Gln Cys Leu Thr Ser Ala Arg Ala Leu Leu Tyr Pro
                        115                 120                 125

Arg Thr Arg Leu Arg Val Leu Met Val Val Asp Gly Asn Arg Ala Glu
                130                 135                 140

Asp Leu Tyr Met Val Asp Met Phe Arg Glu Val Phe Ala Asp Glu Asp
        145                 150                 155                 160

Pro Ala Thr Tyr Val Trp Asp Gly Asn Tyr His Gln Pro Trp Glu Pro
                            165                 170                 175

Ala Glu Ala Ala Gly Ala Val Gly Glu Gly Ala Tyr Arg Glu Val Glu
                        180                 185                 190

Ala Glu Asp Pro Gly Arg Leu Ala Val Glu Ala Leu Val Arg Thr Arg
                        195                 200                 205

Arg Cys Val Cys Val Ala Gln Arg Trp Gly Gly Lys Arg Glu Val Met
                210                 215                 220

Tyr Thr Ala Phe Lys Ala Leu Gly Asp Ser Val Asp Tyr Val Gln Val
        225                 230                 235                 240

Cys Asp Ser Asp Thr Arg Leu Asp Pro Met Ala Leu Leu Glu Leu Val
                            245                 250                 255

Arg Val Leu Asp Glu Asp Pro Arg Val Gly Ala Val Gly Gly Asp Val
                        260                 265                 270

Arg Ile Leu Asn Pro Leu Asp Ser Trp Val Ser Phe Leu Ser Ser Leu
                275                 280                 285

Arg Tyr Trp Val Ala Phe Asn Val Glu Arg Ala Cys Gln Ser Tyr Phe
                290                 295                 300

His Cys Val Ser Cys Ile Ser Gly Pro Leu Gly Leu Tyr Arg Asn Asn
        305                 310                 315                 320

Leu Leu Gln Gln Phe Leu Glu Ala Trp Tyr Asn Gln Lys Phe Leu Gly
                            325                 330                 335

Thr His Cys Thr Phe Gly Asp Asp Arg His Leu Thr Asn Arg Met Leu
                        340                 345                 350

Ser Met Gly Tyr Ala Thr Lys Tyr Thr Ser Arg Ser Arg Cys Tyr Ser
                        355                 360                 365

Glu Thr Pro Ser Ser Phe Leu Arg Trp Leu Ser Gln Gln Thr Arg Trp
                370                 375                 380

Ser Lys Ser Tyr Phe Arg Glu Trp Leu Tyr Asn Ala Leu Trp Trp His
        385                 390                 395                 400

Arg His His Ala Trp Met Thr Tyr Glu Ala Val Val Ser Gly Leu Phe
                            405                 410                 415

Pro Phe Phe Val Ala Ala Thr Val Leu Arg Leu Phe Tyr Ala Gly Arg
                        420                 425                 430

Pro Trp Ala Leu Leu Trp Val Leu Cys Val Gln Gly Val Ala Leu
                        435                 440                 445

Ala Lys Ala Ala Phe Ala Ala Trp Leu Arg Gly Cys Leu Arg Met Val
                450                 455                 460

Leu Leu Ser Leu Tyr Ala Pro Leu Tyr Met Cys Gly Leu Leu Pro Ala
        465                 470                 475                 480

Lys Phe Leu Ala Leu Val Thr Met Asn Gln Ser Gly Trp Gly Thr Ser
                            485                 490                 495
```

```
Gly Arg Lys Lys Leu Ala Ala Asn Tyr Val Pro Val Leu Pro Leu Ala
            500                 505                 510
Leu Trp Ala Leu Leu Leu Gly Leu Ile Arg Ser Val Ala Gln
            515                 520                 525
Glu Val Arg Ala Asp Trp Ser Gly Pro Ser Arg Ala Ala Glu Ala Tyr
530                 535                 540
His Leu Ala Ala Gly Ala Ser Ala Tyr Val Ala Tyr Trp Val Ile Met
545                 550                 555                 560
Leu Thr Ile Tyr Trp Val Gly Val Arg Arg Leu Cys Arg Arg Arg Ser
                565                 570                 575
Gly Gly Tyr Arg Val Gln Val
            580

<210> SEQ ID NO 23
<211> LENGTH: 1659
<212> TYPE: DNA
<213> ORGANISM: Rattus norvegicus
<220> FEATURE:
<221> NAME/KEY: CDS
<222> LOCATION: (1)..(1659)
<223> OTHER INFORMATION: Hyaluronan synthase 2
<300> PUBLICATION INFORMATION:
<308> DATABASE ACCESSION NUMBER: AF008201.1
<309> DATABASE ENTRY DATE: 1997-07-16
<313> RELEVANT RESIDUES IN SEQ ID NO: (507)..(2165)

<400> SEQUENCE: 23 atg cat tgt gag agg ttt cta tgt gtc ctg aga ata atc gga acc aca      48
Met His Cys Glu Arg Phe Leu Cys Val Leu Arg Ile Ile Gly Thr Thr
1               5                   10                  15 ctg ttt gga gtg tct ctc ctc ctc gga atc aca gct gct tat att gtt      96
Leu Phe Gly Val Ser Leu Leu Leu Gly Ile Thr Ala Ala Tyr Ile Val
            20                  25                  30 ggc tac cag ttt atc caa aca gat aat tac tat ttc tcc ttt ggg ctg     144
Gly Tyr Gln Phe Ile Gln Thr Asp Asn Tyr Tyr Phe Ser Phe Gly Leu
        35                  40                  45 tat ggt gcc ttt tta gcc tca cac ctc atc atc caa agc ctc ttt gcc     192
Tyr Gly Ala Phe Leu Ala Ser His Leu Ile Ile Gln Ser Leu Phe Ala
50                  55                  60 ttt ttg gaa cac cgg aaa atg aaa aag tcc ctt gaa acc ccc att aaa     240
Phe Leu Glu His Arg Lys Met Lys Lys Ser Leu Glu Thr Pro Ile Lys
65                  70                  75                  80 ttg aac aaa act gta gct ctc tgc att gct gcg tat caa gaa gac cct     288
Leu Asn Lys Thr Val Ala Leu Cys Ile Ala Ala Tyr Gln Glu Asp Pro
                85                  90                  95 gac tac tta cgg aaa tgt ttg caa tct gtg aaa agg ctg acc tac cct     336
Asp Tyr Leu Arg Lys Cys Leu Gln Ser Val Lys Arg Leu Thr Tyr Pro
            100                 105                 110 ggg atc aaa gtc gtg atg gtc ata gat gga aat tca gat gac gac ctt     384
Gly Ile Lys Val Val Met Val Ile Asp Gly Asn Ser Asp Asp Asp Leu
        115                 120                 125 tac atg atg gac atc ttc agt gaa gtc atg ggc agg gac aaa tca gtc     432
Tyr Met Met Asp Ile Phe Ser Glu Val Met Gly Arg Asp Lys Ser Val
130                 135                 140 act tac atc tgg aag aac aac ttc cat gaa agg gga cct ggt gag aca     480
Thr Tyr Ile Trp Lys Asn Asn Phe His Glu Arg Gly Pro Gly Glu Thr
145                 150                 155                 160 gaa gag tcc cat aaa gaa agt tcg caa cat gta acc caa ttg gtc ttg     528
Glu Glu Ser His Lys Glu Ser Ser Gln His Val Thr Gln Leu Val Leu
                165                 170                 175
```

```
tct aac aag agt att tgc atc atg caa aaa tgg ggt gga aag aga gaa      576
Ser Asn Lys Ser Ile Cys Ile Met Gln Lys Trp Gly Gly Lys Arg Glu
        180                 185                 190 gtc atg tac acc gcc ttc aga gca ctg ggc aga agc gtg gat tat gta      624
Val Met Tyr Thr Ala Phe Arg Ala Leu Gly Arg Ser Val Asp Tyr Val
            195                 200                 205 cag gtg tgt gac tca gac acc atg ctt gac cct gcc tcg tct gtg gag      672
Gln Val Cys Asp Ser Asp Thr Met Leu Asp Pro Ala Ser Ser Val Glu
210                 215                 220 atg gtg aag gtc tta gaa gaa gac ccg atg gtt gga ggt gtt ggg gga      720
Met Val Lys Val Leu Glu Glu Asp Pro Met Val Gly Gly Val Gly Gly
225                 230                 235                 240 gat gtt cag att tta aac aag tat gat tct tgg atc tcc ttc ctc agc      768
Asp Val Gln Ile Leu Asn Lys Tyr Asp Ser Trp Ile Ser Phe Leu Ser
                245                 250                 255 agt gtg aga tac tgg atg gct ttt aat ata gaa agg gcc tgc cag tct      816
Ser Val Arg Tyr Trp Met Ala Phe Asn Ile Glu Arg Ala Cys Gln Ser
            260                 265                 270 tat ttt ggc tgt gtc cag tgc ata agc ggt cct ctg gga atg tac aga      864
Tyr Phe Gly Cys Val Gln Cys Ile Ser Gly Pro Leu Gly Met Tyr Arg
        275                 280                 285 aac tcc ttg ttg cat gag ttt gtg gaa gac tgg tac aat cag gaa ttc      912
Asn Ser Leu Leu His Glu Phe Val Glu Asp Trp Tyr Asn Gln Glu Phe
290                 295                 300 atg ggt aac caa tgc agt ttc ggt gat gat agg cac ctt acc aac agg      960
Met Gly Asn Gln Cys Ser Phe Gly Asp Asp Arg His Leu Thr Asn Arg
305                 310                 315                 320 gta ctg agt ctg ggc tat gca act aaa tac acg gct cgg tcc aag tgc     1008
Val Leu Ser Leu Gly Tyr Ala Thr Lys Tyr Thr Ala Arg Ser Lys Cys
                325                 330                 335 ctt act gaa aca ccc ata gaa tat ctg aga tgg ctg aac cag cag acc     1056
Leu Thr Glu Thr Pro Ile Glu Tyr Leu Arg Trp Leu Asn Gln Gln Thr
            340                 345                 350 cgt tgg agc aag tcc tac ttc cga gag tgg cta tac aat gcc atg tgg     1104
Arg Trp Ser Lys Ser Tyr Phe Arg Glu Trp Leu Tyr Asn Ala Met Trp
        355                 360                 365 ttt cac aag cat cac ttg tgg atg acc tac gaa gct gtt atc act gga     1152
Phe His Lys His His Leu Trp Met Thr Tyr Glu Ala Val Ile Thr Gly
370                 375                 380 ttc ttt cct ttc ttt ctc att gcc aca gtc atc cag ctc ttc tac agg     1200
Phe Phe Pro Phe Phe Leu Ile Ala Thr Val Ile Gln Leu Phe Tyr Arg
385                 390                 395                 400 ggt aaa atc tgg aac atc ctc ctc ttc ctg tta act gtc cag cta gtg     1248
Gly Lys Ile Trp Asn Ile Leu Leu Phe Leu Leu Thr Val Gln Leu Val
                405                 410                 415 ggt ctc atc aag tcg tct ttc gcc agc tgc ctt aga gga aat atc gtc     1296
Gly Leu Ile Lys Ser Ser Phe Ala Ser Cys Leu Arg Gly Asn Ile Val
            420                 425                 430 atg gtc ttc atg tct ctc tac tca gtg ttg tac atg tca agt cta ctt     1344
Met Val Phe Met Ser Leu Tyr Ser Val Leu Tyr Met Ser Ser Leu Leu
        435                 440                 445 cct gcc aag atg ttt gca att gca acc ata aac aaa gct ggg tgg ggc     1392
Pro Ala Lys Met Phe Ala Ile Ala Thr Ile Asn Lys Ala Gly Trp Gly
450                 455                 460 aca tct gga agg aaa acc att gtc gtt aat ttc ata gga ctt att cca     1440
Thr Ser Gly Arg Lys Thr Ile Val Val Asn Phe Ile Gly Leu Ile Pro
465                 470                 475                 480 gtg tcc gtg tgg ttt aca atc ctt cta ggt ggt gtg att ttc acc att     1488
Val Ser Val Trp Phe Thr Ile Leu Leu Gly Gly Val Ile Phe Thr Ile
                485                 490                 495
```

```
tat aag gaa tct aaa aag cca ttt tcc gaa tcc aaa cag act gtt ctc      1536
Tyr Lys Glu Ser Lys Lys Pro Phe Ser Glu Ser Lys Gln Thr Val Leu
            500                 505                 510 att gtg gga acc ttg atc tat gcg tgc tac tgg gtc gtg ctt ttg act      1584
Ile Val Gly Thr Leu Ile Tyr Ala Cys Tyr Trp Val Val Leu Leu Thr
            515                 520                 525 ctg tat gtg gtt ctc atc aat aag tgt ggc agg cgg aag aag gga caa      1632
Leu Tyr Val Val Leu Ile Asn Lys Cys Gly Arg Arg Lys Lys Gly Gln
        530                 535                 540 cag tac gac atg gtg ctt gat gta tga                                  1659
Gln Tyr Asp Met Val Leu Asp Val
545             550

<210> SEQ ID NO 24
<211> LENGTH: 552
<212> TYPE: PRT
<213> ORGANISM: Rattus norvegicus

<400> SEQUENCE: 24

Met His Cys Glu Arg Phe Leu Cys Val Leu Arg Ile Ile Gly Thr Thr
1               5                   10                  15

Leu Phe Gly Val Ser Leu Leu Gly Ile Thr Ala Ala Tyr Ile Val
            20                  25                  30

Gly Tyr Gln Phe Ile Gln Thr Asp Asn Tyr Tyr Phe Ser Phe Gly Leu
        35                  40                  45

Tyr Gly Ala Phe Leu Ala Ser His Leu Ile Ile Gln Ser Leu Phe Ala
    50                  55                  60

Phe Leu Glu His Arg Lys Met Lys Lys Ser Leu Glu Thr Pro Ile Lys
65                  70                  75                  80

Leu Asn Lys Thr Val Ala Leu Cys Ile Ala Ala Tyr Gln Glu Asp Pro
                85                  90                  95

Asp Tyr Leu Arg Lys Cys Leu Gln Ser Val Lys Arg Leu Thr Tyr Pro
            100                 105                 110

Gly Ile Lys Val Val Met Val Ile Asp Gly Asn Ser Asp Asp Asp Leu
        115                 120                 125

Tyr Met Met Asp Ile Phe Ser Glu Val Met Gly Arg Asp Lys Ser Val
    130                 135                 140

Thr Tyr Ile Trp Lys Asn Asn Phe His Glu Arg Gly Pro Gly Glu Thr
145                 150                 155                 160

Glu Glu Ser His Lys Glu Ser Ser Gln His Val Thr Gln Leu Val Leu
                165                 170                 175

Ser Asn Lys Ser Ile Cys Ile Met Gln Lys Trp Gly Gly Lys Arg Glu
            180                 185                 190

Val Met Tyr Thr Ala Phe Arg Ala Leu Gly Arg Ser Val Asp Tyr Val
        195                 200                 205

Gln Val Cys Asp Ser Asp Thr Met Leu Asp Pro Ala Ser Ser Val Glu
    210                 215                 220

Met Val Lys Val Leu Glu Glu Asp Pro Met Val Gly Gly Val Gly Gly
225                 230                 235                 240

Asp Val Gln Ile Leu Asn Lys Tyr Asp Ser Trp Ile Ser Phe Leu Ser
                245                 250                 255

Ser Val Arg Tyr Trp Met Ala Phe Asn Ile Glu Arg Ala Cys Gln Ser
            260                 265                 270

Tyr Phe Gly Cys Val Gln Cys Ile Ser Gly Pro Leu Gly Met Tyr Arg
        275                 280                 285
```

```
Asn Ser Leu Leu His Glu Phe Val Glu Asp Trp Tyr Asn Gln Glu Phe
    290                 295                 300

Met Gly Asn Gln Cys Ser Phe Gly Asp Asp Arg His Leu Thr Asn Arg
305                 310                 315                 320

Val Leu Ser Leu Gly Tyr Ala Thr Lys Tyr Thr Ala Arg Ser Lys Cys
            325                 330                 335

Leu Thr Glu Thr Pro Ile Glu Tyr Leu Arg Trp Leu Asn Gln Gln Thr
        340                 345                 350

Arg Trp Ser Lys Ser Tyr Phe Arg Glu Trp Leu Tyr Asn Ala Met Trp
    355                 360                 365

Phe His Lys His His Leu Trp Met Thr Tyr Glu Ala Val Ile Thr Gly
370                 375                 380

Phe Phe Pro Phe Phe Leu Ile Ala Thr Val Ile Gln Leu Phe Tyr Arg
385                 390                 395                 400

Gly Lys Ile Trp Asn Ile Leu Leu Phe Leu Leu Thr Val Gln Leu Val
            405                 410                 415

Gly Leu Ile Lys Ser Ser Phe Ala Ser Cys Leu Arg Gly Asn Ile Val
        420                 425                 430

Met Val Phe Met Ser Leu Tyr Ser Val Leu Tyr Met Ser Ser Leu Leu
    435                 440                 445

Pro Ala Lys Met Phe Ala Ile Ala Thr Ile Asn Lys Ala Gly Trp Gly
450                 455                 460

Thr Ser Gly Arg Lys Thr Ile Val Val Asn Phe Ile Gly Leu Ile Pro
465                 470                 475                 480

Val Ser Val Trp Phe Thr Ile Leu Leu Gly Gly Val Ile Phe Thr Ile
            485                 490                 495

Tyr Lys Glu Ser Lys Lys Pro Phe Ser Glu Ser Lys Gln Thr Val Leu
        500                 505                 510

Ile Val Gly Thr Leu Ile Tyr Ala Cys Tyr Trp Val Leu Leu Thr
    515                 520                 525

Leu Tyr Val Val Leu Ile Asn Lys Cys Gly Arg Arg Lys Lys Gly Gln
530                 535                 540

Gln Tyr Asp Met Val Leu Asp Val
545                 550

<210> SEQ ID NO 25
<211> LENGTH: 1665
<212> TYPE: DNA
<213> ORGANISM: Rattus norvegicus
<220> FEATURE:
<221> NAME/KEY: CDS
<222> LOCATION: (1)..(1665)
<223> OTHER INFORMATION: Hyaluronan synthase 3
<300> PUBLICATION INFORMATION:
<308> DATABASE ACCESSION NUMBER: NM 172319
<309> DATABASE ENTRY DATE: 2004-08-21

<400> SEQUENCE: 25 atg ccg gtg cag ctg act aca gcc ctt cgt gtg gtg ggc acc agt ctg      48
Met Pro Val Gln Leu Thr Thr Ala Leu Arg Val Val Gly Thr Ser Leu
1               5                   10                  15 ttt gcc ctg gta gtg ctg ggg ggc atc ctg gca gcc tat gtc aca ggc      96
Phe Ala Leu Val Val Leu Gly Gly Ile Leu Ala Ala Tyr Val Thr Gly
            20                  25                  30 tac cag ttt atc cac acg gaa aag cac tat ctg tcc ttc ggc ctc tac     144
Tyr Gln Phe Ile His Thr Glu Lys His Tyr Leu Ser Phe Gly Leu Tyr
        35                  40                  45 ggt gcc atc ctg ggt ctg cat ctg ctc atc cag agc ctg ttt gcc ttc     192
```

-continued

```
                Gly Ala Ile Leu Gly Leu His Leu Leu Ile Gln Ser Leu Phe Ala Phe
                         50                  55                  60 ctg gag cac cgt cgc atg cgc agg gca ggg cgc cca ctg aag ctg cac      240
Leu Glu His Arg Arg Met Arg Arg Ala Gly Arg Pro Leu Lys Leu His
 65                  70                  75                  80 tgc tct cag aga cgg cgt tcg gtg gca ctc tgc atc gct gcc tac caa      288
Cys Ser Gln Arg Arg Arg Ser Val Ala Leu Cys Ile Ala Ala Tyr Gln
                 85                  90                  95 gag gac cct gag tac ttg cgc aag tgc ctt cgc tca gct cag cgc att      336
Glu Asp Pro Glu Tyr Leu Arg Lys Cys Leu Arg Ser Ala Gln Arg Ile
            100                 105                 110 gcc ttc cca aac ctc aag gtg gtc atg gta gtg gat ggc aat cgc cag      384
Ala Phe Pro Asn Leu Lys Val Val Met Val Val Asp Gly Asn Arg Gln
        115                 120                 125 gaa gat gcc tac atg ctg gac atc ttc cat gag gtc ctg ggt ggc act      432
Glu Asp Ala Tyr Met Leu Asp Ile Phe His Glu Val Leu Gly Gly Thr
    130                 135                 140 gag caa gct ggc ttc ttt gtg tgg cgt agc aat ttc cat gag gcg ggt      480
Glu Gln Ala Gly Phe Phe Val Trp Arg Ser Asn Phe His Glu Ala Gly
145                 150                 155                 160 gaa gga gag aca gag gcc agc ttg cag gaa ggc atg gag cgt gtt cga      528
Glu Gly Glu Thr Glu Ala Ser Leu Gln Glu Gly Met Glu Arg Val Arg
                165                 170                 175 gct gtg gtg tgg gcc agc acc ttc tca tgc atc atg cag aag tgg ggg      576
Ala Val Val Trp Ala Ser Thr Phe Ser Cys Ile Met Gln Lys Trp Gly
            180                 185                 190 ggc aag cgt gaa gtc atg tac aca gct ttc aag gcc ctt ggc aac tca      624
Gly Lys Arg Glu Val Met Tyr Thr Ala Phe Lys Ala Leu Gly Asn Ser
        195                 200                 205 gtg gac tac atc cag gtg tgt gac tct gac act gtg ctg gac cca gcc      672
Val Asp Tyr Ile Gln Val Cys Asp Ser Asp Thr Val Leu Asp Pro Ala
    210                 215                 220 tgc acc att gag atg ctt cgg gtc ttg gag gaa gat ccc caa gta gga      720
Cys Thr Ile Glu Met Leu Arg Val Leu Glu Glu Asp Pro Gln Val Gly
225                 230                 235                 240 ggt gtt gga gga gat gtc caa atc ctc aac aaa tac gat tca tgg atc      768
Gly Val Gly Gly Asp Val Gln Ile Leu Asn Lys Tyr Asp Ser Trp Ile
                245                 250                 255 tcc ttc ctg agc agc gtg agg tac tgg atg gcc ttc aac gtg gag cgg      816
Ser Phe Leu Ser Ser Val Arg Tyr Trp Met Ala Phe Asn Val Glu Arg
            260                 265                 270 gcc tgc cag tcc tac ttt ggc tgt gtg cag tgt att agt ggg cct ctg      864
Ala Cys Gln Ser Tyr Phe Gly Cys Val Gln Cys Ile Ser Gly Pro Leu
        275                 280                 285 ggc atg tac cgc aac agc ctc ttg cag cag ttc ctg gag gac tgg tac      912
Gly Met Tyr Arg Asn Ser Leu Leu Gln Gln Phe Leu Glu Asp Trp Tyr
    290                 295                 300 cat cag aag ttc cta ggc agc aag tgc agc ttt ggg gat gat cgg cac      960
His Gln Lys Phe Leu Gly Ser Lys Cys Ser Phe Gly Asp Asp Arg His
305                 310                 315                 320 ctt acc aac cga gtc ctg agt ctt ggc tac cgg act aag tat aca gca     1008
Leu Thr Asn Arg Val Leu Ser Leu Gly Tyr Arg Thr Lys Tyr Thr Ala
                325                 330                 335 cgc tcc aag tgc ctc aca gag acc ccc act aag tat ctc cga tgg ctc     1056
Arg Ser Lys Cys Leu Thr Glu Thr Pro Thr Lys Tyr Leu Arg Trp Leu
            340                 345                 350 aac cag cag acc cgc tgg agc aag tct tac ttt cgg gag tgg ctc tac     1104
Asn Gln Gln Thr Arg Trp Ser Lys Ser Tyr Phe Arg Glu Trp Leu Tyr
        355                 360                 365
```

```
aac tct ctg tgg ttc cat aag cac cac ctg tgg atg acc tat gag tca    1152
Asn Ser Leu Trp Phe His Lys His His Leu Trp Met Thr Tyr Glu Ser
    370             375                 380 gtg gtc aca ggc ttc ttc ccc ttc ttc ctc atc gcc aca gtc ata caa    1200
Val Val Thr Gly Phe Phe Pro Phe Phe Leu Ile Ala Thr Val Ile Gln
385             390                 395                 400 ctt ttc tac cgt ggc cgc atc tgg aac att ctc ctc ttc cta cta acg    1248
Leu Phe Tyr Arg Gly Arg Ile Trp Asn Ile Leu Leu Phe Leu Leu Thr
                405                 410                 415 gtg cag ctg gtg ggc att atc aag gct acc tat gcc tgc ttc ctc cga    1296
Val Gln Leu Val Gly Ile Ile Lys Ala Thr Tyr Ala Cys Phe Leu Arg
            420                 425                 430 ggc aat gca gag atg atc ttc atg tcc ctc tac tcc ctt ctc tat atg    1344
Gly Asn Ala Glu Met Ile Phe Met Ser Leu Tyr Ser Leu Leu Tyr Met
        435                 440                 445 tcc agc ctg ctg cca gcc aag atc ttt gct att gct acc atc aac aag    1392
Ser Ser Leu Leu Pro Ala Lys Ile Phe Ala Ile Ala Thr Ile Asn Lys
    450                 455                 460 tct ggc tgg ggc act tct ggc agg aaa acc att gta gtg aac ttc att    1440
Ser Gly Trp Gly Thr Ser Gly Arg Lys Thr Ile Val Val Asn Phe Ile
465             470                 475                 480 ggc cta atc cct gtg tcc atc tgg gtg gca gtt ctt cta ggg ggg tta    1488
Gly Leu Ile Pro Val Ser Ile Trp Val Ala Val Leu Leu Gly Gly Leu
                485                 490                 495 gcc tac aca gct tat tgt cag gac ctg ttc agt gag act gag cta gcc    1536
Ala Tyr Thr Ala Tyr Cys Gln Asp Leu Phe Ser Glu Thr Glu Leu Ala
            500                 505                 510 ttc ctg gtc tct ggg gcc atc ttg tat ggc tgc tac tgg gtg gcc ctc    1584
Phe Leu Val Ser Gly Ala Ile Leu Tyr Gly Cys Tyr Trp Val Ala Leu
        515                 520                 525 ctc atg ctg tat ttg gcc att att gcc cgg agg tgt ggg aaa aag cca    1632
Leu Met Leu Tyr Leu Ala Ile Ile Ala Arg Arg Cys Gly Lys Lys Pro
    530                 535                 540 gaa cag tat agc ctg gct ttt gct gag gtg tga                        1665
Glu Gln Tyr Ser Leu Ala Phe Ala Glu Val
545             550

<210> SEQ ID NO 26
<211> LENGTH: 554
<212> TYPE: PRT
<213> ORGANISM: Rattus norvegicus

<400> SEQUENCE: 26

Met Pro Val Gln Leu Thr Thr Ala Leu Arg Val Gly Thr Ser Leu
1               5                   10                  15

Phe Ala Leu Val Val Leu Gly Ile Leu Ala Ala Tyr Val Thr Gly
            20                  25                  30

Tyr Gln Phe Ile His Thr Glu Lys His Tyr Leu Ser Phe Gly Leu Tyr
        35                  40                  45

Gly Ala Ile Leu Gly Leu His Leu Leu Ile Gln Ser Leu Phe Ala Phe
    50                  55                  60

Leu Glu His Arg Arg Met Arg Arg Ala Gly Arg Pro Leu Lys Leu His
65              70                  75                  80

Cys Ser Gln Arg Arg Ser Val Ala Leu Cys Ile Ala Ala Tyr Gln
            85                  90                  95

Glu Asp Pro Glu Tyr Leu Arg Lys Cys Leu Arg Ser Ala Gln Arg Ile
            100                 105                 110

Ala Phe Pro Asn Leu Lys Val Val Met Val Val Asp Gly Asn Arg Gln
        115                 120                 125
```

```
Glu Asp Ala Tyr Met Leu Asp Ile Phe His Glu Val Leu Gly Gly Thr
    130                 135                 140

Glu Gln Ala Gly Phe Phe Val Trp Arg Ser Asn Phe His Glu Ala Gly
145                 150                 155                 160

Glu Gly Glu Thr Glu Ala Ser Leu Gln Glu Gly Met Glu Arg Val Arg
                165                 170                 175

Ala Val Val Trp Ala Ser Thr Phe Ser Cys Ile Met Gln Lys Trp Gly
                180                 185                 190

Gly Lys Arg Glu Val Met Tyr Thr Ala Phe Lys Ala Leu Gly Asn Ser
        195                 200                 205

Val Asp Tyr Ile Gln Val Cys Asp Ser Asp Thr Val Leu Asp Pro Ala
    210                 215                 220

Cys Thr Ile Glu Met Leu Arg Val Leu Glu Glu Asp Pro Gln Val Gly
225                 230                 235                 240

Gly Val Gly Gly Asp Val Gln Ile Leu Asn Lys Tyr Asp Ser Trp Ile
                245                 250                 255

Ser Phe Leu Ser Ser Val Arg Tyr Trp Met Ala Phe Asn Val Glu Arg
                260                 265                 270

Ala Cys Gln Ser Tyr Phe Gly Cys Val Gln Cys Ile Ser Gly Pro Leu
        275                 280                 285

Gly Met Tyr Arg Asn Ser Leu Leu Gln Gln Phe Leu Glu Asp Trp Tyr
    290                 295                 300

His Gln Lys Phe Leu Gly Ser Lys Cys Ser Phe Gly Asp Asp Arg His
305                 310                 315                 320

Leu Thr Asn Arg Val Leu Ser Leu Gly Tyr Arg Thr Lys Tyr Thr Ala
                325                 330                 335

Arg Ser Lys Cys Leu Thr Glu Thr Pro Thr Lys Tyr Leu Arg Trp Leu
                340                 345                 350

Asn Gln Gln Thr Arg Trp Ser Lys Ser Tyr Phe Arg Glu Trp Leu Tyr
        355                 360                 365

Asn Ser Leu Trp Phe His Lys His His Leu Trp Met Thr Tyr Glu Ser
    370                 375                 380

Val Val Thr Gly Phe Phe Pro Phe Phe Leu Ile Ala Thr Val Ile Gln
385                 390                 395                 400

Leu Phe Tyr Arg Gly Arg Ile Trp Asn Ile Leu Leu Phe Leu Leu Thr
                405                 410                 415

Val Gln Leu Val Gly Ile Ile Lys Ala Thr Tyr Ala Cys Phe Leu Arg
                420                 425                 430

Gly Asn Ala Glu Met Ile Phe Met Ser Leu Tyr Ser Leu Leu Tyr Met
        435                 440                 445

Ser Ser Leu Leu Pro Ala Lys Ile Phe Ala Ile Ala Thr Ile Asn Lys
    450                 455                 460

Ser Gly Trp Gly Thr Ser Gly Arg Lys Thr Ile Val Val Asn Phe Ile
465                 470                 475                 480

Gly Leu Ile Pro Val Ser Ile Trp Val Ala Val Leu Leu Gly Gly Leu
                485                 490                 495

Ala Tyr Thr Ala Tyr Cys Gln Asp Leu Phe Ser Glu Thr Glu Leu Ala
                500                 505                 510

Phe Leu Val Ser Gly Ala Ile Leu Tyr Gly Cys Tyr Trp Val Ala Leu
        515                 520                 525

Leu Met Leu Tyr Leu Ala Ile Ile Ala Arg Arg Cys Gly Lys Lys Pro
    530                 535                 540
```

-continued

```
Glu Gln Tyr Ser Leu Ala Phe Ala Glu Val
545                 550

<210> SEQ ID NO 27
<211> LENGTH: 1659
<212> TYPE: DNA
<213> ORGANISM: Oryctolagus cuniculus
<220> FEATURE:
<221> NAME/KEY: CDS
<222> LOCATION: (1)..(1659)
<223> OTHER INFORMATION: Hyaluronan synthase 2
<300> PUBLICATION INFORMATION:
<308> DATABASE ACCESSION NUMBER: AB055978
<309> DATABASE ENTRY DATE: 2001-08-21
<313> RELEVANT RESIDUES IN SEQ ID NO: (1)..(1659)

<400> SEQUENCE: 27
```

| | | | | | | | | | | | | | | | | |
|---|---|---|---|---|---|---|---|---|---|---|---|---|---|---|---|---|
| atg | cat | tgt | gag | agg | ttt | ata | tgt | atc | ctg | aga | ata | att | gga | acc | aca | 48 |
| Met | His | Cys | Glu | Arg | Phe | Ile | Cys | Ile | Leu | Arg | Ile | Ile | Gly | Thr | Thr | |
| 1 | | | | 5 | | | | | 10 | | | | | 15 | | |
| ctg | ttt | gga | gtc | tct | ctc | ctt | ctg | gga | atc | aca | gct | gct | tat | att | gtt | 96 |
| Leu | Phe | Gly | Val | Ser | Leu | Leu | Leu | Gly | Ile | Thr | Ala | Ala | Tyr | Ile | Val | |
| | | | 20 | | | | | 25 | | | | | 30 | | | |
| gga | tac | cag | ttt | atc | caa | acg | gat | aat | tac | tat | ttc | tct | ttt | gga | ctg | 144 |
| Gly | Tyr | Gln | Phe | Ile | Gln | Thr | Asp | Asn | Tyr | Tyr | Phe | Ser | Phe | Gly | Leu | |
| | | 35 | | | | | 40 | | | | | 45 | | | | |
| tat | ggt | gcc | ttt | tta | gca | tca | cac | ctc | atc | atc | caa | agc | ctg | ttt | gcc | 192 |
| Tyr | Gly | Ala | Phe | Leu | Ala | Ser | His | Leu | Ile | Ile | Gln | Ser | Leu | Phe | Ala | |
| 50 | | | | | 55 | | | | | 60 | | | | | | |
| ttt | ttg | gag | cac | cga | aaa | atg | aaa | aaa | tcc | cta | gaa | acc | ccc | att | aag | 240 |
| Phe | Leu | Glu | His | Arg | Lys | Met | Lys | Lys | Ser | Leu | Glu | Thr | Pro | Ile | Lys | |
| 65 | | | | | 70 | | | | | 75 | | | | | 80 | |
| ttg | aac | aaa | aca | gtt | gct | ctt | tgc | atc | gct | gcc | tat | caa | gaa | gac | cca | 288 |
| Leu | Asn | Lys | Thr | Val | Ala | Leu | Cys | Ile | Ala | Ala | Tyr | Gln | Glu | Asp | Pro | |
| | | | | 85 | | | | | 90 | | | | | 95 | | |
| gac | tac | tta | agg | aaa | tgt | tta | caa | tct | gtg | aaa | agg | ctg | acc | tac | cct | 336 |
| Asp | Tyr | Leu | Arg | Lys | Cys | Leu | Gln | Ser | Val | Lys | Arg | Leu | Thr | Tyr | Pro | |
| | | | 100 | | | | | 105 | | | | | 110 | | | |
| ggg | att | aaa | gtt | gtc | atg | gtc | att | gat | ggg | aac | tca | gaa | gat | gat | gtt | 384 |
| Gly | Ile | Lys | Val | Val | Met | Val | Ile | Asp | Gly | Asn | Ser | Glu | Asp | Asp | Val | |
| | | 115 | | | | | 120 | | | | | 125 | | | | |
| tac | atg | atg | gac | atc | ttc | agt | gaa | gtc | atg | ggc | agg | gaa | aca | tca | gcc | 432 |
| Tyr | Met | Met | Asp | Ile | Phe | Ser | Glu | Val | Met | Gly | Arg | Glu | Thr | Ser | Ala | |
| | 130 | | | | | 135 | | | | | 140 | | | | | |
| act | tac | atc | tgg | aag | aac | aac | ttt | cat | gaa | aag | ggg | cct | ggg | gag | act | 480 |
| Thr | Tyr | Ile | Trp | Lys | Asn | Asn | Phe | His | Glu | Lys | Gly | Pro | Gly | Glu | Thr | |
| 145 | | | | | 150 | | | | | 155 | | | | | 160 | |
| gat | gag | tca | cat | aaa | gaa | agc | tca | caa | cat | gta | acc | caa | ctg | gtc | ttg | 528 |
| Asp | Glu | Ser | His | Lys | Glu | Ser | Ser | Gln | His | Val | Thr | Gln | Leu | Val | Leu | |
| | | | | 165 | | | | | 170 | | | | | 175 | | |
| tcg | aac | aaa | agt | gtt | tgc | atc | atg | cag | aaa | tgg | ggt | gga | aag | aga | gaa | 576 |
| Ser | Asn | Lys | Ser | Val | Cys | Ile | Met | Gln | Lys | Trp | Gly | Gly | Lys | Arg | Glu | |
| | | | 180 | | | | | 185 | | | | | 190 | | | |
| gtc | atg | tac | aca | gcc | ttc | aga | gca | ctg | gga | cga | agc | gtg | gat | tat | gta | 624 |
| Val | Met | Tyr | Thr | Ala | Phe | Arg | Ala | Leu | Gly | Arg | Ser | Val | Asp | Tyr | Val | |
| | | 195 | | | | | 200 | | | | | 205 | | | | |
| cag | gtt | tgt | gat | tca | gat | acc | atg | ctt | gat | cct | gct | tca | tct | gtg | gag | 672 |
| Gln | Val | Cys | Asp | Ser | Asp | Thr | Met | Leu | Asp | Pro | Ala | Ser | Ser | Val | Glu | |
| | 210 | | | | | 215 | | | | | 220 | | | | | |
| atg | gtg | aaa | gtt | tta | gaa | gaa | gat | ccc | atg | gtg | gga | ggt | gtg | ggg | gga | 720 |
| Met | Val | Lys | Val | Leu | Glu | Glu | Asp | Pro | Met | Val | Gly | Gly | Val | Gly | Gly | |
| 225 | | | | | 230 | | | | | 235 | | | | | 240 | |

```
gat gtc cag att tta aac aag tac gac tcc tgg atc tcc ttc ctc agc        768
Asp Val Gln Ile Leu Asn Lys Tyr Asp Ser Trp Ile Ser Phe Leu Ser
            245                 250                 255 agt gtg aga tac tgg atg gct ttt aat ata gaa agg gcc tgc cag tct        816
Ser Val Arg Tyr Trp Met Ala Phe Asn Ile Glu Arg Ala Cys Gln Ser
                260                 265                 270 tat ttt ggg tgt gtc cag tgc att agt gga cct ctt gga atg tac agg        864
Tyr Phe Gly Cys Val Gln Cys Ile Ser Gly Pro Leu Gly Met Tyr Arg
        275                 280                 285 aac tcc ttg ctg cat gag ttt gtg gaa gac tgg tac aat cag gaa ttt        912
Asn Ser Leu Leu His Glu Phe Val Glu Asp Trp Tyr Asn Gln Glu Phe
    290                 295                 300 atg ggc aac cag tgt agt ttt ggt gat gat agg cat ctg aca aac cga        960
Met Gly Asn Gln Cys Ser Phe Gly Asp Asp Arg His Leu Thr Asn Arg
305                 310                 315                 320 gtg ctg agt ctg ggc tac gca aca aaa tac aca gct cga tcc aag tgc       1008
Val Leu Ser Leu Gly Tyr Ala Thr Lys Tyr Thr Ala Arg Ser Lys Cys
                325                 330                 335 ctt act gaa acc cct ata gaa tat ctc cgg tgg tta aac cag cag acc       1056
Leu Thr Glu Thr Pro Ile Glu Tyr Leu Arg Trp Leu Asn Gln Gln Thr
        340                 345                 350 cgt tgg agc aag tcc tac ttc cga gag tgg ctg tac aat gca atg tgg       1104
Arg Trp Ser Lys Ser Tyr Phe Arg Glu Trp Leu Tyr Asn Ala Met Trp
    355                 360                 365 ttt cat aaa cat cac ttg tgg atg acc tat gaa gcg gtt atc act gga       1152
Phe His Lys His His Leu Trp Met Thr Tyr Glu Ala Val Ile Thr Gly
370                 375                 380 ttc ttc ccc ttc ttt ctc att gcc aca gta atc cag ctc ttc tac cgg       1200
Phe Phe Pro Phe Phe Leu Ile Ala Thr Val Ile Gln Leu Phe Tyr Arg
385                 390                 395                 400 ggt aaa atc tgg aac atc ctc ctc ttc ttg tta act gtc cag cta gta       1248
Gly Lys Ile Trp Asn Ile Leu Leu Phe Leu Leu Thr Val Gln Leu Val
                405                 410                 415 ggt ctc ata aaa tca tct ttt gcc agt tgc ctt aga gga aat atc gtc       1296
Gly Leu Ile Lys Ser Ser Phe Ala Ser Cys Leu Arg Gly Asn Ile Val
        420                 425                 430 atg gtc ttt atg tct ctc tac tca gtg ctg tac atg tca agt tta ctt       1344
Met Val Phe Met Ser Leu Tyr Ser Val Leu Tyr Met Ser Ser Leu Leu
    435                 440                 445 ccg gcc aag atg ttt gca att gca aca ata aac aaa gct ggg tgg ggc       1392
Pro Ala Lys Met Phe Ala Ile Ala Thr Ile Asn Lys Ala Gly Trp Gly
450                 455                 460 act tct gga agg aaa acc att gtt gtt aat ttc ata gga ctc att cca       1440
Thr Ser Gly Arg Lys Thr Ile Val Val Asn Phe Ile Gly Leu Ile Pro
465                 470                 475                 480 gta tca gtt tgg ttt aca att ctg ctg ggt ggt gtc att ttc acc att       1488
Val Ser Val Trp Phe Thr Ile Leu Leu Gly Gly Val Ile Phe Thr Ile
                485                 490                 495 tat aag gaa tct aaa aag cca ttt tca gaa tcc aaa cag aca gtt cta       1536
Tyr Lys Glu Ser Lys Lys Pro Phe Ser Glu Ser Lys Gln Thr Val Leu
        500                 505                 510 att gtt gga acg ttg ctc tat gca tgc tac tgg gtc atg ctt ttg acg       1584
Ile Val Gly Thr Leu Leu Tyr Ala Cys Tyr Trp Val Met Leu Leu Thr
    515                 520                 525 ctg tat gtg gtc ctc atc aat aag tgt ggc cgg cgg aag aag gga caa       1632
Leu Tyr Val Val Leu Ile Asn Lys Cys Gly Arg Arg Lys Lys Gly Gln
530                 535                 540 cag tat gac atg gtg ctt gat gta tga                                   1659
Gln Tyr Asp Met Val Leu Asp Val
545                 550
```

<210> SEQ ID NO 28
<211> LENGTH: 552
<212> TYPE: PRT
<213> ORGANISM: Oryctolagus cuniculus

<400> SEQUENCE: 28

```
Met His Cys Glu Arg Phe Ile Cys Ile Leu Arg Ile Ile Gly Thr Thr
1               5                   10                  15
Leu Phe Gly Val Ser Leu Leu Leu Gly Ile Thr Ala Ala Tyr Ile Val
                20                  25                  30
Gly Tyr Gln Phe Ile Gln Thr Asp Asn Tyr Tyr Phe Ser Phe Gly Leu
            35                  40                  45
Tyr Gly Ala Phe Leu Ala Ser His Leu Ile Ile Gln Ser Leu Phe Ala
 50                  55                  60
Phe Leu Glu His Arg Lys Met Lys Lys Ser Leu Glu Thr Pro Ile Lys
65                  70                  75                  80
Leu Asn Lys Thr Val Ala Leu Cys Ile Ala Ala Tyr Gln Glu Asp Pro
                85                  90                  95
Asp Tyr Leu Arg Lys Cys Leu Gln Ser Val Lys Arg Leu Thr Tyr Pro
            100                 105                 110
Gly Ile Lys Val Val Met Val Ile Asp Gly Asn Ser Glu Asp Asp Val
        115                 120                 125
Tyr Met Met Asp Ile Phe Ser Glu Val Met Gly Arg Glu Thr Ser Ala
130                 135                 140
Thr Tyr Ile Trp Lys Asn Asn Phe His Glu Lys Gly Pro Gly Glu Thr
145                 150                 155                 160
Asp Glu Ser His Lys Glu Ser Ser Gln His Val Thr Gln Leu Val Leu
                165                 170                 175
Ser Asn Lys Ser Val Cys Ile Met Gln Lys Trp Gly Gly Lys Arg Glu
            180                 185                 190
Val Met Tyr Thr Ala Phe Arg Ala Leu Gly Arg Ser Val Asp Tyr Val
        195                 200                 205
Gln Val Cys Asp Ser Asp Thr Met Leu Asp Pro Ala Ser Ser Val Glu
210                 215                 220
Met Val Lys Val Leu Glu Glu Asp Pro Met Val Gly Gly Val Gly Gly
225                 230                 235                 240
Asp Val Gln Ile Leu Asn Lys Tyr Asp Ser Trp Ile Ser Phe Leu Ser
                245                 250                 255
Ser Val Arg Tyr Trp Met Ala Phe Asn Ile Glu Arg Ala Cys Gln Ser
            260                 265                 270
Tyr Phe Gly Cys Val Gln Cys Ile Ser Gly Pro Leu Gly Met Tyr Arg
        275                 280                 285
Asn Ser Leu Leu His Glu Phe Val Glu Asp Trp Tyr Asn Gln Glu Phe
290                 295                 300
Met Gly Asn Gln Cys Ser Phe Gly Asp Asp Arg His Leu Thr Asn Arg
305                 310                 315                 320
Val Leu Ser Leu Gly Tyr Ala Thr Lys Tyr Thr Ala Arg Ser Lys Cys
                325                 330                 335
Leu Thr Glu Thr Pro Ile Glu Tyr Leu Arg Trp Leu Asn Gln Gln Thr
            340                 345                 350
Arg Trp Ser Lys Ser Tyr Phe Arg Glu Trp Leu Tyr Asn Ala Met Trp
        355                 360                 365
Phe His Lys His His Leu Trp Met Thr Tyr Glu Ala Val Ile Thr Gly
```

```
                    370                 375                 380
Phe Phe Pro Phe Phe Leu Ile Ala Thr Val Ile Gln Leu Phe Tyr Arg
385                 390                 395                 400

Gly Lys Ile Trp Asn Ile Leu Leu Phe Leu Leu Thr Val Gln Leu Val
                    405                 410                 415

Gly Leu Ile Lys Ser Ser Phe Ala Ser Cys Leu Arg Gly Asn Ile Val
                420                 425                 430

Met Val Phe Met Ser Leu Tyr Ser Val Leu Tyr Met Ser Ser Leu Leu
                435                 440                 445

Pro Ala Lys Met Phe Ala Ile Ala Thr Ile Asn Lys Ala Gly Trp Gly
        450                 455                 460

Thr Ser Gly Arg Lys Thr Ile Val Val Asn Phe Ile Gly Leu Ile Pro
465                 470                 475                 480

Val Ser Val Trp Phe Thr Ile Leu Leu Gly Gly Val Ile Phe Thr Ile
                485                 490                 495

Tyr Lys Glu Ser Lys Lys Pro Phe Ser Glu Ser Lys Gln Thr Val Leu
                500                 505                 510

Ile Val Gly Thr Leu Leu Tyr Ala Cys Tyr Trp Val Met Leu Leu Thr
            515                 520                 525

Leu Tyr Val Val Leu Ile Asn Lys Cys Gly Arg Arg Lys Lys Gly Gln
        530                 535                 540

Gln Tyr Asp Met Val Leu Asp Val
545                 550

<210> SEQ ID NO 29
<211> LENGTH: 1659
<212> TYPE: DNA
<213> ORGANISM: Oryctolagus cuniculus
<220> FEATURE:
<221> NAME/KEY: CDS
<222> LOCATION: (1)..(1659)
<223> OTHER INFORMATION: Hyaluronan synthase 3
<300> PUBLICATION INFORMATION:
<308> DATABASE ACCESSION NUMBER: AB055979.1
<309> DATABASE ENTRY DATE: 2001-08-21
<313> RELEVANT RESIDUES IN SEQ ID NO: (1)..(1659)

<400> SEQUENCE: 29 atg cca gtg caa ctg aca aca gcc ttg cgt gtg gtg ggc acc agc ctg      48
Met Pro Val Gln Leu Thr Thr Ala Leu Arg Val Val Gly Thr Ser Leu
1               5                   10                  15 ttt gcc ttg gcg gtg ctg ggt ggc atc ctg gca gcc tat gtg aca ggc      96
Phe Ala Leu Ala Val Leu Gly Gly Ile Leu Ala Ala Tyr Val Thr Gly
            20                  25                  30 tac cag ttc atc cac aca gag aag cac tac ctg tcc ttc ggc ctg tac     144
Tyr Gln Phe Ile His Thr Glu Lys His Tyr Leu Ser Phe Gly Leu Tyr
        35                  40                  45 ggc gct atc ctg ggc ctg cac ctg ctc atc cag agc ctg ttt gcc ttc     192
Gly Ala Ile Leu Gly Leu His Leu Leu Ile Gln Ser Leu Phe Ala Phe
    50                  55                  60 ctg gag cac cgg cgc atg cgg cgg gcc agg cgg ccg ctg aag ctg ccc     240
Leu Glu His Arg Arg Met Arg Arg Ala Arg Arg Pro Leu Lys Leu Pro
65                  70                  75                  80 tca cgg cgg cgc tct gtg gcg ctc tgc atc gcc gcc tac cag gag gac     288
Ser Arg Arg Arg Ser Val Ala Leu Cys Ile Ala Ala Tyr Gln Glu Asp
                85                  90                  95 ccc gac tac ttg cgc aag tgc ctg cgc tca gcc cag cgc atc gcc ttc     336
Pro Asp Tyr Leu Arg Lys Cys Leu Arg Ser Ala Gln Arg Ile Ala Phe
            100                 105                 110
```

-continued

| | |
|---|---|
| cct gac ctc aag gtg gtt atg gtg gtc gat ggc aac cgc cag gaa gac<br>Pro Asp Leu Lys Val Val Met Val Val Asp Gly Asn Arg Gln Glu Asp<br>115                    120                    125 | 384 |
| gcc tac atg ctg gac atc ttc cat gag gtg ctg ggt ggc act gag cag<br>Ala Tyr Met Leu Asp Ile Phe His Glu Val Leu Gly Gly Thr Glu Gln<br>130                    135                    140 | 432 |
| gcc ggc ttc ttt gtg tgg cgc agc aac ttc cac gag gca ggc gag ggc<br>Ala Gly Phe Phe Val Trp Arg Ser Asn Phe His Glu Ala Gly Glu Gly<br>145                    150                    155                    160 | 480 |
| gag acc gag gcc agc ctg cag gaa ggc atg gag cgc gtg cgg gct gtg<br>Glu Thr Glu Ala Ser Leu Gln Glu Gly Met Glu Arg Val Arg Ala Val<br>                    165                    170                    175 | 528 |
| gtg cgg acc agc acc ttc tcg tgc atc atg cag aag tgg gga ggc aag<br>Val Arg Thr Ser Thr Phe Ser Cys Ile Met Gln Lys Trp Gly Gly Lys<br>180                    185                    190 | 576 |
| cgt gag gtc atg tac aca gcc ttc aag gcc ctc ggc gat tca gtg gac<br>Arg Glu Val Met Tyr Thr Ala Phe Lys Ala Leu Gly Asp Ser Val Asp<br>                    195                    200                    205 | 624 |
| tac atc cag gta tgt gac tcg gac acg gtg ctg gac cca gcc tgt acc<br>Tyr Ile Gln Val Cys Asp Ser Asp Thr Val Leu Asp Pro Ala Cys Thr<br>210                    215                    220 | 672 |
| atc gag atg ctt cgc gtc ctg gaa gag gat ccc caa gta ggg gga gtc<br>Ile Glu Met Leu Arg Val Leu Glu Glu Asp Pro Gln Val Gly Gly Val<br>225                    230                    235                    240 | 720 |
| ggg gga gat gtc caa atc ctc aac aag tat gac tca tgg atc tcg ttc<br>Gly Gly Asp Val Gln Ile Leu Asn Lys Tyr Asp Ser Trp Ile Ser Phe<br>                    245                    250                    255 | 768 |
| ctg agc agt gtg cgg tac tgg atg gcc ttc aac gtg gag cgg gcg tgc<br>Leu Ser Ser Val Arg Tyr Trp Met Ala Phe Asn Val Glu Arg Ala Cys<br>260                    265                    270 | 816 |
| cag tcc tac ttt ggc tgt gtg cag tgt atc agt ggg ccc ttg ggc atg<br>Gln Ser Tyr Phe Gly Cys Val Gln Cys Ile Ser Gly Pro Leu Gly Met<br>                    275                    280                    285 | 864 |
| tac cgc aac agt ctc ctc cag caa ttc ctg gag gac tgg tac cat cag<br>Tyr Arg Asn Ser Leu Leu Gln Gln Phe Leu Glu Asp Trp Tyr His Gln<br>290                    295                    300 | 912 |
| aag ttc cta ggc agc aag tgc agc ttt ggg gat gac agg cac ctc acc<br>Lys Phe Leu Gly Ser Lys Cys Ser Phe Gly Asp Asp Arg His Leu Thr<br>305                    310                    315                    320 | 960 |
| aac cga gtc ctg agt ctt ggc tac cga act aag tat aca gca cgc tcc<br>Asn Arg Val Leu Ser Leu Gly Tyr Arg Thr Lys Tyr Thr Ala Arg Ser<br>                    325                    330                    335 | 1008 |
| aag tgc ctc act gag acc cct acc aag tac cta cgg tgg ctc aac caa<br>Lys Cys Leu Thr Glu Thr Pro Thr Lys Tyr Leu Arg Trp Leu Asn Gln<br>340                    345                    350 | 1056 |
| cag acg cgc tgg agc aag tct tac ttc cgg gag tgg ctc tac aac tct<br>Gln Thr Arg Trp Ser Lys Ser Tyr Phe Arg Glu Trp Leu Tyr Asn Ser<br>                    355                    360                    365 | 1104 |
| ctg tgg ttc cat aag cac cat ctc tgg atg acc tac gag tcg gtg gtc<br>Leu Trp Phe His Lys His His Leu Trp Met Thr Tyr Glu Ser Val Val<br>370                    375                    380 | 1152 |
| aca ggt ttc ttc ccc ttc ttc ctc atc gcc aca gtg ata cag ctt ttc<br>Thr Gly Phe Phe Pro Phe Phe Leu Ile Ala Thr Val Ile Gln Leu Phe<br>385                    390                    395                    400 | 1200 |
| tac cgt ggc cgc atc tgg aac atc ctc ctc ttc ctg ctg acc gtg cag<br>Tyr Arg Gly Arg Ile Trp Asn Ile Leu Leu Phe Leu Leu Thr Val Gln<br>                    405                    410                    415 | 1248 |
| ctg gtg ggc atc atc aaa gct acc tat gcc tgc ttc ctt cgg ggc aat<br>Leu Val Gly Ile Ile Lys Ala Thr Tyr Ala Cys Phe Leu Arg Gly Asn<br>420                    425                    430 | 1296 |

```
gca gag atg atc ttc atg tcc ctc tac tcc ctt ctc tac atg tct agc      1344
Ala Glu Met Ile Phe Met Ser Leu Tyr Ser Leu Leu Tyr Met Ser Ser
        435                 440                 445 ctc ctg ccc gcc aag atc ttt gcc att gct acc atc aac aag tct ggc      1392
Leu Leu Pro Ala Lys Ile Phe Ala Ile Ala Thr Ile Asn Lys Ser Gly
450                 455                 460 tgg ggc act tct ggc cga aaa aca att gtg gtg aac ttc att ggc ctc      1440
Trp Gly Thr Ser Gly Arg Lys Thr Ile Val Val Asn Phe Ile Gly Leu
465                 470                 475                 480 atc cct gtg tcc atc tgg gtg gca gtt ctt ttg ggg ggt ctg gcc tac      1488
Ile Pro Val Ser Ile Trp Val Ala Val Leu Leu Gly Gly Leu Ala Tyr
                485                 490                 495 acg gct tat tgc cag gac ctg ttc agt gag aca gag tta gcc ttc ctt      1536
Thr Ala Tyr Cys Gln Asp Leu Phe Ser Glu Thr Glu Leu Ala Phe Leu
            500                 505                 510 gtt tca ggg gcc att ctg tat ggc tgc tac tgg gtg gcc ctc ctc atg      1584
Val Ser Gly Ala Ile Leu Tyr Gly Cys Tyr Trp Val Ala Leu Leu Met
        515                 520                 525 ctg tat ctg gcc atc ata gcc cgg aga tgt ggg aag aag cca gaa caa      1632
Leu Tyr Leu Ala Ile Ile Ala Arg Arg Cys Gly Lys Lys Pro Glu Gln
530                 535                 540 tat agc ttg gcc ttt gct gag gtg tga                                  1659
Tyr Ser Leu Ala Phe Ala Glu Val
545                 550

<210> SEQ ID NO 30
<211> LENGTH: 552
<212> TYPE: PRT
<213> ORGANISM: Oryctolagus cuniculus

<400> SEQUENCE: 30

Met Pro Val Gln Leu Thr Thr Ala Leu Arg Val Val Gly Thr Ser Leu
1               5                   10                  15

Phe Ala Leu Ala Val Leu Gly Gly Ile Leu Ala Ala Tyr Val Thr Gly
                20                  25                  30

Tyr Gln Phe Ile His Thr Glu Lys His Tyr Leu Ser Phe Gly Leu Tyr
            35                  40                  45

Gly Ala Ile Leu Gly Leu His Leu Leu Ile Gln Ser Leu Phe Ala Phe
        50                  55                  60

Leu Glu His Arg Arg Met Arg Arg Ala Arg Pro Leu Lys Leu Pro
65                  70                  75                  80

Ser Arg Arg Arg Ser Val Ala Leu Cys Ile Ala Ala Tyr Gln Glu Asp
                85                  90                  95

Pro Asp Tyr Leu Arg Lys Cys Leu Arg Ser Ala Gln Arg Ile Ala Phe
            100                 105                 110

Pro Asp Leu Lys Val Val Met Val Val Asp Gly Asn Arg Gln Glu Asp
        115                 120                 125

Ala Tyr Met Leu Asp Ile Phe His Glu Val Leu Gly Thr Glu Gln
    130                 135                 140

Ala Gly Phe Phe Val Trp Arg Ser Asn Phe His Glu Ala Gly Glu Gly
145                 150                 155                 160

Glu Thr Glu Ala Ser Leu Gln Glu Gly Met Arg Val Arg Ala Val
                165                 170                 175

Val Arg Thr Ser Thr Phe Ser Cys Ile Met Gln Lys Trp Gly Gly Lys
            180                 185                 190

Arg Glu Val Met Tyr Thr Ala Phe Lys Ala Leu Gly Asp Ser Val Asp
        195                 200                 205
```

```
Tyr Ile Gln Val Cys Asp Ser Asp Thr Val Leu Asp Pro Ala Cys Thr
    210                 215                 220
Ile Glu Met Leu Arg Val Leu Glu Glu Asp Pro Gln Val Gly Gly Val
225                 230                 235                 240
Gly Gly Asp Val Gln Ile Leu Asn Lys Tyr Asp Ser Trp Ile Ser Phe
                245                 250                 255
Leu Ser Ser Val Arg Tyr Trp Met Ala Phe Asn Val Glu Arg Ala Cys
            260                 265                 270
Gln Ser Tyr Phe Gly Cys Val Gln Cys Ile Ser Gly Pro Leu Gly Met
        275                 280                 285
Tyr Arg Asn Ser Leu Leu Gln Gln Phe Leu Glu Asp Trp Tyr His Gln
    290                 295                 300
Lys Phe Leu Gly Ser Lys Cys Ser Phe Gly Asp Asp Arg His Leu Thr
305                 310                 315                 320
Asn Arg Val Leu Ser Leu Gly Tyr Arg Thr Lys Tyr Thr Ala Arg Ser
                325                 330                 335
Lys Cys Leu Thr Glu Thr Pro Thr Lys Tyr Leu Arg Trp Leu Asn Gln
            340                 345                 350
Gln Thr Arg Trp Ser Lys Ser Tyr Phe Arg Glu Trp Leu Tyr Asn Ser
        355                 360                 365
Leu Trp Phe His Lys His His Leu Trp Met Thr Tyr Glu Ser Val Val
    370                 375                 380
Thr Gly Phe Phe Pro Phe Phe Leu Ile Ala Thr Val Ile Gln Leu Phe
385                 390                 395                 400
Tyr Arg Gly Arg Ile Trp Asn Ile Leu Leu Phe Leu Leu Thr Val Gln
                405                 410                 415
Leu Val Gly Ile Ile Lys Ala Thr Tyr Ala Cys Phe Leu Arg Gly Asn
            420                 425                 430
Ala Glu Met Ile Phe Met Ser Leu Tyr Ser Leu Leu Tyr Met Ser Ser
        435                 440                 445
Leu Leu Pro Ala Lys Ile Phe Ala Ile Ala Thr Ile Asn Lys Ser Gly
    450                 455                 460
Trp Gly Thr Ser Gly Arg Lys Thr Ile Val Val Asn Phe Ile Gly Leu
465                 470                 475                 480
Ile Pro Val Ser Ile Trp Val Ala Val Leu Leu Gly Gly Leu Ala Tyr
                485                 490                 495
Thr Ala Tyr Cys Gln Asp Leu Phe Ser Glu Thr Glu Leu Ala Phe Leu
            500                 505                 510
Val Ser Gly Ala Ile Leu Tyr Gly Cys Tyr Trp Val Ala Leu Leu Met
        515                 520                 525
Leu Tyr Leu Ala Ile Ile Ala Arg Arg Cys Gly Lys Lys Pro Glu Gln
    530                 535                 540
Tyr Ser Leu Ala Phe Ala Glu Val
545                 550

<210> SEQ ID NO 31
<211> LENGTH: 1659
<212> TYPE: DNA
<213> ORGANISM: Equus caballus
<220> FEATURE:
<221> NAME/KEY: CDS
<222> LOCATION: (1)..(1659)
<223> OTHER INFORMATION: Hyaluronan synthase 2
<300> PUBLICATION INFORMATION:
<308> DATABASE ACCESSION NUMBER: AY056582.1
<309> DATABASE ENTRY DATE: 2002-11-05
```

-continued

<313> RELEVANT RESIDUES IN SEQ ID NO: (437)..(2095)

<400> SEQUENCE: 31

| | | | | | | | | | | | | | | | | |
|---|---|---|---|---|---|---|---|---|---|---|---|---|---|---|---|---|
| atg | cat | tgt | gag | agg | ttt | ata | tgt | atc | ctg | aga | ata | att | gga | acc | aca | 48 |
| Met | His | Cys | Glu | Arg | Phe | Ile | Cys | Ile | Leu | Arg | Ile | Ile | Gly | Thr | Thr | |
| 1 | | | | 5 | | | | | 10 | | | | | 15 | | |
| ctt | ttt | gga | gtc | tct | ctc | cta | ctt | gga | atc | aca | gct | gct | tat | att | gtt | 96 |
| Leu | Phe | Gly | Val | Ser | Leu | Leu | Leu | Gly | Ile | Thr | Ala | Ala | Tyr | Ile | Val | |
| | | | 20 | | | | | 25 | | | | | 30 | | | |
| ggc | tac | caa | ttt | atc | caa | aca | gat | aat | tac | tat | ttc | tct | ttt | gga | cta | 144 |
| Gly | Tyr | Gln | Phe | Ile | Gln | Thr | Asp | Asn | Tyr | Tyr | Phe | Ser | Phe | Gly | Leu | |
| | | 35 | | | | | 40 | | | | | 45 | | | | |
| tat | ggt | gcc | ttt | tta | gca | tca | cac | ctc | atc | atc | caa | agc | ctg | ttt | gcc | 192 |
| Tyr | Gly | Ala | Phe | Leu | Ala | Ser | His | Leu | Ile | Ile | Gln | Ser | Leu | Phe | Ala | |
| | 50 | | | | | 55 | | | | | 60 | | | | | |
| ttt | ttg | gag | cat | cga | aaa | atg | aaa | aaa | tcc | cta | gaa | acc | ccc | att | aag | 240 |
| Phe | Leu | Glu | His | Arg | Lys | Met | Lys | Lys | Ser | Leu | Glu | Thr | Pro | Ile | Lys | |
| 65 | | | | | 70 | | | | | 75 | | | | | 80 | |
| ttg | aac | aaa | act | gtt | gct | ctt | tgc | atc | gct | gcg | tat | caa | gaa | gat | cca | 288 |
| Leu | Asn | Lys | Thr | Val | Ala | Leu | Cys | Ile | Ala | Ala | Tyr | Gln | Glu | Asp | Pro | |
| | | | | 85 | | | | | 90 | | | | | 95 | | |
| gac | tac | tta | cgg | aaa | tgc | ttg | caa | tct | gtg | aaa | agg | cta | acc | tac | cct | 336 |
| Asp | Tyr | Leu | Arg | Lys | Cys | Leu | Gln | Ser | Val | Lys | Arg | Leu | Thr | Tyr | Pro | |
| | | | 100 | | | | | 105 | | | | | 110 | | | |
| ggg | att | aaa | gtt | gtc | atg | gtc | ata | gat | ggg | aac | tca | gaa | gat | gat | ctt | 384 |
| Gly | Ile | Lys | Val | Val | Met | Val | Ile | Asp | Gly | Asn | Ser | Glu | Asp | Asp | Leu | |
| | | 115 | | | | | 120 | | | | | 125 | | | | |
| tac | atg | atg | gac | atc | ttc | agt | gaa | gtc | atg | ggc | agg | gac | aaa | tca | gcc | 432 |
| Tyr | Met | Met | Asp | Ile | Phe | Ser | Glu | Val | Met | Gly | Arg | Asp | Lys | Ser | Ala | |
| | 130 | | | | | 135 | | | | | 140 | | | | | |
| act | tac | atc | tgg | aag | aac | aac | ttc | cac | gag | aag | ggt | cct | ggt | gag | acg | 480 |
| Thr | Tyr | Ile | Trp | Lys | Asn | Asn | Phe | His | Glu | Lys | Gly | Pro | Gly | Glu | Thr | |
| 145 | | | | | 150 | | | | | 155 | | | | | 160 | |
| gat | gag | tca | cat | aaa | gaa | agc | tct | caa | cat | gtt | acc | caa | ttg | gtc | ttg | 528 |
| Asp | Glu | Ser | His | Lys | Glu | Ser | Ser | Gln | His | Val | Thr | Gln | Leu | Val | Leu | |
| | | | | 165 | | | | | 170 | | | | | 175 | | |
| tcc | aac | aaa | agt | att | tgc | atc | atg | caa | aaa | tgg | ggt | gga | aaa | aga | gaa | 576 |
| Ser | Asn | Lys | Ser | Ile | Cys | Ile | Met | Gln | Lys | Trp | Gly | Gly | Lys | Arg | Glu | |
| | | | 180 | | | | | 185 | | | | | 190 | | | |
| gtc | atg | tac | acg | gcc | ttc | aga | gca | ctg | gga | cga | agt | gtg | gat | tat | gtg | 624 |
| Val | Met | Tyr | Thr | Ala | Phe | Arg | Ala | Leu | Gly | Arg | Ser | Val | Asp | Tyr | Val | |
| | | 195 | | | | | 200 | | | | | 205 | | | | |
| cag | gtt | tgt | gat | tca | gat | acc | atg | ctt | gac | cct | gcc | tcg | tct | gtg | gag | 672 |
| Gln | Val | Cys | Asp | Ser | Asp | Thr | Met | Leu | Asp | Pro | Ala | Ser | Ser | Val | Glu | |
| | 210 | | | | | 215 | | | | | 220 | | | | | |
| atg | gta | aaa | gtt | tta | gaa | gaa | gac | ccc | atg | gtt | gga | ggt | gtc | gga | gga | 720 |
| Met | Val | Lys | Val | Leu | Glu | Glu | Asp | Pro | Met | Val | Gly | Gly | Val | Gly | Gly | |
| 225 | | | | | 230 | | | | | 235 | | | | | 240 | |
| gat | gtc | cag | att | tta | aac | aag | tac | gat | tcc | tgg | atc | tcc | ttc | ctc | agc | 768 |
| Asp | Val | Gln | Ile | Leu | Asn | Lys | Tyr | Asp | Ser | Trp | Ile | Ser | Phe | Leu | Ser | |
| | | | | 245 | | | | | 250 | | | | | 255 | | |
| agt | gtg | aga | tac | tgg | atg | gct | ttt | aac | ata | gaa | aga | gcc | tgt | cag | tct | 816 |
| Ser | Val | Arg | Tyr | Trp | Met | Ala | Phe | Asn | Ile | Glu | Arg | Ala | Cys | Gln | Ser | |
| | | | 260 | | | | | 265 | | | | | 270 | | | |
| tat | ttt | ggg | tgc | gtc | cag | tgc | att | agt | gga | ccc | ctg | gga | atg | tac | aga | 864 |
| Tyr | Phe | Gly | Cys | Val | Gln | Cys | Ile | Ser | Gly | Pro | Leu | Gly | Met | Tyr | Arg | |
| | | 275 | | | | | 280 | | | | | 285 | | | | |
| aac | tcc | ttg | ctg | cat | gaa | ttc | gta | gaa | gac | tgg | tac | aat | cag | gaa | ttt | 912 |
| Asn | Ser | Leu | Leu | His | Glu | Phe | Val | Glu | Asp | Trp | Tyr | Asn | Gln | Glu | Phe | |
| | 290 | | | | | 295 | | | | | 300 | | | | | |

| | | |
|---|---|---|
| atg ggc agc caa tgt agt ttt ggc gat gac cgg cat cta acg aac cga<br>Met Gly Ser Gln Cys Ser Phe Gly Asp Asp Arg His Leu Thr Asn Arg<br>305                    310                   315               320 | 960 |
| gtg ctg agt ctg ggt tat gca aca aaa tac aca gct cga tcc aag tgc<br>Val Leu Ser Leu Gly Tyr Ala Thr Lys Tyr Thr Ala Arg Ser Lys Cys<br>               325                   330               335 | 1008 |
| ctt act gaa aca cct ata gaa tat ctc aga tgg tta aac cag cag acc<br>Leu Thr Glu Thr Pro Ile Glu Tyr Leu Arg Trp Leu Asn Gln Gln Thr<br>           340                 345               350 | 1056 |
| cgt tgg agc aag tcc tac ttc cga gag tgg ctg tac aat gcg atg tgg<br>Arg Trp Ser Lys Ser Tyr Phe Arg Glu Trp Leu Tyr Asn Ala Met Trp<br>      355                 360               365 | 1104 |
| ttt cat aaa cat cac ttg tgg atg acc tac gaa gcg gtt atc act gga<br>Phe His Lys His His Leu Trp Met Thr Tyr Glu Ala Val Ile Thr Gly<br>370                    375                   380 | 1152 |
| ttc ttc cct ttc ttt ctc att gcc aca gta atc cag ctc ttc tac cgg<br>Phe Phe Pro Phe Phe Leu Ile Ala Thr Val Ile Gln Leu Phe Tyr Arg<br>385                    390                   395               400 | 1200 |
| ggt aaa att tgg aat atc ctc ctc ttc ttg tta aca gtc cag tta gta<br>Gly Lys Ile Trp Asn Ile Leu Leu Phe Leu Leu Thr Val Gln Leu Val<br>                    405               410               415 | 1248 |
| ggt ctc ata aag tct tcc ttt gcc agc tgc ctt aga gga aac atc gtc<br>Gly Leu Ile Lys Ser Ser Phe Ala Ser Cys Leu Arg Gly Asn Ile Val<br>           420                 425               430 | 1296 |
| atg gtc ttc atg tcc ctc tac tca gtg tta tac atg tca agt tta ctg<br>Met Val Phe Met Ser Leu Tyr Ser Val Leu Tyr Met Ser Ser Leu Leu<br>      435                 440               445 | 1344 |
| ccc gcc aaa atg ttt gct att gcc acg ata aac aaa gct ggg tgg ggc<br>Pro Ala Lys Met Phe Ala Ile Ala Thr Ile Asn Lys Ala Gly Trp Gly<br>450                    455                   460 | 1392 |
| aca tct gga agg aaa acc att gtt gtt aat ttc ata gga ctc att cca<br>Thr Ser Gly Arg Lys Thr Ile Val Val Asn Phe Ile Gly Leu Ile Pro<br>465                    470                   475               480 | 1440 |
| gta tca gtg tgg ttt aca atc ctc ctg ggt gga gtc att ttc acc att<br>Val Ser Val Trp Phe Thr Ile Leu Leu Gly Gly Val Ile Phe Thr Ile<br>                    485               490               495 | 1488 |
| tat atg gaa tct aaa aag cca ttc tca gaa tcc aaa cag aca gtt cta<br>Tyr Met Glu Ser Lys Lys Pro Phe Ser Glu Ser Lys Gln Thr Val Leu<br>           500                 505               510 | 1536 |
| atc gtt gga acg ttg ctc tat gca tgc tat tgg gtc atg ctt ttg acg<br>Ile Val Gly Thr Leu Leu Tyr Ala Cys Tyr Trp Val Met Leu Leu Thr<br>      515                 520               525 | 1584 |
| ctg tac gtg gtt ctc atc aac aaa tgt ggc agg cgg aag aag gga caa<br>Leu Tyr Val Val Leu Ile Asn Lys Cys Gly Arg Arg Lys Lys Gly Gln<br>530                    535                   540 | 1632 |
| cag tat gac atg gtg ctt gat gta tga<br>Gln Tyr Asp Met Val Leu Asp Val<br>545                    550 | 1659 |

<210> SEQ ID NO 32
<211> LENGTH: 552
<212> TYPE: PRT
<213> ORGANISM: Equus caballus

<400> SEQUENCE: 32

Met His Cys Glu Arg Phe Ile Cys Ile Leu Arg Ile Ile Gly Thr Thr
1               5                   10                 15

Leu Phe Gly Val Ser Leu Leu Leu Gly Ile Thr Ala Ala Tyr Ile Val
                 20                   25                 30

-continued

```
Gly Tyr Gln Phe Ile Gln Thr Asp Asn Tyr Tyr Phe Ser Phe Gly Leu
         35                  40                  45

Tyr Gly Ala Phe Leu Ala Ser His Leu Ile Ile Gln Ser Leu Phe Ala
 50                  55                  60

Phe Leu Glu His Arg Lys Met Lys Lys Ser Leu Glu Thr Pro Ile Lys
 65                  70                  75                  80

Leu Asn Lys Thr Val Ala Leu Cys Ile Ala Ala Tyr Gln Glu Asp Pro
                 85                  90                  95

Asp Tyr Leu Arg Lys Cys Leu Gln Ser Val Lys Arg Leu Thr Tyr Pro
                100                 105                 110

Gly Ile Lys Val Val Met Val Ile Asp Gly Asn Ser Glu Asp Asp Leu
            115                 120                 125

Tyr Met Met Asp Ile Phe Ser Glu Val Met Gly Arg Asp Lys Ser Ala
130                 135                 140

Thr Tyr Ile Trp Lys Asn Asn Phe His Glu Lys Gly Pro Gly Glu Thr
145                 150                 155                 160

Asp Glu Ser His Lys Glu Ser Ser Gln His Val Thr Gln Leu Val Leu
                165                 170                 175

Ser Asn Lys Ser Ile Cys Ile Met Gln Lys Trp Gly Gly Lys Arg Glu
            180                 185                 190

Val Met Tyr Thr Ala Phe Arg Ala Leu Gly Arg Ser Val Asp Tyr Val
        195                 200                 205

Gln Val Cys Asp Ser Asp Thr Met Leu Asp Pro Ala Ser Ser Val Glu
    210                 215                 220

Met Val Lys Val Leu Glu Glu Asp Pro Met Val Gly Gly Val Gly Gly
225                 230                 235                 240

Asp Val Gln Ile Leu Asn Lys Tyr Asp Ser Trp Ile Ser Phe Leu Ser
                245                 250                 255

Ser Val Arg Tyr Trp Met Ala Phe Asn Ile Glu Arg Ala Cys Gln Ser
            260                 265                 270

Tyr Phe Gly Cys Val Gln Cys Ile Ser Gly Pro Leu Gly Met Tyr Arg
        275                 280                 285

Asn Ser Leu Leu His Glu Phe Val Glu Asp Trp Tyr Asn Gln Glu Phe
    290                 295                 300

Met Gly Ser Gln Cys Ser Phe Gly Asp Asp Arg His Leu Thr Asn Arg
305                 310                 315                 320

Val Leu Ser Leu Gly Tyr Ala Thr Lys Tyr Thr Ala Arg Ser Lys Cys
                325                 330                 335

Leu Thr Glu Thr Pro Ile Glu Tyr Leu Arg Trp Leu Asn Gln Gln Thr
            340                 345                 350

Arg Trp Ser Lys Ser Tyr Phe Arg Glu Trp Leu Tyr Asn Ala Met Trp
        355                 360                 365

Phe His Lys His His Leu Trp Met Thr Tyr Glu Ala Val Ile Thr Gly
    370                 375                 380

Phe Phe Pro Phe Leu Ile Ala Thr Val Ile Gln Leu Phe Tyr Arg
385                 390                 395                 400

Gly Lys Ile Trp Asn Ile Leu Leu Phe Leu Leu Thr Val Gln Leu Val
                405                 410                 415

Gly Leu Ile Lys Ser Ser Phe Ala Ser Cys Leu Arg Gly Asn Ile Val
            420                 425                 430

Met Val Phe Met Ser Leu Tyr Ser Val Leu Tyr Met Ser Ser Leu Leu
        435                 440                 445

Pro Ala Lys Met Phe Ala Ile Ala Thr Ile Asn Lys Ala Gly Trp Gly
```

```
                450             455             460
Thr Ser Gly Arg Lys Thr Ile Val Val Asn Phe Ile Gly Leu Ile Pro
465                 470                 475                 480

Val Ser Val Trp Phe Thr Ile Leu Leu Gly Val Ile Phe Thr Ile
                    485                 490                 495

Tyr Met Glu Ser Lys Lys Pro Phe Ser Glu Ser Lys Gln Thr Val Leu
                500                 505                 510

Ile Val Gly Thr Leu Leu Tyr Ala Cys Tyr Trp Val Met Leu Leu Thr
            515                 520                 525

Leu Tyr Val Val Leu Ile Asn Lys Cys Gly Arg Arg Lys Lys Gly Gln
        530                 535                 540

Gln Tyr Asp Met Val Leu Asp Val
545                 550

<210> SEQ ID NO 33
<211> LENGTH: 1659
<212> TYPE: DNA
<213> ORGANISM: Sus scrofa
<220> FEATURE:
<221> NAME/KEY: CDS
<222> LOCATION: (1)..(1659)
<223> OTHER INFORMATION: Hyaluronan synthase 2
<300> PUBLICATION INFORMATION:
<308> DATABASE ACCESSION NUMBER: NM_214053.1
<309> DATABASE ENTRY DATE: 2004-08-23
<313> RELEVANT RESIDUES IN SEQ ID NO: (568)..(2226)

<400> SEQUENCE: 33 atg cat tgt gag agg ttt cta tgt atc ctg aga ata att gga acc aca      48
Met His Cys Glu Arg Phe Leu Cys Ile Leu Arg Ile Ile Gly Thr Thr
1               5                   10                  15 ctt ttt gga gtt tct ctc ctc ctt gga att acc gct gct tat atc gtt      96
Leu Phe Gly Val Ser Leu Leu Leu Gly Ile Thr Ala Ala Tyr Ile Val
                20                  25                  30 ggc tac caa ttt atc caa aca gat aat tac tat ttc ttt ttt ggg cta     144
Gly Tyr Gln Phe Ile Gln Thr Asp Asn Tyr Tyr Phe Phe Phe Gly Leu
            35                  40                  45 tat ggt gcc ttt tta gca tca cac ctt atc atc caa agc ttg ttt gcc     192
Tyr Gly Ala Phe Leu Ala Ser His Leu Ile Ile Gln Ser Leu Phe Ala
        50                  55                  60 ttt ttg gag cac cgg aaa atg aaa aaa tct cta gaa acc ccc att aaa     240
Phe Leu Glu His Arg Lys Met Lys Lys Ser Leu Glu Thr Pro Ile Lys
65                  70                  75                  80 ttg aac aaa act gtc gct ctt tgc atc gcg gcc tat caa gaa gat cca     288
Leu Asn Lys Thr Val Ala Leu Cys Ile Ala Ala Tyr Gln Glu Asp Pro
                85                  90                  95 gac tac ttg cga aag tgt ttg caa tct gtg aaa agg cta acc tac cct     336
Asp Tyr Leu Arg Lys Cys Leu Gln Ser Val Lys Arg Leu Thr Tyr Pro
            100                 105                 110 gga att aaa gtg gtc atg gtc ata gat ggg aac tcg gaa gat gac ctt     384
Gly Ile Lys Val Val Met Val Ile Asp Gly Asn Ser Glu Asp Asp Leu
        115                 120                 125 tac atg atg gac atc ttc agt gaa gtc atg ggc agg gac aat tca gcc     432
Tyr Met Met Asp Ile Phe Ser Glu Val Met Gly Arg Asp Asn Ser Ala
130                 135                 140 act tat atc tgg aag aac aac ttc cac gaa aag ggc cct ggt gag acg     480
Thr Tyr Ile Trp Lys Asn Asn Phe His Glu Lys Gly Pro Gly Glu Thr
145                 150                 155                 160 gat gag tca cat aaa gaa agc tcc caa cat gtc acc caa ctg gtc ttg     528
Asp Glu Ser His Lys Glu Ser Ser Gln His Val Thr Gln Leu Val Leu
                165                 170                 175
```

```
tcc aac aaa agt att tgc atc atg caa aaa tgg ggt gga aaa aga gaa    576
Ser Asn Lys Ser Ile Cys Ile Met Gln Lys Trp Gly Gly Lys Arg Glu
            180                 185                 190 gtc atg tac acg gcc ttc aga gct ctg gga cga agt gtg gat tat gta    624
Val Met Tyr Thr Ala Phe Arg Ala Leu Gly Arg Ser Val Asp Tyr Val
            195                 200                 205 cag gtt tgt gat tca gac acc atg ctt gac cct gcc tca tct gtg gag    672
Gln Val Cys Asp Ser Asp Thr Met Leu Asp Pro Ala Ser Ser Val Glu
            210                 215                 220 atg gtg aaa gtt tta gaa gaa gac ccc atg gtt gga ggt gtc gga gga    720
Met Val Lys Val Leu Glu Glu Asp Pro Met Val Gly Gly Val Gly Gly
225                 230                 235                 240 gat gtc cag att tta aac aag tat gat tcc tgg atc tcc ttc ctc agc    768
Asp Val Gln Ile Leu Asn Lys Tyr Asp Ser Trp Ile Ser Phe Leu Ser
            245                 250                 255 agt gtg aga tac tgg atg gct ttt aac ata gaa agg gcc tgc cag tct    816
Ser Val Arg Tyr Trp Met Ala Phe Asn Ile Glu Arg Ala Cys Gln Ser
            260                 265                 270 tat ttt gga tgt gtc cag tgc att agt gga cct ctg ggg atg tac aga    864
Tyr Phe Gly Cys Val Gln Cys Ile Ser Gly Pro Leu Gly Met Tyr Arg
            275                 280                 285 aac tcc tta ctg cat gaa ttt gtg gaa gac tgg tac aat caa gag ttt    912
Asn Ser Leu Leu His Glu Phe Val Glu Asp Trp Tyr Asn Gln Glu Phe
            290                 295                 300 atg ggc agc caa tgt agt ttt gga gat gac agg cat cta acg aac cga    960
Met Gly Ser Gln Cys Ser Phe Gly Asp Asp Arg His Leu Thr Asn Arg
305                 310                 315                 320 gtg ctg agt ctg ggc tat gca aca aaa tac aca gct cgg tcc aag tgc   1008
Val Leu Ser Leu Gly Tyr Ala Thr Lys Tyr Thr Ala Arg Ser Lys Cys
            325                 330                 335 ctt act gag acg cct ata gaa tat ctc aga tgg tta aac cag cag acc   1056
Leu Thr Glu Thr Pro Ile Glu Tyr Leu Arg Trp Leu Asn Gln Gln Thr
            340                 345                 350 cgt tgg agc aag tcc tac ttc cga gag tgg ctg tac aat gcg atg tgg   1104
Arg Trp Ser Lys Ser Tyr Phe Arg Glu Trp Leu Tyr Asn Ala Met Trp
            355                 360                 365 ttt cat aag cat cat ttg tgg atg acc tat gag gca gtt atc acc ggg   1152
Phe His Lys His His Leu Trp Met Thr Tyr Glu Ala Val Ile Thr Gly
370                 375                 380 ttc ttc cct ttc ttt ctc att gcc aca gta atc cag ctc ttc tac agg   1200
Phe Phe Pro Phe Phe Leu Ile Ala Thr Val Ile Gln Leu Phe Tyr Arg
385                 390                 395                 400 ggt aaa att tgg aac atc ctc ctc ttc ttg tta act gtc cag tta gta   1248
Gly Lys Ile Trp Asn Ile Leu Leu Phe Leu Leu Thr Val Gln Leu Val
            405                 410                 415 ggt ctc ata aaa tca tcc ttt gcc agc tgc ctt aga gga aat atc gtc   1296
Gly Leu Ile Lys Ser Ser Phe Ala Ser Cys Leu Arg Gly Asn Ile Val
            420                 425                 430 atg gtc ttc atg tcc ctc tac tcg gtt ttg tac atg tca agt tta ctt   1344
Met Val Phe Met Ser Leu Tyr Ser Val Leu Tyr Met Ser Ser Leu Leu
            435                 440                 445 ccc gcc aag atg ttt gcc att gca acg ata aac aaa gct ggc tgg ggc   1392
Pro Ala Lys Met Phe Ala Ile Ala Thr Ile Asn Lys Ala Gly Trp Gly
450                 455                 460 aca tct gga agg aaa acc atc gtt gtg aat ttc ata gga ctc att cca   1440
Thr Ser Gly Arg Lys Thr Ile Val Val Asn Phe Ile Gly Leu Ile Pro
465                 470                 475                 480 gtg tca gtt tgg ttt aca atc ctc ctg ggt ggt gtg att ttc acc att   1488
Val Ser Val Trp Phe Thr Ile Leu Leu Gly Gly Val Ile Phe Thr Ile
```

```
                    485            490            495
tat aag gaa tct aaa aag cca ttc tca gaa tcc aaa cag aca gtt tta    1536
Tyr Lys Glu Ser Lys Lys Pro Phe Ser Glu Ser Lys Gln Thr Val Leu
            500                 505                 510 att gtt gga acg ttg ctc tat gca tgc tat tgg gtc atg ctt ttg aca    1584
Ile Val Gly Thr Leu Leu Tyr Ala Cys Tyr Trp Val Met Leu Leu Thr
            515                 520                 525 ctg tat gtg gtt ctc atc aat aaa tgt ggc cgg cgg aag aag gga caa    1632
Leu Tyr Val Val Leu Ile Asn Lys Cys Gly Arg Arg Lys Lys Gly Gln
        530                 535                 540 cag tac gac atg gtg ctt gat gta tga                                1659
Gln Tyr Asp Met Val Leu Asp Val
545                 550

<210> SEQ ID NO 34
<211> LENGTH: 552
<212> TYPE: PRT
<213> ORGANISM: Sus scrofa

<400> SEQUENCE: 34

Met His Cys Glu Arg Phe Leu Cys Ile Leu Arg Ile Ile Gly Thr Thr
1               5                   10                  15

Leu Phe Gly Val Ser Leu Leu Leu Gly Ile Thr Ala Ala Tyr Ile Val
            20                  25                  30

Gly Tyr Gln Phe Ile Gln Thr Asp Asn Tyr Tyr Phe Phe Gly Leu
        35                  40                  45

Tyr Gly Ala Phe Leu Ala Ser His Leu Ile Ile Gln Ser Leu Phe Ala
    50                  55                  60

Phe Leu Glu His Arg Lys Met Lys Lys Ser Leu Glu Thr Pro Ile Lys
65                  70                  75                  80

Leu Asn Lys Thr Val Ala Leu Cys Ile Ala Ala Tyr Gln Glu Asp Pro
                85                  90                  95

Asp Tyr Leu Arg Lys Cys Leu Gln Ser Val Lys Arg Leu Thr Tyr Pro
            100                 105                 110

Gly Ile Lys Val Val Met Val Ile Asp Gly Asn Ser Glu Asp Asp Leu
        115                 120                 125

Tyr Met Met Asp Ile Phe Ser Glu Val Met Gly Arg Asp Asn Ser Ala
    130                 135                 140

Thr Tyr Ile Trp Lys Asn Asn Phe His Glu Lys Gly Pro Gly Glu Thr
145                 150                 155                 160

Asp Glu Ser His Lys Glu Ser Ser Gln His Val Thr Gln Leu Val Leu
                165                 170                 175

Ser Asn Lys Ser Ile Cys Ile Met Gln Lys Trp Gly Gly Lys Arg Glu
            180                 185                 190

Val Met Tyr Thr Ala Phe Arg Ala Leu Gly Arg Ser Val Asp Tyr Val
        195                 200                 205

Gln Val Cys Asp Ser Asp Thr Met Leu Asp Pro Ala Ser Ser Val Glu
    210                 215                 220

Met Val Lys Val Leu Glu Glu Asp Pro Met Val Gly Val Gly Gly
225                 230                 235                 240

Asp Val Gln Ile Leu Asn Lys Tyr Asp Ser Trp Ile Ser Phe Leu Ser
                245                 250                 255

Ser Val Arg Tyr Trp Met Ala Phe Asn Ile Glu Arg Ala Cys Gln Ser
            260                 265                 270

Tyr Phe Gly Cys Val Gln Cys Ile Ser Gly Pro Leu Gly Met Tyr Arg
        275                 280                 285
```

-continued

```
Asn Ser Leu Leu His Glu Phe Val Glu Asp Trp Tyr Asn Gln Glu Phe
            290                 295                 300

Met Gly Ser Gln Cys Ser Phe Gly Asp Asp Arg His Leu Thr Asn Arg
305                 310                 315                 320

Val Leu Ser Leu Gly Tyr Ala Thr Lys Tyr Thr Ala Arg Ser Lys Cys
                325                 330                 335

Leu Thr Glu Thr Pro Ile Glu Tyr Leu Arg Trp Leu Asn Gln Gln Thr
            340                 345                 350

Arg Trp Ser Lys Ser Tyr Phe Arg Glu Trp Leu Tyr Asn Ala Met Trp
        355                 360                 365

Phe His Lys His His Leu Trp Met Thr Tyr Glu Ala Val Ile Thr Gly
    370                 375                 380

Phe Phe Pro Phe Phe Leu Ile Ala Thr Val Ile Gln Leu Phe Tyr Arg
385                 390                 395                 400

Gly Lys Ile Trp Asn Ile Leu Leu Phe Leu Leu Thr Val Gln Leu Val
                405                 410                 415

Gly Leu Ile Lys Ser Ser Phe Ala Ser Cys Leu Arg Gly Asn Ile Val
            420                 425                 430

Met Val Phe Met Ser Leu Tyr Ser Val Leu Tyr Met Ser Ser Leu Leu
        435                 440                 445

Pro Ala Lys Met Phe Ala Ile Ala Thr Ile Asn Lys Ala Gly Trp Gly
    450                 455                 460

Thr Ser Gly Arg Lys Thr Ile Val Val Asn Phe Ile Gly Leu Ile Pro
465                 470                 475                 480

Val Ser Val Trp Phe Thr Ile Leu Leu Gly Gly Val Ile Phe Thr Ile
                485                 490                 495

Tyr Lys Glu Ser Lys Lys Pro Phe Ser Glu Ser Lys Gln Thr Val Leu
            500                 505                 510

Ile Val Gly Thr Leu Leu Tyr Ala Cys Tyr Trp Val Met Leu Leu Thr
        515                 520                 525

Leu Tyr Val Val Leu Ile Asn Lys Cys Gly Arg Arg Lys Lys Gly Gln
    530                 535                 540

Gln Tyr Asp Met Val Leu Asp Val
545                 550
```

<210> SEQ ID NO 35
<211> LENGTH: 1662
<212> TYPE: DNA
<213> ORGANISM: Sus scrofa
<220> FEATURE:
<221> NAME/KEY: CDS
<222> LOCATION: (1)..(1662)
<223> OTHER INFORMATION: Hyaluronan synthase 3
<300> PUBLICATION INFORMATION:
<308> DATABASE ACCESSION NUMBER: AB159675
<309> DATABASE ENTRY DATE: 2004-05-08
<313> RELEVANT RESIDUES IN SEQ ID NO: (1)..(1662)

<400> SEQUENCE: 35

```
atg ccg gtt cag ctg acg aca gcc ctg cgt gtg gtg ggc acc agc ctg      48
Met Pro Val Gln Leu Thr Thr Ala Leu Arg Val Val Gly Thr Ser Leu
1               5                   10                  15 ttt gcc ctg gca gtg ctg ggc ggc att ctg gca gca tat gtg aca ggc      96
Phe Ala Leu Ala Val Leu Gly Gly Ile Leu Ala Ala Tyr Val Thr Gly
                20                  25                  30 tac cag ttc atc cac aca gaa aag cac tac ctg tcc ttt ggg ctg tat     144
Tyr Gln Phe Ile His Thr Glu Lys His Tyr Leu Ser Phe Gly Leu Tyr
            35                  40                  45
```

```
ggt gcc atc ctg ggc ctg cac ctg ctc atc cag agc ctg ttt gcc ttc      192
Gly Ala Ile Leu Gly Leu His Leu Leu Ile Gln Ser Leu Phe Ala Phe
 50              55                  60 ctg gag cac cgg cgc atg cgg cgg gca ggc cgg cca ctg aag ctg ccc      240
Leu Glu His Arg Arg Met Arg Arg Ala Gly Arg Pro Leu Lys Leu Pro
 65              70                  75                  80 tcc ccg ctg cag cgc tca gtg gcg ctc tgc atc gcc gcg tac cag gag      288
Ser Pro Leu Gln Arg Ser Val Ala Leu Cys Ile Ala Ala Tyr Gln Glu
                 85                  90                  95 gac ccc gac tac ttg cgc aag tgc ctg cgc tcg gcc cag cgc atc gcc      336
Asp Pro Asp Tyr Leu Arg Lys Cys Leu Arg Ser Ala Gln Arg Ile Ala
            100                 105                 110 ttc ccc gat ctc aag gtg gtc atg gtg gtg gac ggc aat cgc cag gag      384
Phe Pro Asp Leu Lys Val Val Met Val Val Asp Gly Asn Arg Gln Glu
        115                 120                 125 gat gcc tac atg ttg gac atc ttc cac gag gtg cta ggt ggc aac gag      432
Asp Ala Tyr Met Leu Asp Ile Phe His Glu Val Leu Gly Gly Asn Glu
130                 135                 140 caa gcc ggc ttc ttt gtg tgg cgc agc aac ttc cat gag gcg ggt gag      480
Gln Ala Gly Phe Phe Val Trp Arg Ser Asn Phe His Glu Ala Gly Glu
145                 150                 155                 160 ggc gag acg gag gcc agc ctg cag gag ggc atg gac cgt gtg cgg aat      528
Gly Glu Thr Glu Ala Ser Leu Gln Glu Gly Met Asp Arg Val Arg Asn
                165                 170                 175 gtg gtg cgg gcc agc acc ttc tcc tgc atc atg cag aag tgg gga gga      576
Val Val Arg Ala Ser Thr Phe Ser Cys Ile Met Gln Lys Trp Gly Gly
            180                 185                 190 aag cga gag gtc atg tac acg gcc ttc aag gcc ctt ggt gac tcc gtg      624
Lys Arg Glu Val Met Tyr Thr Ala Phe Lys Ala Leu Gly Asp Ser Val
        195                 200                 205 gac tac att cag gtg tgt gac tct gac act gta ctg gat cca gcc tgt      672
Asp Tyr Ile Gln Val Cys Asp Ser Asp Thr Val Leu Asp Pro Ala Cys
210                 215                 220 acc ttc gag atg ctt cga gtc ttg gag gag gac ccc caa gta ggg gga      720
Thr Phe Glu Met Leu Arg Val Leu Glu Glu Asp Pro Gln Val Gly Gly
225                 230                 235                 240 gtt ggg gga gat gtc caa atc ctc aat aag tat gac tcc tgg atc tcc      768
Val Gly Gly Asp Val Gln Ile Leu Asn Lys Tyr Asp Ser Trp Ile Ser
                245                 250                 255 ttc ctg agc agt gtg cgg tac tgg atg gcc ttc aac gtg gaa cgg gct      816
Phe Leu Ser Ser Val Arg Tyr Trp Met Ala Phe Asn Val Glu Arg Ala
            260                 265                 270 tgc cag tcc tac ttc ggc tgt gtg cag tgt atc agt ggg ccc ctg ggc      864
Cys Gln Ser Tyr Phe Gly Cys Val Gln Cys Ile Ser Gly Pro Leu Gly
        275                 280                 285 atg tac cgg aac agc ctg ctt cag cag ttc ttg gag gac tgg tac cat      912
Met Tyr Arg Asn Ser Leu Leu Gln Gln Phe Leu Glu Asp Trp Tyr His
290                 295                 300 cag aag ttc cta ggt agc aag tgc agt ttt ggg gat gac cgg cac ctc      960
Gln Lys Phe Leu Gly Ser Lys Cys Ser Phe Gly Asp Asp Arg His Leu
305                 310                 315                 320 acc aac cga gtc ctg agt ctc ggc tac agg act aag tac aca gca cgc     1008
Thr Asn Arg Val Leu Ser Leu Gly Tyr Arg Thr Lys Tyr Thr Ala Arg
                325                 330                 335 tct aaa tgc ctc aca gag acc ccc acc aag tac ctc cgg tgg ctc aac     1056
Ser Lys Cys Leu Thr Glu Thr Pro Thr Lys Tyr Leu Arg Trp Leu Asn
            340                 345                 350 caa cag acc cgc tgg agc aag tct tac ttc cgg gag tgg ctc tac aac     1104
Gln Gln Thr Arg Trp Ser Lys Ser Tyr Phe Arg Glu Trp Leu Tyr Asn
```

```
              355                 360                 365
tct ctg tgg ttc cac aag cac cac ctc tgg atg acc tac gag tca gtg      1152
Ser Leu Trp Phe His Lys His His Leu Trp Met Thr Tyr Glu Ser Val
370                 375                 380 gtc aca ggt ttt ttc ccc ttc ttc ctt att gcc aca gtc ata cag ctt      1200
Val Thr Gly Phe Phe Pro Phe Phe Leu Ile Ala Thr Val Ile Gln Leu
385                 390                 395                 400 ttc tac cgt ggc cgc atc tgg aac att ctc ctc ttc ctg ctg aca gtg      1248
Phe Tyr Arg Gly Arg Ile Trp Asn Ile Leu Leu Phe Leu Leu Thr Val
                405                 410                 415 cag ttg gta ggc atc atc aag gct acc tat gcc tgc ttt ctt cgg ggc      1296
Gln Leu Val Gly Ile Ile Lys Ala Thr Tyr Ala Cys Phe Leu Arg Gly
            420                 425                 430 aat gca gag atg atc ttc atg tct ctc tac tcc ctt ctc tac atg tcc      1344
Asn Ala Glu Met Ile Phe Met Ser Leu Tyr Ser Leu Leu Tyr Met Ser
        435                 440                 445 agc ctc ctg cca gcc aag atc ttc gcc att gct acc atc aac aaa tct      1392
Ser Leu Leu Pro Ala Lys Ile Phe Ala Ile Ala Thr Ile Asn Lys Ser
    450                 455                 460 ggc tgg ggc act tct ggc cga aaa acc att gtg gtg aac ttc att ggc      1440
Gly Trp Gly Thr Ser Gly Arg Lys Thr Ile Val Val Asn Phe Ile Gly
465                 470                 475                 480 ctc atc cct gtg tcc atc tgg gtg gca gtc ctt ctg ggg gga ctg gcc      1488
Leu Ile Pro Val Ser Ile Trp Val Ala Val Leu Leu Gly Gly Leu Ala
                485                 490                 495 tat aca gct tac tgt cag gac ctg ttc agt gag acg gag cta gcc ttc      1536
Tyr Thr Ala Tyr Cys Gln Asp Leu Phe Ser Glu Thr Glu Leu Ala Phe
            500                 505                 510 ctg gtc tca ggg gcc atc ctt tat ggc tgc tac tgg gtg gcc ctc ctt      1584
Leu Val Ser Gly Ala Ile Leu Tyr Gly Cys Tyr Trp Val Ala Leu Leu
        515                 520                 525 atg ctg tat ctg gcc atc atc gcc cgg cgg tgc ggg aag aag ccg gag      1632
Met Leu Tyr Leu Ala Ile Ile Ala Arg Arg Cys Gly Lys Lys Pro Glu
    530                 535                 540 cag tat agc tta gct ttt gct gag gtg tga                              1662
Gln Tyr Ser Leu Ala Phe Ala Glu Val
545                 550

<210> SEQ ID NO 36
<211> LENGTH: 553
<212> TYPE: PRT
<213> ORGANISM: Sus scrofa

<400> SEQUENCE: 36

Met Pro Val Gln Leu Thr Thr Ala Leu Arg Val Val Gly Thr Ser Leu
1               5                   10                  15

Phe Ala Leu Ala Val Leu Gly Gly Ile Leu Ala Ala Tyr Val Thr Gly
            20                  25                  30

Tyr Gln Phe Ile His Thr Glu Lys His Tyr Leu Ser Phe Gly Leu Tyr
        35                  40                  45

Gly Ala Ile Leu Gly Leu His Leu Leu Ile Gln Ser Leu Phe Ala Phe
    50                  55                  60

Leu Glu His Arg Arg Met Arg Arg Ala Gly Arg Pro Leu Lys Leu Pro
65                  70                  75                  80

Ser Pro Leu Gln Arg Ser Val Ala Leu Cys Ile Ala Ala Tyr Gln Glu
                85                  90                  95

Asp Pro Asp Tyr Leu Arg Lys Cys Leu Arg Ser Ala Gln Arg Ile Ala
            100                 105                 110
```

```
Phe Pro Asp Leu Lys Val Val Met Val Val Asp Gly Asn Arg Gln Glu
            115                 120                 125
Asp Ala Tyr Met Leu Asp Ile Phe His Glu Val Leu Gly Gly Asn Glu
            130                 135                 140
Gln Ala Gly Phe Phe Val Trp Arg Ser Asn Phe His Glu Ala Gly Glu
145                 150                 155                 160
Gly Glu Thr Glu Ala Ser Leu Gln Glu Gly Met Asp Arg Val Arg Asn
                165                 170                 175
Val Val Arg Ala Ser Thr Phe Ser Cys Ile Met Gln Lys Trp Gly Gly
            180                 185                 190
Lys Arg Glu Val Met Tyr Thr Ala Phe Lys Ala Leu Gly Asp Ser Val
            195                 200                 205
Asp Tyr Ile Gln Val Cys Asp Ser Asp Thr Val Leu Asp Pro Ala Cys
            210                 215                 220
Thr Phe Glu Met Leu Arg Val Leu Glu Glu Asp Pro Gln Val Gly Gly
225                 230                 235                 240
Val Gly Gly Asp Val Gln Ile Leu Asn Lys Tyr Asp Ser Trp Ile Ser
                245                 250                 255
Phe Leu Ser Ser Val Arg Tyr Trp Met Ala Phe Asn Val Glu Arg Ala
            260                 265                 270
Cys Gln Ser Tyr Phe Gly Cys Val Gln Cys Ile Ser Gly Pro Leu Gly
            275                 280                 285
Met Tyr Arg Asn Ser Leu Leu Gln Gln Phe Leu Glu Asp Trp Tyr His
            290                 295                 300
Gln Lys Phe Leu Gly Ser Lys Cys Ser Phe Gly Asp Asp Arg His Leu
305                 310                 315                 320
Thr Asn Arg Val Leu Ser Leu Gly Tyr Arg Thr Lys Tyr Thr Ala Arg
                325                 330                 335
Ser Lys Cys Leu Thr Glu Thr Pro Thr Lys Tyr Leu Arg Trp Leu Asn
            340                 345                 350
Gln Gln Thr Arg Trp Ser Lys Ser Tyr Phe Arg Glu Trp Leu Tyr Asn
            355                 360                 365
Ser Leu Trp Phe His Lys His His Leu Trp Met Thr Tyr Glu Ser Val
370                 375                 380
Val Thr Gly Phe Phe Pro Phe Phe Leu Ile Ala Thr Val Ile Gln Leu
385                 390                 395                 400
Phe Tyr Arg Gly Arg Ile Trp Asn Ile Leu Phe Leu Leu Thr Val
                405                 410                 415
Gln Leu Val Gly Ile Ile Lys Ala Thr Tyr Ala Cys Phe Leu Arg Gly
            420                 425                 430
Asn Ala Glu Met Ile Phe Met Ser Leu Tyr Ser Leu Leu Tyr Met Ser
            435                 440                 445
Ser Leu Leu Pro Ala Lys Ile Phe Ala Ile Ala Thr Ile Asn Lys Ser
450                 455                 460
Gly Trp Gly Thr Ser Gly Arg Lys Thr Ile Val Val Asn Phe Ile Gly
465                 470                 475                 480
Leu Ile Pro Val Ser Ile Trp Val Ala Val Leu Leu Gly Gly Leu Ala
                485                 490                 495
Tyr Thr Ala Tyr Cys Gln Asp Leu Phe Ser Glu Thr Glu Leu Ala Phe
            500                 505                 510
Leu Val Ser Gly Ala Ile Leu Tyr Gly Cys Tyr Trp Val Ala Leu Leu
            515                 520                 525
Met Leu Tyr Leu Ala Ile Ile Ala Arg Arg Cys Gly Lys Lys Pro Glu
```

Gln Tyr Ser Leu Ala Phe Ala Glu Val
545             550

<210> SEQ ID NO 37
<211> LENGTH: 1659
<212> TYPE: DNA
<213> ORGANISM: Bos taurus
<220> FEATURE:
<221> NAME/KEY: CDS
<222> LOCATION: (1)..(1659)
<223> OTHER INFORMATION: Hyaluronan synthase 2
<300> PUBLICATION INFORMATION:
<308> DATABASE ACCESSION NUMBER: AJ004951.1
<309> DATABASE ENTRY DATE: 1998-11-24
<313> RELEVANT RESIDUES IN SEQ ID NO: (545)..(2203)

<400> SEQUENCE: 37

| | | |
|---|---|---|
| atg cat tgt gag aga ttt cta tgt atc ctg aga ata att gga acc aca<br>Met His Cys Glu Arg Phe Leu Cys Ile Leu Arg Ile Ile Gly Thr Thr<br>1               5                   10                  15 | 48 | |
| ctt ttt gga gtc tct ctc ctc ctt gga atc aca gct gct tat att gtt<br>Leu Phe Gly Val Ser Leu Leu Leu Gly Ile Thr Ala Ala Tyr Ile Val<br>            20                  25                  30 | 96 | |
| ggc tat caa ttt atc caa aca gat aat tac tat ttc tct ttt gga ctg<br>Gly Tyr Gln Phe Ile Gln Thr Asp Asn Tyr Tyr Phe Ser Phe Gly Leu<br>        35                  40                  45 | 144 | |
| tat ggt gcc ttt tta gca tca cac ctc atc atc caa agc ctg ttt gcc<br>Tyr Gly Ala Phe Leu Ala Ser His Leu Ile Ile Gln Ser Leu Phe Ala<br>    50                  55                  60 | 192 | |
| ttt ttg gag cac cgg aaa atg aaa aaa tct cta gaa acc ccc att aag<br>Phe Leu Glu His Arg Lys Met Lys Lys Ser Leu Glu Thr Pro Ile Lys<br>65                  70                  75                  80 | 240 | |
| ttg aac aaa act gtt gct ctt tgc att gct gca tat caa gaa gat cca<br>Leu Asn Lys Thr Val Ala Leu Cys Ile Ala Ala Tyr Gln Glu Asp Pro<br>                85                  90                  95 | 288 | |
| gac tat ttg cgg aaa tgt ttg caa tct gtg aaa agg cta acc tac ccc<br>Asp Tyr Leu Arg Lys Cys Leu Gln Ser Val Lys Arg Leu Thr Tyr Pro<br>            100                 105                 110 | 336 | |
| gga att aaa gtt gtc atg gtc ata gat gga aac tcg gaa gat gac ctt<br>Gly Ile Lys Val Val Met Val Ile Asp Gly Asn Ser Glu Asp Asp Leu<br>        115                 120                 125 | 384 | |
| tac atg atg gac atc ttc agt gaa gtc atg ggc agg gac aag tca gcc<br>Tyr Met Met Asp Ile Phe Ser Glu Val Met Gly Arg Asp Lys Ser Ala<br>    130                 135                 140 | 432 | |
| act tat atc tgg aag aac aac tac cat gtg aag ggt cct gga gag acg<br>Thr Tyr Ile Trp Lys Asn Asn Tyr His Val Lys Gly Pro Gly Glu Thr<br>145                 150                 155                 160 | 480 | |
| gat gag tcg cac aaa gaa agc tca cag cat gtc acc cag ttg gtc ttg<br>Asp Glu Ser His Lys Glu Ser Ser Gln His Val Thr Gln Leu Val Leu<br>                165                 170                 175 | 528 | |
| tcc aac aag agt att tgc acc atg caa aaa tgg ggt gga aaa aga gaa<br>Ser Asn Lys Ser Ile Cys Thr Met Gln Lys Trp Gly Gly Lys Arg Glu<br>            180                 185                 190 | 576 | |
| gtc atg tac aca gcc ttc aga gca ctg ggg cga agt gtg gat tat gta<br>Val Met Tyr Thr Ala Phe Arg Ala Leu Gly Arg Ser Val Asp Tyr Val<br>        195                 200                 205 | 624 | |
| cag gtt tgt gat tca gac acc atg ctt gac cca gca tca tct gtg gag<br>Gln Val Cys Asp Ser Asp Thr Met Leu Asp Pro Ala Ser Ser Val Glu<br>    210                 215                 220 | 672 | |
| atg gta aaa gtt tta gaa gaa gat ccc atg gtt gga ggt gtc ggg gga<br>Met Val Lys Val Leu Glu Glu Asp Pro Met Val Gly Gly Val Gly Gly<br>225                 230                 235                 240 | 720 | |

```
                225                 230                 235                 240 gat gtc cag att tta aac aag tat gat tcc tgg atc tcc ttc ctc agc     768
Asp Val Gln Ile Leu Asn Lys Tyr Asp Ser Trp Ile Ser Phe Leu Ser
                        245                 250                 255 agt gtg aga tac tgg atg gct ttt aac ata gaa agg gcc tgt cag tct     816
Ser Val Arg Tyr Trp Met Ala Phe Asn Ile Glu Arg Ala Cys Gln Ser
            260                 265                 270 tat ttc gga tgt gtc cag tgc att agc gga cct ctg gga atg tac aga     864
Tyr Phe Gly Cys Val Gln Cys Ile Ser Gly Pro Leu Gly Met Tyr Arg
                275                 280                 285 aac tcc tta ctg cat gaa ttt gtg gaa gac tgg tac aat caa gaa ttt     912
Asn Ser Leu Leu His Glu Phe Val Glu Asp Trp Tyr Asn Gln Glu Phe
    290                 295                 300 atg ggc agc caa tgt agt ttt gga gat gac agg cat cta acg aac cga     960
Met Gly Ser Gln Cys Ser Phe Gly Asp Asp Arg His Leu Thr Asn Arg
305                 310                 315                 320 gtg ctg agt ctg ggc tat gca acg aaa tac aca gct cga tcc aag tgc    1008
Val Leu Ser Leu Gly Tyr Ala Thr Lys Tyr Thr Ala Arg Ser Lys Cys
                    325                 330                 335 ctt act gaa aca cct ata gaa tat ctc aga tgg tta aac cag cag acc    1056
Leu Thr Glu Thr Pro Ile Glu Tyr Leu Arg Trp Leu Asn Gln Gln Thr
                340                 345                 350 cgc tgg agc aag tcg tac ttc cga gag tgg ctg tac aac gct atg tgg    1104
Arg Trp Ser Lys Ser Tyr Phe Arg Glu Trp Leu Tyr Asn Ala Met Trp
            355                 360                 365 ttt cat aaa cat cac ttg tgg atg acc tat gaa gcc gtc atc act ggg    1152
Phe His Lys His His Leu Trp Met Thr Tyr Glu Ala Val Ile Thr Gly
        370                 375                 380 ttc ttc cct ttc ttt ctc att gcc acg gta atc cag ctc ttc tac agg    1200
Phe Phe Pro Phe Phe Leu Ile Ala Thr Val Ile Gln Leu Phe Tyr Arg
385                 390                 395                 400 ggt aaa att tgg aac acc ctc ctc ttc ttg tta act gtc cag tta gtg    1248
Gly Lys Ile Trp Asn Thr Leu Leu Phe Leu Leu Thr Val Gln Leu Val
                    405                 410                 415 ggt ctc ata aaa tca tct ttt gcc agc tgc ctt aga gga aac att gtc    1296
Gly Leu Ile Lys Ser Ser Phe Ala Ser Cys Leu Arg Gly Asn Ile Val
                420                 425                 430 atg gtc ttc atg tcc ctc tac tca gtg tta tac atg tca agt tta ctt    1344
Met Val Phe Met Ser Leu Tyr Ser Val Leu Tyr Met Ser Ser Leu Leu
            435                 440                 445 ccg gcc aag atg ttt gca att gca aca ata aac aaa gct ggg tgg ggc    1392
Pro Ala Lys Met Phe Ala Ile Ala Thr Ile Asn Lys Ala Gly Trp Gly
        450                 455                 460 aca tct gga agg aaa acc att gtc gtt aat ttc ata gga ctc att ccc    1440
Thr Ser Gly Arg Lys Thr Ile Val Val Asn Phe Ile Gly Leu Ile Pro
465                 470                 475                 480 gta tcg gtt tgg ttt aca ata ctc ctg ggt ggt gtg att ttc acc att    1488
Val Ser Val Trp Phe Thr Ile Leu Leu Gly Gly Val Ile Phe Thr Ile
                    485                 490                 495 tat aag gaa tct aaa aag cca ttc tca gaa tcc aaa cag aca gtt tta    1536
Tyr Lys Glu Ser Lys Lys Pro Phe Ser Glu Ser Lys Gln Thr Val Leu
                500                 505                 510 att gtt gga acg ttg ctg tat gca tgc tat tgg gtc atg ctt ttg aca    1584
Ile Val Gly Thr Leu Leu Tyr Ala Cys Tyr Trp Val Met Leu Leu Thr
            515                 520                 525 ctg tac gtg gtt ctc atc aat aaa tgt ggc agg cgg aag aag gga caa    1632
Leu Tyr Val Val Leu Ile Asn Lys Cys Gly Arg Arg Lys Lys Gly Gln
        530                 535                 540 cag tac gac atg gtg ctt gat gta tga                                1659
```

```
Gln Tyr Asp Met Val Leu Asp Val
545                 550
```

<210> SEQ ID NO 38
<211> LENGTH: 552
<212> TYPE: PRT
<213> ORGANISM: Bos taurus

<400> SEQUENCE: 38

```
Met His Cys Glu Arg Phe Leu Cys Ile Leu Arg Ile Ile Gly Thr Thr
1               5                   10                  15

Leu Phe Gly Val Ser Leu Leu Leu Gly Ile Thr Ala Ala Tyr Ile Val
                20                  25                  30

Gly Tyr Gln Phe Ile Gln Thr Asp Asn Tyr Tyr Phe Ser Phe Gly Leu
            35                  40                  45

Tyr Gly Ala Phe Leu Ala Ser His Leu Ile Ile Gln Ser Leu Phe Ala
50                  55                  60

Phe Leu Glu His Arg Lys Met Lys Lys Ser Leu Glu Thr Pro Ile Lys
65                  70                  75                  80

Leu Asn Lys Thr Val Ala Leu Cys Ile Ala Ala Tyr Gln Glu Asp Pro
                85                  90                  95

Asp Tyr Leu Arg Lys Cys Leu Gln Ser Val Lys Arg Leu Thr Tyr Pro
            100                 105                 110

Gly Ile Lys Val Val Met Val Ile Asp Gly Asn Ser Glu Asp Asp Leu
        115                 120                 125

Tyr Met Met Asp Ile Phe Ser Glu Val Met Gly Arg Asp Lys Ser Ala
130                 135                 140

Thr Tyr Ile Trp Lys Asn Asn Tyr His Val Lys Gly Pro Gly Glu Thr
145                 150                 155                 160

Asp Glu Ser His Lys Glu Ser Ser Gln His Val Thr Gln Leu Val Leu
                165                 170                 175

Ser Asn Lys Ser Ile Cys Thr Met Gln Lys Trp Gly Gly Lys Arg Glu
            180                 185                 190

Val Met Tyr Thr Ala Phe Arg Ala Leu Gly Arg Ser Val Asp Tyr Val
        195                 200                 205

Gln Val Cys Asp Ser Asp Thr Met Leu Asp Pro Ala Ser Ser Val Glu
210                 215                 220

Met Val Lys Val Leu Glu Glu Asp Pro Met Val Gly Gly Val Gly Gly
225                 230                 235                 240

Asp Val Gln Ile Leu Asn Lys Tyr Asp Ser Trp Ile Ser Phe Leu Ser
                245                 250                 255

Ser Val Arg Tyr Trp Met Ala Phe Asn Ile Glu Arg Ala Cys Gln Ser
            260                 265                 270

Tyr Phe Gly Cys Val Gln Cys Ile Ser Gly Pro Leu Gly Met Tyr Arg
        275                 280                 285

Asn Ser Leu Leu His Glu Phe Val Glu Asp Trp Tyr Asn Gln Glu Phe
290                 295                 300

Met Gly Ser Gln Cys Ser Phe Gly Asp Asp Arg His Leu Thr Asn Arg
305                 310                 315                 320

Val Leu Ser Leu Gly Tyr Ala Thr Lys Tyr Thr Ala Arg Ser Lys Cys
                325                 330                 335

Leu Thr Glu Thr Pro Ile Glu Tyr Leu Arg Trp Leu Asn Gln Gln Thr
            340                 345                 350

Arg Trp Ser Lys Ser Tyr Phe Arg Glu Trp Leu Tyr Asn Ala Met Trp
        355                 360                 365
```

```
Phe His Lys His His Leu Trp Met Thr Tyr Glu Ala Val Ile Thr Gly
        370                 375                 380

Phe Phe Pro Phe Phe Leu Ile Ala Thr Val Ile Gln Leu Phe Tyr Arg
385                 390                 395                 400

Gly Lys Ile Trp Asn Thr Leu Leu Phe Leu Leu Thr Val Gln Leu Val
                405                 410                 415

Gly Leu Ile Lys Ser Ser Phe Ala Ser Cys Leu Arg Gly Asn Ile Val
                420                 425                 430

Met Val Phe Met Ser Leu Tyr Ser Val Leu Tyr Met Ser Ser Leu Leu
            435                 440                 445

Pro Ala Lys Met Phe Ala Ile Ala Thr Ile Asn Lys Ala Gly Trp Gly
            450                 455                 460

Thr Ser Gly Arg Lys Thr Ile Val Val Asn Phe Ile Gly Leu Ile Pro
465                 470                 475                 480

Val Ser Val Trp Phe Thr Ile Leu Leu Gly Gly Val Ile Phe Thr Ile
                485                 490                 495

Tyr Lys Glu Ser Lys Lys Pro Phe Ser Glu Ser Lys Gln Thr Val Leu
                500                 505                 510

Ile Val Gly Thr Leu Leu Tyr Ala Cys Tyr Trp Val Met Leu Leu Thr
            515                 520                 525

Leu Tyr Val Val Leu Ile Asn Lys Cys Gly Arg Arg Lys Lys Gly Gln
            530                 535                 540

Gln Tyr Asp Met Val Leu Asp Val
545                 550

<210> SEQ ID NO 39
<211> LENGTH: 1659
<212> TYPE: DNA
<213> ORGANISM: Gallus gallus
<220> FEATURE:
<221> NAME/KEY: CDS
<222> LOCATION: (1)..(1659)
<223> OTHER INFORMATION: Hyaluronan synthase 2
<300> PUBLICATION INFORMATION:
<308> DATABASE ACCESSION NUMBER: AF106940.1
<309> DATABASE ENTRY DATE: 1999-12-10
<313> RELEVANT RESIDUES IN SEQ ID NO: (563)..(2221)

<400> SEQUENCE: 39 atg tat tgt gag agg ttt ata tgt atc ctg aga ata ctt gga acc aca      48
Met Tyr Cys Glu Arg Phe Ile Cys Ile Leu Arg Ile Leu Gly Thr Thr
1               5                   10                  15 ctc ttt gga gtg tcc ctc ctg ctg gga atc acc gct gct tac att gtg      96
Leu Phe Gly Val Ser Leu Leu Leu Gly Ile Thr Ala Ala Tyr Ile Val
                20                  25                  30 ggc tac cag ttt atc caa aca gac aat tac tac ttc tcc ttt gga ctc     144
Gly Tyr Gln Phe Ile Gln Thr Asp Asn Tyr Tyr Phe Ser Phe Gly Leu
            35                  40                  45 tat ggt gct atc ctg gca tca cat ctc atc atc caa agc ctg ttt gcc     192
Tyr Gly Ala Ile Leu Ala Ser His Leu Ile Ile Gln Ser Leu Phe Ala
        50                  55                  60 tac cta gag cac agg aaa atg aag cgg tcg cta gag act cca atc aag     240
Tyr Leu Glu His Arg Lys Met Lys Arg Ser Leu Glu Thr Pro Ile Lys
65                  70                  75                  80 ctg aac aaa act gtt gcc ctt tgt att gct gcc tat caa gag gat cct     288
Leu Asn Lys Thr Val Ala Leu Cys Ile Ala Ala Tyr Gln Glu Asp Pro
                85                  90                  95 gac tac tta aga aaa tgt tta ctt tct gtg aaa aga ttg acc tac cct     336
Asp Tyr Leu Arg Lys Cys Leu Leu Ser Val Lys Arg Leu Thr Tyr Pro
```

|  |  |  |  |  |  |  |  |  |  |  |  |  |  |  |  |
|---|---|---|---|---|---|---|---|---|---|---|---|---|---|---|---|
|  |  |  | 100 |  |  |  | 105 |  |  |  | 110 |  |  |  |  |
| gga | att | aaa | gtt | gtt | atg | gtc | att | gat | ggg | aac | tca | gaa | gat | gac | gtt | 384 |
| Gly | Ile | Lys | Val | Val | Met | Val | Ile | Asp | Gly | Asn | Ser | Glu | Asp | Asp | Val |
|  |  | 115 |  |  |  |  | 120 |  |  |  |  | 125 |  |  |  |
| tac | atg | atg | gac | att | ttt | act | gaa | atc | atg | ggg | agg | gac | aaa | tct | gcc | 432 |
| Tyr | Met | Met | Asp | Ile | Phe | Thr | Glu | Ile | Met | Gly | Arg | Asp | Lys | Ser | Ala |
| 130 |  |  |  |  | 135 |  |  |  |  | 140 |  |  |  |  |  |
| act | tat | atc | tgg | agt | aac | aac | ttc | cat | gac | aaa | ggt | cca | ggt | gag | acg | 480 |
| Thr | Tyr | Ile | Trp | Ser | Asn | Asn | Phe | His | Asp | Lys | Gly | Pro | Gly | Glu | Thr |
| 145 |  |  |  | 150 |  |  |  |  | 155 |  |  |  |  | 160 |  |
| gag | gag | tct | cac | aga | gag | agc | atg | cag | cac | gta | tct | cag | ctg | gtc | ctg | 528 |
| Glu | Glu | Ser | His | Arg | Glu | Ser | Met | Gln | His | Val | Ser | Gln | Leu | Val | Leu |
|  |  |  |  | 165 |  |  |  |  | 170 |  |  |  |  | 175 |  |
| tcc | aac | aaa | agt | gtt | tgc | atc | atg | cag | aaa | tgg | ggt | gga | aaa | aga | gaa | 576 |
| Ser | Asn | Lys | Ser | Val | Cys | Ile | Met | Gln | Lys | Trp | Gly | Gly | Lys | Arg | Glu |
|  |  |  | 180 |  |  |  |  | 185 |  |  |  |  | 190 |  |  |
| gta | atg | tac | aca | gca | ttc | aaa | gca | ctg | gga | gaa | gcg | tgg | aat | tat | gta | 624 |
| Val | Met | Tyr | Thr | Ala | Phe | Lys | Ala | Leu | Gly | Glu | Ala | Trp | Asn | Tyr | Val |
|  |  | 195 |  |  |  |  | 200 |  |  |  |  | 205 |  |  |  |
| cag | gtc | tgt | gat | tca | gac | aca | atg | ctc | gat | cca | gct | tca | tca | gtg | gaa | 672 |
| Gln | Val | Cys | Asp | Ser | Asp | Thr | Met | Leu | Asp | Pro | Ala | Ser | Ser | Val | Glu |
| 210 |  |  |  |  | 215 |  |  |  |  | 220 |  |  |  |  |  |
| atg | gta | aag | gtc | tta | gaa | gaa | gat | cca | atg | gtt | gga | gga | gtt | gga | ggc | 720 |
| Met | Val | Lys | Val | Leu | Glu | Glu | Asp | Pro | Met | Val | Gly | Gly | Val | Gly | Gly |
| 225 |  |  |  | 230 |  |  |  |  | 235 |  |  |  |  | 240 |  |
| gat | gtg | cag | att | ttg | aac | aag | tat | gat | tcc | tgg | atc | tcc | ttt | ctg | agc | 768 |
| Asp | Val | Gln | Ile | Leu | Asn | Lys | Tyr | Asp | Ser | Trp | Ile | Ser | Phe | Leu | Ser |
|  |  |  |  | 245 |  |  |  |  | 250 |  |  |  |  | 255 |  |
| agt | gtg | aga | tac | tgg | atg | gca | ttt | aac | ata | gaa | aga | gcc | tgc | cag | tcc | 816 |
| Ser | Val | Arg | Tyr | Trp | Met | Ala | Phe | Asn | Ile | Glu | Arg | Ala | Cys | Gln | Ser |
|  |  |  | 260 |  |  |  |  | 265 |  |  |  |  | 270 |  |  |
| tat | ttt | ggc | tgc | gta | cag | tgc | atc | agt | gga | cct | ctg | gga | atg | tac | aga | 864 |
| Tyr | Phe | Gly | Cys | Val | Gln | Cys | Ile | Ser | Gly | Pro | Leu | Gly | Met | Tyr | Arg |
|  |  | 275 |  |  |  |  | 280 |  |  |  |  | 285 |  |  |  |
| aac | tct | tta | ctc | cat | gaa | ttt | gtg | gaa | gat | tgg | tac | aat | caa | gaa | ttt | 912 |
| Asn | Ser | Leu | Leu | His | Glu | Phe | Val | Glu | Asp | Trp | Tyr | Asn | Gln | Glu | Phe |
|  | 290 |  |  |  |  | 295 |  |  |  |  | 300 |  |  |  |  |
| atg | ggc | tcc | cag | tgc | agc | ttt | gga | gac | gac | agg | cat | cta | act | aac | cga | 960 |
| Met | Gly | Ser | Gln | Cys | Ser | Phe | Gly | Asp | Asp | Arg | His | Leu | Thr | Asn | Arg |
| 305 |  |  |  |  | 310 |  |  |  |  | 315 |  |  |  |  | 320 |
| gtg | cta | agt | ctg | ggc | tat | gca | aca | aaa | tac | aca | gct | aga | tcc | aag | tgc | 1008 |
| Val | Leu | Ser | Leu | Gly | Tyr | Ala | Thr | Lys | Tyr | Thr | Ala | Arg | Ser | Lys | Cys |
|  |  |  |  | 325 |  |  |  |  | 330 |  |  |  |  | 335 |  |
| ctt | act | gaa | aca | cca | ata | gag | tat | ctc | agg | tgg | ctg | aat | cag | cag | acc | 1056 |
| Leu | Thr | Glu | Thr | Pro | Ile | Glu | Tyr | Leu | Arg | Trp | Leu | Asn | Gln | Gln | Thr |
|  |  |  |  | 340 |  |  |  |  | 345 |  |  |  |  | 350 |  |
| cgc | tgg | agt | aaa | tcg | tat | ttt | aga | gag | tgg | ctt | tat | aat | gca | atg | tgg | 1104 |
| Arg | Trp | Ser | Lys | Ser | Tyr | Phe | Arg | Glu | Trp | Leu | Tyr | Asn | Ala | Met | Trp |
|  |  | 355 |  |  |  |  | 360 |  |  |  |  | 365 |  |  |  |
| ttc | cac | aag | cac | cat | ttg | tgg | atg | acc | tat | gaa | gct | gta | atc | act | gga | 1152 |
| Phe | His | Lys | His | His | Leu | Trp | Met | Thr | Tyr | Glu | Ala | Val | Ile | Thr | Gly |
|  | 370 |  |  |  |  | 375 |  |  |  |  | 380 |  |  |  |  |
| ttc | ttt | cct | ttc | ttc | ctt | atc | gct | aca | gtc | att | cag | ctc | ttc | tac | agg | 1200 |
| Phe | Phe | Pro | Phe | Phe | Leu | Ile | Ala | Thr | Val | Ile | Gln | Leu | Phe | Tyr | Arg |
| 385 |  |  |  |  | 390 |  |  |  |  | 395 |  |  |  |  | 400 |
| gga | aaa | atc | tgg | aac | atc | ctc | ctt | ttc | ttg | ttg | aca | gtt | cag | tta | gtg | 1248 |
| Gly | Lys | Ile | Trp | Asn | Ile | Leu | Leu | Phe | Leu | Leu | Thr | Val | Gln | Leu | Val |
|  |  |  |  | 405 |  |  |  |  | 410 |  |  |  |  | 415 |  |
| ggc | ctg | ata | aag | tct | tcc | ttt | gcc | agt | ttc | ctt | agg | ggc | aac | att | gtc | 1296 |

```
Gly Leu Ile Lys Ser Ser Phe Ala Ser Phe Leu Arg Gly Asn Ile Val
                420                 425                 430 atg gtt ttc atg tca ctc tac tca gtg ttg tat atg tcg agt tta ctg      1344
Met Val Phe Met Ser Leu Tyr Ser Val Leu Tyr Met Ser Ser Leu Leu
            435                 440                 445 cca gca aag atg ttt gca atc gcc acg ata aac aaa gca ggg tgg ggc      1392
Pro Ala Lys Met Phe Ala Ile Ala Thr Ile Asn Lys Ala Gly Trp Gly
450                 455                 460 aca tca gga aga aaa acc att gta gtt aat ttt ata gga ctc att cca      1440
Thr Ser Gly Arg Lys Thr Ile Val Val Asn Phe Ile Gly Leu Ile Pro
465                 470                 475                 480 gtc tcc att tgg ttt aca atc ctc cta ggt cgc gta att ttc act atc      1488
Val Ser Ile Trp Phe Thr Ile Leu Leu Gly Arg Val Ile Phe Thr Ile
            485                 490                 495 tac aag gaa tca aaa aag cca ttc tct gag tca aaa aca aca gtt ctc      1536
Tyr Lys Glu Ser Lys Lys Pro Phe Ser Glu Ser Lys Thr Thr Val Leu
                500                 505                 510 gtc att ggt aca atc ctc tat gca tgt tac tgg gtt ctt cta ttg act      1584
Val Ile Gly Thr Ile Leu Tyr Ala Cys Tyr Trp Val Leu Leu Leu Thr
            515                 520                 525 ttg tac ttg gtt ctc atc acc aaa tgt ggc agg cgg aag aaa gag caa      1632
Leu Tyr Leu Val Leu Ile Thr Lys Cys Gly Arg Arg Lys Lys Glu Gln
530                 535                 540 cac tat gac atg gtg cta gat gta tga                                  1659
His Tyr Asp Met Val Leu Asp Val
545                 550

<210> SEQ ID NO 40
<211> LENGTH: 552
<212> TYPE: PRT
<213> ORGANISM: Gallus gallus

<400> SEQUENCE: 40

Met Tyr Cys Glu Arg Phe Ile Cys Ile Leu Arg Ile Leu Gly Thr Thr
1               5                   10                  15

Leu Phe Gly Val Ser Leu Leu Leu Gly Ile Thr Ala Ala Tyr Ile Val
            20                  25                  30

Gly Tyr Gln Phe Ile Gln Thr Asp Asn Tyr Tyr Phe Ser Phe Gly Leu
        35                  40                  45

Tyr Gly Ala Ile Leu Ala Ser His Leu Ile Ile Gln Ser Leu Phe Ala
    50                  55                  60

Tyr Leu Glu His Arg Lys Met Lys Arg Ser Leu Glu Thr Pro Ile Lys
65                  70                  75                  80

Leu Asn Lys Thr Val Ala Leu Cys Ile Ala Ala Tyr Gln Glu Asp Pro
                85                  90                  95

Asp Tyr Leu Arg Lys Cys Leu Leu Ser Val Lys Arg Leu Thr Tyr Pro
            100                 105                 110

Gly Ile Lys Val Val Met Val Ile Asp Gly Asn Ser Glu Asp Asp Val
        115                 120                 125

Tyr Met Met Asp Ile Phe Thr Glu Ile Met Gly Arg Asp Lys Ser Ala
    130                 135                 140

Thr Tyr Ile Trp Ser Asn Asn Phe His Asp Lys Gly Pro Gly Glu Thr
145                 150                 155                 160

Glu Glu Ser His Arg Glu Ser Met Gln His Val Ser Gln Leu Val Leu
                165                 170                 175

Ser Asn Lys Ser Val Cys Ile Met Gln Lys Trp Gly Gly Lys Arg Glu
            180                 185                 190
```

```
Val Met Tyr Thr Ala Phe Lys Ala Leu Gly Glu Ala Trp Asn Tyr Val
        195                 200                 205

Gln Val Cys Asp Ser Asp Thr Met Leu Asp Pro Ala Ser Ser Val Glu
210                 215                 220

Met Val Lys Val Leu Glu Glu Asp Pro Met Val Gly Val Gly Gly
225                 230                 235                 240

Asp Val Gln Ile Leu Asn Lys Tyr Asp Ser Trp Ile Ser Phe Leu Ser
                245                 250                 255

Ser Val Arg Tyr Trp Met Ala Phe Asn Ile Glu Arg Ala Cys Gln Ser
            260                 265                 270

Tyr Phe Gly Cys Val Gln Cys Ile Ser Gly Pro Leu Gly Met Tyr Arg
        275                 280                 285

Asn Ser Leu Leu His Glu Phe Val Glu Asp Trp Tyr Asn Gln Glu Phe
290                 295                 300

Met Gly Ser Gln Cys Ser Phe Gly Asp Asp Arg His Leu Thr Asn Arg
305                 310                 315                 320

Val Leu Ser Leu Gly Tyr Ala Thr Lys Tyr Thr Ala Arg Ser Lys Cys
                325                 330                 335

Leu Thr Glu Thr Pro Ile Glu Tyr Leu Arg Trp Leu Asn Gln Gln Thr
            340                 345                 350

Arg Trp Ser Lys Ser Tyr Phe Arg Glu Trp Leu Tyr Asn Ala Met Trp
        355                 360                 365

Phe His Lys His His Leu Trp Met Thr Tyr Glu Ala Val Ile Thr Gly
370                 375                 380

Phe Phe Pro Phe Phe Leu Ile Ala Thr Val Ile Gln Leu Phe Tyr Arg
385                 390                 395                 400

Gly Lys Ile Trp Asn Ile Leu Leu Phe Leu Leu Thr Val Gln Leu Val
                405                 410                 415

Gly Leu Ile Lys Ser Ser Phe Ala Ser Phe Leu Arg Gly Asn Ile Val
            420                 425                 430

Met Val Phe Met Ser Leu Tyr Ser Val Leu Tyr Met Ser Ser Leu Leu
        435                 440                 445

Pro Ala Lys Met Phe Ala Ile Ala Thr Ile Asn Lys Ala Gly Trp Gly
450                 455                 460

Thr Ser Gly Arg Lys Thr Ile Val Val Asn Phe Ile Gly Leu Ile Pro
465                 470                 475                 480

Val Ser Ile Trp Phe Thr Ile Leu Leu Gly Arg Val Ile Phe Thr Ile
                485                 490                 495

Tyr Lys Glu Ser Lys Lys Pro Phe Ser Glu Ser Lys Thr Thr Val Leu
            500                 505                 510

Val Ile Gly Thr Ile Leu Tyr Ala Cys Tyr Trp Val Leu Leu Leu Thr
        515                 520                 525

Leu Tyr Leu Val Leu Ile Thr Lys Cys Gly Arg Arg Lys Lys Glu Gln
530                 535                 540

His Tyr Asp Met Val Leu Asp Val
545                 550

<210> SEQ ID NO 41
<211> LENGTH: 1767
<212> TYPE: DNA
<213> ORGANISM: Xenopus laevis
<220> FEATURE:
<221> NAME/KEY: CDS
<222> LOCATION: (1)..(1767)
<223> OTHER INFORMATION: Hyaluronan synthase 1
<300> PUBLICATION INFORMATION:
```

-continued

<308> DATABASE ACCESSION NUMBER: M22249.1
<309> DATABASE ENTRY DATE: 1989-04-22
<313> RELEVANT RESIDUES IN SEQ ID NO: (527)..(2293)

<400> SEQUENCE: 41

```
atg aag gaa aaa gct gca gaa aca atg gag att cct gaa ggg atc ccc         48
Met Lys Glu Lys Ala Ala Glu Thr Met Glu Ile Pro Glu Gly Ile Pro
1               5                   10                  15 aaa gat cta gag cca aaa cac ccc acc ctt tgg agg ata att tat tat         96
Lys Asp Leu Glu Pro Lys His Pro Thr Leu Trp Arg Ile Ile Tyr Tyr
                20                  25                  30 tct ttt ggt gtg gtg cta tta gct acc att aca gca gcc tat gtg gca        144
Ser Phe Gly Val Val Leu Leu Ala Thr Ile Thr Ala Ala Tyr Val Ala
            35                  40                  45 gag ttc cag gtc ctc aaa cat gaa gcc att ctc ttc tcc ctt ggg ctt        192
Glu Phe Gln Val Leu Lys His Glu Ala Ile Leu Phe Ser Leu Gly Leu
        50                  55                  60 tat ggt ctt gca atg ctt ctc cac ctg atg atg cag agc ctc ttt gcc        240
Tyr Gly Leu Ala Met Leu Leu His Leu Met Met Gln Ser Leu Phe Ala
65                  70                  75                  80 ttc ctg gag ata cgc agg gta aat aag agt gag ctt cct tgc agc ttt        288
Phe Leu Glu Ile Arg Arg Val Asn Lys Ser Glu Leu Pro Cys Ser Phe
                85                  90                  95 aag aag aca gtg gct ctg acc att gct ggg tat cag gag aac cct gag        336
Lys Lys Thr Val Ala Leu Thr Ile Ala Gly Tyr Gln Glu Asn Pro Glu
            100                 105                 110 tac ctg ata aag tgc ttg gaa tcc tgc aag tat gtg aaa tac ccc aaa        384
Tyr Leu Ile Lys Cys Leu Glu Ser Cys Lys Tyr Val Lys Tyr Pro Lys
        115                 120                 125 gat aaa ctc aag atc att ttg gtc atc gat ggg aac aca gag gat gat        432
Asp Lys Leu Lys Ile Ile Leu Val Ile Asp Gly Asn Thr Glu Asp Asp
    130                 135                 140 gcc tac atg atg gag atg ttc aaa gac gtg ttc cac ggt gaa gat gta        480
Ala Tyr Met Met Glu Met Phe Lys Asp Val Phe His Gly Glu Asp Val
145                 150                 155                 160 ggc acc tac gta tgg aag gga aat tac cac act gtt aaa aag cct gag        528
Gly Thr Tyr Val Trp Lys Gly Asn Tyr His Thr Val Lys Lys Pro Glu
                165                 170                 175 gag acc aat aag gga tcc tgt cct gag gtt tct aag ccc ttg aat gaa        576
Glu Thr Asn Lys Gly Ser Cys Pro Glu Val Ser Lys Pro Leu Asn Glu
            180                 185                 190 gat gaa ggt atc aat atg gtg gaa gaa ctt gtt aga aac aag aga tgt        624
Asp Glu Gly Ile Asn Met Val Glu Glu Leu Val Arg Asn Lys Arg Cys
        195                 200                 205 gtg tgc atc atg caa cag tgg ggc gga aaa aga gag gtc atg tac aca        672
Val Cys Ile Met Gln Gln Trp Gly Gly Lys Arg Glu Val Met Tyr Thr
    210                 215                 220 gca ttc cag gcc att ggg act tct gtg gac tat gta cag gtc tgt gac        720
Ala Phe Gln Ala Ile Gly Thr Ser Val Asp Tyr Val Gln Val Cys Asp
225                 230                 235                 240 tcg gac acc aaa ctg gat gaa ctg gca aca gtg gaa atg gtg aag gtt        768
Ser Asp Thr Lys Leu Asp Glu Leu Ala Thr Val Glu Met Val Lys Val
                245                 250                 255 ctg gaa tcc aat gac atg tac ggc gca gtg gga gga gac gtt cgc att        816
Leu Glu Ser Asn Asp Met Tyr Gly Ala Val Gly Gly Asp Val Arg Ile
            260                 265                 270 ctg aac cct tat gat tcc ttc att agt ttc atg agc agc ctg cgt tac        864
Leu Asn Pro Tyr Asp Ser Phe Ile Ser Phe Met Ser Ser Leu Arg Tyr
        275                 280                 285 tgg atg gcg ttt aac gtg gag agg gcc tgc cag tct tac ttc gac tgc        912
```

```
Trp Met Ala Phe Asn Val Glu Arg Ala Cys Gln Ser Tyr Phe Asp Cys
    290                 295                 300 gtg tcc tgt ata agt gga cct ctg gga atg tac cgg aac aac att ctc        960
Val Ser Cys Ile Ser Gly Pro Leu Gly Met Tyr Arg Asn Asn Ile Leu
305                 310                 315                 320 cag gtg ttt ttg gaa gcc tgg tac aga cag aaa ttt ttg gga acc tat       1008
Gln Val Phe Leu Glu Ala Trp Tyr Arg Gln Lys Phe Leu Gly Thr Tyr
                325                 330                 335 tgt act ttg gga gat gat aga cat ctg aca aac cga gtg ctc agc atg       1056
Cys Thr Leu Gly Asp Asp Arg His Leu Thr Asn Arg Val Leu Ser Met
            340                 345                 350 gga tat cgc acc aaa tac acc cac aaa tcc aga gca ttc tcc gaa act       1104
Gly Tyr Arg Thr Lys Tyr Thr His Lys Ser Arg Ala Phe Ser Glu Thr
        355                 360                 365 cca tcc ctg tat ctc cgg tgg ttg aac cag caa acc cgg tgg acc aag       1152
Pro Ser Leu Tyr Leu Arg Trp Leu Asn Gln Gln Thr Arg Trp Thr Lys
    370                 375                 380 tcc tac ttc cga gag tgg ctg tat aat gcc cag tgg tgg cac aag cat       1200
Ser Tyr Phe Arg Glu Trp Leu Tyr Asn Ala Gln Trp Trp His Lys His
385                 390                 395                 400 cac atc tgg atg acc tat gag tct gtg gtg tcc ttc atc ttt ccc ttc       1248
His Ile Trp Met Thr Tyr Glu Ser Val Val Ser Phe Ile Phe Pro Phe
                405                 410                 415 ttc atc act gcc act gtt atc cgc ctc atc tat gcc ggc acc ata tgg       1296
Phe Ile Thr Ala Thr Val Ile Arg Leu Ile Tyr Ala Gly Thr Ile Trp
            420                 425                 430 aat gtt gtg tgg ctc ctc ctg tgc atc cag atc atg tct ctc ttc aaa       1344
Asn Val Val Trp Leu Leu Leu Cys Ile Gln Ile Met Ser Leu Phe Lys
        435                 440                 445 tcc atc tat gcc tgc tgg ctc cgc ggc aac ttc att atg ctc ctg atg       1392
Ser Ile Tyr Ala Cys Trp Leu Arg Gly Asn Phe Ile Met Leu Leu Met
    450                 455                 460 tct ctc tac tcc atg ctg tac atg act ggg ctt ctg cca tcc aag tac       1440
Ser Leu Tyr Ser Met Leu Tyr Met Thr Gly Leu Leu Pro Ser Lys Tyr
465                 470                 475                 480 ttt gcc ttg ttg acc tta aac aag acc ggt tgg gga aca tct ggg cgc       1488
Phe Ala Leu Leu Thr Leu Asn Lys Thr Gly Trp Gly Thr Ser Gly Arg
                485                 490                 495 aag aag ata gta ggc aac tac atg cca ata ctg ccc ctg tcc ata tgg       1536
Lys Lys Ile Val Gly Asn Tyr Met Pro Ile Leu Pro Leu Ser Ile Trp
            500                 505                 510 gca gct gtt ctg tgt gga ggg gtg ggt tat agt atc tat atg gac tgt       1584
Ala Ala Val Leu Cys Gly Gly Val Gly Tyr Ser Ile Tyr Met Asp Cys
        515                 520                 525 caa aat gac tgg agc acc cct gaa aag caa aag gag atg tac cat cta       1632
Gln Asn Asp Trp Ser Thr Pro Glu Lys Gln Lys Glu Met Tyr His Leu
    530                 535                 540 ttg tat ggg tgt gtg ggc tat gta atg tac tgg gta atc atg gct gtg       1680
Leu Tyr Gly Cys Val Gly Tyr Val Met Tyr Trp Val Ile Met Ala Val
545                 550                 555                 560 atg tac tgg gtc tgg gtg aag agg tgc tgc agg aag agg tcc caa act       1728
Met Tyr Trp Val Trp Val Lys Arg Cys Cys Arg Lys Arg Ser Gln Thr
                565                 570                 575 gtc acc ctg gtc cat gac att cct gat atg tgt gtt taa                   1767
Val Thr Leu Val His Asp Ile Pro Asp Met Cys Val
            580                 585

<210> SEQ ID NO 42
<211> LENGTH: 588
<212> TYPE: PRT
```

<213> ORGANISM: Xenopus laevis

<400> SEQUENCE: 42

```
Met Lys Glu Lys Ala Ala Glu Thr Met Glu Ile Pro Glu Gly Ile Pro
1               5                   10                  15

Lys Asp Leu Glu Pro Lys His Pro Thr Leu Trp Arg Ile Ile Tyr Tyr
            20                  25                  30

Ser Phe Gly Val Val Leu Leu Ala Thr Ile Thr Ala Ala Tyr Val Ala
        35                  40                  45

Glu Phe Gln Val Leu Lys His Glu Ala Ile Leu Phe Ser Leu Gly Leu
    50                  55                  60

Tyr Gly Leu Ala Met Leu Leu His Leu Met Met Gln Ser Leu Phe Ala
65                  70                  75                  80

Phe Leu Glu Ile Arg Arg Val Asn Lys Ser Glu Leu Pro Cys Ser Phe
                85                  90                  95

Lys Lys Thr Val Ala Leu Thr Ile Ala Gly Tyr Gln Glu Asn Pro Glu
            100                 105                 110

Tyr Leu Ile Lys Cys Leu Glu Ser Cys Lys Tyr Val Lys Tyr Pro Lys
        115                 120                 125

Asp Lys Leu Lys Ile Ile Leu Val Ile Asp Gly Asn Thr Glu Asp Asp
    130                 135                 140

Ala Tyr Met Met Glu Met Phe Lys Asp Val Phe His Gly Glu Asp Val
145                 150                 155                 160

Gly Thr Tyr Val Trp Lys Gly Asn Tyr His Thr Val Lys Lys Pro Glu
                165                 170                 175

Glu Thr Asn Lys Gly Ser Cys Pro Glu Val Ser Lys Pro Leu Asn Glu
            180                 185                 190

Asp Glu Gly Ile Asn Met Val Glu Glu Leu Val Arg Asn Lys Arg Cys
        195                 200                 205

Val Cys Ile Met Gln Gln Trp Gly Gly Lys Arg Glu Val Met Tyr Thr
    210                 215                 220

Ala Phe Gln Ala Ile Gly Thr Ser Val Asp Tyr Val Gln Val Cys Asp
225                 230                 235                 240

Ser Asp Thr Lys Leu Asp Glu Leu Ala Thr Val Glu Met Val Lys Val
                245                 250                 255

Leu Glu Ser Asn Asp Met Tyr Gly Ala Val Gly Gly Asp Val Arg Ile
            260                 265                 270

Leu Asn Pro Tyr Asp Ser Phe Ile Ser Phe Met Ser Ser Leu Arg Tyr
        275                 280                 285

Trp Met Ala Phe Asn Val Glu Arg Ala Cys Gln Ser Tyr Phe Asp Cys
    290                 295                 300

Val Ser Cys Ile Ser Gly Pro Leu Gly Met Tyr Arg Asn Asn Ile Leu
305                 310                 315                 320

Gln Val Phe Leu Glu Ala Trp Tyr Arg Gln Lys Phe Leu Gly Thr Tyr
                325                 330                 335

Cys Thr Leu Gly Asp Asp Arg His Leu Thr Asn Arg Val Leu Ser Met
            340                 345                 350

Gly Tyr Arg Thr Lys Tyr Thr His Lys Ser Arg Ala Phe Ser Glu Thr
        355                 360                 365

Pro Ser Leu Tyr Leu Arg Trp Leu Asn Gln Gln Thr Arg Trp Thr Lys
    370                 375                 380

Ser Tyr Phe Arg Glu Trp Leu Tyr Asn Ala Gln Trp Trp His Lys His
385                 390                 395                 400
```

```
His Ile Trp Met Thr Tyr Glu Ser Val Val Ser Phe Ile Phe Pro Phe
                405                 410                 415

Phe Ile Thr Ala Thr Val Ile Arg Leu Ile Tyr Ala Gly Thr Ile Trp
            420                 425                 430

Asn Val Val Trp Leu Leu Leu Cys Ile Gln Ile Met Ser Leu Phe Lys
        435                 440                 445

Ser Ile Tyr Ala Cys Trp Leu Arg Gly Asn Phe Ile Met Leu Leu Met
450                 455                 460

Ser Leu Tyr Ser Met Leu Tyr Met Thr Gly Leu Leu Pro Ser Lys Tyr
465                 470                 475                 480

Phe Ala Leu Leu Thr Leu Asn Lys Thr Gly Trp Gly Thr Ser Gly Arg
                485                 490                 495

Lys Lys Ile Val Gly Asn Tyr Met Pro Ile Leu Pro Leu Ser Ile Trp
            500                 505                 510

Ala Ala Val Leu Cys Gly Gly Val Gly Tyr Ser Ile Tyr Met Asp Cys
        515                 520                 525

Gln Asn Asp Trp Ser Thr Pro Glu Lys Gln Lys Glu Met Tyr His Leu
530                 535                 540

Leu Tyr Gly Cys Val Gly Tyr Val Met Tyr Trp Val Ile Met Ala Val
545                 550                 555                 560

Met Tyr Trp Val Trp Val Lys Arg Cys Cys Arg Lys Arg Ser Gln Thr
                565                 570                 575

Val Thr Leu Val His Asp Ile Pro Asp Met Cys Val
            580                 585
```

```
<210> SEQ ID NO 43
<211> LENGTH: 1656
<212> TYPE: DNA
<213> ORGANISM: Xenopus laevis
<220> FEATURE:
<221> NAME/KEY: CDS
<222> LOCATION: (1)..(1656)
<223> OTHER INFORMATION: Hyaluronan synthase 2
<220> FEATURE:
<221> NAME/KEY: misc_feature
<222> LOCATION: (724)..(726)
<223> OTHER INFORMATION: gtr: gtg, gta
<220> FEATURE:
<221> NAME/KEY: misc_feature
<222> LOCATION: (796)..(798)
<223> OTHER INFORMATION: aty: att, atc

<400> SEQUENCE: 43
```

```
atg cac tgt gaa cgg ttt ata tgc atc ctg aga ata att ggg aca act    48
Met His Cys Glu Arg Phe Ile Cys Ile Leu Arg Ile Ile Gly Thr Thr
1               5                   10                  15 ctc ttc gga gtc tcc ttg tta ctt gga atc tca gct gct tat atc gtt    96
Leu Phe Gly Val Ser Leu Leu Leu Gly Ile Ser Ala Ala Tyr Ile Val
            20                  25                  30 ggt tac caa ttt atc caa aca gac aac tat tat ttc tca ttt gga ctc   144
Gly Tyr Gln Phe Ile Gln Thr Asp Asn Tyr Tyr Phe Ser Phe Gly Leu
        35                  40                  45 tat ggg gcg att tta gcc ctc cac ctt att atc caa agc ctt ttt gcc   192
Tyr Gly Ala Ile Leu Ala Leu His Leu Ile Ile Gln Ser Leu Phe Ala
50                  55                  60 ttt ctg gaa cac cga aaa atg aaa cga tct cta gaa acc ccc att aaa   240
Phe Leu Glu His Arg Lys Met Lys Arg Ser Leu Glu Thr Pro Ile Lys
65                  70                  75                  80 ctg aat aaa tca gtt gcc cta tgt att gct gca tat caa gag gac gaa   288
Leu Asn Lys Ser Val Ala Leu Cys Ile Ala Ala Tyr Gln Glu Asp Glu
                85                  90                  95
```

```
gac tac tta cgg aaa tgt tta ctt tcg gtc aag cgc ttg acg tac cca      336
Asp Tyr Leu Arg Lys Cys Leu Leu Ser Val Lys Arg Leu Thr Tyr Pro
            100                 105                 110 gga atg aaa gtc atc atg gtg atc gat gga aac tcg gac gat gat ctc      384
Gly Met Lys Val Ile Met Val Ile Asp Gly Asn Ser Asp Asp Asp Leu
            115                 120                 125 tac atg atg aat atc ttt cgt gag att atg ggg aat gac agc tgc gcc      432
Tyr Met Met Asn Ile Phe Arg Glu Ile Met Gly Asn Asp Ser Cys Ala
130                 135                 140 act tac gta tgg aaa aat aac ttc cac atg aaa ggc ccc aac gag acg      480
Thr Tyr Val Trp Lys Asn Asn Phe His Met Lys Gly Pro Asn Glu Thr
145                 150                 155                 160 gac gaa acg cac aga gag agc atg cag cac gta acg cag atg gtt ctc      528
Asp Glu Thr His Arg Glu Ser Met Gln His Val Thr Gln Met Val Leu
            165                 170                 175 tcc aat aga aac gtg tgc atc atg cag aaa tgg aat ggg aag aga gaa      576
Ser Asn Arg Asn Val Cys Ile Met Gln Lys Trp Asn Gly Lys Arg Glu
            180                 185                 190 gtc atg tac acc gcg ttc aag gca ctg ggg aga agt gtg gat tat gtg      624
Val Met Tyr Thr Ala Phe Lys Ala Leu Gly Arg Ser Val Asp Tyr Val
            195                 200                 205 cag gta tgt gat tct gac aca gtg ctt gat ccg gcg tca tca gtg gag      672
Gln Val Cys Asp Ser Asp Thr Val Leu Asp Pro Ala Ser Ser Val Glu
210                 215                 220 atg gtc aaa gta ctg gag gaa gac atc atg gtt gga gga gtg ggt gga      720
Met Val Lys Val Leu Glu Glu Asp Ile Met Val Gly Gly Val Gly Gly
225                 230                 235                 240 gat gtr cag att tta aac aag tac gac tca tgg att tcc ttc ctg agt      768
Asp Xaa Gln Ile Leu Asn Lys Tyr Asp Ser Trp Ile Ser Phe Leu Ser
            245                 250                 255 agc gtc aga tac tgg atg gcg ttt aac aty gag aga gca tgc cag tct      816
Ser Val Arg Tyr Trp Met Ala Phe Asn Xaa Glu Arg Ala Cys Gln Ser
            260                 265                 270 tac ttt ggc tgt gtg caa tgc att agc ggc ccg ttg ggg atg tac cgc      864
Tyr Phe Gly Cys Val Gln Cys Ile Ser Gly Pro Leu Gly Met Tyr Arg
            275                 280                 285 aat tcc ctt ctc cac gaa ttc att gaa gac tgg tac aac caa gaa ttt      912
Asn Ser Leu Leu His Glu Phe Ile Glu Asp Trp Tyr Asn Gln Glu Phe
290                 295                 300 ttg ggt tcc cag tgc agt ttt ggg gat gac cgt cac cta acc aat cga      960
Leu Gly Ser Gln Cys Ser Phe Gly Asp Asp Arg His Leu Thr Asn Arg
305                 310                 315                 320 gtt ttg agt ctg ggc tat gca acc aaa tac acg gcc aga tcc aaa tgc     1008
Val Leu Ser Leu Gly Tyr Ala Thr Lys Tyr Thr Ala Arg Ser Lys Cys
            325                 330                 335 ctt act gaa aca ccc acc gag tac ctg cgg tgg ctc aac cag caa acg     1056
Leu Thr Glu Thr Pro Thr Glu Tyr Leu Arg Trp Leu Asn Gln Gln Thr
            340                 345                 350 cga tgg agc aag tcc tac ttc cga gaa tgg ctg tac aat tca ttg tgg     1104
Arg Trp Ser Lys Ser Tyr Phe Arg Glu Trp Leu Tyr Asn Ser Leu Trp
            355                 360                 365 ttc cat aaa cat cac tta tgg atg acc tac gaa gct gtg att act gga     1152
Phe His Lys His His Leu Trp Met Thr Tyr Glu Ala Val Ile Thr Gly
370                 375                 380 ttc ttt cct ttc ttc ctc atc gcc act gtc atc cag ctc ttc tac cgt     1200
Phe Phe Pro Phe Phe Leu Ile Ala Thr Val Ile Gln Leu Phe Tyr Arg
385                 390                 395                 400 gga agg atc tgg aac atc ctc ctg ttc ttg ctg aca gta caa ctt gta     1248
Gly Arg Ile Trp Asn Ile Leu Leu Phe Leu Leu Thr Val Gln Leu Val
```

-continued

```
                        405                 410                 415
ggc ctt atc aaa tct tcc ttt gct agt gcc ctc cga ggg aac ata gtc    1296
Gly Leu Ile Lys Ser Ser Phe Ala Ser Ala Leu Arg Gly Asn Ile Val
            420                 425                 430 atg gtc ttc atg tcc ttc tac tca gtg tta tac atg tcc agt tta cta    1344
Met Val Phe Met Ser Phe Tyr Ser Val Leu Tyr Met Ser Ser Leu Leu
        435                 440                 445 cct gcc aaa atg ttt gcc att gcc acc atc aac aag gca ggt tgg ggc    1392
Pro Ala Lys Met Phe Ala Ile Ala Thr Ile Asn Lys Ala Gly Trp Gly
450                 455                 460 aca tca gga agg aag aca ata gtt gtg aat ttt ata gga ctg att cct    1440
Thr Ser Gly Arg Lys Thr Ile Val Val Asn Phe Ile Gly Leu Ile Pro
465                 470                 475                 480 ata acc gtt tgg ttt aca att ctc ctt ggg ggc gtc tgc tac act att    1488
Ile Thr Val Trp Phe Thr Ile Leu Leu Gly Gly Val Cys Tyr Thr Ile
                485                 490                 495 tgg agg gaa aca aaa aag cca ttt tca gaa tct gaa aag ata gtt ctc    1536
Trp Arg Glu Thr Lys Lys Pro Phe Ser Glu Ser Glu Lys Ile Val Leu
            500                 505                 510 gcc gtt ggt gca ata ctt tac gca tgc tac tgg gtc atg ctt ttg act    1584
Ala Val Gly Ala Ile Leu Tyr Ala Cys Tyr Trp Val Met Leu Leu Thr
        515                 520                 525 atg tat gtt tct ctc gtc atg aar tgt ggc agg cgg aga aag gaa cca    1632
Met Tyr Val Ser Leu Val Met Lys Cys Gly Arg Arg Arg Lys Glu Pro
530                 535                 540 caa cat gac ttg gtg ctt gct tga                                    1656
Gln His Asp Leu Val Leu Ala
545                 550

<210> SEQ ID NO 44
<211> LENGTH: 551
<212> TYPE: PRT
<213> ORGANISM: Xenopus laevis
<220> FEATURE:
<221> NAME/KEY: misc_feature
<222> LOCATION: (242)..(242)
<223> OTHER INFORMATION: Xaa: Val
<220> FEATURE:
<221> NAME/KEY: misc_feature
<222> LOCATION: (266)..(266)
<223> OTHER INFORMATION: Xaa: Ile
<220> FEATURE:
<221> NAME/KEY: misc_feature
<222> LOCATION: (724)..(726)
<223> OTHER INFORMATION: gtr: gtg, gta
<220> FEATURE:
<221> NAME/KEY: misc_feature
<222> LOCATION: (796)..(798)
<223> OTHER INFORMATION: aty: att, atc

<400> SEQUENCE: 44

Met His Cys Glu Arg Phe Ile Cys Ile Leu Arg Ile Ile Gly Thr Thr
1               5                   10                  15

Leu Phe Gly Val Ser Leu Leu Gly Ile Ser Ala Ala Tyr Ile Val
            20                  25                  30

Gly Tyr Gln Phe Ile Gln Thr Asp Asn Tyr Tyr Phe Ser Phe Gly Leu
        35                  40                  45

Tyr Gly Ala Ile Leu Ala Leu His Leu Ile Gln Ser Leu Phe Ala
    50                  55                  60

Phe Leu Glu His Arg Lys Met Lys Arg Ser Leu Glu Thr Pro Ile Lys
65                  70                  75                  80

Leu Asn Lys Ser Val Ala Leu Cys Ile Ala Ala Tyr Gln Glu Asp Glu
                85                  90                  95
```

```
Asp Tyr Leu Arg Lys Cys Leu Leu Ser Val Lys Arg Leu Thr Tyr Pro
            100                 105                 110

Gly Met Lys Val Ile Met Val Ile Asp Gly Asn Ser Asp Asp Asp Leu
        115                 120                 125

Tyr Met Met Asn Ile Phe Arg Glu Ile Met Gly Asn Asp Ser Cys Ala
    130                 135                 140

Thr Tyr Val Trp Lys Asn Asn Phe His Met Lys Gly Pro Asn Glu Thr
145                 150                 155                 160

Asp Glu Thr His Arg Glu Ser Met Gln His Val Thr Gln Met Val Leu
                165                 170                 175

Ser Asn Arg Asn Val Cys Ile Met Gln Lys Trp Asn Gly Lys Arg Glu
            180                 185                 190

Val Met Tyr Thr Ala Phe Lys Ala Leu Gly Arg Ser Val Asp Tyr Val
        195                 200                 205

Gln Val Cys Asp Ser Asp Thr Val Leu Asp Pro Ala Ser Ser Val Glu
    210                 215                 220

Met Val Lys Val Leu Glu Glu Asp Ile Met Val Gly Gly Val Gly Gly
225                 230                 235                 240

Asp Xaa Gln Ile Leu Asn Lys Tyr Asp Ser Trp Ile Ser Phe Leu Ser
                245                 250                 255

Ser Val Arg Tyr Trp Met Ala Phe Asn Xaa Glu Arg Ala Cys Gln Ser
            260                 265                 270

Tyr Phe Gly Cys Val Gln Cys Ile Ser Gly Pro Leu Gly Met Tyr Arg
        275                 280                 285

Asn Ser Leu Leu His Glu Phe Ile Glu Asp Trp Tyr Asn Gln Glu Phe
    290                 295                 300

Leu Gly Ser Gln Cys Ser Phe Gly Asp Asp Arg His Leu Thr Asn Arg
305                 310                 315                 320

Val Leu Ser Leu Gly Tyr Ala Thr Lys Tyr Thr Ala Arg Ser Lys Cys
                325                 330                 335

Leu Thr Glu Thr Pro Thr Glu Tyr Leu Arg Trp Leu Asn Gln Gln Thr
            340                 345                 350

Arg Trp Ser Lys Ser Tyr Phe Arg Glu Trp Leu Tyr Asn Ser Leu Trp
        355                 360                 365

Phe His Lys His His Leu Trp Met Thr Tyr Glu Ala Val Ile Thr Gly
    370                 375                 380

Phe Phe Pro Phe Phe Leu Ile Ala Thr Val Ile Gln Leu Phe Tyr Arg
385                 390                 395                 400

Gly Arg Ile Trp Asn Ile Leu Leu Phe Leu Leu Thr Val Gln Leu Val
                405                 410                 415

Gly Leu Ile Lys Ser Ser Phe Ala Ser Ala Leu Arg Gly Asn Ile Val
            420                 425                 430

Met Val Phe Met Ser Phe Tyr Ser Val Leu Tyr Met Ser Ser Leu Leu
        435                 440                 445

Pro Ala Lys Met Phe Ala Ile Ala Thr Ile Asn Lys Ala Gly Trp Gly
    450                 455                 460

Thr Ser Gly Arg Lys Thr Ile Val Val Asn Phe Ile Gly Leu Ile Pro
465                 470                 475                 480

Ile Thr Val Trp Phe Thr Ile Leu Leu Gly Gly Val Cys Tyr Thr Ile
                485                 490                 495

Trp Arg Glu Thr Lys Lys Pro Phe Ser Glu Ser Glu Lys Ile Val Leu
            500                 505                 510
```

| | |
|---|---|
| Ala Val Gly Ala Ile Leu Tyr Ala Cys Tyr Trp Val Met Leu Leu Thr<br>     515                   520                   525 | |
| Met Tyr Val Ser Leu Val Met Lys Cys Gly Arg Arg Arg Lys Glu Pro<br>530                   535               540 | |
| Gln His Asp Leu Val Leu Ala<br>545                 550 | |

<210> SEQ ID NO 45
<211> LENGTH: 1674
<212> TYPE: DNA
<213> ORGANISM: Xenopus laevis
<220> FEATURE:
<221> NAME/KEY: CDS
<222> LOCATION: (1)..(1674)
<223> OTHER INFORMATION: Hyaluronan synthase 3
<300> PUBLICATION INFORMATION:
<308> DATABASE ACCESSION NUMBER: AY302252.1
<309> DATABASE ENTRY DATE: 2003-11-30
<313> RELEVANT RESIDUES IN SEQ ID NO: (102)..(1775)

<400> SEQUENCE: 45

| | |
|---|---:|
| atg cct ggg aag ttt cag acc ggc ctt agg gtg cta gcc act tgc ctc<br>Met Pro Gly Lys Phe Gln Thr Gly Leu Arg Val Leu Ala Thr Cys Leu<br>1                 5                    10                 15 | 48 |
| ttt gct ctg ctg gtg ttg ggg ggc atc ttg gtt gca tat gtg aca ggg<br>Phe Ala Leu Leu Val Leu Gly Gly Ile Leu Val Ala Tyr Val Thr Gly<br>                 20                    25                    30 | 96 |
| tac caa ttt att cat acc gat cgc cac cat ctc tca ttt ggc cta tac<br>Tyr Gln Phe Ile His Thr Asp Arg His His Leu Ser Phe Gly Leu Tyr<br>                 35                    40                   45 | 144 |
| gga gcc atc ctg ggt ctc cat tta ctc tct cag agc ctc ttt gct ttt<br>Gly Ala Ile Leu Gly Leu His Leu Leu Ser Gln Ser Leu Phe Ala Phe<br>50                   55                 60 | 192 |
| ttg gag cac agg aag atg cga gga ggt ggg cgg tgt cct tca gga aag<br>Leu Glu His Arg Lys Met Arg Gly Gly Gly Arg Cys Pro Ser Gly Lys<br>65                   70                    75                80 | 240 |
| tcc aca gtg gtg ctt tgt att gca gca tat caa gag gac cca gag tac<br>Ser Thr Val Val Leu Cys Ile Ala Ala Tyr Gln Glu Asp Pro Glu Tyr<br>                 85                    90                   95 | 288 |
| tta cgg aaa tgt ctg cga tca gtg cgc cgc ctc tca tat cct cac ctt<br>Leu Arg Lys Cys Leu Arg Ser Val Arg Arg Leu Ser Tyr Pro His Leu<br>                 100                  105              110 | 336 |
| cgt gtg atc atg gtg gtg gat ggg aat aca gaa gag gac aga tat atg<br>Arg Val Ile Met Val Val Asp Gly Asn Thr Glu Glu Asp Arg Tyr Met<br>                 115                  120              125 | 384 |
| atg gac ata ttc cga gag gtc atg gga tca gag gga acc tgc tgc tac<br>Met Asp Ile Phe Arg Glu Val Met Gly Ser Glu Gly Thr Cys Cys Tyr<br>130                   135                    140 | 432 |
| att tgg gac aaa aat tac cat gaa tca gag gag gga caa gag ggt<br>Ile Trp Asp Lys Asn Tyr His Glu Ser Glu Glu Gly Gln Glu Gly<br>145                  150                155              160 | 480 |
| gag agg gga gta cag gag atg gtg aag aac ttc cag tat gtc tgc atc<br>Glu Arg Gly Val Gln Glu Met Val Lys Asn Phe Gln Tyr Val Cys Ile<br>                 165                  170              175 | 528 |
| atg cag aag tgg ggt gga aaa agg gaa gtc acg tat act gcg ttt cgt<br>Met Gln Lys Trp Gly Gly Lys Arg Glu Val Thr Tyr Thr Ala Phe Arg<br>180                   185                    190 | 576 |
| gca ctt gga gac agt gtg gct tat gtg cag gtc tgt gac tct gac act<br>Ala Leu Gly Asp Ser Val Ala Tyr Val Gln Val Cys Asp Ser Asp Thr<br>                 195                  200              205 | 624 |
| gtg tta gac cca gct tgc acc gct gag atg ctg cgc att ttg gaa gaa<br>Val Leu Asp Pro Ala Cys Thr Ala Glu Met Leu Arg Ile Leu Glu Glu | 672 |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     |     | 210 |     |     |     |     | 215 |     |     |     |     | 220 |     |     |     |      |
| gat | cct | gaa | gtg | ggg | gga | gta | ggt | gga | gat | gtg | cag | atc | ctg | aat | aag | 720  |
| Asp | Pro | Glu | Val | Gly | Gly | Val | Gly | Gly | Asp | Val | Gln | Ile | Leu | Asn | Lys |      |
| 225 |     |     |     |     | 230 |     |     |     |     | 235 |     |     |     |     | 240 |      |
| tac | gaa | tcg | tgg | atc | tca | ttt | ctg | agc | agt | ttc | cgc | tac | tgg | atg | gca | 768  |
| Tyr | Glu | Ser | Trp | Ile | Ser | Phe | Leu | Ser | Ser | Phe | Arg | Tyr | Trp | Met | Ala |      |
|     |     |     |     | 245 |     |     |     |     | 250 |     |     |     |     | 255 |     |      |
| ttc | aat | gtg | gaa | cgg | gcc | tgc | cag | tcc | tac | ttt | ggc | tgt | gtc | cag | tgc | 816  |
| Phe | Asn | Val | Glu | Arg | Ala | Cys | Gln | Ser | Tyr | Phe | Gly | Cys | Val | Gln | Cys |      |
|     |     |     | 260 |     |     |     |     | 265 |     |     |     |     | 270 |     |     |      |
| atc | agt | ggc | cca | ctg | gga | atg | tat | agg | aac | agt | ctt | ttg | cag | tac | ttt | 864  |
| Ile | Ser | Gly | Pro | Leu | Gly | Met | Tyr | Arg | Asn | Ser | Leu | Leu | Gln | Tyr | Phe |      |
|     |     | 275 |     |     |     |     | 280 |     |     |     |     | 285 |     |     |     |      |
| tta | gaa | gat | tgg | tac | cat | caa | aca | ttt | ttg | ggg | cag | aag | tgt | agc | ttt | 912  |
| Leu | Glu | Asp | Trp | Tyr | His | Gln | Thr | Phe | Leu | Gly | Gln | Lys | Cys | Ser | Phe |      |
|     | 290 |     |     |     |     | 295 |     |     |     |     | 300 |     |     |     |     |      |
| gga | gat | gac | aga | cat | ctc | acg | aac | cgt | gta | cta | agc | atg | gga | ttc | cga | 960  |
| Gly | Asp | Asp | Arg | His | Leu | Thr | Asn | Arg | Val | Leu | Ser | Met | Gly | Phe | Arg |      |
| 305 |     |     |     |     | 310 |     |     |     |     | 315 |     |     |     |     | 320 |      |
| acg | aag | tat | aca | gct | cgc | tct | cgt | tgc | ctg | aca | gag | aca | cca | acg | cgg | 1008 |
| Thr | Lys | Tyr | Thr | Ala | Arg | Ser | Arg | Cys | Leu | Thr | Glu | Thr | Pro | Thr | Arg |      |
|     |     |     |     | 325 |     |     |     |     | 330 |     |     |     |     | 335 |     |      |
| tat | ttg | cgc | tgg | ttg | aac | caa | caa | acg | cgc | tgg | agc | aaa | tca | tac | ttc | 1056 |
| Tyr | Leu | Arg | Trp | Leu | Asn | Gln | Gln | Thr | Arg | Trp | Ser | Lys | Ser | Tyr | Phe |      |
|     |     |     | 340 |     |     |     |     | 345 |     |     |     |     | 350 |     |     |      |
| cgt | gag | tgg | cta | tac | aat | gca | ctg | tgg | ttc | cac | aaa | cac | cac | ctt | tgg | 1104 |
| Arg | Glu | Trp | Leu | Tyr | Asn | Ala | Leu | Trp | Phe | His | Lys | His | His | Leu | Trp |      |
|     |     | 355 |     |     |     |     | 360 |     |     |     |     | 365 |     |     |     |      |
| atg | acc | tat | gaa | tct | gtg | gtt | act | ggc | ttc | ttt | ccc | ttc | ttc | ttg | gtg | 1152 |
| Met | Thr | Tyr | Glu | Ser | Val | Val | Thr | Gly | Phe | Phe | Pro | Phe | Phe | Leu | Val |      |
|     | 370 |     |     |     |     | 375 |     |     |     |     | 380 |     |     |     |     |      |
| gcc | aca | gtg | gtt | caa | cta | ttt | tat | cgt | ggc | cgt | gtt | tgg | aat | att | ctt | 1200 |
| Ala | Thr | Val | Val | Gln | Leu | Phe | Tyr | Arg | Gly | Arg | Val | Trp | Asn | Ile | Leu |      |
| 385 |     |     |     |     | 390 |     |     |     |     | 395 |     |     |     |     | 400 |      |
| ctt | ttt | cta | ttg | acc | gta | cag | ctt | gtt | ggt | att | ttg | aag | gca | acc | tat | 1248 |
| Leu | Phe | Leu | Leu | Thr | Val | Gln | Leu | Val | Gly | Ile | Leu | Lys | Ala | Thr | Tyr |      |
|     |     |     |     | 405 |     |     |     |     | 410 |     |     |     |     | 415 |     |      |
| gcc | tgt | atc | ctt | cga | ggt | aat | gct | gaa | atg | att | ttc | atg | tca | ctt | tat | 1296 |
| Ala | Cys | Ile | Leu | Arg | Gly | Asn | Ala | Glu | Met | Ile | Phe | Met | Ser | Leu | Tyr |      |
|     |     |     | 420 |     |     |     |     | 425 |     |     |     |     | 430 |     |     |      |
| tca | ctt | ctc | tac | atg | act | agc | ctt | ctg | cct | gcc | aaa | ata | ttc | gca | gtg | 1344 |
| Ser | Leu | Leu | Tyr | Met | Thr | Ser | Leu | Leu | Pro | Ala | Lys | Ile | Phe | Ala | Val |      |
|     |     | 435 |     |     |     |     | 440 |     |     |     |     | 445 |     |     |     |      |
| atc | acc | atc | aaa | aag | tct | ggc | tgg | ggg | act | tca | ggg | cgc | agg | aag | ctg | 1392 |
| Ile | Thr | Ile | Lys | Lys | Ser | Gly | Trp | Gly | Thr | Ser | Gly | Arg | Arg | Lys | Leu |      |
|     | 450 |     |     |     |     | 455 |     |     |     |     | 460 |     |     |     |     |      |
| gtg | gtg | aat | ttt | atg | ggt | atg | gtg | ccc | gtg | tct | gtc | tgg | ttt | tgc | att | 1440 |
| Val | Val | Asn | Phe | Met | Gly | Met | Val | Pro | Val | Ser | Val | Trp | Phe | Cys | Ile |      |
| 465 |     |     |     |     | 470 |     |     |     |     | 475 |     |     |     |     | 480 |      |
| ctg | ctg | gga | gga | tta | gta | tac | aca | gca | tat | tgt | cag | agt | cat | gat | ccg | 1488 |
| Leu | Leu | Gly | Gly | Leu | Val | Tyr | Thr | Ala | Tyr | Cys | Gln | Ser | His | Asp | Pro |      |
|     |     |     |     | 485 |     |     |     |     | 490 |     |     |     |     | 495 |     |      |
| ttc | acc | gaa | aca | gaa | ctg | tta | ttc | ctg | ttg | aca | ggt | gcc | atc | tta | tac | 1536 |
| Phe | Thr | Glu | Thr | Glu | Leu | Leu | Phe | Leu | Leu | Thr | Gly | Ala | Ile | Leu | Tyr |      |
|     |     |     | 500 |     |     |     |     | 505 |     |     |     |     | 510 |     |     |      |
| gga | tgt | tat | tgg | gtg | gca | ctt | ctc | agt | tta | tat | ctt | gct | tta | att | gcc | 1584 |
| Gly | Cys | Tyr | Trp | Val | Ala | Leu | Leu | Ser | Leu | Tyr | Leu | Ala | Leu | Ile | Ala |      |
|     |     | 515 |     |     |     |     | 520 |     |     |     |     | 525 |     |     |     |      |
| cgg | cgg | tgt | ggg | aag | aga | caa | gag | ctg | tac | aac | tta | gca | ttg | gag | gaa | 1632 |

```
Arg Arg Cys Gly Lys Arg Gln Glu Leu Tyr Asn Leu Ala Leu Glu Glu
            530                 535                 540 gtc tca gaa cca gag cca gct gcc aaa gca ata aag cct taa              1674
Val Ser Glu Pro Glu Pro Ala Ala Lys Ala Ile Lys Pro
545                 550                 555
```

<210> SEQ ID NO 46
<211> LENGTH: 557
<212> TYPE: PRT
<213> ORGANISM: Xenopus laevis

<400> SEQUENCE: 46

```
Met Pro Gly Lys Phe Gln Thr Gly Leu Arg Val Leu Ala Thr Cys Leu
1               5                   10                  15

Phe Ala Leu Leu Val Leu Gly Gly Ile Leu Val Ala Tyr Val Thr Gly
                20                  25                  30

Tyr Gln Phe Ile His Thr Asp Arg His His Leu Ser Phe Gly Leu Tyr
            35                  40                  45

Gly Ala Ile Leu Gly Leu His Leu Leu Ser Gln Ser Leu Phe Ala Phe
        50                  55                  60

Leu Glu His Arg Lys Met Arg Gly Gly Arg Cys Pro Ser Gly Lys
65                  70                  75                  80

Ser Thr Val Val Leu Cys Ile Ala Ala Tyr Gln Glu Asp Pro Glu Tyr
                85                  90                  95

Leu Arg Lys Cys Leu Arg Ser Val Arg Arg Leu Ser Tyr Pro His Leu
            100                 105                 110

Arg Val Ile Met Val Val Asp Gly Asn Thr Glu Glu Asp Arg Tyr Met
        115                 120                 125

Met Asp Ile Phe Arg Glu Val Met Gly Ser Glu Gly Thr Cys Cys Tyr
130                 135                 140

Ile Trp Asp Lys Asn Tyr His Glu Ser Glu Glu Gly Gln Glu Gly
145                 150                 155                 160

Glu Arg Gly Val Gln Glu Met Val Lys Asn Phe Gln Tyr Val Cys Ile
                165                 170                 175

Met Gln Lys Trp Gly Gly Lys Arg Glu Val Thr Tyr Thr Ala Phe Arg
            180                 185                 190

Ala Leu Gly Asp Ser Val Ala Tyr Val Gln Val Cys Asp Ser Asp Thr
        195                 200                 205

Val Leu Asp Pro Ala Cys Thr Ala Glu Met Leu Arg Ile Leu Glu Glu
210                 215                 220

Asp Pro Glu Val Gly Gly Val Gly Gly Asp Val Gln Ile Leu Asn Lys
225                 230                 235                 240

Tyr Glu Ser Trp Ile Ser Phe Leu Ser Ser Phe Arg Tyr Trp Met Ala
                245                 250                 255

Phe Asn Val Glu Arg Ala Cys Gln Ser Tyr Phe Gly Cys Val Gln Cys
            260                 265                 270

Ile Ser Gly Pro Leu Gly Met Tyr Arg Asn Ser Leu Leu Gln Tyr Phe
        275                 280                 285

Leu Glu Asp Trp Tyr His Gln Thr Phe Leu Gly Gln Lys Cys Ser Phe
    290                 295                 300

Gly Asp Asp Arg His Leu Thr Asn Arg Val Leu Ser Met Gly Phe Arg
305                 310                 315                 320

Thr Lys Tyr Thr Ala Arg Ser Arg Cys Leu Thr Glu Thr Pro Thr Arg
                325                 330                 335

Tyr Leu Arg Trp Leu Asn Gln Gln Thr Arg Trp Ser Lys Ser Tyr Phe
```

-continued

```
                    340                 345                 350
Arg Glu Trp Leu Tyr Asn Ala Leu Trp Phe His Lys His His Leu Trp
                355                 360                 365

Met Thr Tyr Glu Ser Val Val Thr Gly Phe Phe Pro Phe Phe Leu Val
            370                 375                 380

Ala Thr Val Val Gln Leu Phe Tyr Arg Gly Arg Val Trp Asn Ile Leu
385                 390                 395                 400

Leu Phe Leu Leu Thr Val Gln Leu Val Gly Ile Leu Lys Ala Thr Tyr
                405                 410                 415

Ala Cys Ile Leu Arg Gly Asn Ala Glu Met Ile Phe Met Ser Leu Tyr
            420                 425                 430

Ser Leu Leu Tyr Met Thr Ser Leu Leu Pro Ala Lys Ile Phe Ala Val
                435                 440                 445

Ile Thr Ile Lys Lys Ser Gly Trp Gly Thr Ser Gly Arg Arg Lys Leu
            450                 455                 460

Val Val Asn Phe Met Gly Met Val Pro Val Ser Val Trp Phe Cys Ile
465                 470                 475                 480

Leu Leu Gly Gly Leu Val Tyr Thr Ala Tyr Cys Gln Ser His Asp Pro
                485                 490                 495

Phe Thr Glu Thr Glu Leu Leu Phe Leu Leu Thr Gly Ala Ile Leu Tyr
            500                 505                 510

Gly Cys Tyr Trp Val Ala Leu Leu Ser Leu Tyr Leu Ala Leu Ile Ala
                515                 520                 525

Arg Arg Cys Gly Lys Arg Gln Glu Leu Tyr Asn Leu Ala Leu Glu Glu
            530                 535                 540

Val Ser Glu Pro Glu Pro Ala Ala Lys Ala Ile Lys Pro
545                 550                 555
```

<210> SEQ ID NO 47
<211> LENGTH: 1659
<212> TYPE: DNA
<213> ORGANISM: Danio rerio
<220> FEATURE:
<221> NAME/KEY: CDS
<222> LOCATION: (1)..(1659)
<223> OTHER INFORMATION: Hyaluronan synthase 2
<300> PUBLICATION INFORMATION:
<308> DATABASE ACCESSION NUMBER: AF190742.1
<309> DATABASE ENTRY DATE: 2000-10-02
<313> RELEVANT RESIDUES IN SEQ ID NO: (34)..(1692)

<400> SEQUENCE: 47

```
atg aga tgt gat aaa gcg gtc agc tac tta agg att gtt ggg acg aca        48
Met Arg Cys Asp Lys Ala Val Ser Tyr Leu Arg Ile Val Gly Thr Thr
1               5                   10                  15 ctg ttc ggc att tca ctg ctt gtg gga atc tct act gct tat atc atg        96
Leu Phe Gly Ile Ser Leu Leu Val Gly Ile Ser Thr Ala Tyr Ile Met
            20                  25                  30 ggg tat aag ctt gta aca act ccg ggc aac tat ttg tcc ttt ggt ctt       144
Gly Tyr Lys Leu Val Thr Thr Pro Gly Asn Tyr Leu Ser Phe Gly Leu
        35                  40                  45 tat gga gca att ctt gtc atc cac ctc atc atc caa agt gtg ttt gcc       192
Tyr Gly Ala Ile Leu Val Ile His Leu Ile Ile Gln Ser Val Phe Ala
    50                  55                  60 cta ctg gaa cac agg aac atg aaa cgc tcc ctg gaa aca cca atc aaa       240
Leu Leu Glu His Arg Asn Met Lys Arg Ser Leu Glu Thr Pro Ile Lys
65                  70                  75                  80 ctc aac aag tca ctg gcc cta tgc atc gca gcc tat cag gaa gac ccc       288
Leu Asn Lys Ser Leu Ala Leu Cys Ile Ala Ala Tyr Gln Glu Asp Pro
```

```
                     85                   90                   95
aac tac ctg aga aag tgt tta ata tca gtg aag agg ctc acg tat ccg       336
Asn Tyr Leu Arg Lys Cys Leu Ile Ser Val Lys Arg Leu Thr Tyr Pro
            100                 105                 110 ggt ata aag gtc ata atg gtt atc gat ggg aac aac gat gat gac tgc       384
Gly Ile Lys Val Ile Met Val Ile Asp Gly Asn Asn Asp Asp Asp Cys
        115                 120                 125 tac atg atg gag atc ttt cga gaa atc atg ggc cgg gac aag gca gcc       432
Tyr Met Met Glu Ile Phe Arg Glu Ile Met Gly Arg Asp Lys Ala Ala
    130                 135                 140 acg tac att tgg aaa agc aac tat cac cat aga gga ccc gaa gaa act       480
Thr Tyr Ile Trp Lys Ser Asn Tyr His His Arg Gly Pro Glu Glu Thr
145                 150                 155                 160 gaa gaa tca tac gca aca agc ttg cag cat gtt tct cac ctg gtt ctc       528
Glu Glu Ser Tyr Ala Thr Ser Leu Gln His Val Ser His Leu Val Leu
                165                 170                 175 aat aat aag tgt gtg tgc atc atg cag aag tgg ggc ggg aaa aga gag       576
Asn Asn Lys Cys Val Cys Ile Met Gln Lys Trp Gly Gly Lys Arg Glu
            180                 185                 190 gtc atg tac acc gcc ttc aaa gcc ctg gga aga agt gtt gac tat gta       624
Val Met Tyr Thr Ala Phe Lys Ala Leu Gly Arg Ser Val Asp Tyr Val
        195                 200                 205 cag gtt tgt gat tca gac acc atg ctg gac ccg gcc tcc tct gta gag       672
Gln Val Cys Asp Ser Asp Thr Met Leu Asp Pro Ala Ser Ser Val Glu
    210                 215                 220 atg gtg aag gtt cta gaa gaa gat ccc aat gtt gga gga gta ggt gga       720
Met Val Lys Val Leu Glu Glu Asp Pro Asn Val Gly Gly Val Gly Gly
225                 230                 235                 240 gat gtg cag ata ttg aac aaa tat gag tcg tgg gtc tcc ttc ctg agc       768
Asp Val Gln Ile Leu Asn Lys Tyr Glu Ser Trp Val Ser Phe Leu Ser
                245                 250                 255 agc gtg agg tat tgg atg gcg ttc aac att gaa aga gcc tgc cag tca       816
Ser Val Arg Tyr Trp Met Ala Phe Asn Ile Glu Arg Ala Cys Gln Ser
            260                 265                 270 tat ttc ggg tgc gtt caa tgt atc agc gga ccc ttg gga atg tac agg       864
Tyr Phe Gly Cys Val Gln Cys Ile Ser Gly Pro Leu Gly Met Tyr Arg
        275                 280                 285 aac tcc ctc ctc cat gag ttc ctg gag gac tgg tat gat cag aca ttc       912
Asn Ser Leu Leu His Glu Phe Leu Glu Asp Trp Tyr Asp Gln Thr Phe
    290                 295                 300 atg gga agc cac tgc agt ttt ggc gat gac cgc cat ctg acc aat cga       960
Met Gly Ser His Cys Ser Phe Gly Asp Asp Arg His Leu Thr Asn Arg
305                 310                 315                 320 gta ctg agc ttg gga tat gcc acg aaa tac acc gcg cgc tcc aag tgc      1008
Val Leu Ser Leu Gly Tyr Ala Thr Lys Tyr Thr Ala Arg Ser Lys Cys
                325                 330                 335 ttg acc gag acg ccc att acc tac ctg cgc tgg ctc aac caa caa acc      1056
Leu Thr Glu Thr Pro Ile Thr Tyr Leu Arg Trp Leu Asn Gln Gln Thr
            340                 345                 350 cgc tgg agt aaa tcc tat ttc aga gag tgg ctt tac aac tcc ttg tgg      1104
Arg Trp Ser Lys Ser Tyr Phe Arg Glu Trp Leu Tyr Asn Ser Leu Trp
        355                 360                 365 ttc cac aag cac cac ttg tgg atg acc tac gag gcc gtc atc acc ggc      1152
Phe His Lys His His Leu Trp Met Thr Tyr Glu Ala Val Ile Thr Gly
    370                 375                 380 ttc ttc ccg ttc ttc ctt atc gcc act gcc att caa ctg ttc tac cag      1200
Phe Phe Pro Phe Phe Leu Ile Ala Thr Ala Ile Gln Leu Phe Tyr Gln
385                 390                 395                 400 ggc agg atc tgg aat atc ctt ctg ttc ctg ctg atc gtc cag gtc gtg      1248
```

```
Gly Arg Ile Trp Asn Ile Leu Leu Phe Leu Leu Ile Val Gln Val Val
                405                 410                 415 gca ctc ata aag tcc tca ttt gcc agt tgc ctc cga ggc aac ata gtc    1296
Ala Leu Ile Lys Ser Ser Phe Ala Ser Cys Leu Arg Gly Asn Ile Val
                420                 425                 430 atg gtc ttc atg tca ttc tac tca gtg tta tac atg tca agt ctg cta   1344
Met Val Phe Met Ser Phe Tyr Ser Val Leu Tyr Met Ser Ser Leu Leu
                435                 440                 445 ccg gca aaa atg ttt gca ata gcc acc ata aac aaa tcc gga tgg gga   1392
Pro Ala Lys Met Phe Ala Ile Ala Thr Ile Asn Lys Ser Gly Trp Gly
    450                 455                 460 acg tct gga agg aag acc gtg gtg gtg aac ttc atc gga ctc att cca   1440
Thr Ser Gly Arg Lys Thr Val Val Val Asn Phe Ile Gly Leu Ile Pro
465                 470                 475                 480 atc tca att tgg ttc act att ctt ttc gtt ggc att att tat acc ata   1488
Ile Ser Ile Trp Phe Thr Ile Leu Phe Val Gly Ile Ile Tyr Thr Ile
                485                 490                 495 atc caa gag acg cga aaa ccc ttt cct gaa tcc gaa aag gtg gtt ttg   1536
Ile Gln Glu Thr Arg Lys Pro Phe Pro Glu Ser Glu Lys Val Val Leu
                500                 505                 510 ata att ggc gca atc gtt tat atc agc tac tgg gtt gtg ttt ttg act   1584
Ile Ile Gly Ala Ile Val Tyr Ile Ser Tyr Trp Val Val Phe Leu Thr
                515                 520                 525 ttg tac gct gtc ctc att atg aag tgt ggc aag agg aag aaa gga cag   1632
Leu Tyr Ala Val Leu Ile Met Lys Cys Gly Lys Arg Lys Lys Gly Gln
    530                 535                 540 cag tat gac atg gtt ctt gac gta tag                                1659
Gln Tyr Asp Met Val Leu Asp Val
545                 550

<210> SEQ ID NO 48
<211> LENGTH: 552
<212> TYPE: PRT
<213> ORGANISM: Danio rerio

<400> SEQUENCE: 48

Met Arg Cys Asp Lys Ala Val Ser Tyr Leu Arg Ile Val Gly Thr Thr
1               5                   10                  15

Leu Phe Gly Ile Ser Leu Leu Val Gly Ile Ser Thr Ala Tyr Ile Met
                20                  25                  30

Gly Tyr Lys Leu Val Thr Thr Pro Gly Asn Tyr Leu Ser Phe Gly Leu
            35                  40                  45

Tyr Gly Ala Ile Leu Val Ile His Leu Ile Ile Gln Ser Val Phe Ala
        50                  55                  60

Leu Leu Glu His Arg Asn Met Lys Arg Ser Leu Glu Thr Pro Ile Lys
65                  70                  75                  80

Leu Asn Lys Ser Leu Ala Leu Cys Ile Ala Ala Tyr Gln Glu Asp Pro
                85                  90                  95

Asn Tyr Leu Arg Lys Cys Leu Ile Ser Val Lys Arg Leu Thr Tyr Pro
            100                 105                 110

Gly Ile Lys Val Ile Met Val Ile Asp Gly Asn Asn Asp Asp Asp Cys
        115                 120                 125

Tyr Met Met Glu Ile Phe Arg Glu Ile Met Gly Arg Asp Lys Ala Ala
    130                 135                 140

Thr Tyr Ile Trp Lys Ser Asn Tyr His His Arg Gly Pro Glu Glu Thr
145                 150                 155                 160

Glu Glu Ser Tyr Ala Thr Ser Leu Gln His Val Ser His Leu Val Leu
                165                 170                 175
```

```
Asn Asn Lys Cys Val Cys Ile Met Gln Lys Trp Gly Gly Lys Arg Glu
            180                 185                 190

Val Met Tyr Thr Ala Phe Lys Ala Leu Gly Arg Ser Val Asp Tyr Val
        195                 200                 205

Gln Val Cys Asp Ser Asp Thr Met Leu Asp Pro Ala Ser Ser Val Glu
    210                 215                 220

Met Val Lys Val Leu Glu Glu Asp Pro Asn Val Gly Val Gly Gly
225                 230                 235                 240

Asp Val Gln Ile Leu Asn Lys Tyr Glu Ser Trp Val Ser Phe Leu Ser
                245                 250                 255

Ser Val Arg Tyr Trp Met Ala Phe Asn Ile Glu Arg Ala Cys Gln Ser
            260                 265                 270

Tyr Phe Gly Cys Val Gln Cys Ile Ser Gly Pro Leu Gly Met Tyr Arg
        275                 280                 285

Asn Ser Leu Leu His Glu Phe Leu Glu Asp Trp Tyr Asp Gln Thr Phe
    290                 295                 300

Met Gly Ser His Cys Ser Phe Gly Asp Asp Arg His Leu Thr Asn Arg
305                 310                 315                 320

Val Leu Ser Leu Gly Tyr Ala Thr Lys Tyr Thr Ala Arg Ser Lys Cys
                325                 330                 335

Leu Thr Glu Thr Pro Ile Thr Tyr Leu Arg Trp Leu Asn Gln Gln Thr
            340                 345                 350

Arg Trp Ser Lys Ser Tyr Phe Arg Glu Trp Leu Tyr Asn Ser Leu Trp
        355                 360                 365

Phe His Lys His His Leu Trp Met Thr Tyr Glu Ala Val Ile Thr Gly
    370                 375                 380

Phe Phe Pro Phe Phe Leu Ile Ala Thr Ala Ile Gln Leu Phe Tyr Gln
385                 390                 395                 400

Gly Arg Ile Trp Asn Ile Leu Leu Phe Leu Leu Ile Val Gln Val Val
                405                 410                 415

Ala Leu Ile Lys Ser Ser Phe Ala Ser Cys Leu Arg Gly Asn Ile Val
            420                 425                 430

Met Val Phe Met Ser Phe Tyr Ser Val Leu Tyr Met Ser Ser Leu Leu
        435                 440                 445

Pro Ala Lys Met Phe Ala Ile Ala Thr Ile Asn Lys Ser Gly Trp Gly
    450                 455                 460

Thr Ser Gly Arg Lys Thr Val Val Asn Phe Ile Gly Leu Ile Pro
465                 470                 475                 480

Ile Ser Ile Trp Phe Thr Ile Leu Phe Val Gly Ile Ile Tyr Thr Ile
                485                 490                 495

Ile Gln Glu Thr Arg Lys Pro Phe Pro Glu Ser Glu Lys Val Val Leu
            500                 505                 510

Ile Ile Gly Ala Ile Val Tyr Ile Ser Tyr Trp Val Val Phe Leu Thr
        515                 520                 525

Leu Tyr Ala Val Leu Ile Met Lys Cys Gly Lys Arg Lys Lys Gly Gln
    530                 535                 540

Gln Tyr Asp Met Val Leu Asp Val
545                 550

<210> SEQ ID NO 49
<211> LENGTH: 2994
<212> TYPE: DNA
<213> ORGANISM: Danio rerio
<220> FEATURE:
```

```
<221> NAME/KEY: CDS
<222> LOCATION: (1)..(633)
<223> OTHER INFORMATION: Hyaluronan synthase (Exon)
<220> FEATURE:
<221> NAME/KEY: CDS
<222> LOCATION: (1059)..(1160)
<223> OTHER INFORMATION: Hyaluronan synthase (Exon)
<220> FEATURE:
<221> NAME/KEY: CDS
<222> LOCATION: (2065)..(2991)
<223> OTHER INFORMATION: Hyaluronan synthase (Exon)
<220> FEATURE:
<221> NAME/KEY: misc_feature
<222> LOCATION: (1425)..(1425)
<223> OTHER INFORMATION: n: a, c, g, or t
<220> FEATURE:
<221> NAME/KEY: misc_feature
<222> LOCATION: (1481)..(1481)
<223> OTHER INFORMATION: n: a, c, g, or t
<220> FEATURE:
<221> NAME/KEY: misc_feature
<222> LOCATION: (1632)..(1632)
<223> OTHER INFORMATION: n: a, c, g, or t
<220> FEATURE:
<221> NAME/KEY: misc_feature
<222> LOCATION: (1834)..(1834)
<223> OTHER INFORMATION: n: a, c, g, or t
<220> FEATURE:
<221> NAME/KEY: misc_feature
<222> LOCATION: (2295)..(2295)
<223> OTHER INFORMATION: n: a, c, g, or t

<400> SEQUENCE: 49 atg ccc tct cgc ttt ggc act gcg gtg cgg atc ttc atc acc acc tta      48
Met Pro Ser Arg Phe Gly Thr Ala Val Arg Ile Phe Ile Thr Thr Leu
1               5                   10                  15 ttt gca gca gtg gtg ctt ttc gca atc cta cta gcc tat gtg aca ggt      96
Phe Ala Ala Val Val Leu Phe Ala Ile Leu Leu Ala Tyr Val Thr Gly
            20                  25                  30 tac cag ttc atc cac aca gag cag cac cat ctg tct ttt ggc ttg tac     144
Tyr Gln Phe Ile His Thr Glu Gln His His Leu Ser Phe Gly Leu Tyr
        35                  40                  45 ggt gca ttt cta tcc ctc cac ctt ctc ctg cag agt ctc ttc gcc tac     192
Gly Ala Phe Leu Ser Leu His Leu Leu Leu Gln Ser Leu Phe Ala Tyr
    50                  55                  60 ctg gag cac aga caa atg cga ggc ccc tcc aga ccg cag cac ctg cgc     240
Leu Glu His Arg Gln Met Arg Gly Pro Ser Arg Pro Gln His Leu Arg
65                  70                  75                  80 cgc act gtg gcc ctc tgc att gca gcc tat cag gaa gat cca gac tac     288
Arg Thr Val Ala Leu Cys Ile Ala Ala Tyr Gln Glu Asp Pro Asp Tyr
                85                  90                  95 ctt cgc aag tgt ctg cgg agt tcg cgc att tct ttt ccc ggg ctg aaa     336
Leu Arg Lys Cys Leu Arg Ser Ser Arg Ile Ser Phe Pro Gly Leu Lys
            100                 105                 110 gtg gtg ttg gtg gtg gat ggc aat cgg cag gag gat gcc tac atg atg     384
Val Val Leu Val Val Asp Gly Asn Arg Gln Glu Asp Ala Tyr Met Met
        115                 120                 125 gat atc ttc cag gag gtg atg ggg gga gtg gag cag aca ggc tgt gtg     432
Asp Ile Phe Gln Glu Val Met Gly Gly Val Glu Gln Thr Gly Cys Val
    130                 135                 140 gtg tgg aaa ggg aat tac cac agt aac ggg gat gga gga gga gga          480
Val Trp Lys Gly Asn Tyr His Ser Asn Gly Asp Gly Gly Gly Gly Gly
145                 150                 155                 160 ggg aaa ggc tcg gtg cat gcc gaa gag gct gca cga gtg gcc aga gtg     528
Gly Lys Gly Ser Val His Ala Glu Glu Ala Ala Arg Val Ala Arg Val
                165                 170                 175 gtg cgg agc tgc cgt tac tcc tgc atc atg cag gaa tgg ggt ggc aag     576
```

```
                Val Arg Ser Cys Arg Tyr Ser Cys Ile Met Gln Glu Trp Gly Gly Lys
                            180                 185                 190 agg gaa gtg atg tat aca gcc ttc aaa gca ctt gga gat aca gtg gat         624
Arg Glu Val Met Tyr Thr Ala Phe Lys Ala Leu Gly Asp Thr Val Asp
            195                 200                 205 tac atg cag gtaagtctaa acctcattta acaaccaaaa aaaaaaatcg                 673
Tyr Met Gln
        210 gaaacatacc tctatgcttt ttgatcttgt tactcttttt tttatgccta caattaacca       733 acggttcata ctctagtcat ctcaatgtcc ctgtaatctg aatccttgca acactaaggt       793 caaaggtcag tcctttaaat tcacctgtag ttccgagcac acctgtgtgc tgtcatcaac       853 tattcattgt ttcggcgtat aatgtgtatg ttcagaaaca gaaatgacct tgaaacatct       913 gtgaacctct ctttacaaca gtccttgcat tgttcacaca gtgattgtta acatgagcct       973 taccttctgg aaattagtca atatttgtat acgagttagt gaggaagtct tccaagtaag      1033 tatctcttgc tttgtttgtt tgcag gta tgt gat tca gac act gta ctt gat        1085
               Val Cys Asp Ser Asp Thr Val Leu Asp
               215                 220 cca gca tgc act att gag atg ttg aag att cta gag gag gat cct gat        1133
Pro Ala Cys Thr Ile Glu Met Leu Lys Ile Leu Glu Glu Asp Pro Asp
                        225                 230                 235 gtg gga gga gtt gga gga gat gtt cag gtaataattt taaggcaatt              1180
Val Gly Gly Val Gly Gly Asp Val Gln
                240                 245 tgtaaatatg tagaaacatt tcaacaaatt aatttgagag gattacattt gatctcatag      1240
atatatacat tagatatcgc ctggcctatt gtctattgga cggaatccaa agccagagat      1300
atacacatat atctatgatc gggagttttc ctggatgtta gtatgtaatt ttttttttct      1360
aattacgaaa attataattt tacatcactt ttctacattg atggatcagt caccgaacgg      1420
gcatncctga caaaaagctt gtgtttgtgt gtacagaaat gtactattca ccctccctat      1480
naaatttgat ctaatcatgt cctgaaacac agctcctctc ctgctttcac ttctcatact      1540
gacggaggga gcgattcgtt tgtgaatgaa tccccggaac gactcttttca ctaacgttag     1600 ccgacaataa tacgagtttc tggcagcgca gnatctcgtt gtcatatttc ttttgcattg      1660
tttgctgatt ttattcaaca aaactagcat aagccgagtg tttaatgcga gttggagctg     1720
ctttgcctta tatggtgaat gcagtaagtg actgttatca tcaataacgt tacctgatta     1780
gcacaaaagt tcagaacata caaaaacaga aaaaaacgta atattaccta tganatgttc     1840
tgcctttgtg ctttgttttc tttgtttgct cgttactaca accgtagaca gcgctaaagt     1900
cccgcatctt cacgtaataa cactgtcttg actagtgcgg ttgaatgaca ttctcctggg     1960
agcactgtac caatgtggct gtgctattga cgcatgctca gggtccctat gcgatatcta     2020
gtgtatatat ctatgatttg ttctctgttc attgtttcct tcag att ctg aac aag      2076
                                                    Ile Leu Asn Lys tat gac tcc tgg atc tcc ttc ctg agc agt gtc cgc tat tgg atg gcc       2124
Tyr Asp Ser Trp Ile Ser Phe Leu Ser Ser Val Arg Tyr Trp Met Ala
250                 255                 260                 265 ttc aat gtg gag cgg gcc tgc cag tct tat ttc gga tgt gtg cag tgc       2172
Phe Asn Val Glu Arg Ala Cys Gln Ser Tyr Phe Gly Cys Val Gln Cys
                    270                 275                 280 atc agt gga cct cta gga atg tac cgt aac tct ctc ctt cag cag ttc       2220
Ile Ser Gly Pro Leu Gly Met Tyr Arg Asn Ser Leu Leu Gln Gln Phe
                285                 290                 295
```

```
tta gag ccc tgg tac cac cag acc ttc cta gga agc aag tgc agt ttt    2268
Leu Glu Pro Trp Tyr His Gln Thr Phe Leu Gly Ser Lys Cys Ser Phe
        300                 305                 310 ggt gat gat cga cat ctc acc aac cgn gtc ctt agc ttt ggc ttc aaa    2316
Gly Asp Asp Arg His Leu Thr Asn Arg Val Leu Ser Phe Gly Phe Lys
    315                 320                 325 acc aag ttc acg gca cgc tct caa tgc cag acc gag acc cca aca caa    2364
Thr Lys Phe Thr Ala Arg Ser Gln Cys Gln Thr Glu Thr Pro Thr Gln
330                 335                 340                 345 tac ctg cgt tgg ctc aat cag cag acc cgc tgg agc aag tct tac ttt    2412
Tyr Leu Arg Trp Leu Asn Gln Gln Thr Arg Trp Ser Lys Ser Tyr Phe
                350                 355                 360 cga gag tgg ctc tac aat gct ctt tgg ttc cac aag cac agc ctg tgg    2460
Arg Glu Trp Leu Tyr Asn Ala Leu Trp Phe His Lys His Ser Leu Trp
            365                 370                 375 atg acc tat gaa tct gtg gtt act ggg ttc ttc ccc ttc ttt ctg gtg    2508
Met Thr Tyr Glu Ser Val Val Thr Gly Phe Phe Pro Phe Phe Leu Val
        380                 385                 390 gct aca gtc atc cac ctg ttc tac aga ggc cgg ttg tgg aac atc tta    2556
Ala Thr Val Ile His Leu Phe Tyr Arg Gly Arg Leu Trp Asn Ile Leu
    395                 400                 405 ctc ttc ttg ttg acg gtc cag ctg gtg ggt atg gtg aag gcc acc tac    2604
Leu Phe Leu Leu Thr Val Gln Leu Val Gly Met Val Lys Ala Thr Tyr
410                 415                 420                 425 gcc tgc ttc ctg cgg ggc agc ctt gtc atg atc ttc atg tca ctc tac    2652
Ala Cys Phe Leu Arg Gly Ser Leu Val Met Ile Phe Met Ser Leu Tyr
                430                 435                 440 tca ctg ctc tac atg tca agc ctg ctc cct gct aag atc ttt gcc ctg    2700
Ser Leu Leu Tyr Met Ser Ser Leu Leu Pro Ala Lys Ile Phe Ala Leu
            445                 450                 455 ctg act att aac aaa gca gga tgg ggc aca tca ggc agg aaa aag atg    2748
Leu Thr Ile Asn Lys Ala Gly Trp Gly Thr Ser Gly Arg Lys Lys Met
        460                 465                 470 gta gta aac ctt att gga gct gtg cct gtt act gtg tgg aca gcc att    2796
Val Val Asn Leu Ile Gly Ala Val Pro Val Thr Val Trp Thr Ala Ile
    475                 480                 485 ctg ctt ggt gga gtg gtt tac acc att tac tgc gag gtt caa gaa cct    2844
Leu Leu Gly Gly Val Val Tyr Thr Ile Tyr Cys Glu Val Gln Glu Pro
490                 495                 500                 505 ttt acc gcg act gag aag gct ctt ctt atc gca ggc acc att gtc tat    2892
Phe Thr Ala Thr Glu Lys Ala Leu Leu Ile Ala Gly Thr Ile Val Tyr
                510                 515                 520 gcc tct tac tgg ctt ata ctc ctg gtc ctc tac ctg gcc ata gtg gcc    2940
Ala Ser Tyr Trp Leu Ile Leu Leu Val Leu Tyr Leu Ala Ile Val Ala
            525                 530                 535 aaa cgt tgt aac aaa aga gaa gaa cag ttc cac ctt tcc tat gcc gaa    2988
Lys Arg Cys Asn Lys Arg Glu Glu Gln Phe His Leu Ser Tyr Ala Glu
        540                 545                 550 gcc tag                                                            2994
Ala

<210> SEQ ID NO 50
<211> LENGTH: 554
<212> TYPE: PRT
<213> ORGANISM: Danio rerio

<400> SEQUENCE: 50

Met Pro Ser Arg Phe Gly Thr Ala Val Arg Ile Phe Ile Thr Thr Leu
1               5                   10                  15
```

```
Phe Ala Ala Val Val Leu Phe Ala Ile Leu Ala Tyr Val Thr Gly
            20                  25                  30

Tyr Gln Phe Ile His Thr Glu Gln His His Leu Ser Phe Gly Leu Tyr
        35                  40                  45

Gly Ala Phe Leu Ser Leu His Leu Leu Leu Gln Ser Leu Phe Ala Tyr
    50                  55                  60

Leu Glu His Arg Gln Met Arg Gly Pro Ser Arg Pro Gln His Leu Arg
65                  70                  75                  80

Arg Thr Val Ala Leu Cys Ile Ala Ala Tyr Gln Glu Asp Pro Asp Tyr
                85                  90                  95

Leu Arg Lys Cys Leu Arg Ser Ser Arg Ile Ser Phe Pro Gly Leu Lys
            100                 105                 110

Val Val Leu Val Val Asp Gly Asn Arg Gln Glu Asp Ala Tyr Met Met
        115                 120                 125

Asp Ile Phe Gln Glu Val Met Gly Gly Val Glu Gln Thr Gly Cys Val
    130                 135                 140

Val Trp Lys Gly Asn Tyr His Ser Asn Gly Asp Gly Gly Gly Gly Gly
145                 150                 155                 160

Gly Lys Gly Ser Val His Ala Glu Glu Ala Ala Arg Val Ala Arg Val
                165                 170                 175

Val Arg Ser Cys Arg Tyr Ser Cys Ile Met Gln Glu Trp Gly Gly Lys
            180                 185                 190

Arg Glu Val Met Tyr Thr Ala Phe Lys Ala Leu Gly Asp Thr Val Asp
        195                 200                 205

Tyr Met Gln Val Cys Asp Ser Asp Thr Val Leu Asp Pro Ala Cys Thr
    210                 215                 220

Ile Glu Met Leu Lys Ile Leu Glu Glu Asp Pro Asp Val Gly Gly Val
225                 230                 235                 240

Gly Gly Asp Val Gln Ile Leu Asn Lys Tyr Asp Ser Trp Ile Ser Phe
                245                 250                 255

Leu Ser Ser Val Arg Tyr Trp Met Ala Phe Asn Val Glu Arg Ala Cys
            260                 265                 270

Gln Ser Tyr Phe Gly Cys Val Gln Cys Ile Ser Gly Pro Leu Gly Met
        275                 280                 285

Tyr Arg Asn Ser Leu Leu Gln Gln Phe Leu Glu Pro Trp Tyr His Gln
    290                 295                 300

Thr Phe Leu Gly Ser Lys Cys Ser Phe Gly Asp Asp Arg His Leu Thr
305                 310                 315                 320

Asn Arg Val Leu Ser Phe Gly Phe Lys Thr Lys Phe Thr Ala Arg Ser
                325                 330                 335

Gln Cys Gln Thr Glu Thr Pro Thr Gln Tyr Leu Arg Trp Leu Asn Gln
            340                 345                 350

Gln Thr Arg Trp Ser Lys Ser Tyr Phe Arg Glu Trp Leu Tyr Asn Ala
        355                 360                 365

Leu Trp Phe His Lys His Ser Leu Trp Met Thr Tyr Glu Ser Val Val
    370                 375                 380

Thr Gly Phe Phe Pro Phe Phe Leu Val Ala Thr Val Ile His Leu Phe
385                 390                 395                 400

Tyr Arg Gly Arg Leu Trp Asn Ile Leu Leu Phe Leu Leu Thr Val Gln
                405                 410                 415

Leu Val Gly Met Val Lys Ala Thr Tyr Ala Cys Phe Leu Arg Gly Ser
            420                 425                 430

Leu Val Met Ile Phe Met Ser Leu Tyr Ser Leu Leu Tyr Met Ser Ser
```

```
        435                 440                 445

Leu Leu Pro Ala Lys Ile Phe Ala Leu Leu Thr Ile Asn Lys Ala Gly
    450                 455                 460

Trp Gly Thr Ser Gly Arg Lys Lys Met Val Val Asn Leu Ile Gly Ala
465                 470                 475                 480

Val Pro Val Thr Val Trp Thr Ala Ile Leu Leu Gly Gly Val Val Tyr
                485                 490                 495

Thr Ile Tyr Cys Glu Val Gln Glu Pro Phe Thr Ala Thr Glu Lys Ala
            500                 505                 510

Leu Leu Ile Ala Gly Thr Ile Val Tyr Ala Ser Tyr Trp Leu Ile Leu
        515                 520                 525

Leu Val Leu Tyr Leu Ala Ile Val Ala Lys Arg Cys Asn Lys Arg Glu
    530                 535                 540

Glu Gln Phe His Leu Ser Tyr Ala Glu Ala
545                 550

<210> SEQ ID NO 51
<211> LENGTH: 2919
<212> TYPE: DNA
<213> ORGANISM: Pasteurella multocida
<220> FEATURE:
<221> NAME/KEY: CDS
<222> LOCATION: (1)..(2919)
<223> OTHER INFORMATION: Hyaluronan synthase
<300> PUBLICATION INFORMATION:
<308> DATABASE ACCESSION NUMBER: AF036004.2
<309> DATABASE ENTRY DATE: 1998-04-15
<313> RELEVANT RESIDUES IN SEQ ID NO: (1)..(2919)

<400> SEQUENCE: 51 atg aat aca tta tca caa gca ata aaa gca tat aac agc aat gac tat       48
Met Asn Thr Leu Ser Gln Ala Ile Lys Ala Tyr Asn Ser Asn Asp Tyr
1               5                   10                  15 caa tta gca ctc aaa tta ttt gaa aag tcg gcg gaa atc tat gga cgg       96
Gln Leu Ala Leu Lys Leu Phe Glu Lys Ser Ala Glu Ile Tyr Gly Arg
            20                  25                  30 aaa att gtt gaa ttt caa att acc aaa tgc aaa gaa aaa ctc tca gca      144
Lys Ile Val Glu Phe Gln Ile Thr Lys Cys Lys Glu Lys Leu Ser Ala
        35                  40                  45 cat cct tct gtt aat tca gca cat ctt tct gta aat aaa gaa gaa aaa      192
His Pro Ser Val Asn Ser Ala His Leu Ser Val Asn Lys Glu Glu Lys
    50                  55                  60 gtc aat gtt tgc gat agt ccg tta gat att gca aca caa ctg tta ctt      240
Val Asn Val Cys Asp Ser Pro Leu Asp Ile Ala Thr Gln Leu Leu Leu
65                  70                  75                  80 tcc aac gta aaa aaa tta gta ctt tct gac tcg gaa aaa aac acg tta      288
Ser Asn Val Lys Lys Leu Val Leu Ser Asp Ser Glu Lys Asn Thr Leu
                85                  90                  95 aaa aat aaa tgg aaa ttg ctc act gag aag aaa tct gaa aat gcg gag      336
Lys Asn Lys Trp Lys Leu Leu Thr Glu Lys Lys Ser Glu Asn Ala Glu
            100                 105                 110 gta aga gcg gtc gcc ctt gta cca aaa gat ttt ccc aaa gat ctg gtt      384
Val Arg Ala Val Ala Leu Val Pro Lys Asp Phe Pro Lys Asp Leu Val
        115                 120                 125 tta gcg cct tta cct gat cat gtt aat gat ttt aca tgg tac aaa aag      432
Leu Ala Pro Leu Pro Asp His Val Asn Asp Phe Thr Trp Tyr Lys Lys
    130                 135                 140 cga aag aaa aga ctt ggc ata aaa cct gaa cat caa cat gtt ggt ctt      480
Arg Lys Lys Arg Leu Gly Ile Lys Pro Glu His Gln His Val Gly Leu
145                 150                 155                 160
```

```
tct att atc gtt aca aca ttc aat cga cca gca att tta tcg att aca    528
Ser Ile Ile Val Thr Thr Phe Asn Arg Pro Ala Ile Leu Ser Ile Thr
            165                 170                 175 tta gcc tgt tta gta aac caa aaa aca cat tac ccg ttt gaa gtt atc    576
Leu Ala Cys Leu Val Asn Gln Lys Thr His Tyr Pro Phe Glu Val Ile
            180                 185                 190 gtg aca gat gat ggt agt cag gaa gat cta tca ccg atc att cgc caa    624
Val Thr Asp Asp Gly Ser Gln Glu Asp Leu Ser Pro Ile Ile Arg Gln
            195                 200                 205 tat gaa aat aaa ttg gat att cgc tac gtc aga caa aaa gat aac ggt    672
Tyr Glu Asn Lys Leu Asp Ile Arg Tyr Val Arg Gln Lys Asp Asn Gly
            210                 215                 220 ttt caa gcc agt gcc gct cgg aat atg gga tta cgc tta gca aaa tat    720
Phe Gln Ala Ser Ala Ala Arg Asn Met Gly Leu Arg Leu Ala Lys Tyr
225             230                 235                 240 gac ttt att ggc tta ctc gac tgt gat atg gcg cca aat cca tta tgg    768
Asp Phe Ile Gly Leu Leu Asp Cys Asp Met Ala Pro Asn Pro Leu Trp
            245                 250                 255 gtt cat tct tat gtt gca gag cta tta gaa gat gat gat tta aca atc    816
Val His Ser Tyr Val Ala Glu Leu Leu Glu Asp Asp Asp Leu Thr Ile
            260                 265                 270 att ggt cca aga aaa tac atc gat aca caa cat att gac cca aaa gac    864
Ile Gly Pro Arg Lys Tyr Ile Asp Thr Gln His Ile Asp Pro Lys Asp
            275                 280                 285 ttc tta aat aac gcg agt ttg ctt gaa tca tta cca gaa gtg aaa acc    912
Phe Leu Asn Asn Ala Ser Leu Leu Glu Ser Leu Pro Glu Val Lys Thr
            290                 295                 300 aat aat agt gtt gcc gca aaa ggg gaa gga aca gtt tct ctg gat tgg    960
Asn Asn Ser Val Ala Ala Lys Gly Glu Gly Thr Val Ser Leu Asp Trp
305             310                 315                 320 cgc tta gaa caa ttc gaa aaa aca gaa aat ctc cgc tta tcc gat tcg   1008
Arg Leu Glu Gln Phe Glu Lys Thr Glu Asn Leu Arg Leu Ser Asp Ser
            325                 330                 335 cct ttc cgt ttt ttt gcg gcg ggt aat gtt gct ttc gct aaa aaa tgg   1056
Pro Phe Arg Phe Phe Ala Ala Gly Asn Val Ala Phe Ala Lys Lys Trp
            340                 345                 350 cta aat aaa tcc ggt ttc ttt gat gag gaa ttt aat cac tgg ggt gga   1104
Leu Asn Lys Ser Gly Phe Phe Asp Glu Glu Phe Asn His Trp Gly Gly
            355                 360                 365 gaa gat gtg gaa ttt gga tat cgc tta ttc cgt tac ggt agt ttc ttt   1152
Glu Asp Val Glu Phe Gly Tyr Arg Leu Phe Arg Tyr Gly Ser Phe Phe
            370                 375                 380 aaa act att gat ggc att atg gcc tac cat caa gag cca cca ggt aaa   1200
Lys Thr Ile Asp Gly Ile Met Ala Tyr His Gln Glu Pro Pro Gly Lys
385             390                 395                 400 gaa aat gaa acc gat cgt gaa gcg gga aaa aat att acg ctc gat att   1248
Glu Asn Glu Thr Asp Arg Glu Ala Gly Lys Asn Ile Thr Leu Asp Ile
            405                 410                 415 atg aga gaa aag gtc cct tat atc tat aga aaa ctt tta cca ata gaa   1296
Met Arg Glu Lys Val Pro Tyr Ile Tyr Arg Lys Leu Leu Pro Ile Glu
            420                 425                 430 gat tcg cat atc aat aga gta cct tta gtt tca att tat atc cca gct   1344
Asp Ser His Ile Asn Arg Val Pro Leu Val Ser Ile Tyr Ile Pro Ala
            435                 440                 445 tat aac tgt gca aac tat att caa cgt tgc gta gat agt gca ctg aat   1392
Tyr Asn Cys Ala Asn Tyr Ile Gln Arg Cys Val Asp Ser Ala Leu Asn
450             455                 460 cag act gtt gtt gat ctc gag gtt tgt att tgt aac gat ggt tca aca   1440
Gln Thr Val Val Asp Leu Glu Val Cys Ile Cys Asn Asp Gly Ser Thr
465             470                 475                 480
```

```
gat aat acc tta gaa gtg atc aat aag ctt tat ggt aat aat cct agg    1488
Asp Asn Thr Leu Glu Val Ile Asn Lys Leu Tyr Gly Asn Asn Pro Arg
            485                 490                 495 gta cgc atc atg tct aaa cca aat ggc gga ata gcc tca gca tca aat    1536
Val Arg Ile Met Ser Lys Pro Asn Gly Gly Ile Ala Ser Ala Ser Asn
            500                 505                 510 gca gcc gtt tct ttt gct aaa ggt tat tac att ggg cag tta gat tca    1584
Ala Ala Val Ser Phe Ala Lys Gly Tyr Tyr Ile Gly Gln Leu Asp Ser
            515                 520                 525 gat tat ctt gag cct gat gca gtt gaa ctg tgt tta aaa gaa ttt        1632
Asp Asp Tyr Leu Glu Pro Asp Ala Val Glu Leu Cys Leu Lys Glu Phe
        530                 535                 540 tta aaa gat aaa acg cta gct tgt gtt tat acc act aat aga aac gtc    1680
Leu Lys Asp Lys Thr Leu Ala Cys Val Tyr Thr Thr Asn Arg Asn Val
545                 550                 555                 560 aat ccg gat ggt agc tta atc gct aat ggt tac aat tgg cca gaa ttt    1728
Asn Pro Asp Gly Ser Leu Ile Ala Asn Gly Tyr Asn Trp Pro Glu Phe
                565                 570                 575 tca cga gaa aaa ctc aca acg gct atg att gct cac cac ttt aga atg    1776
Ser Arg Glu Lys Leu Thr Thr Ala Met Ile Ala His His Phe Arg Met
            580                 585                 590 ttc acg att aga gct tgg cat tta act gat gga ttc aat gaa aaa att    1824
Phe Thr Ile Arg Ala Trp His Leu Thr Asp Gly Phe Asn Glu Lys Ile
            595                 600                 605 gaa aat gcc gta gac tat gac atg ttc ctc aaa ctc agt gaa gtt gga    1872
Glu Asn Ala Val Asp Tyr Asp Met Phe Leu Lys Leu Ser Glu Val Gly
            610                 615                 620 aaa ttt aaa cat ctt aat aaa atc tgc tat aac cgt gta tta cat ggt    1920
Lys Phe Lys His Leu Asn Lys Ile Cys Tyr Asn Arg Val Leu His Gly
625                 630                 635                 640 gat aac aca tca att aag aaa ctt ggc att caa aag aaa aac cat ttt    1968
Asp Asn Thr Ser Ile Lys Lys Leu Gly Ile Gln Lys Lys Asn His Phe
                645                 650                 655 gtt gta gtc aat cag tca tta aat aga caa ggc ata act tat tat aat    2016
Val Val Val Asn Gln Ser Leu Asn Arg Gln Gly Ile Thr Tyr Tyr Asn
            660                 665                 670 tat gac gaa ttt gat gat tta gat gaa agt aga aag tat att ttc aat    2064
Tyr Asp Glu Phe Asp Asp Leu Asp Glu Ser Arg Lys Tyr Ile Phe Asn
            675                 680                 685 aaa acc gct gaa tat caa gaa gag att gat atc tta aaa gat att aaa    2112
Lys Thr Ala Glu Tyr Gln Glu Glu Ile Asp Ile Leu Lys Asp Ile Lys
            690                 695                 700 atc atc cag aat aaa gat gcc aaa atc gca gtc agt att ttt tat ccc    2160
Ile Ile Gln Asn Lys Asp Ala Lys Ile Ala Val Ser Ile Phe Tyr Pro
705                 710                 715                 720 aat aca tta aac ggc tta gtg aaa aaa cta aac aat att att gaa tat    2208
Asn Thr Leu Asn Gly Leu Val Lys Lys Leu Asn Asn Ile Ile Glu Tyr
                725                 730                 735 aat aaa aat ata ttc gtt att gtt cta cat gtt gat aag aat cat ctt    2256
Asn Lys Asn Ile Phe Val Ile Val Leu His Val Asp Lys Asn His Leu
            740                 745                 750 aca cca gat atc aaa aaa gaa ata cta gcc ttc tat cat aaa cat caa    2304
Thr Pro Asp Ile Lys Lys Glu Ile Leu Ala Phe Tyr His Lys His Gln
            755                 760                 765 gtg aat att tta cta aat aat gat atc tca tat tac acg agt aat aga    2352
Val Asn Ile Leu Leu Asn Asn Asp Ile Ser Tyr Tyr Thr Ser Asn Arg
            770                 775                 780 tta ata aaa act gag gcg cat tta agt aat att aat aaa tta agt cag    2400
Leu Ile Lys Thr Glu Ala His Leu Ser Asn Ile Asn Lys Leu Ser Gln
```

```
                  785                 790                 795                 800
tta aat cta aat tgt gaa tac atc att ttt gat aat cat gac agc cta   2448
Leu Asn Leu Asn Cys Glu Tyr Ile Ile Phe Asp Asn His Asp Ser Leu
                805                 810                 815 ttc gtt aaa aat gac agc tat gct tat atg aaa aaa tat gat gtc ggc   2496
Phe Val Lys Asn Asp Ser Tyr Ala Tyr Met Lys Lys Tyr Asp Val Gly
            820                 825                 830 atg aat ttc tca gca tta aca cat gat tgg atc gag aaa atc aat gcg   2544
Met Asn Phe Ser Ala Leu Thr His Asp Trp Ile Glu Lys Ile Asn Ala
        835                 840                 845 cat cca cca ttt aaa aag ctc att aaa act tat ttt aat gac aat gac   2592
His Pro Pro Phe Lys Lys Leu Ile Lys Thr Tyr Phe Asn Asp Asn Asp
    850                 855                 860 tta aaa agt atg aat gtg aaa ggg gca tca caa ggt atg ttt atg acg   2640
Leu Lys Ser Met Asn Val Lys Gly Ala Ser Gln Gly Met Phe Met Thr
865                 870                 875                 880 tat gcg cta gcg cat gag ctt ctg acg att att aaa gaa gtc atc aca   2688
Tyr Ala Leu Ala His Glu Leu Leu Thr Ile Ile Lys Glu Val Ile Thr
                885                 890                 895 tct tgc cag tca att gat agt gtg cca gaa tat aac act gag gat att   2736
Ser Cys Gln Ser Ile Asp Ser Val Pro Glu Tyr Asn Thr Glu Asp Ile
            900                 905                 910 tgg ttc caa ttt gca ctt tta atc tta gaa aag aaa acc ggc cat gta   2784
Trp Phe Gln Phe Ala Leu Leu Ile Leu Glu Lys Lys Thr Gly His Val
        915                 920                 925 ttt aat aaa aca tcg acc ctg act tat atg cct tgg gaa cga aaa tta   2832
Phe Asn Lys Thr Ser Thr Leu Thr Tyr Met Pro Trp Glu Arg Lys Leu
    930                 935                 940 caa tgg aca aat gaa caa att gaa agt gca aaa aga gga gaa aat ata   2880
Gln Trp Thr Asn Glu Gln Ile Glu Ser Ala Lys Arg Gly Glu Asn Ile
945                 950                 955                 960 cct gtt aac aag ttc att att aat agt ata act cta taa               2919
Pro Val Asn Lys Phe Ile Ile Asn Ser Ile Thr Leu
                965                 970

<210> SEQ ID NO 52
<211> LENGTH: 972
<212> TYPE: PRT
<213> ORGANISM: Pasteurella multocida

<400> SEQUENCE: 52

Met Asn Thr Leu Ser Gln Ala Ile Lys Ala Tyr Asn Ser Asn Asp Tyr
1               5                   10                  15

Gln Leu Ala Leu Lys Leu Phe Glu Lys Ser Ala Glu Ile Tyr Gly Arg
            20                  25                  30

Lys Ile Val Glu Phe Gln Ile Thr Lys Cys Lys Glu Lys Leu Ser Ala
        35                  40                  45

His Pro Ser Val Asn Ser Ala His Leu Ser Val Asn Lys Glu Glu Lys
    50                  55                  60

Val Asn Val Cys Asp Ser Pro Leu Asp Ile Ala Thr Gln Leu Leu Leu
65                  70                  75                  80

Ser Asn Val Lys Lys Leu Val Leu Ser Asp Ser Glu Lys Asn Thr Leu
                85                  90                  95

Lys Asn Lys Trp Lys Leu Leu Thr Glu Lys Lys Ser Glu Asn Ala Glu
            100                 105                 110

Val Arg Ala Val Ala Leu Val Pro Lys Asp Phe Pro Lys Asp Leu Val
        115                 120                 125

Leu Ala Pro Leu Pro Asp His Val Asn Asp Phe Thr Trp Tyr Lys Lys
```

-continued

```
            130                 135                 140
Arg Lys Lys Arg Leu Gly Ile Lys Pro Glu His Gln His Val Gly Leu
145                 150                 155                 160

Ser Ile Ile Val Thr Thr Phe Asn Arg Pro Ala Ile Leu Ser Ile Thr
                165                 170                 175

Leu Ala Cys Leu Val Asn Gln Lys Thr His Tyr Pro Phe Glu Val Ile
                180                 185                 190

Val Thr Asp Asp Gly Ser Gln Glu Asp Leu Ser Pro Ile Ile Arg Gln
                195                 200                 205

Tyr Glu Asn Lys Leu Asp Ile Arg Tyr Val Arg Gln Lys Asp Asn Gly
                210                 215                 220

Phe Gln Ala Ser Ala Ala Arg Asn Met Gly Leu Arg Leu Ala Lys Tyr
225                 230                 235                 240

Asp Phe Ile Gly Leu Leu Asp Cys Asp Met Ala Pro Asn Pro Leu Trp
                245                 250                 255

Val His Ser Tyr Val Ala Glu Leu Leu Glu Asp Asp Asp Leu Thr Ile
                260                 265                 270

Ile Gly Pro Arg Lys Tyr Ile Asp Thr Gln His Ile Asp Pro Lys Asp
                275                 280                 285

Phe Leu Asn Asn Ala Ser Leu Leu Glu Ser Leu Pro Glu Val Lys Thr
                290                 295                 300

Asn Asn Ser Val Ala Ala Lys Gly Glu Gly Thr Val Ser Leu Asp Trp
305                 310                 315                 320

Arg Leu Glu Gln Phe Glu Lys Thr Glu Asn Leu Arg Leu Ser Asp Ser
                325                 330                 335

Pro Phe Arg Phe Phe Ala Ala Gly Asn Val Ala Phe Ala Lys Lys Trp
                340                 345                 350

Leu Asn Lys Ser Gly Phe Phe Asp Glu Glu Phe Asn His Trp Gly Gly
                355                 360                 365

Glu Asp Val Glu Phe Gly Tyr Arg Leu Phe Arg Tyr Gly Ser Phe Phe
                370                 375                 380

Lys Thr Ile Asp Gly Ile Met Ala Tyr His Gln Glu Pro Pro Gly Lys
385                 390                 395                 400

Glu Asn Glu Thr Asp Arg Glu Ala Gly Lys Asn Ile Thr Leu Asp Ile
                405                 410                 415

Met Arg Glu Lys Val Pro Tyr Ile Tyr Arg Lys Leu Leu Pro Ile Glu
                420                 425                 430

Asp Ser His Ile Asn Arg Val Pro Leu Val Ser Ile Tyr Ile Pro Ala
                435                 440                 445

Tyr Asn Cys Ala Asn Tyr Ile Gln Arg Cys Val Asp Ser Ala Leu Asn
                450                 455                 460

Gln Thr Val Val Asp Leu Glu Val Cys Ile Cys Asn Asp Gly Ser Thr
465                 470                 475                 480

Asp Asn Thr Leu Glu Val Ile Asn Lys Leu Tyr Gly Asn Asn Pro Arg
                485                 490                 495

Val Arg Ile Met Ser Lys Pro Asn Gly Gly Ile Ala Ser Ala Ser Asn
                500                 505                 510

Ala Ala Val Ser Phe Ala Lys Gly Tyr Tyr Ile Gly Gln Leu Asp Ser
                515                 520                 525

Asp Asp Tyr Leu Glu Pro Asp Ala Val Glu Leu Cys Leu Lys Glu Phe
                530                 535                 540

Leu Lys Asp Lys Thr Leu Ala Cys Val Tyr Thr Thr Asn Arg Asn Val
545                 550                 555                 560
```

```
Asn Pro Asp Gly Ser Leu Ile Ala Asn Gly Tyr Asn Trp Pro Glu Phe
                565                 570                 575

Ser Arg Glu Lys Leu Thr Thr Ala Met Ile Ala His His Phe Arg Met
            580                 585                 590

Phe Thr Ile Arg Ala Trp His Leu Thr Asp Gly Phe Asn Glu Lys Ile
        595                 600                 605

Glu Asn Ala Val Asp Tyr Asp Met Phe Leu Lys Leu Ser Glu Val Gly
    610                 615                 620

Lys Phe Lys His Leu Asn Lys Ile Cys Tyr Asn Arg Val Leu His Gly
625                 630                 635                 640

Asp Asn Thr Ser Ile Lys Lys Leu Gly Ile Gln Lys Lys Asn His Phe
                645                 650                 655

Val Val Val Asn Gln Ser Leu Asn Arg Gln Gly Ile Thr Tyr Tyr Asn
            660                 665                 670

Tyr Asp Glu Phe Asp Asp Leu Asp Glu Ser Arg Lys Tyr Ile Phe Asn
        675                 680                 685

Lys Thr Ala Glu Tyr Gln Glu Glu Ile Asp Ile Leu Lys Asp Ile Lys
    690                 695                 700

Ile Ile Gln Asn Lys Asp Ala Lys Ile Ala Val Ser Ile Phe Tyr Pro
705                 710                 715                 720

Asn Thr Leu Asn Gly Leu Val Lys Lys Leu Asn Asn Ile Ile Glu Tyr
                725                 730                 735

Asn Lys Asn Ile Phe Val Ile Val Leu His Val Asp Lys Asn His Leu
            740                 745                 750

Thr Pro Asp Ile Lys Lys Glu Ile Leu Ala Phe Tyr His Lys His Gln
        755                 760                 765

Val Asn Ile Leu Leu Asn Asn Asp Ile Ser Tyr Tyr Thr Ser Asn Arg
    770                 775                 780

Leu Ile Lys Thr Glu Ala His Leu Ser Asn Ile Asn Lys Leu Ser Gln
785                 790                 795                 800

Leu Asn Leu Asn Cys Glu Tyr Ile Ile Phe Asp Asn His Asp Ser Leu
                805                 810                 815

Phe Val Lys Asn Asp Ser Tyr Ala Tyr Met Lys Lys Tyr Asp Val Gly
            820                 825                 830

Met Asn Phe Ser Ala Leu Thr His Asp Trp Ile Glu Lys Ile Asn Ala
        835                 840                 845

His Pro Pro Phe Lys Lys Leu Ile Lys Thr Tyr Phe Asn Asp Asn Asp
    850                 855                 860

Leu Lys Ser Met Asn Val Lys Gly Ala Ser Gln Gly Met Phe Met Thr
865                 870                 875                 880

Tyr Ala Leu Ala His Glu Leu Leu Thr Ile Ile Lys Glu Val Ile Thr
                885                 890                 895

Ser Cys Gln Ser Ile Asp Ser Val Pro Glu Tyr Asn Thr Glu Asp Ile
            900                 905                 910

Trp Phe Gln Phe Ala Leu Leu Ile Leu Glu Lys Lys Thr Gly His Val
        915                 920                 925

Phe Asn Lys Thr Ser Thr Leu Thr Tyr Met Pro Trp Glu Arg Lys Leu
    930                 935                 940

Gln Trp Thr Asn Glu Gln Ile Glu Ser Ala Lys Arg Gly Glu Asn Ile
945                 950                 955                 960

Pro Val Asn Lys Phe Ile Ile Asn Ser Ile Thr Leu
                965                 970
```

<210> SEQ ID NO 53
<211> LENGTH: 1260
<212> TYPE: DNA
<213> ORGANISM: Streptococcus pyogenes
<220> FEATURE:
<221> NAME/KEY: CDS
<222> LOCATION: (1)..(1260)
<223> OTHER INFORMATION: Hyaluronan synthase
<300> PUBLICATION INFORMATION:
<308> DATABASE ACCESSION NUMBER: L21187.1
<309> DATABASE ENTRY DATE: 1993-07-23
<313> RELEVANT RESIDUES IN SEQ ID NO: (79)..(1338)

<400> SEQUENCE: 53

```
gtg cct att ttt aaa aaa act tta att gtt tta tcc ttt att ttt ttg     48
Met Pro Ile Phe Lys Lys Thr Leu Ile Val Leu Ser Phe Ile Phe Leu
1               5                   10                  15 ata tct atc ttg att tat cta aat atg tat cta ttt gga aca tca act     96
Ile Ser Ile Leu Ile Tyr Leu Asn Met Tyr Leu Phe Gly Thr Ser Thr
            20                  25                  30 gta gga att tat gga gta ata tta ata acc tat cta gtt atc aaa ctt    144
Val Gly Ile Tyr Gly Val Ile Leu Ile Thr Tyr Leu Val Ile Lys Leu
        35                  40                  45 gga tta tct ttc ctt tat gag cca ttt aaa gga aag cca cat gac tat    192
Gly Leu Ser Phe Leu Tyr Glu Pro Phe Lys Gly Lys Pro His Asp Tyr
50                  55                  60 aaa gtt gct gct gta att cct tct tat aat gaa gat gcc gag tca tta    240
Lys Val Ala Ala Val Ile Pro Ser Tyr Asn Glu Asp Ala Glu Ser Leu
65                  70                  75                  80 tta gaa aca ctt aaa agt gtg tta gca cag acc tat ccg tta tca gaa    288
Leu Glu Thr Leu Lys Ser Met Leu Ala Gln Thr Tyr Pro Leu Ser Glu
                85                  90                  95 att tat att gtt gat gat ggg agt tca aac aca gat gca ata caa tta    336
Ile Tyr Ile Val Asp Asp Gly Ser Ser Asn Thr Asp Ala Ile Gln Leu
            100                 105                 110 att gaa gag tat gta aat aga gaa gtg gat att tgt cga aac gtt atc    384
Ile Glu Glu Tyr Val Asn Arg Glu Met Asp Ile Cys Arg Asn Val Ile
        115                 120                 125 gtt cac cgt tcc ctt gtc aat aaa gga aaa cgc cat gct caa gcg tgg    432
Val His Arg Ser Leu Val Asn Lys Gly Lys Arg His Ala Gln Ala Trp
130                 135                 140 gca ttt gaa aga tct gac gct gac gtt ttt tta acc gta gat tca gat    480
Ala Phe Glu Arg Ser Asp Ala Asp Val Phe Leu Thr Val Asp Ser Asp
145                 150                 155                 160 act tat atc tat cca aat gcc tta gaa gaa ctc cta aaa agc ttc aat    528
Thr Tyr Ile Tyr Pro Asn Ala Leu Glu Glu Leu Leu Lys Ser Phe Asn
                165                 170                 175 gat gag aca gtt tat gct gca aca gga cat ttg aat gct aga aac aga    576
Asp Glu Thr Val Tyr Ala Ala Thr Gly His Leu Asn Ala Arg Asn Arg
            180                 185                 190 caa act aat cta tta acg cga ctt aca gat atc cgt tac gat aat gcc    624
Gln Thr Asn Leu Leu Thr Arg Leu Thr Asp Ile Arg Tyr Asp Asn Ala
        195                 200                 205 ttt ggg gtg gag cgt gct gct caa tca tta aca ggt aat att tta gtt    672
Phe Gly Met Glu Arg Ala Ala Gln Ser Leu Thr Gly Asn Ile Leu Val
210                 215                 220 tgc tca gga cca ttg agt att tat cga cgt gaa gtg att att cct aac    720
Cys Ser Gly Pro Leu Ser Ile Tyr Arg Arg Glu Val Ile Ile Pro Asn
225                 230                 235                 240 tta gag cgc tat aaa aat caa aca ttc cta ggt tta cct gtt agc att    768
Leu Glu Arg Tyr Lys Asn Gln Thr Phe Leu Gly Leu Pro Val Ser Ile
                245                 250                 255
```

```
ggg gat gat cga tgt tta aca aat tat gct att gat tta gga cgc act    816
Gly Asp Asp Arg Cys Leu Thr Asn Tyr Ala Ile Asp Leu Gly Arg Thr
        260                 265                 270 gtc tac caa tca aca gct aga tgt gat act gat gta cct ttc caa tta    864
Val Tyr Gln Ser Thr Ala Arg Cys Asp Thr Asp Val Pro Phe Gln Leu
    275                 280                 285 aaa agt tat tta aag caa caa aat cga tgg aat aaa tct ttt ttt aga    912
Lys Ser Tyr Leu Lys Gln Gln Asn Arg Trp Asn Lys Ser Phe Phe Arg
290                 295                 300 gaa tct att att tct gtt aaa aaa att ctt tct aat ccc atc gtt gcc    960
Glu Ser Ile Ile Ser Val Lys Lys Ile Leu Ser Asn Pro Ile Val Ala
305                 310                 315                 320 tta tgg act att ttc gaa gtc gtt atg ttt atg atg ttg att gtc gca   1008
Leu Trp Thr Ile Phe Glu Val Val Met Phe Met Met Leu Ile Val Ala
                325                 330                 335 att ggg aat ctt ttg ttt aat caa gct att caa tta gac ctt att aaa   1056
Ile Gly Asn Leu Leu Phe Asn Gln Ala Ile Gln Leu Asp Leu Ile Lys
            340                 345                 350 ctt ttt gcc ttt tta tcc atc atc ttt atc gtt gct tta tgt cgt aat   1104
Leu Phe Ala Phe Leu Ser Ile Ile Phe Ile Val Ala Leu Cys Arg Asn
        355                 360                 365 gtt cat tat atg gtc aaa cat cct gct agt ttt ttg tta tct cct ctg   1152
Val His Tyr Met Val Lys His Pro Ala Ser Phe Leu Leu Ser Pro Leu
370                 375                 380 tat gga ata tta cac ttg ttt gtc tta cag ccc cta aaa ctt tat tct   1200
Tyr Gly Ile Leu His Leu Phe Val Leu Gln Pro Leu Lys Leu Tyr Ser
385                 390                 395                 400 tta tgc acc att aaa aat acg gaa tgg gga aca cgt aaa aag gtc act   1248
Leu Cys Thr Ile Lys Asn Thr Glu Trp Gly Thr Arg Lys Lys Val Thr
                405                 410                 415 att ttt aaa taa                                                   1260
Ile Phe Lys <210> SEQ ID NO 54
<211> LENGTH: 419
<212> TYPE: PRT
<213> ORGANISM: Streptococcus pyogenes

<400> SEQUENCE: 54

Met Pro Ile Phe Lys Lys Thr Leu Ile Val Leu Ser Phe Ile Phe Leu
1               5                   10                  15

Ile Ser Ile Leu Ile Tyr Leu Asn Met Tyr Leu Phe Gly Thr Ser Thr
            20                  25                  30

Val Gly Ile Tyr Gly Val Ile Leu Ile Thr Tyr Leu Val Ile Lys Leu
        35                  40                  45

Gly Leu Ser Phe Leu Tyr Glu Pro Phe Lys Gly Lys Pro His Asp Tyr
    50                  55                  60

Lys Val Ala Ala Val Ile Pro Ser Tyr Asn Glu Asp Ala Glu Ser Leu
65                  70                  75                  80

Leu Glu Thr Leu Lys Ser Met Leu Ala Gln Thr Tyr Pro Leu Ser Glu
                85                  90                  95

Ile Tyr Ile Val Asp Asp Gly Ser Ser Asn Thr Asp Ala Ile Gln Leu
            100                 105                 110

Ile Glu Glu Tyr Val Asn Arg Glu Met Asp Ile Cys Arg Asn Val Ile
        115                 120                 125

Val His Arg Ser Leu Val Asn Lys Gly Lys Arg His Ala Gln Ala Trp
    130                 135                 140
```

```
Ala Phe Glu Arg Ser Asp Ala Asp Val Phe Leu Thr Val Asp Ser Asp
145                 150                 155                 160

Thr Tyr Ile Tyr Pro Asn Ala Leu Glu Glu Leu Leu Lys Ser Phe Asn
            165                 170                 175

Asp Glu Thr Val Tyr Ala Ala Thr Gly His Leu Asn Ala Arg Asn Arg
        180                 185                 190

Gln Thr Asn Leu Leu Thr Arg Leu Thr Asp Ile Arg Tyr Asp Asn Ala
    195                 200                 205

Phe Gly Met Glu Arg Ala Ala Gln Ser Leu Thr Gly Asn Ile Leu Val
210                 215                 220

Cys Ser Gly Pro Leu Ser Ile Tyr Arg Arg Glu Met Ile Ile Pro Asn
225                 230                 235                 240

Leu Glu Arg Tyr Lys Asn Gln Thr Phe Leu Gly Leu Pro Val Ser Ile
                245                 250                 255

Gly Asp Asp Arg Cys Leu Thr Asn Tyr Ala Ile Asp Leu Gly Arg Thr
                260                 265                 270

Val Tyr Gln Ser Thr Ala Arg Cys Asp Thr Asp Val Pro Phe Gln Leu
        275                 280                 285

Lys Ser Tyr Leu Lys Gln Gln Asn Arg Trp Asn Lys Ser Phe Phe Arg
290                 295                 300

Glu Ser Ile Ile Ser Val Lys Lys Ile Leu Ser Asn Pro Ile Val Ala
305                 310                 315                 320

Leu Trp Thr Ile Phe Glu Val Val Met Phe Met Met Leu Ile Val Ala
                325                 330                 335

Ile Gly Asn Leu Leu Phe Asn Gln Ala Ile Gln Leu Asp Leu Ile Lys
                340                 345                 350

Leu Phe Ala Phe Leu Ser Ile Ile Phe Ile Val Ala Leu Cys Arg Asn
        355                 360                 365

Val His Tyr Met Val Lys His Pro Ala Ser Phe Leu Leu Ser Pro Leu
    370                 375                 380

Tyr Gly Ile Leu His Leu Phe Val Leu Gln Pro Leu Lys Leu Tyr Ser
385                 390                 395                 400

Leu Cys Thr Ile Lys Asn Thr Glu Trp Gly Thr Arg Lys Lys Val Thr
                405                 410                 415

Ile Phe Lys

<210> SEQ ID NO 55
<211> LENGTH: 1254
<212> TYPE: DNA
<213> ORGANISM: Streptococcus equi
<220> FEATURE:
<221> NAME/KEY: CDS
<222> LOCATION: (1)..(1254)
<223> OTHER INFORMATION: Hyaluronan synthase
<300> PUBLICATION INFORMATION:
<308> DATABASE ACCESSION NUMBER: AF347022.1
<309> DATABASE ENTRY DATE: 2002-11-13
<313> RELEVANT RESIDUES IN SEQ ID NO: (531)..(1784)

<400> SEQUENCE: 55 atg aga aca tta aaa aac ctc ata act gtt gtg gcc ttt agt att ttt      48
Met Arg Thr Leu Lys Asn Leu Ile Thr Val Val Ala Phe Ser Ile Phe
1               5                   10                  15 tgg gta ctg ttg att tac gtc aat gtt tat ctc ttt ggt gct aaa gga      96
Trp Val Leu Leu Ile Tyr Val Asn Val Tyr Leu Phe Gly Ala Lys Gly
            20                  25                  30 agc ttg tca att tat ggc ttt ttg ctg ata gct tac cta tta gtc aaa     144
Ser Leu Ser Ile Tyr Gly Phe Leu Leu Ile Ala Tyr Leu Leu Val Lys
```

```
              35                  40                  45
atg tcc tta tcc ttt ttt tac aag cca ttt aag gga agg gct ggg caa    192
Met Ser Leu Ser Phe Phe Tyr Lys Pro Phe Lys Gly Arg Ala Gly Gln
 50                  55                  60 tat aag gtt gca gcc att att ccc tct tat aac gaa gat gct gag tca    240
Tyr Lys Val Ala Ala Ile Ile Pro Ser Tyr Asn Glu Asp Ala Glu Ser
 65                  70                  75                  80 ttg cta gag acc tta aaa agt gtt cag cag caa acc tat ccc cta gca    288
Leu Leu Glu Thr Leu Lys Ser Val Gln Gln Gln Thr Tyr Pro Leu Ala
                 85                  90                  95 gaa att tat gtt gtt gac gat gga agt gct gat gag aca ggt att aag    336
Glu Ile Tyr Val Val Asp Asp Gly Ser Ala Asp Glu Thr Gly Ile Lys
                100                 105                 110 cgc att gaa gac tat gtg cgt gac act ggt gac cta tca agc aat gtc    384
Arg Ile Glu Asp Tyr Val Arg Asp Thr Gly Asp Leu Ser Ser Asn Val
            115                 120                 125 att gtt cac cgg tca gaa aaa aat caa gga aag cgt cat gca cag gcc    432
Ile Val His Arg Ser Glu Lys Asn Gln Gly Lys Arg His Ala Gln Ala
        130                 135                 140 tgg gcc ttt gaa aga tca gac gct gat gtc ttt ttg acc gtt gac tca    480
Trp Ala Phe Glu Arg Ser Asp Ala Asp Val Phe Leu Thr Val Asp Ser
145                 150                 155                 160 gat act tat atc tac cct gat gct tta gag gag ttg tta aaa acc ttt    528
Asp Thr Tyr Ile Tyr Pro Asp Ala Leu Glu Glu Leu Leu Lys Thr Phe
                165                 170                 175 aat gac cca act gtt ttt gct gcg acg ggt cac ctt aat gtc aga aat    576
Asn Asp Pro Thr Val Phe Ala Ala Thr Gly His Leu Asn Val Arg Asn
                180                 185                 190 aga caa acc aat ctc tta aca cgc ttg aca gat att cgc tat gat aat    624
Arg Gln Thr Asn Leu Leu Thr Arg Leu Thr Asp Ile Arg Tyr Asp Asn
            195                 200                 205 gct ttt ggc gtt gaa cga gct gcc caa tcc gtt aca ggt aat att ctc    672
Ala Phe Gly Val Glu Arg Ala Ala Gln Ser Val Thr Gly Asn Ile Leu
        210                 215                 220 gtt tgc tca ggc ccg ctt agc gtt tac aga cgc gag gtg gtt gtt cct    720
Val Cys Ser Gly Pro Leu Ser Val Tyr Arg Arg Glu Val Val Val Pro
225                 230                 235                 240 aac ata gat aga tac atc aac cag acc ttc ctg ggt att cct gta agt    768
Asn Ile Asp Arg Tyr Ile Asn Gln Thr Phe Leu Gly Ile Pro Val Ser
                245                 250                 255 atc ggt gat gac agg tgc ttg acc aac tat gca act gat tta gga aag    816
Ile Gly Asp Asp Arg Cys Leu Thr Asn Tyr Ala Thr Asp Leu Gly Lys
                260                 265                 270 act gtt tat caa tcc act gct aaa tgt att aca gat gtt cct gac aag    864
Thr Val Tyr Gln Ser Thr Ala Lys Cys Ile Thr Asp Val Pro Asp Lys
            275                 280                 285 atg tct act tac ttg aag cag caa aac cgc tgg aac aag tcc ttc ttt    912
Met Ser Thr Tyr Leu Lys Gln Gln Asn Arg Trp Asn Lys Ser Phe Phe
        290                 295                 300 aga gag tcc att att tct gtt aag aaa atc atg aac aat cct ttt gta    960
Arg Glu Ser Ile Ile Ser Val Lys Lys Ile Met Asn Asn Pro Phe Val
305                 310                 315                 320 gcc cta tgg acc ata ctt gag gtg tct atg ttt atg atg ctt gtt tat   1008
Ala Leu Trp Thr Ile Leu Glu Val Ser Met Phe Met Met Leu Val Tyr
                325                 330                 335 tct gtg gtg gat ttc ttt gta gac aat gtc aga gaa ttt gat tgg ctc   1056
Ser Val Val Asp Phe Phe Val Asp Asn Val Arg Glu Phe Asp Trp Leu
                340                 345                 350 agg gtt ttg gcc ttt ctg gtg att atc ttc att gtt gct ctt tgt cgt   1104
Arg Val Leu Ala Phe Leu Val Ile Ile Phe Ile Val Ala Leu Cys Arg
```

```
                Arg Val Leu Ala Phe Leu Val Ile Ile Phe Ile Val Ala Leu Cys Arg
                                355                 360                 365 aat att cac tat atg ctt aag cac ccg ctg tcc ttc ttg tta tct ccg          1152
Asn Ile His Tyr Met Leu Lys His Pro Leu Ser Phe Leu Leu Ser Pro
    370                 375                 380 ttt tat ggg gta ctg cat ttg ttt gtc cta cag ccc ttg aaa ttg tat          1200
Phe Tyr Gly Val Leu His Leu Phe Val Leu Gln Pro Leu Lys Leu Tyr
385                 390                 395                 400 tct ctt ttt act att aga aat gct gac tgg gga aca cgt aaa aaa tta          1248
Ser Leu Phe Thr Ile Arg Asn Ala Asp Trp Gly Thr Arg Lys Lys Leu
                405                 410                 415 tta taa                                                                  1254
Leu <210> SEQ ID NO 56
<211> LENGTH: 417
<212> TYPE: PRT
<213> ORGANISM: Streptococcus equi

<400> SEQUENCE: 56
```

Met Arg Thr Leu Lys Asn Leu Ile Thr Val Ala Phe Ser Ile Phe
1               5                   10                  15

Trp Val Leu Leu Ile Tyr Val Asn Val Tyr Leu Phe Gly Ala Lys Gly
            20                  25                  30

Ser Leu Ser Ile Tyr Gly Phe Leu Leu Ile Ala Tyr Leu Leu Val Lys
        35                  40                  45

Met Ser Leu Ser Phe Phe Tyr Lys Pro Phe Lys Gly Arg Ala Gly Gln
    50                  55                  60

Tyr Lys Val Ala Ala Ile Ile Pro Ser Tyr Asn Glu Asp Ala Glu Ser
65                  70                  75                  80

Leu Leu Glu Thr Leu Lys Ser Val Gln Gln Gln Thr Tyr Pro Leu Ala
                85                  90                  95

Glu Ile Tyr Val Val Asp Asp Gly Ser Ala Asp Glu Thr Gly Ile Lys
            100                 105                 110

Arg Ile Glu Asp Tyr Val Arg Asp Thr Gly Asp Leu Ser Ser Asn Val
        115                 120                 125

Ile Val His Arg Ser Glu Lys Asn Gln Gly Lys Arg His Ala Gln Ala
    130                 135                 140

Trp Ala Phe Glu Arg Ser Asp Ala Asp Val Phe Leu Thr Val Asp Ser
145                 150                 155                 160

Asp Thr Tyr Ile Tyr Pro Asp Ala Leu Glu Glu Leu Leu Lys Thr Phe
                165                 170                 175

Asn Asp Pro Thr Val Phe Ala Ala Thr Gly His Leu Asn Val Arg Asn
            180                 185                 190

Arg Gln Thr Asn Leu Leu Thr Arg Leu Thr Asp Ile Arg Tyr Asp Asn
        195                 200                 205

Ala Phe Gly Val Glu Arg Ala Ala Gln Ser Val Thr Gly Asn Ile Leu
    210                 215                 220

Val Cys Ser Gly Pro Leu Ser Val Tyr Arg Arg Glu Val Val Val Pro
225                 230                 235                 240

Asn Ile Asp Arg Tyr Ile Asn Gln Thr Phe Leu Gly Ile Pro Val Ser
                245                 250                 255

Ile Gly Asp Asp Arg Cys Leu Thr Asn Tyr Ala Thr Asp Leu Gly Lys
            260                 265                 270

Thr Val Tyr Gln Ser Thr Ala Lys Cys Ile Thr Asp Val Pro Asp Lys
        275                 280                 285

```
Met Ser Thr Tyr Leu Lys Gln Gln Asn Arg Trp Asn Lys Ser Phe Phe
        290                 295                 300
Arg Glu Ser Ile Ile Ser Val Lys Lys Ile Met Asn Asn Pro Phe Val
305                 310                 315                 320
Ala Leu Trp Thr Ile Leu Glu Val Ser Met Phe Met Met Leu Val Tyr
                325                 330                 335
Ser Val Val Asp Phe Phe Val Asp Asn Val Arg Glu Phe Asp Trp Leu
            340                 345                 350
Arg Val Leu Ala Phe Leu Val Ile Ile Phe Ile Val Ala Leu Cys Arg
                355                 360                 365
Asn Ile His Tyr Met Leu Lys His Pro Leu Ser Phe Leu Leu Ser Pro
370                 375                 380
Phe Tyr Gly Val Leu His Leu Phe Val Leu Gln Pro Leu Lys Leu Tyr
385                 390                 395                 400
Ser Leu Phe Thr Ile Arg Asn Ala Asp Trp Gly Thr Arg Lys Lys Leu
                405                 410                 415
Leu

<210> SEQ ID NO 57
<211> LENGTH: 1254
<212> TYPE: DNA
<213> ORGANISM: Streptococcus uberis
<220> FEATURE:
<221> NAME/KEY: CDS
<222> LOCATION: (1)..(1254)
<223> OTHER INFORMATION: Hyaluronan synthase
<300> PUBLICATION INFORMATION:
<308> DATABASE ACCESSION NUMBER: AJ242946.2
<309> DATABASE ENTRY DATE: 1999-07-07
<313> RELEVANT RESIDUES IN SEQ ID NO: (23)..(1276)

<400> SEQUENCE: 57 atg gaa aaa cta aaa aat ctc att aca ttt atg act ttt att ttc ctg      48
Met Glu Lys Leu Lys Asn Leu Ile Thr Phe Met Thr Phe Ile Phe Leu
1               5                   10                  15 tgg ctc ata att att ggg ctt aat gtt ttt gta ttt gga act aaa gga      96
Trp Leu Ile Ile Ile Gly Leu Asn Val Phe Val Phe Gly Thr Lys Gly
            20                  25                  30 agt cta aca gtg tat ggg att att cta tta acc tat ttg tcg ata aaa     144
Ser Leu Thr Val Tyr Gly Ile Ile Leu Leu Thr Tyr Leu Ser Ile Lys
        35                  40                  45 atg gga tta tct ttt ttt tat cgt ccc tat aaa gga agt gta ggt caa     192
Met Gly Leu Ser Phe Phe Tyr Arg Pro Tyr Lys Gly Ser Val Gly Gln
    50                  55                  60 tat aag gta gca gct att atc cca tct tat aat gag gat ggt gtc ggt     240
Tyr Lys Val Ala Ala Ile Ile Pro Ser Tyr Asn Glu Asp Gly Val Gly
65                  70                  75                  80 tta cta gaa act cta aag agt gtt caa aaa caa aca tat cca att gca     288
Leu Leu Glu Thr Leu Lys Ser Val Gln Lys Gln Thr Tyr Pro Ile Ala
                85                  90                  95 gaa att ttc gta att gac gat ggg tca gta gat aaa aca ggt ata aaa     336
Glu Ile Phe Val Ile Asp Asp Gly Ser Val Asp Lys Thr Gly Ile Lys
            100                 105                 110 ttg gtc gaa gac tat gtg aag tta aat ggc ttt gga gac caa gtt atc     384
Leu Val Glu Asp Tyr Val Lys Leu Asn Gly Phe Gly Asp Gln Val Ile
        115                 120                 125 gtt cat cag atg cct gaa aat gtt ggt aaa aga cat gct cag gct tgg     432
Val His Gln Met Pro Glu Asn Val Gly Lys Arg His Ala Gln Ala Trp
    130                 135                 140
```

```
gca ttt gaa agg tct gat gct gat gtt ttc tta aca gtg gat tca gat      480
Ala Phe Glu Arg Ser Asp Ala Asp Val Phe Leu Thr Val Asp Ser Asp
145                 150                 155                 160 acc tac atc tat cct gat gct ctt gaa gaa tta tta aag aca ttt aat      528
Thr Tyr Ile Tyr Pro Asp Ala Leu Glu Glu Leu Leu Lys Thr Phe Asn
            165                 170                 175 gat cca gag gtc tac gct gca act ggt cat tta aat gca aga aat aga      576
Asp Pro Glu Val Tyr Ala Ala Thr Gly His Leu Asn Ala Arg Asn Arg
        180                 185                 190 caa act aat ctc tta act aga ctg act gat att cgt tac gat aat gca      624
Gln Thr Asn Leu Leu Thr Arg Leu Thr Asp Ile Arg Tyr Asp Asn Ala
    195                 200                 205 ttt ggt gta gaa cgt gct gct cag tct gtt acg gga aat att ttg gtt      672
Phe Gly Val Glu Arg Ala Ala Gln Ser Val Thr Gly Asn Ile Leu Val
210                 215                 220 tgt tcc gga cct tta agt att tat aga cgt tcc gtc ggt att cca aat      720
Cys Ser Gly Pro Leu Ser Ile Tyr Arg Arg Ser Val Gly Ile Pro Asn
225                 230                 235                 240 ctt gaa cgc tat acc tca caa aca ttt ctt ggt gtc cct gta agc ata      768
Leu Glu Arg Tyr Thr Ser Gln Thr Phe Leu Gly Val Pro Val Ser Ile
            245                 250                 255 ggg gat gac cgt tgt ttg aca aat tat gca act gat ttg gga aaa acg      816
Gly Asp Asp Arg Cys Leu Thr Asn Tyr Ala Thr Asp Leu Gly Lys Thr
        260                 265                 270 gtt tat cag tca act gca aga tgt gat act gac gtt cca gat aag ttt      864
Val Tyr Gln Ser Thr Ala Arg Cys Asp Thr Asp Val Pro Asp Lys Phe
    275                 280                 285 aag gtt ttc atc aaa caa caa aat cgt tgg aat aag tca ttt ttt agg      912
Lys Val Phe Ile Lys Gln Gln Asn Arg Trp Asn Lys Ser Phe Phe Arg
290                 295                 300 gag tct att atc tct gtt aag aag tta tta gcc aca cca agt gtt gct      960
Glu Ser Ile Ile Ser Val Lys Lys Leu Leu Ala Thr Pro Ser Val Ala
305                 310                 315                 320 gtt tgg act att aca gaa gtt tcc atg ttc atc atg cta gtt tat tct     1008
Val Trp Thr Ile Thr Glu Val Ser Met Phe Ile Met Leu Val Tyr Ser
            325                 330                 335 atc ttt agc tta ttg ata gga gag gct caa gaa ttt aat ctc ata aaa     1056
Ile Phe Ser Leu Leu Ile Gly Glu Ala Gln Glu Phe Asn Leu Ile Lys
        340                 345                 350 ctg gtt gct ttt tta gtt att att ttc ata gta gct ctt tgt aga aat     1104
Leu Val Ala Phe Leu Val Ile Ile Phe Ile Val Ala Leu Cys Arg Asn
    355                 360                 365 gtt cat tac atg gtt aag cat cca ttt gct ttt tta ttg tca ccg ttt     1152
Val His Tyr Met Val Lys His Pro Phe Ala Phe Leu Leu Ser Pro Phe
370                 375                 380 tat gga ttg ata cat cta ttc gtt ttg caa cct ctt aag ata tat tcg     1200
Tyr Gly Leu Ile His Leu Phe Val Leu Gln Pro Leu Lys Ile Tyr Ser
385                 390                 395                 400 tta ttt act ata aga aat gct aca tgg gga act cgt aaa aag aca agt     1248
Leu Phe Thr Ile Arg Asn Ala Thr Trp Gly Thr Arg Lys Lys Thr Ser
            405                 410                 415 aaa taa                                                              1254
Lys

<210> SEQ ID NO 58
<211> LENGTH: 417
<212> TYPE: PRT
<213> ORGANISM: Streptococcus uberis

<400> SEQUENCE: 58
```

```
Met Glu Lys Leu Lys Asn Leu Ile Thr Phe Met Thr Phe Ile Phe Leu
 1               5                  10                  15
Trp Leu Ile Ile Ile Gly Leu Asn Val Phe Val Phe Gly Thr Lys Gly
                20                  25                  30
Ser Leu Thr Val Tyr Gly Ile Ile Leu Leu Thr Tyr Leu Ser Ile Lys
                35                  40                  45
Met Gly Leu Ser Phe Phe Tyr Arg Pro Tyr Lys Gly Ser Val Gly Gln
 50                  55                  60
Tyr Lys Val Ala Ala Ile Ile Pro Ser Tyr Asn Glu Asp Gly Val Gly
 65                  70                  75                  80
Leu Leu Glu Thr Leu Lys Ser Val Gln Lys Gln Thr Tyr Pro Ile Ala
                85                  90                  95
Glu Ile Phe Val Ile Asp Asp Gly Ser Val Asp Lys Thr Gly Ile Lys
                100                 105                 110
Leu Val Glu Asp Tyr Val Lys Leu Asn Gly Phe Gly Asp Gln Val Ile
                115                 120                 125
Val His Gln Met Pro Glu Asn Val Gly Lys Arg His Ala Gln Ala Trp
                130                 135                 140
Ala Phe Glu Arg Ser Asp Ala Asp Val Phe Leu Thr Val Asp Ser Asp
145                 150                 155                 160
Thr Tyr Ile Tyr Pro Asp Ala Leu Glu Glu Leu Leu Lys Thr Phe Asn
                165                 170                 175
Asp Pro Glu Val Tyr Ala Ala Thr Gly His Leu Asn Ala Arg Asn Arg
                180                 185                 190
Gln Thr Asn Leu Leu Thr Arg Leu Thr Asp Ile Arg Tyr Asp Asn Ala
                195                 200                 205
Phe Gly Val Glu Arg Ala Ala Gln Ser Val Thr Gly Asn Ile Leu Val
                210                 215                 220
Cys Ser Gly Pro Leu Ser Ile Tyr Arg Arg Ser Val Gly Ile Pro Asn
225                 230                 235                 240
Leu Glu Arg Tyr Thr Ser Gln Thr Phe Leu Gly Val Pro Val Ser Ile
                245                 250                 255
Gly Asp Asp Arg Cys Leu Thr Asn Tyr Ala Thr Asp Leu Gly Lys Thr
                260                 265                 270
Val Tyr Gln Ser Thr Ala Arg Cys Asp Thr Asp Val Pro Asp Lys Phe
                275                 280                 285
Lys Val Phe Ile Lys Gln Gln Asn Arg Trp Asn Lys Ser Phe Phe Arg
                290                 295                 300
Glu Ser Ile Ile Ser Val Lys Lys Leu Leu Ala Thr Pro Ser Val Ala
305                 310                 315                 320
Val Trp Thr Ile Thr Glu Val Ser Met Phe Ile Met Leu Val Tyr Ser
                325                 330                 335
Ile Phe Ser Leu Leu Ile Gly Glu Ala Gln Glu Phe Asn Leu Ile Lys
                340                 345                 350
Leu Val Ala Phe Leu Val Ile Phe Ile Val Ala Leu Cys Arg Asn
                355                 360                 365
Val His Tyr Met Val Lys His Pro Phe Ala Phe Leu Leu Ser Pro Phe
                370                 375                 380
Tyr Gly Leu Ile His Leu Phe Val Leu Gln Pro Leu Lys Ile Tyr Ser
385                 390                 395                 400
Leu Phe Thr Ile Arg Asn Ala Thr Trp Gly Thr Arg Lys Lys Thr Ser
                405                 410                 415
Lys
```

<210> SEQ ID NO 59
<211> LENGTH: 1254
<212> TYPE: DNA
<213> ORGANISM: Streptococcus equisimilis
<220> FEATURE:
<221> NAME/KEY: CDS
<222> LOCATION: (1)..(1254)
<223> OTHER INFORMATION: Hyaluronan synthase
<300> PUBLICATION INFORMATION:
<308> DATABASE ACCESSION NUMBER: AF023876.1
<309> DATABASE ENTRY DATE: 1997-12-04
<313> RELEVANT RESIDUES IN SEQ ID NO: (1)..(1254)

<400> SEQUENCE: 59

```
atg aga aca tta aaa aac ctc ata act gtt gtg gcc ttt agt att ttt      48
Met Arg Thr Leu Lys Asn Leu Ile Thr Val Val Ala Phe Ser Ile Phe
1               5                   10                  15 tgg gta ctg ttg att tac gtc aat gtt tat ctc ttt ggt gct aaa gga      96
Trp Val Leu Leu Ile Tyr Val Asn Val Tyr Leu Phe Gly Ala Lys Gly
            20                  25                  30 agc ttg tca att tat ggc ttt ttg ctg ata gct tac cta tta gtc aaa     144
Ser Leu Ser Ile Tyr Gly Phe Leu Leu Ile Ala Tyr Leu Leu Val Lys
        35                  40                  45 atg tcc tta tcc ttt ttt tac aag cca ttt aag gga agg gct ggg caa     192
Met Ser Leu Ser Phe Phe Tyr Lys Pro Phe Lys Gly Arg Ala Gly Gln
    50                  55                  60 tat aag gtt gca gcc att att ccc tct tat aac gaa gat gct gag tca     240
Tyr Lys Val Ala Ala Ile Ile Pro Ser Tyr Asn Glu Asp Ala Glu Ser
65                  70                  75                  80 ttg cta gag acc tta aaa agt gtt cag cag caa acc tat ccc cta gca     288
Leu Leu Glu Thr Leu Lys Ser Val Gln Gln Gln Thr Tyr Pro Leu Ala
                85                  90                  95 gaa att tat gtt gtt gac gat gga agt gct gat gag aca ggt att aag     336
Glu Ile Tyr Val Val Asp Asp Gly Ser Ala Asp Glu Thr Gly Ile Lys
            100                 105                 110 cgc att gaa gac tat gtg cgt gac act ggt gac cta tca agc aat gtc     384
Arg Ile Glu Asp Tyr Val Arg Asp Thr Gly Asp Leu Ser Ser Asn Val
        115                 120                 125 att gtt cat cgg tca gag aaa aat caa gga aag cgt cat gca cag gcc     432
Ile Val His Arg Ser Glu Lys Asn Gln Gly Lys Arg His Ala Gln Ala
    130                 135                 140 tgg gcc ttt gaa aga tca gac gct gat gtc ttt ttg acc gtt gac tca     480
Trp Ala Phe Glu Arg Ser Asp Ala Asp Val Phe Leu Thr Val Asp Ser
145                 150                 155                 160 gat act tat atc tac cct gat gct tta gag gag ttg tta aaa acc ttt     528
Asp Thr Tyr Ile Tyr Pro Asp Ala Leu Glu Glu Leu Leu Lys Thr Phe
                165                 170                 175 aat gac cca act gtt ttt gct gcg acg ggt cac ctt aat gtc aga aat     576
Asn Asp Pro Thr Val Phe Ala Ala Thr Gly His Leu Asn Val Arg Asn
            180                 185                 190 aga caa acc aat ctc tta aca cgc ttg aca gat att cgc tat gat aat     624
Arg Gln Thr Asn Leu Leu Thr Arg Leu Thr Asp Ile Arg Tyr Asp Asn
        195                 200                 205 gct ttt ggc gtt gaa cga gct gcc caa tcc gtt aca ggt aat atc ctt     672
Ala Phe Gly Val Glu Arg Ala Ala Gln Ser Val Thr Gly Asn Ile Leu
    210                 215                 220 gtt tgc tca ggt ccg ctt agc gtt tac aga cgc gag gtg gtt gtt cct     720
Val Cys Ser Gly Pro Leu Ser Val Tyr Arg Arg Glu Val Val Val Pro
225                 230                 235                 240 aac ata gat aga tac atc aac cag acc ttc ctg ggt att cct gta agt     768
Asn Ile Asp Arg Tyr Ile Asn Gln Thr Phe Leu Gly Ile Pro Val Ser
```

-continued

```
                    245                 250                 255
att ggt gat gac agg tgc ttg acc aac tat gca act gat tta gga aag      816
Ile Gly Asp Asp Arg Cys Leu Thr Asn Tyr Ala Thr Asp Leu Gly Lys
            260                 265                 270 act gtt tat caa tcc act gct aaa tgt att aca gat gtt cct gac aag      864
Thr Val Tyr Gln Ser Thr Ala Lys Cys Ile Thr Asp Val Pro Asp Lys
        275                 280                 285 atg tct act tac ttg aag cag caa aac cgc tgg aac aag tcc ttc ttt      912
Met Ser Thr Tyr Leu Lys Gln Gln Asn Arg Trp Asn Lys Ser Phe Phe
290                 295                 300 aga gag tcc att att tct gtt aag aaa atc atg aac aat cct ttt gta      960
Arg Glu Ser Ile Ile Ser Val Lys Lys Ile Met Asn Asn Pro Phe Val
305                 310                 315                 320 gcc cta tgg acc ata ctt gag gtg tct atg ttt atg atg ctt gtt tat     1008
Ala Leu Trp Thr Ile Leu Glu Val Ser Met Phe Met Met Leu Val Tyr
                325                 330                 335 tct gtg gtg gat ttc ttt gta ggc aat gtc aga gaa ttt gat tgg ctc     1056
Ser Val Val Asp Phe Phe Val Gly Asn Val Arg Glu Phe Asp Trp Leu
            340                 345                 350 agg gtt tta gcc ttt ctg gtg att atc ttc att gtt gcc ctg tgt cgg     1104
Arg Val Leu Ala Phe Leu Val Ile Ile Phe Ile Val Ala Leu Cys Arg
        355                 360                 365 aac att cat tac atg ctt aag cac ccg ctg tcc ttc ttg tta tct ccg     1152
Asn Ile His Tyr Met Leu Lys His Pro Leu Ser Phe Leu Leu Ser Pro
370                 375                 380 ttt tat ggg gtg ctg cat ttg ttt gtc cta cag ccc ttg aaa tta tat     1200
Phe Tyr Gly Val Leu His Leu Phe Val Leu Gln Pro Leu Lys Leu Tyr
385                 390                 395                 400 tct ctt ttt act att aga aat gct gac tgg gga aca cgt aaa aaa tta     1248
Ser Leu Phe Thr Ile Arg Asn Ala Asp Trp Gly Thr Arg Lys Lys Leu
                405                 410                 415 tta taa                                                              1254
Leu

<210> SEQ ID NO 60
<211> LENGTH: 417
<212> TYPE: PRT
<213> ORGANISM: Streptococcus equisimilis

<400> SEQUENCE: 60

Met Arg Thr Leu Lys Asn Leu Ile Thr Val Val Ala Phe Ser Ile Phe
1               5                   10                  15

Trp Val Leu Leu Ile Tyr Val Asn Val Tyr Leu Phe Gly Ala Lys Gly
            20                  25                  30

Ser Leu Ser Ile Tyr Gly Phe Leu Leu Ile Ala Tyr Leu Leu Val Lys
        35                  40                  45

Met Ser Leu Ser Phe Phe Tyr Lys Pro Phe Lys Gly Arg Ala Gly Gln
    50                  55                  60

Tyr Lys Val Ala Ala Ile Ile Pro Ser Tyr Asn Glu Asp Ala Glu Ser
65                  70                  75                  80

Leu Leu Glu Thr Leu Lys Ser Val Gln Gln Gln Thr Tyr Pro Leu Ala
                85                  90                  95

Glu Ile Tyr Val Val Asp Asp Gly Ser Ala Asp Glu Thr Gly Ile Lys
            100                 105                 110

Arg Ile Glu Asp Tyr Val Arg Asp Thr Gly Asp Leu Ser Ser Asn Val
        115                 120                 125

Ile Val His Arg Ser Glu Lys Asn Gln Gly Lys Arg His Ala Gln Ala
    130                 135                 140
```

```
Trp Ala Phe Glu Arg Ser Asp Ala Asp Val Phe Leu Thr Val Asp Ser
145                 150                 155                 160

Asp Thr Tyr Ile Tyr Pro Asp Ala Leu Glu Glu Leu Leu Lys Thr Phe
                165                 170                 175

Asn Asp Pro Thr Val Phe Ala Ala Thr Gly His Leu Asn Val Arg Asn
            180                 185                 190

Arg Gln Thr Asn Leu Leu Thr Arg Leu Thr Asp Ile Arg Tyr Asp Asn
        195                 200                 205

Ala Phe Gly Val Glu Arg Ala Ala Gln Ser Val Thr Gly Asn Ile Leu
    210                 215                 220

Val Cys Ser Gly Pro Leu Ser Val Tyr Arg Arg Glu Val Val Val Pro
225                 230                 235                 240

Asn Ile Asp Arg Tyr Ile Asn Gln Thr Phe Leu Gly Ile Pro Val Ser
                245                 250                 255

Ile Gly Asp Asp Arg Cys Leu Thr Asn Tyr Ala Thr Asp Leu Gly Lys
            260                 265                 270

Thr Val Tyr Gln Ser Thr Ala Lys Cys Ile Thr Asp Val Pro Asp Lys
        275                 280                 285

Met Ser Thr Tyr Leu Lys Gln Gln Asn Arg Trp Asn Lys Ser Phe Phe
    290                 295                 300

Arg Glu Ser Ile Ile Ser Val Lys Lys Ile Met Asn Asn Pro Phe Val
305                 310                 315                 320

Ala Leu Trp Thr Ile Leu Glu Val Ser Met Phe Met Met Leu Val Tyr
                325                 330                 335

Ser Val Val Asp Phe Phe Val Gly Asn Val Arg Glu Phe Asp Trp Leu
            340                 345                 350

Arg Val Leu Ala Phe Leu Val Ile Ile Phe Ile Val Ala Leu Cys Arg
        355                 360                 365

Asn Ile His Tyr Met Leu Lys His Pro Leu Ser Phe Leu Leu Ser Pro
    370                 375                 380

Phe Tyr Gly Val Leu His Leu Phe Val Leu Gln Pro Leu Lys Leu Tyr
385                 390                 395                 400

Ser Leu Phe Thr Ile Arg Asn Ala Asp Trp Gly Thr Arg Lys Lys Leu
                405                 410                 415

Leu
```

<210> SEQ ID NO 61
<211> LENGTH: 1248
<212> TYPE: DNA
<213> ORGANISM: Sulfolobus tokodaii str. 7
<220> FEATURE:
<221> NAME/KEY: CDS
<222> LOCATION: (1)..(1248)
<223> OTHER INFORMATION: Hyaluronan synthase
<300> PUBLICATION INFORMATION:
<308> DATABASE ACCESSION NUMBER: AP000988
<309> DATABASE ENTRY DATE: 2001-09-17
<313> RELEVANT RESIDUES IN SEQ ID NO: (173392)..(174639)

<400> SEQUENCE: 61

```
gtg gtg att atg ttt cac tta ttt cac gga gtc tca tat ttc att tat      48
Met Met Ile Met Phe His Leu Phe His Gly Val Ser Tyr Phe Ile Tyr
1               5                   10                  15 tct ctt tca ttc aca att ata act att ctt tat ttc ttt ttg aat tca      96
Ser Leu Ser Phe Thr Ile Ile Thr Ile Leu Tyr Phe Phe Leu Asn Ser
            20                  25                  30 ttt ttt gca gta ata agt aat aat aga aaa act caa cac tca agt ttt     144
```

|     |     |     |     |     |     |     |     |     |     |     |     |     |     |     |
|---|---|---|---|---|---|---|---|---|---|---|---|---|---|---|
| Phe | Phe | Ala | Val | Ile | Ser | Asn | Asn | Arg | Lys | Thr | Gln | His | Ser | Ser | Phe |
|     |     |     | 35  |     |     |     | 40  |     |     |     |     | 45  |     |     |     |

| tat | aat | ctc | tct | gat | ctt | aca | gtt | gtg | ata | cca | gtt | tat | aag | gag | gaa | 192 |
|---|---|---|---|---|---|---|---|---|---|---|---|---|---|---|---|---|
| Tyr | Asn | Leu | Ser | Asp | Leu | Thr | Val | Met | Ile | Pro | Val | Tyr | Lys | Glu | Glu |     |
|     | 50  |     |     |     |     | 55  |     |     |     |     | 60  |     |     |     |     |     |

| ata | gat | att | ttt | gaa | aaa | gtg | ata | agg | act | tta | tat | gac | aca | agg | tta | 240 |
|---|---|---|---|---|---|---|---|---|---|---|---|---|---|---|---|---|
| Ile | Asp | Ile | Phe | Glu | Lys | Met | Ile | Arg | Thr | Leu | Tyr | Asp | Thr | Arg | Leu |     |
| 65  |     |     |     |     | 70  |     |     |     |     | 75  |     |     |     |     | 80  |     |

| gaa | ttt | att | gtt | gta | ggg | gat | agt | gtt | cta | gaa | cca | tac | aaa | tca | att | 288 |
|---|---|---|---|---|---|---|---|---|---|---|---|---|---|---|---|---|
| Glu | Phe | Ile | Val | Val | Gly | Asp | Ser | Val | Leu | Glu | Pro | Tyr | Lys | Ser | Ile |     |
|     |     |     |     | 85  |     |     |     |     | 90  |     |     |     |     | 95  |     |     |

| acg | gaa | aga | tat | ggt | ggt | aaa | ttt | att | tat | atg | cgt | gaa | cat | aag | ggg | 336 |
|---|---|---|---|---|---|---|---|---|---|---|---|---|---|---|---|---|
| Thr | Glu | Arg | Tyr | Gly | Gly | Lys | Phe | Ile | Tyr | Met | Arg | Glu | His | Lys | Gly |     |
|     |     |     | 100 |     |     |     |     | 105 |     |     |     |     | 110 |     |     |     |

| aaa | aga | tac | gcg | tta | gcc | gag | gga | gtt | aag | tat | gta | aga | tct | cct | cta | 384 |
|---|---|---|---|---|---|---|---|---|---|---|---|---|---|---|---|---|
| Lys | Arg | Tyr | Ala | Leu | Ala | Glu | Gly | Val | Lys | Tyr | Val | Arg | Ser | Pro | Leu |     |
|     |     | 115 |     |     |     |     | 120 |     |     |     |     | 125 |     |     |     |     |

| gtg | atg | ttt | cta | gat | agt | gat | acg | att | att | tat | aaa | gac | tct | ata | cta | 432 |
|---|---|---|---|---|---|---|---|---|---|---|---|---|---|---|---|---|
| Met | Met | Phe | Leu | Asp | Ser | Asp | Thr | Ile | Ile | Tyr | Lys | Asp | Ser | Ile | Leu |     |
|     | 130 |     |     |     |     | 135 |     |     |     |     | 140 |     |     |     |     |     |

| aag | atg | tta | agt | gtt | ttt | gat | gag | tca | gta | ggt | gga | gta | ggg | cca | aat | 480 |
|---|---|---|---|---|---|---|---|---|---|---|---|---|---|---|---|---|
| Lys | Met | Leu | Ser | Val | Phe | Asp | Glu | Ser | Val | Gly | Gly | Val | Gly | Pro | Asn |     |
| 145 |     |     |     |     | 150 |     |     |     |     | 155 |     |     |     |     | 160 |     |

| att | aga | att | atg | tat | gac | gag | aaa | aat | aaa | tat | gca | tat | tat | tat | ggt | 528 |
|---|---|---|---|---|---|---|---|---|---|---|---|---|---|---|---|---|
| Ile | Arg | Ile | Met | Tyr | Asp | Glu | Lys | Asn | Lys | Tyr | Ala | Tyr | Tyr | Tyr | Gly |     |
|     |     |     |     | 165 |     |     |     |     | 170 |     |     |     |     | 175 |     |     |

| gaa | ttc | ttt | gag | aga | ata | agt | gag | ata | gta | aac | agg | gcg | gta | aac | tat | 576 |
|---|---|---|---|---|---|---|---|---|---|---|---|---|---|---|---|---|
| Glu | Phe | Phe | Glu | Arg | Ile | Ser | Glu | Ile | Val | Asn | Arg | Ala | Val | Asn | Tyr |     |
|     |     |     | 180 |     |     |     |     | 185 |     |     |     |     | 190 |     |     |     |

| ttt | gga | agt | gct | ata | ata | tta | agt | gga | caa | tgt | gta | ata | tat | agg | acc | 624 |
|---|---|---|---|---|---|---|---|---|---|---|---|---|---|---|---|---|
| Phe | Gly | Ser | Ala | Ile | Ile | Leu | Ser | Gly | Gln | Cys | Val | Ile | Tyr | Arg | Thr |     |
|     |     | 195 |     |     |     |     | 200 |     |     |     |     | 205 |     |     |     |     |

| gaa | ctc | gta | aaa | cca | tat | ata | tta | tct | aaa | gag | ttt | tta | gag | ccg | aaa | 672 |
|---|---|---|---|---|---|---|---|---|---|---|---|---|---|---|---|---|
| Glu | Leu | Val | Lys | Pro | Tyr | Ile | Leu | Ser | Lys | Glu | Phe | Leu | Glu | Pro | Lys |     |
|     | 210 |     |     |     |     | 215 |     |     |     |     | 220 |     |     |     |     |     |

| atg | ttt | gga | aga | cca | att | aaa | att | tcc | gat | gat | aga | gat | tta | acc | gat | 720 |
|---|---|---|---|---|---|---|---|---|---|---|---|---|---|---|---|---|
| Met | Phe | Gly | Arg | Pro | Ile | Lys | Ile | Ser | Asp | Asp | Arg | Asp | Leu | Thr | Asp |     |
| 225 |     |     |     |     | 230 |     |     |     |     | 235 |     |     |     |     | 240 |     |

| ttt | gtt | ata | aaa | aaa | ggg | tat | agg | gct | gta | aaa | gtc | ttt | gat | gca | gtg | 768 |
|---|---|---|---|---|---|---|---|---|---|---|---|---|---|---|---|---|
| Phe | Val | Ile | Lys | Lys | Gly | Tyr | Arg | Ala | Val | Lys | Val | Phe | Asp | Ala | Met |     |
|     |     |     |     | 245 |     |     |     |     | 250 |     |     |     |     | 255 |     |     |

| gca | tat | aca | aaa | ccc | cct | aga | gac | ata | aaa | atg | ttt | acg | aaa | caa | gta | 816 |
|---|---|---|---|---|---|---|---|---|---|---|---|---|---|---|---|---|
| Ala | Tyr | Thr | Lys | Pro | Pro | Arg | Asp | Ile | Lys | Met | Phe | Thr | Lys | Gln | Val |     |
|     |     |     | 260 |     |     |     |     | 265 |     |     |     |     | 270 |     |     |     |

| act | aga | tgg | aca | aga | gca | aat | tat | ctt | aat | ttt | ata | agg | gag | ata | gct | 864 |
|---|---|---|---|---|---|---|---|---|---|---|---|---|---|---|---|---|
| Thr | Arg | Trp | Thr | Arg | Ala | Asn | Tyr | Leu | Asn | Phe | Ile | Arg | Glu | Ile | Ala |     |
|     |     | 275 |     |     |     |     | 280 |     |     |     |     | 285 |     |     |     |     |

| gac | ggt | agt | ata | agt | aaa | agg | ggt | tca | tta | tac | gtt | ttt | aat | atg | ata | 912 |
|---|---|---|---|---|---|---|---|---|---|---|---|---|---|---|---|---|
| Asp | Gly | Ser | Ile | Ser | Lys | Arg | Gly | Ser | Leu | Tyr | Val | Phe | Asn | Met | Ile |     |
|     | 290 |     |     |     |     | 295 |     |     |     |     | 300 |     |     |     |     |     |

| tac | acc | aat | ctg | tta | cca | tta | ttt | acg | ctc | ttg | ttc | ctt | tat | atg | agt | 960 |
|---|---|---|---|---|---|---|---|---|---|---|---|---|---|---|---|---|
| Tyr | Thr | Asn | Leu | Leu | Pro | Leu | Phe | Thr | Leu | Leu | Phe | Leu | Tyr | Met | Ser |     |
| 305 |     |     |     |     | 310 |     |     |     |     | 315 |     |     |     |     | 320 |     |

| ttc | act | aga | att | ctt | aag | atc | tat | tcc | tca | att | aat | gta | att | aat | act | 1008 |
|---|---|---|---|---|---|---|---|---|---|---|---|---|---|---|---|---|
| Phe | Thr | Arg | Ile | Leu | Lys | Ile | Tyr | Ser | Ser | Ile | Asn | Val | Ile | Asn | Thr |     |
|     |     |     |     | 325 |     |     |     |     | 330 |     |     |     |     | 335 |     |     |

| aag | ctc | tta | tta | cta | ttg | tat | ctg | cca | acc | cgt | tac | cat | tcc | gac | ttc | 1056 |
|---|---|---|---|---|---|---|---|---|---|---|---|---|---|---|---|---|
| Lys | Leu | Leu | Leu | Leu | Leu | Tyr | Leu | Pro | Thr | Arg | Tyr | His | Ser | Asp | Phe |     |
|     |     |     | 340 |     |     |     |     | 345 |     |     |     |     | 350 |     |     |     |

| | | | | | | | | | | | | | | | |
|---|---|---|---|---|---|---|---|---|---|---|---|---|---|---|---|
| ttt | atc | ttt | tat | tta | ttc | ttg | cat | tac | gga | gga | ttt | ata | gct | ata | ata | 1104 |
| Phe | Ile | Phe | Tyr | Leu | Phe | Leu | His | Tyr | Gly | Gly | Phe | Ile | Ala | Ile | Ile |
| | 355 | | | | | 360 | | | | | 365 | | | | |
| ccc | ttt | gta | atg | acc | atg | att | tat | tta | att | cca | gaa | gat | aaa | ttg | aaa | 1152 |
| Pro | Phe | Val | Met | Thr | Met | Ile | Tyr | Leu | Ile | Pro | Glu | Asp | Lys | Leu | Lys |
| 370 | | | | | 375 | | | | | 380 | | | | | |
| act | cta | ata | tac | ggt | tct | atc | gca | cta | gca | gtg | caa | tat | att | gct | tcc | 1200 |
| Thr | Leu | Ile | Tyr | Gly | Ser | Ile | Ala | Leu | Ala | Met | Gln | Tyr | Ile | Ala | Ser |
| 385 | | | | | 390 | | | | | 395 | | | | | 400 |
| cta | tat | gct | atg | ata | act | ttc | tgg | tgg | caa | gat | tgg | tta | act | aga | taa | 1248 |
| Leu | Tyr | Ala | Met | Ile | Thr | Phe | Trp | Trp | Gln | Asp | Trp | Leu | Thr | Arg |
| | | | | 405 | | | | | 410 | | | | | 415 | |

<210> SEQ ID NO 62
<211> LENGTH: 415
<212> TYPE: PRT
<213> ORGANISM: Sulfolobus tokodaii str. 7

<400> SEQUENCE: 62

Met Met Ile Met Phe His Leu Phe His Gly Val Ser Tyr Phe Ile Tyr
1               5                   10                  15

Ser Leu Ser Phe Thr Ile Ile Thr Ile Leu Tyr Phe Phe Leu Asn Ser
            20                  25                  30

Phe Phe Ala Val Ile Ser Asn Asn Arg Lys Thr Gln His Ser Ser Phe
        35                  40                  45

Tyr Asn Leu Ser Asp Leu Thr Val Met Ile Pro Val Tyr Lys Glu Glu
    50                  55                  60

Ile Asp Ile Phe Glu Lys Met Ile Arg Thr Leu Tyr Asp Thr Arg Leu
65                  70                  75                  80

Glu Phe Ile Val Val Gly Asp Ser Val Leu Glu Pro Tyr Lys Ser Ile
                85                  90                  95

Thr Glu Arg Tyr Gly Gly Lys Phe Ile Tyr Met Arg Glu His Lys Gly
            100                 105                 110

Lys Arg Tyr Ala Leu Ala Glu Gly Val Lys Tyr Val Arg Ser Pro Leu
        115                 120                 125

Met Met Phe Leu Asp Ser Asp Thr Ile Ile Tyr Lys Asp Ser Ile Leu
130                 135                 140

Lys Met Leu Ser Val Phe Asp Glu Ser Val Gly Gly Val Gly Pro Asn
145                 150                 155                 160

Ile Arg Ile Met Tyr Asp Glu Lys Asn Lys Tyr Ala Tyr Tyr Tyr Gly
                165                 170                 175

Glu Phe Phe Glu Arg Ile Ser Glu Ile Val Asn Arg Ala Val Asn Tyr
            180                 185                 190

Phe Gly Ser Ala Ile Ile Leu Ser Gly Gln Cys Val Ile Tyr Arg Thr
        195                 200                 205

Glu Leu Val Lys Pro Tyr Ile Leu Ser Lys Glu Phe Leu Glu Pro Lys
    210                 215                 220

Met Phe Gly Arg Pro Ile Lys Ile Ser Asp Asp Arg Asp Leu Thr Asp
225                 230                 235                 240

Phe Val Ile Lys Lys Gly Tyr Arg Ala Val Lys Val Phe Asp Ala Met
                245                 250                 255

Ala Tyr Thr Lys Pro Pro Arg Asp Ile Lys Met Phe Thr Lys Gln Val
            260                 265                 270

Thr Arg Trp Thr Arg Ala Asn Tyr Leu Asn Phe Ile Arg Glu Ile Ala
        275                 280                 285

Asp Gly Ser Ile Ser Lys Arg Gly Ser Leu Tyr Val Phe Asn Met Ile

```
                   290                 295                 300
Tyr Thr Asn Leu Leu Pro Leu Phe Thr Leu Leu Phe Leu Tyr Met Ser
305                 310                 315                 320

Phe Thr Arg Ile Leu Lys Ile Tyr Ser Ser Ile Asn Val Ile Asn Thr
                325                 330                 335

Lys Leu Leu Leu Leu Leu Tyr Leu Pro Thr Arg Tyr His Ser Asp Phe
                340                 345                 350

Phe Ile Phe Tyr Leu Phe Leu His Tyr Gly Gly Phe Ile Ala Ile Ile
            355                 360                 365

Pro Phe Val Met Thr Met Ile Tyr Leu Ile Pro Glu Asp Lys Leu Lys
        370                 375                 380

Thr Leu Ile Tyr Gly Ser Ile Ala Leu Ala Met Gln Tyr Ile Ala Ser
385                 390                 395                 400

Leu Tyr Ala Met Ile Thr Phe Trp Trp Gln Asp Trp Leu Thr Arg
                405                 410                 415

<210> SEQ ID NO 63
<211> LENGTH: 1767
<212> TYPE: DNA
<213> ORGANISM: Artificial Sequence
<220> FEATURE:
<221> NAME/KEY: CDS
<222> LOCATION: (1)..(1767)
<223> OTHER INFORMATION: Synthetic sequence encoding HAS 1 from Xenopus
      laevis

<400> SEQUENCE: 63 atg aaa gag aaa gcc gct gaa aca atg gaa ata ccg gaa gga atc cct      48
Met Lys Glu Lys Ala Ala Glu Thr Met Glu Ile Pro Glu Gly Ile Pro
1               5                   10                  15 aaa gat tta gaa ccc aag cac cct acg ttg tgg cgc att atc tac tat      96
Lys Asp Leu Glu Pro Lys His Pro Thr Leu Trp Arg Ile Ile Tyr Tyr
            20                  25                  30 tcc ttc ggt gtt gtc ctc ctt gcg acg att act gct gcc tac gtt gca     144
Ser Phe Gly Val Val Leu Leu Ala Thr Ile Thr Ala Ala Tyr Val Ala
        35                  40                  45 gag ttc caa gtc ctc aaa cat gaa gcc atc ctg ttc tcc ctt ggc ctg     192
Glu Phe Gln Val Leu Lys His Glu Ala Ile Leu Phe Ser Leu Gly Leu
    50                  55                  60 tat ggg ctc gca atg ttg ctc cat ctc atg atg caa tca cta ttc gcg     240
Tyr Gly Leu Ala Met Leu Leu His Leu Met Met Gln Ser Leu Phe Ala
65                  70                  75                  80 ttc ttg gag atc cgt cgc gtc aac aaa tcg gag ctc cct tgc tca ttc     288
Phe Leu Glu Ile Arg Arg Val Asn Lys Ser Glu Leu Pro Cys Ser Phe
                85                  90                  95 aag aag acg gtc gcc ctc act atc gca ggc tat caa gag aat ccc gaa     336
Lys Lys Thr Val Ala Leu Thr Ile Ala Gly Tyr Gln Glu Asn Pro Glu
            100                 105                 110 tac ctt atc aag tgc ctc gaa agt tgt aag tac gtc aag tac cca aag     384
Tyr Leu Ile Lys Cys Leu Glu Ser Cys Lys Tyr Val Lys Tyr Pro Lys
        115                 120                 125 gac aaa ttg aag atc atc ttg gtt atc gac ggc aac aca gag gat gac     432
Asp Lys Leu Lys Ile Ile Leu Val Ile Asp Gly Asn Thr Glu Asp Asp
    130                 135                 140 gct tac atg atg gaa atg ttc aag gat gtg ttc cac gga gag gat gta     480
Ala Tyr Met Met Glu Met Phe Lys Asp Val Phe His Gly Glu Asp Val
145                 150                 155                 160 ggt act tac gtc tgg aag gga aac tac cat acc gtg aag aaa ccc gag     528
Gly Thr Tyr Val Trp Lys Gly Asn Tyr His Thr Val Lys Lys Pro Glu
                165                 170                 175
```

-continued

| | | |
|---|---|---|
| gag aca aac aag gga agc tgt ccc gag gta tcg aaa cct ttg aac gaa<br>Glu Thr Asn Lys Gly Ser Cys Pro Glu Val Ser Lys Pro Leu Asn Glu<br>180 185 190 | 576 | |
| gat gaa ggt atc aac atg gtt gaa gag tta gtc cgt aac aag agg tgc<br>Asp Glu Gly Ile Asn Met Val Glu Glu Leu Val Arg Asn Lys Arg Cys<br>195 200 205 | 624 | |
| gtt tgc att atg caa cag tgg gga ggt aaa cga gaa gtg atg tat act<br>Val Cys Ile Met Gln Gln Trp Gly Gly Lys Arg Glu Val Met Tyr Thr<br>210 215 220 | 672 | |
| gcc ttc caa gca ata ggt act tcc gtt gac tac gtt caa gtc tgt gac<br>Ala Phe Gln Ala Ile Gly Thr Ser Val Asp Tyr Val Gln Val Cys Asp<br>225 230 235 240 | 720 | |
| agc gac acc aag ctc gac gag ctt gcc acc gtt gag atg gtg aaa gtt<br>Ser Asp Thr Lys Leu Asp Glu Leu Ala Thr Val Glu Met Val Lys Val<br>245 250 255 | 768 | |
| ctg gag tca aac gac atg tat ggt gcg gtc ggc ggt gat gtt cga atc<br>Leu Glu Ser Asn Asp Met Tyr Gly Ala Val Gly Gly Asp Val Arg Ile<br>260 265 270 | 816 | |
| ttg aat cca tac gac tcg ttc atc agt ttc atg agc tca ctt agg tac<br>Leu Asn Pro Tyr Asp Ser Phe Ile Ser Phe Met Ser Ser Leu Arg Tyr<br>275 280 285 | 864 | |
| tgg atg gct ttc aat gtc gag cgc gct tgt caa agc tat ttc gat tgc<br>Trp Met Ala Phe Asn Val Glu Arg Ala Cys Gln Ser Tyr Phe Asp Cys<br>290 295 300 | 912 | |
| gta tct tgc att agt gga cct ctc ggt atg tat aga aat aac att ctt<br>Val Ser Cys Ile Ser Gly Pro Leu Gly Met Tyr Arg Asn Asn Ile Leu<br>305 310 315 320 | 960 | |
| cag gtg ttc ctc gaa gct tgg tat cgg cag aag ttc ttg ggc acc tac<br>Gln Val Phe Leu Glu Ala Trp Tyr Arg Gln Lys Phe Leu Gly Thr Tyr<br>325 330 335 | 1008 | |
| tgt acc cta ggc gat gac cgt cac ctc acc aat cgt gtt ctc tcc atg<br>Cys Thr Leu Gly Asp Asp Arg His Leu Thr Asn Arg Val Leu Ser Met<br>340 345 350 | 1056 | |
| gga tac aga act aag tat acc cat aag tct cgt gct ttc tcc gag acc<br>Gly Tyr Arg Thr Lys Tyr Thr His Lys Ser Arg Ala Phe Ser Glu Thr<br>355 360 365 | 1104 | |
| ccg tct ctt tat ctc aga tgg ctg aac cag caa act cgg tgg acc aag<br>Pro Ser Leu Tyr Leu Arg Trp Leu Asn Gln Gln Thr Arg Trp Thr Lys<br>370 375 380 | 1152 | |
| tct tac ttc cgc gaa tgg ctc tac aac gca caa tgg tgg cac aaa cac<br>Ser Tyr Phe Arg Glu Trp Leu Tyr Asn Ala Gln Trp Trp His Lys His<br>385 390 395 400 | 1200 | |
| cat atc tgg atg aca tat gaa tcc gtc gtt agc ttt atc ttc ccc ttc<br>His Ile Trp Met Thr Tyr Glu Ser Val Val Ser Phe Ile Phe Pro Phe<br>405 410 415 | 1248 | |
| ttc atc acg gcg act gtt atc cga ctc ata tac gcc ggc act att tgg<br>Phe Ile Thr Ala Thr Val Ile Arg Leu Ile Tyr Ala Gly Thr Ile Trp<br>420 425 430 | 1296 | |
| aat gtc gta tgg ctc tta ctt tgt atc cag att atg tct ctg ttc aag<br>Asn Val Val Trp Leu Leu Leu Cys Ile Gln Ile Met Ser Leu Phe Lys<br>435 440 445 | 1344 | |
| agc atc tac gct tgc tgg cta cgc gga aac ttc att atg ctc ctt atg<br>Ser Ile Tyr Ala Cys Trp Leu Arg Gly Asn Phe Ile Met Leu Leu Met<br>450 455 460 | 1392 | |
| tct ctt tac tcg atg ctc tat atg acc ggc ctg ctc cca tct aag tac<br>Ser Leu Tyr Ser Met Leu Tyr Met Thr Gly Leu Leu Pro Ser Lys Tyr<br>465 470 475 480 | 1440 | |
| ttc gcc ctg ttg act ttg aac aag aca ggt tgg ggt act tcc ggt cgc<br>Phe Ala Leu Leu Thr Leu Asn Lys Thr Gly Trp Gly Thr Ser Gly Arg | 1488 | |

|  |  |  |  |  |  |  |  |  |  |  |  |
|---|---|---|---|---|---|---|---|---|---|---|---|
|  |  | 485 |  |  |  | 490 |  |  |  | 495 |  |
| aag | aag | att | gtc | gga | aac | tat | atg | cct | att | ctg | ccg | ctt | agt | atc | tgg | 1536 |
| Lys | Lys | Ile | Val | Gly | Asn | Tyr | Met | Pro | Ile | Leu | Pro | Leu | Ser | Ile | Trp |  |
|  |  | 500 |  |  |  | 505 |  |  |  | 510 |  |

```
            485                 490                 495
aag aag att gtc gga aac tat atg cct att ctg ccg ctt agt atc tgg      1536
Lys Lys Ile Val Gly Asn Tyr Met Pro Ile Leu Pro Leu Ser Ile Trp
            500                 505                 510 gct gct gtc cta tgc ggt ggc gtc ggg tat tcg atc tat atg gat tgc      1584
Ala Ala Val Leu Cys Gly Gly Val Gly Tyr Ser Ile Tyr Met Asp Cys
            515                 520                 525 cag aac gat tgg tcc acg ccc gag aag cag aaa gaa atg tat cac ctt      1632
Gln Asn Asp Trp Ser Thr Pro Glu Lys Gln Lys Glu Met Tyr His Leu
            530                 535                 540 ctc tat ggg tgc gtg ggt tac gtc atg tac tgg gtc atc atg gct gtc      1680
Leu Tyr Gly Cys Val Gly Tyr Val Met Tyr Trp Val Ile Met Ala Val
545                 550                 555                 560 atg tac tgg gtt tgg gtc aaa cgt tgt tgc cgt aag agg tct cag act      1728
Met Tyr Trp Val Trp Val Lys Arg Cys Cys Arg Lys Arg Ser Gln Thr
            565                 570                 575 gtt acc ctt gtg cat gac atc cct gat atg tgt gtt taa                  1767
Val Thr Leu Val His Asp Ile Pro Asp Met Cys Val
            580                 585

<210> SEQ ID NO 64
<211> LENGTH: 588
<212> TYPE: PRT
<213> ORGANISM: Artificial Sequence
<220> FEATURE:
<223> OTHER INFORMATION: Synthetic sequence encoding HAS 1 from Xenopus
      laevis

<400> SEQUENCE: 64

Met Lys Glu Lys Ala Ala Glu Thr Met Glu Ile Pro Glu Gly Ile Pro
1               5                   10                  15

Lys Asp Leu Glu Pro Lys His Pro Thr Leu Trp Arg Ile Ile Tyr Tyr
            20                  25                  30

Ser Phe Gly Val Val Leu Leu Ala Thr Ile Thr Ala Ala Tyr Val Ala
        35                  40                  45

Glu Phe Gln Val Leu Lys His Glu Ala Ile Leu Phe Ser Leu Gly Leu
    50                  55                  60

Tyr Gly Leu Ala Met Leu Leu His Leu Met Met Gln Ser Leu Phe Ala
65                  70                  75                  80

Phe Leu Glu Ile Arg Arg Val Asn Lys Ser Glu Leu Pro Cys Ser Phe
                85                  90                  95

Lys Lys Thr Val Ala Leu Thr Ile Ala Gly Tyr Gln Glu Asn Pro Glu
            100                 105                 110

Tyr Leu Ile Lys Cys Leu Glu Ser Cys Lys Tyr Val Lys Tyr Pro Lys
        115                 120                 125

Asp Lys Leu Lys Ile Ile Leu Val Ile Asp Gly Asn Thr Glu Asp Asp
    130                 135                 140

Ala Tyr Met Met Glu Met Phe Lys Asp Val Phe His Gly Glu Asp Val
145                 150                 155                 160

Gly Thr Tyr Val Trp Lys Gly Asn Tyr His Thr Val Lys Lys Pro Glu
                165                 170                 175

Glu Thr Asn Lys Gly Ser Cys Pro Glu Val Ser Lys Pro Leu Asn Glu
            180                 185                 190

Asp Glu Gly Ile Asn Met Val Glu Glu Leu Val Arg Asn Lys Arg Cys
        195                 200                 205

Val Cys Ile Met Gln Gln Trp Gly Gly Lys Arg Glu Val Met Tyr Thr
    210                 215                 220
```

```
Ala Phe Gln Ala Ile Gly Thr Ser Val Asp Tyr Val Gln Val Cys Asp
225                 230                 235                 240

Ser Asp Thr Lys Leu Asp Glu Leu Ala Thr Val Glu Met Val Lys Val
            245                 250                 255

Leu Glu Ser Asn Asp Met Tyr Gly Ala Val Gly Gly Asp Val Arg Ile
                260                 265                 270

Leu Asn Pro Tyr Asp Ser Phe Ile Ser Phe Met Ser Ser Leu Arg Tyr
            275                 280                 285

Trp Met Ala Phe Asn Val Glu Arg Ala Cys Gln Ser Tyr Phe Asp Cys
        290                 295                 300

Val Ser Cys Ile Ser Gly Pro Leu Gly Met Tyr Arg Asn Asn Ile Leu
305                 310                 315                 320

Gln Val Phe Leu Glu Ala Trp Tyr Arg Gln Lys Phe Leu Gly Thr Tyr
                325                 330                 335

Cys Thr Leu Gly Asp Asp Arg His Leu Thr Asn Arg Val Leu Ser Met
            340                 345                 350

Gly Tyr Arg Thr Lys Tyr Thr His Lys Ser Arg Ala Phe Ser Glu Thr
        355                 360                 365

Pro Ser Leu Tyr Leu Arg Trp Leu Asn Gln Thr Arg Trp Thr Lys
370                 375                 380

Ser Tyr Phe Arg Glu Trp Leu Tyr Asn Ala Gln Trp Trp His Lys His
385                 390                 395                 400

His Ile Trp Met Thr Tyr Glu Ser Val Val Ser Phe Ile Phe Pro Phe
                405                 410                 415

Phe Ile Thr Ala Thr Val Ile Arg Leu Ile Tyr Ala Gly Thr Ile Trp
            420                 425                 430

Asn Val Val Trp Leu Leu Leu Cys Ile Gln Ile Met Ser Leu Phe Lys
        435                 440                 445

Ser Ile Tyr Ala Cys Trp Leu Arg Gly Asn Phe Ile Met Leu Leu Met
450                 455                 460

Ser Leu Tyr Ser Met Leu Tyr Met Thr Gly Leu Leu Pro Ser Lys Tyr
465                 470                 475                 480

Phe Ala Leu Leu Thr Leu Asn Lys Thr Gly Trp Gly Thr Ser Gly Arg
                485                 490                 495

Lys Lys Ile Val Gly Asn Tyr Met Pro Ile Leu Pro Leu Ser Ile Trp
            500                 505                 510

Ala Ala Val Leu Cys Gly Gly Val Gly Tyr Ser Ile Tyr Met Asp Cys
        515                 520                 525

Gln Asn Asp Trp Ser Thr Pro Glu Lys Gln Lys Glu Met Tyr His Leu
        530                 535                 540

Leu Tyr Gly Cys Val Gly Tyr Val Met Tyr Trp Val Ile Met Ala Val
545                 550                 555                 560

Met Tyr Trp Val Trp Val Lys Arg Cys Cys Arg Lys Arg Ser Gln Thr
                565                 570                 575

Val Thr Leu Val His Asp Ile Pro Asp Met Cys Val
            580                 585

<210> SEQ ID NO 65
<211> LENGTH: 658
```

```
<212> TYPE: DNA
<213> ORGANISM: Artificial sequence
<220> FEATURE:
<223> OTHER INFORMATION: Chemically synthesized
<220> FEATURE:
<221> NAME/KEY: misc_feature
<222> LOCATION: (1)..(12)
<223> OTHER INFORMATION: Polylinker comprising restriction enzyme
      recognition sites for SalI, HpaI
<220> FEATURE:
<221> NAME/KEY: misc_feature
<222> LOCATION: (13)..(15)
<223> OTHER INFORMATION: Spacer nucleotides between Polylinker and
      promotor
<220> FEATURE:
<221> NAME/KEY: promoter
<222> LOCATION: (16)..(269)
<223> OTHER INFORMATION: glyceraldehyde 3-phospate dehydrogenase (gpd)
      promoter
<220> FEATURE:
<221> NAME/KEY: misc_feature
<222> LOCATION: (271)..(296)
<223> OTHER INFORMATION: Polylinker comprising restriction enzyme
      recognition sites for PacI, KpnI, SpeI, BamHI
<220> FEATURE:
<221> NAME/KEY: Intron
<222> LOCATION: (298)..(352)
<223> OTHER INFORMATION: Intron with an appropriate donor and acceptor
      recoginition sequence
<220> FEATURE:
<221> NAME/KEY: polyA_signal
<222> LOCATION: (356)..(491)
<223> OTHER INFORMATION: First polyadenylation signal of the manganese
      peroxidase isoenzyme 1
<220> FEATURE:
<221> NAME/KEY: polyA_signal
<222> LOCATION: (492)..(540)
<223> OTHER INFORMATION: Second polyadenylation signal
<220> FEATURE:
<221> NAME/KEY: pause_signal
<222> LOCATION: (541)..(632)
<223> OTHER INFORMATION: Transcription blocker
<220> FEATURE:
<221> NAME/KEY: misc_feature
<222> LOCATION: (633)..(658)
<223> OTHER INFORMATION: Polylinker comprising restriction enzyme
      recognition sites for StuI, SbfI, HpaI

<400> SEQUENCE: 65
gtcgacgtta actttaagag gtccgcaagt agattgaaag ttcagtacgt ttttaacaat      60
agagcatttt cgaggcttgc gtcattctgt gtcaggctag cagtttataa gcgttgagga     120
tctagagctg ctgttcccgc gtctcgaatg ttctcggtgt ttaggggtta gcaatctgat     180
atgataataa tttgtgatga catcgatagt acaaaaaccc caattccggt cacatccacc     240
atctccgttt tctcccatct acacacaaca ttaattaagg taccactagt ggatccggtc     300
agtacaccac acagcccgac cgcgacgacc gcgtgctgac ttcgctttcc aggtcattca     360
tattccacgc ggtttcttac ctggtcacgg ctactcgttg atggattaaa ggtcttcgct     420 tgttttctg tacgctgccc tggattgttg gaaactggtc ttttggtaat acatgaggtt     480
catctctgtt caataaaata tctttatttt cattacatct gtgtgttggt tttttgtgtg     540
aacatacgct ctccatcaaa acaaaacgaa acaaaacaaa ctagcaaaat aggctgtccc     600
cagtgcaagt gcaggtgcca gaacatttct ctatcgaaag gcctcctgca gggttaac     658
```

METHODS AND MEANS FOR PRODUCING HYALURONAN

CROSS-REFERENCE TO RELATED APPLICATIONS

This application is the U.S. National Stage filing PCT/EP2006/002913, filed Feb. 22, 2006, which claims priority to EP 05090042.2, filed Feb. 23, 2005, and U.S. Provisional Patent Application No. 60/657,107, filed Feb. 28, 2005, the disclosures of each of which are hereby incorporated by reference.

BACKGROUND OF THE INVENTION (i) Field of the Invention

The present invention relates to fungal cells and fungi which synthesize hyaluronan, and to methods for preparing such fungi, and also to methods for preparing hyaluronan with the aid of these fungal cells or fungi. Furthermore the present invention relates to the use of fungi for preparing hyaluronan and hyaluronan-containing food or feed.

(ii) Description of the Related Art

Hyaluronan is a naturally occurring unbranched, linear mucopolysaccharide (glucosaminoglucan) which is constructed of alternating molecules of glucuronic acid and N-acetyl-glucosamine. The basic building block of hyaluronan consists of the disaccharide glucuronic acid-beta-1,3-N-acetyl-glucosamine. In hyaluronan, these repeating units are attached to one another by beta-1,4 linkages.

In pharmacy, use is frequently made of the term hyaluronic acid. Since hyaluronan is in most cases present as polyanion and not as free acid, hereinbelow, the term hyaluronan is preferably used, but each term is to be understood as embracing both molecular forms.

Hyaluronan has unusual physico-chemical properties, such as, for example, properties of polyelectrolytes, viscoelastic properties, a high capacity to bind water, properties of gel formation, which, in addition to further properties of hyaluronan, are described in a review article by Lapcik et al. (1998, Chemical Reviews 98(8), 2663-2684). The specific properties of hyaluronan are determined inter alia by the molecular weight and the molecular weight distribution of the hyaluronan in question.

Hyaluronan is a component of extracellular connective tissue and bodily fluids of vertebrates. In humans, hyaluronic acid is synthesized by the cell membrane of all body cells, especially mesenchymal cells, and ubiquitously present in the body with a particularly high concentration in the connective tissues, the extracellular matrix, the umbilical cord, the joint fluid, the cartilageous tissue, the skin and the vitreous body of the eye (Bernhard Gebauer, 1998, Inaugural-Dissertation, Virchow-Kinikum Medizinische Fakultät Charité der Humboldt Universität zu Berlin; Fraser et al., 1997, Journal of Internal Medicine 242, 27-33).

Recently, hyaluronan was also found in animal non-vertebrate organisms (molluscs) (Volpi and Maccari, 2003, Biochimie 85, 619-625).

Furthermore, some pathogenic gram-positive bacteria (Streptococcus group A and C) and gram-negative bacteria (Pasteurella) synthesize hyaluronan as exopolysaccharides which protect these bacteria against attack by the immune system of their host, since hyaluronan is a non-immunogenic substance.

Viruses which infect single-cell green algae of the genus Chlorella, some of which are present as endosymbionts in Paramecium species, bestow upon the single-cell green algae the ability to synthesize hyaluronan after infection by the virus (Graves et al., 1999, Virology 257, 15-23). Hitherto, this is the only example from the systematic realm of the plants where the synthesis of hyaluronan was demonstrated.

Organisms from the realm of the fungi (mycota) which synthesize hyaluronan have hitherto not been described. WO 03 060063 does describe the use of Saccharomyces cerevisiae for preparing a recombinantly expressed hyaluronan synthase, but not the preparation of hyaluronan with the aid of transgenic yeasts. The synthesis of hyaluronan with the aid of genetically altered Saccharomyces cerevisiae cells seems impossible even, as they obviously lack the enzyme UDP-glucose 6-dehydrogenase which is necessary for the preparation of a substrate of hyaluronan synthase (UDP-glucuronic acid) (DeAngelis and Achyuthan, 1996, J Biological Chemistry 271(39), 23657-23660).

The catalysis of the hyaluronan synthesis is effected by a single membrane-integrated or membrane-associated enzyme, hyaluronan synthase. The hyaluronan synthases which have hitherto been studied can be classified into two groups: hyaluronan synthases of Class I and hyaluronan synthases of Class II (DeAngelis, 1999, CMLS, Cellular and Molecular Life Sciences 56, 670-682).

The hyaluronan synthases of vertebrates are further distinguished by the identified isoenzymes. The different isoenzymes are referred to in the order of their identification using Arabic numbers (for example, hsHAS1, hsHAS2, hsHAS3).

The mechanism of the transfer of synthetic hyaluronan molecules across the cytoplasmic membrane into the medium surrounding the cell has not yet been fully elucidated. Earlier hypotheses assumed that the transport across the cell membrane would be carried out by the hyaluronan synthase itself. However more recent results indicate that the transport of hyaluronan molecules via the cytoplasmic membrane takes place by way of an energy-dependent transport by means of relevant transport proteins. Thus Streptococcus strains in which synthesis of an active transport protein was inhibited were generated by mutagenesis. These strains synthesized less hyaluronan than corresponding wild-type bacterial strains (Ouskova et al., 2004, Glycobiology 14(10), 931-938). It was shown, with the aid of agents acting in a specific inhibiting manner on known transport proteins in human fibroblast cells, that it is possible to reduce both the amount of hyaluronan produced and the activity of hyaluronan synthases (Prehm and Schumacher, 2004, Biochemical Pharmacology 68, 1401-1410).

The unusual properties of hyaluronan offer a wealth of possibilities for application in various fields, such as, for example, pharmacy, the cosmetics industry, in the production of food and feed, in technical applications (for example as lubricants), etc. The most important applications where hyaluronan is currently being used are in the medicinal and cosmetics field (see, for example, Lapcik et al., 1998, Chemical Reviews 98(8), 2663-2684, Goa and Benfield, 1994, Drugs 47(3), 536-566).

In the medical field, hyaluronan-containing products are currently used for the intraarticular treatment of arthrosis and in ophthalmics used for eye surgery. Derivatized, so-called cross-linked hyaluronan is used for treating joint diseases (Fong Chong et al., 2005), Appl Microbiol Biotechnol 66, 341-351). Hyaluronan is also used for treating joint disorders in racehorses. In addition, hyaluronic acid is a component of some rhinologics which, for example in the form of eye drops and nasalia, serve to moisten dry mucous membranes. Hyaluronan-containing solutions for injection are used as analgesics and antirheumatics. Patches comprising hyaluronan or derivatized hyaluronan are employed in wound healing. As dermatics, hyaluronan-containing gel imfungi are used for correcting skin deformations in plastic surgery.

For pharmacological applications, preference is given to using hyaluronan having a high molecular weight.

In cosmetic medicine, hyaluronan preparations are among the most suitable skin filler materials. By injecting hyaluronan, for a limited period of time, it is possible to smooth wrinkles or to increase the volume of lips.

In cosmetic products, in particular in skin creams and lotions, hyaluronan is frequently used as moisturizer by virtue of its high water-binding capacity. Further possibilities of application in the medicinal and cosmetics field, such as, for example, the use of hyaluronan as carrier for active compounds which ensures a controlled release of the active compound over a long period of time, as carrier for active compounds which transports the active compounds in a targeted manner into the lymphatic system or as active compound which, after application as an ointment, ensures that the active compound remains in the skin for a relatively long period of time, are described in Lapcik et al. (1998, Chemical Reviews 98(8), 2663-2684). The use of hyaluronan derivatives in the medicinal field requires further research efforts; however, first results have already revealed a large potential (Lapcik et al. 1998, Chemical Reviews 98(8), 2663-2684).

Furthermore, hyaluronan-containing preparations are sold as so-called nutraceuticals (food supplements) which can also be used in animals (for example dogs, horses) for the prophylaxis and alleviation of arthrosis.

Hyaluronan used for commercial purposes is currently isolated from animal tissues (roostercombs) or prepared fermentatively using bacterial cultures. U.S. Pat. No. 4,141,973 describes a process for isolating hyaluronan from roostercombs or alternatively from umbilical cords. In addition to hyaluronan, animal tissues (for example roostercombs, umbilical cords) also contain further mucopolysaccharides related to hyaluronan, such as chondroitin sulphate, dermatan sulphate, keratan sulphate, heparan sulphate and heparin. Furthermore, animal organisms contain proteins (hyaladherins) which bind specifically to hyaluronan and which are required for the widest range of functions in the organism, such as, for example, the degradation of hyaluronan in the liver, the function of hyaluronan as lead structure for cell migration, the regulation of endocytosis, the anchoring of hyaluronan on the cell surface or the formation of hyaluronan networks (Turley, 1991, Adv Drug Delivery Rev 7, 257 ff.; Laurent and Fraser, 1992, FASEB J. 6, 183 ff.; Stamenkovic and Aruffo, 1993, Methods Enzymol. 245, 195 ff; Knudson and Knudson, 1993, FASEB 7, 1233 ff.).

The *Streptococcus* strains used for the bacterial production of hyaluronan are exclusively pathogenic bacteria. During cultivation, too, these bacteria produce (pyrogenic) exotoxins and haemolysins (streptolysin, (in particular alpha- and beta-haemolysin) (Kilian, M.: *Streptococcus* and *Enterococcus*. In: Medical Microbiology. Greenwood, D.; Slack, RCA; Peutherer, J. F. (Eds.). Chapter 16. Churchill Livingstone, Edinburgh, UK: pp. 174-188, 2002, ISBN 0443070776) which are released into the culture medium. This renders purification and isolation of the hyaluronan prepared with the aid of *Streptococcus* strains more difficult. In particular for pharmaceutical applications, the presence of exotoxins and haemolysins in the preparations is a problem.

U.S. Pat. No. 4,801,539 describes the preparation of hyaluronan by fermentation of a mutagenized bacterial strain (*Streptococcus zooedemicus*). The mutagenized bacteria strain used no longer synthesizes beta-haemolysin. The yield achieved was 3.6 g of hyaluronan per litre of culture.

EP 0694616 describes a method for cultivating *Streptococcus zooedemicus* or *Streptococcus equi*, where, under the culture conditions employed, no streptolysin, but increased amounts of hyaluronan are synthesized. The yield achieved was 3.5 g of hyaluronan per litre of culture.

During cultivation, *Streptococcus* strains release the enzyme hyaluronidase into the culture medium, as a consequence of which, in this production system, too, the molecular weight is reduced during purification. The use of hyaluronidase-negative *Streptococcus* strains or of methods for the production of hyaluronan where the production of hyaluronidase during cultivation is inhibited are described in U.S. Pat. No. 4,782,046. The yield achieved was up to 2.5 g of hyaluronan per litre of culture, and the maximum mean molecular weight achieved was $3.8 \times 10^6$ Da, at a molecular weight distribution of from $2.4 \times 10^6$ to $4.0 \times 10^6$.

US 20030175902 and WO 03 054163 describe the preparation of hyaluronan with the aid of heterologous expression of a hyaluronan synthase from *Streptococcus equisimilis* in *Bacillus subtilis*. To achieve the production of sufficient amounts of hyaluronan, in addition to heterologous expression of a hyaluronan synthase, simultaneous expression of a UDP-glucose dehydrogenase in the *Bacillus* cells is also required. US 20030175902 and WO 03 054163 do not state the absolute amount of hyaluronan obtained in the production with the aid of *Bacillus subtilis*. However, the amounts of hyaluronan achieved are not higher than the amounts which are obtained by means of fermentation of *Streptococcus* strains. (Fong Chong et al., 2005), Appl Microbiol Biotechnol 66, 341-351). In the production of hyaluronan with the aid of *Bacillus subtilis* a maximum mean molecular weight of about $4.2 \times 10^6$ Da is achieved. However, this mean molecular weight was only achieved for the recombinant *Bacillus* strain where a gene coding for the hyaluronan synthase gene from *Streptococcus equisimilis* and the gene coding for the UDP-glucose dehydrogenase from *Bacillus subtilis* were integrated into the *Bacillus subtilis* genome under the control of the amyQ promoter, where at the same time the *Bacillus subtilis-endogenous* cxpy gene (which codes for a P450 cytochrome oxidase) was inactivated. The molecular weight of the hyaluronan produced with the aid of *Bacillus* strains could also not be increased with respect to the hyaluronan produced by means of *Streptococcus* strains (Fong Chong et al., 2005), Appl Microbiol Biotechnol 66, 341-351).

The production of hyaluronan by fermentation of bacteria strains is associated with high costs, since the bacteria have to be fermented in sealed sterile containers under expensive controlled culture conditions (see, for example, U.S. Pat. No. 4,897,349). Furthermore, the amount of hyaluronan which can be produced by fermentation of bacteria strains is limited by the production facilities present in each case. Here, it also has to be taken into account that fermenters, as a consequence of physical laws, cannot be built for excessively large culture volumes. Particular mention may be made here homogeneous mixing of the substances fed in from the outside (for example essential nutrient sources for bacteria, reagents for regulating the pH, oxygen) with the culture medium required for efficient production, which, in large fermenters, can be ensured only with great technical expenditure, if at all.

The purification of hyaluronan from animal organisms is complicated owing to the presence, in animal tissues, of other mucopolysaccharides and proteins which specifically bind to hyaluronan. In patients, the use of hyaluronan-containing medicinal preparations contaminated by animal proteins can result in unwanted immunological reactions of the body (U.S. Pat. No. 4,141,973), in particular if the patient is allergic to animal proteins (for example chicken egg white). Furthermore, the amounts (yields) of hyaluronan which can be obtained from animal tissues in satisfactory quality and purity are low (roostercomb: 0.079% w/w, EP 0144019, U.S. Pat. No. 4,782,046), which necessitates the processing of large amounts of animal tissues. A further problem in the isolation of hyaluronan from animal tissues consists in the fact that the molecular weight of hyaluronan during purification is reduced since animal tissues also contain a hyaluronan-degrading enzyme (hyaluronidase).

In addition to the hyaluronidases and exotoxins already mentioned, Streptococcus strains also produce endotoxins which, when present in pharmacological products, pose risks for the health of the patient. In a scientific study, it was shown that even hyaluronan-containing medicinal products on the market contain detectable amounts of bacterial endotoxins (Dick et al., 2003, Eur J. Opthalmol. 13(2), 176-184). A further disadvantage of the hyaluronan produced with the aid of Streptococcus strains is the fact that the isolated hyaluronan has a lower molecular weight than hyaluronan isolated from roostercombs (Lapcik et al. 1998, Chemical Reviews 98(8), 2663-2684). US 20030134393 describes the use of a Streptococcus strain for producing hyaluronan which synthesizes a particularly pronounced hyaluronan capsule (supercapsulated). The hyaluronan isolated after fermentation had a molecular weight of $9.1 \times 10^6$ Da. However, the yield was only 350 mg per litre.

Although hyaluronan has unusual properties, it is, owing to its scarcity and the high price, rarely, if at all, used for industrial applications.

SUMMARY OF THE INVENTION

Accordingly, it is an object of the present invention to provide means and methods which permit the provision of hyaluronan in sufficient amounts and quality and which make it possible to provide hyaluronan even for industrial applications and applications in the field of food and feed.

This object is achieved by the embodiments outlined in the claims.

Thus, the present invention relates to fungal cells or fungi, particularly fungal cells or fungi of the systematic division Basidiomycota, characterized in that they comprise a nucleic acid molecule coding for a hyaluronan synthase.

In a preferred embodiment, the nucleic acid coding for a hyaluronan synthase is integrated into the genome of fungal cells according to the invention or fungi according to the invention.

The present invention also provides fungal cells or fungi, preferably fungal cells or fungi of the systematic division Basidiomycota, which synthesize hyaluronan. A preferred embodiment are fungal cells according to the invention or fungi according to the invention which synthesize hyaluronan.

Hyaluronan can be isolated from fungal cells according to the invention or fungi according to the invention. Accordingly, fungal cells according to the invention or fungi according to the invention offer, compared to the prior art, the advantage that they can be cultivated on large areas for producing hyaluronan at little expense. This leads to the possibility to provide hyaluronan in sufficient amounts even for industrial applications where it is currently not used owing to its scarcity and the high price.

A further advantage of the present invention consists in the fact that fungi can be cultivated on substrates which are relatively reasonably priced and occur frequently as waste products in agriculture and/or forestry, for example.

DETAILED DESCRIPTION OF THE INVENTION

In the context of the present invention, the term "hyaluronan" is to be understood as meaning both a free acid (hyaluronic acid) and the polyanion form of a linear glucosamine comprising a plurality of basic building blocks of the disaccharide glucuronic acid beta-1,3-N-acetyl-glucosamine linked to one another by beta-1,4 linkages.

In the context of the present invention, the term "hyaluronan synthase" (EC 2.4.1.212) is to be understood as meaning a protein which synthesizes hyaluronan from the substrates UDP-glucuronic acid (UDP-GlcA) and N-acetyl-glucosamine (UDP-GlcNAc). The hyaluronan synthesis is catalysed according to the reaction schemes below:

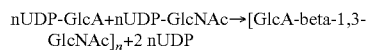

Nucleic acid molecules and corresponding protein sequences coding for hyaluronan synthases have been described, inter alia, for the following organisms: rabbit (*Oryctolagus cuniculus*) ocHas2 (EMBL AB055978.1, US 20030235893), ocHas3 (EMBL AB055979.1, US 20030235893); baboon (*Papio anubis*) paHas1 (EMBL AY463695.1); frog (*Xenopus laevis*) xlHas1 (DG42) (EMBL M22249.1, US 20030235893), xlHas2 (EMBL AF168465.1), xlHas3 (EMBL AY302252.1); human (*Homo sapiens*) hsHAS1 (EMBL D84424.1, US 20030235893), hsHAS2 (EMBL U54804.1, US 20030235893), hsHAS3 (EMBL AF232772.1, US 20030235893); mouse (*Mus musculus*), mmHas1 (EMBL D82964.1, US 20030235893), mmHAS2 (EMBL U52524.2, US 20030235893), mmHas3 (EMBL U86408.2, US 20030235893); cattle (*Bos taurus*) btHas2 (EMBL AJ004951.1, US 20030235893); chicken (*Gallus gallus*) ggHas2 (EMBL AF106940.1, US 20030235893); rat (*Rattus norvegicus*) rnHas 1 (EMBL AB097568.1, Itano et al., 2004, J. Biol. Chem. 279(18) 18679-18678), rnHas2 (EMBL AF008201.1); rnHas 3 (NCBI NM__172319.1, Itano et al., 2004, J. Biol. Chem. 279(18) 18679-18678) horse (*Equus caballus*) ecHAS2 (EMBL AY056582.1, GI:23428486), pig (*Sus scrofa*) sscHAS2 (NCBI NM__214053.1, GI:47522921), sscHas 3 (EMBLAB159675), zebra fish (*Danio rerio*) brHas1 (EMBL AY437-407), brHas2 (EMBL AF190742.1) brHas3 (EMBL AF190743.1); *Pasteurella multocida* pmHas (EMBL AF036004.2); *Streptococcus pyogenes* spHas (EMBL, L20853.1, L21187.1, U.S. Pat. No. 6,455,304, US 20030235893); *Streptococcus equis* seHas (EMBL AF347022.1, AY173078.1), *Streptococcus uberis* suHasA (EMBL AJ242946.2, US 20030235893), *Streptococcus equisimilis* seqHas (EMBL AF023876.1, US 20030235893); *Sulfolobus solfataricus* ssHAS (US 20030235893), *Sulfolobus tokodaii* stHas (AP000988.1), *Paramecium bursaria Chlorella* virus 1, cvHAS (EMBL U42580.3, PB42580, US 20030235893).

In the context of the present invention, the term "genome" is to be understood as meaning the entire genetic material present in a fungal cell. It is known to the person skilled in the art that, in addition to the nucleus, other compartments (for example mitochondria) also contain genetic material.

In the context of the present invention, the term "stably integrated nucleic acid molecule" is to be understood as meaning the integration of a nucleic acid molecule into the genome of the fungus. A stably integrated nucleic acid molecule is characterized in that, during the replication of the corresponding integration site, it is multiplied together with the nucleic acid sequences of the host which border on the integration site, so that the integration site in the replicated DNA strand is surrounded by the same nucleic acid sequences as on the read strand which serves as a matrix for the replication. Preferably, the nucleic acid molecule is stably integrated into the nuclear-genome.

The stable integration of a nucleic acid molecule into the genome of a fungal cell or fungus can be demonstrated by genetic methods and/or methods of molecular biology. A stable integration of a nucleic acid molecule into the genome of a fungal cell or the genome of a fungus is characterized in that in the progeny which has inherited said nucleic acid molecule, the stably integrated nucleic acid molecule is present in the same genomic environment as in the parent generation. The presence of a stable integration of a nucleic acid sequence in the genome of a fungal cell or in the genome of a fungus can be demonstrated using methods known to the person skilled in the art, inter alia with the aid of southern blot analysis or with the aid of RFLP analysis (Restriction Fragment Length Polymorphism) (Nam et al., 1989, The Plant cell 1, 699-705; Leister and Dean, 1993, The Plant Journal 4 (4), 745-750), with methods based on PCR, such as, for example, the analysis of differences in length in the amplified fragment (Amplified Fragment Length Polymorphism, AFLP) (Castiglioni et al., 1998, Genetics 149, 2039-2056; Meksem et al., 2001, Molecular Genetics and Genomics 265, 207-214; Meyer et al., 1998, Molecular and General Genetics 259, 150-160) or using amplified fragments cleaved using restriction endonucleases (Cleaved Amplified Polymorphic Sequences, CAPS) (Konieczny and Ausubel, 1993, The Plant Journal 4, 403-410; Jarvis et al., 1994, Plant Molecular Biology 24, 685-687; Bachem et al., 1996, The Plant Journal 9 (5), 745-753).

In a further preferred embodiment, the present invention relates to fungal cells according to the invention or fungi according to the invention where the nucleic acid molecule coding for hyaluronan synthase is characterized in that it codes for a hyaluronan synthase Class I.

The hyaluronan synthases which have hitherto been investigated can be classified into two groups: hyaluronan synthases of Class I and hyaluronan synthases of Class II (DeAngelis, 1999, CMLS, Cellular and Molecular Life Sciences 56, 670-682). This classification is based essentially on biochemical studies of the reaction mechanism and the analysis of the amino acid sequences coding for the hyaluronan synthases in question. Class I includes inter alia the hyaluronan synthases from *Streptococcus pyogenes* (spHas), *Streptococcus equisimilis* (seHas), *Paramecium bursaria Chlorella* virus 1 (cvHas) and the known hyaluronan synthases of the vertebrates (*Xenopus laevis*, xlHas; *Homo sapiens*, hsHAS, *Mus musculus*, mmHas). Class I hyaluronan synthases have an amino acid sequence of from 417 to 588 amino acids. Class I hyaluronan synthases are proteins which are integrated into the cytoplasmic membrane and have multiple (five to seven) membrane-associated regions. Elongation of the hyaluronan with further molecular building blocks probably takes place at the reducing end of the polymer. Suitable acceptor molecules used by hyaluronan synthases of Class I have hitherto not been disclosed.

To date, the hyaluronan synthase from *Pasteurella* is the only known representative of Class II hyaluronan synthases. Its protein sequence has 972 amino acids. It is a soluble protein which, on its C-terminus, contains amino acid sequences responsible for localization at the cytoplasmic membrane (Jing and DeAngelis, 2000, Glycobiology 10, 883-889). Interaction probably takes place via molecules associated with the cytoplasmic membrane. In the case of the enzyme of Class II, the hyaluronan is synthesized by extension at the non-reducing end (DeAngelis, 1999, J. Biol. Chem 274, 26557-26562). The synthesis of hyaluronan by the Class II enzyme does not require an acceptor molecule; however, it was shown that hyaluronan oligomers (DP4) are used as acceptor and the rate of synthesis is increased by adding the acceptors (DeAngelis, 1999, J. Biol. Chem. 274, 26557-26562).

In a preferred embodiment, the present invention relates to fungal cells according to the invention or fungi according to the invention where the nucleic acid molecule coding for hyaluronan synthase is characterized in that it codes for a hyaluronan synthase from vertebrates or a viral hyaluronan synthase. Preferably, the nucleic acid molecule coding for the hyaluronan synthase codes for a hyaluronan synthase from amphibians or a hyaluronan synthase of a virus which infects algae.

With regard to a virus which infects algae, the nucleic acid molecule coding for hyaluronan synthase particularly preferably codes for a hyaluronan synthase of a *Chlorella*-infecting virus, especially preferably a hyaluronan synthase of a *Paramecium bursaria Chlorella* virus 1.

With regard to the nucleic acid molecule which codes for a hyaluronan synthase from amphibians, preference is given to a frog hyaluronan synthase, in particular a hyaluronan synthase 1 from *Xenopus laevis*.

In a further preferred embodiment, the present invention relates to fungal cells according to the invention or fungi according to the invention where the nucleic acid molecule coding for hyaluronan synthase is characterized in that the codons of the nucleic acid molecule coding for a hyaluronan synthase are modified compared to the codons of the nucleic acid molecule coding for the hyaluronan synthase of the parent organism of the hyaluronan synthase. Particularly preferably, the codons of the hyaluronan synthase are modified such that they are adapted to the frequency of the use of the codons of the fungal cell or fungus into whose genome they are or will be integrated. Especially preferably the codons of the hyaluronan synthase are modified such that the nucleic acid sequence coding for the hyaluronan synthase does not have any AT-rich regions. A person skilled in the art knows that AT-rich regions, which are present within a coding nucleic acid sequence, can lead to a reduced rate of expression in fungi (Scholtmeijer et al., 2001, Applied and Environmental Microbiology 67(1), 481-483).

Owing to the degeneracy of the genetic code, amino acids can be encoded by one or more codons. In different organisms, the codons coding for a respective amino acid are used at different frequencies. Adapting the codons of a coding nucleic acid sequence to the frequency of their use in the fungal cell or in the fungus into whose genome the sequence to be expressed is to be integrated may contribute to an increased amount of translated protein and/or to the stability of the mRNA in question in the particular fungal cells or fungi. The frequency of use of codons in the fungal cells or fungi in question can be determined by the person skilled in the art by examining as many coding nucleic acid sequences of the organism in question as possible for the frequency with which certain codons are used for coding for a certain amino acid. The frequency of the use of codons of certain organisms is known to the person skilled in the art and can be determined in a simple and rapid manner using computer programs. Suitable computer programs are publicly accessible and provided for free inter alia on the Internet (for example, on the world wide web at gcua.schoedl.de/; kazusa.or.jp/codon/; entelechon.com/eng/cutanalysis).

Adapting the codons of a coding nucleic acid sequence to the frequency of their use in the fungal cell or in the fungus into whose genome the sequence to be expressed is to be integrated can be carried out by in vitro mutagenesis or, preferably, by de novo synthesis of the gene sequence. Methods for the de novo synthesis of nucleic acid sequences are known to the person skilled in the art. A de novo synthesis can be carried out, for example, by initially synthesizing individual nucleic acid oligonucleotides, hybridizing these with oligonucleotides complementary thereto, so that they form a DNA double strand, and then ligating the individual double-stranded oligonucleotides to one another such that the desired nucleic acid sequence is obtained. The de novo synthesis of nucleic acid sequences including the adaptation of the frequency with which the codons are used to a certain target organism can also be sourced out to companies offering this service (for example Entelechon GmbH, Regensburg, Germany).

In a further preferred embodiment, the present invention relates to fungal cells according to the invention or fungi according to the invention where the nucleic acid molecule coding for hyaluronan synthase is characterized in that it codes for a hyaluronan synthase having the amino acid sequence shown under SEQ ID NO 2, SEQ ID NO 4, SEQ ID NO 6, SEQ ID NO 8, SEQ ID NO 10, SEQ ID NO 12, SEQ ID NO 14, SEQ ID NO 16, SEQ ID NO 18, SEQ ID NO 20, SEQ ID NO 22, SEQ ID NO 24, SEQ ID NO 26, SEQ ID NO 28, SEQ ID NO 30, SEQ ID NO 32, SEQ ID NO 34, SEQ ID NO 36, SEQ ID NO 38, SEQ ID NO 40, SEQ ID NO 42, SEQ ID NO 44, SEQ ID NO 46, SEQ ID NO 48, SEQ ID NO 50, SEQ ID NO 52, SEQ ID NO 54, SEQ ID NO 56, SEQ ID NO 58, SEQ ID NO 60, SEQ ID NO 62 or SEQ ID NO 64. Particularly preferably, the nucleic acid molecule coding for the hyaluronan synthase is characterized in that it codes for a hyaluronan synthase having the amino acid sequence shown under SEQ ID NO 2 or SEQ ID NO 42.

In a further preferred embodiment, the present invention relates to fungal cells according to the invention or fungi according to the invention where the nucleic acid molecule coding for the hyaluronan synthase is characterized in that it comprises a nucleic acid sequence shown under SEQ ID NO 1, SEQ ID NO 3, SEQ ID NO 5, SEQ ID NO 7, SEQ ID NO 9, SEQ ID NO 11, SEQ ID NO 13, SEQ ID NO 15, SEQ ID NO 17, SEQ ID NO 19, SEQ ID NO 21, SEQ ID NO 23, SEQ ID NO 25, SEQ ID NO 27, SEQ ID NO 29, SEQ ID NO 31, SEQ ID NO 33, SEQ ID NO 35, SEQ ID NO 37, SEQ ID NO 39, SEQ ID NO 41, SEQ ID NO 43, SEQ ID NO 45, SEQ ID NO 47, SEQ ID NO 49, SEQ ID NO 51, SEQ ID NO 53, SEQ ID NO 55, SEQ ID NO 57, SEQ ID NO 59, SEQ ID NO 61 or SEQ ID NO 63. Particularly preferably, the nucleic acid molecule coding for the hyaluronan synthase is characterized in that it comprises a nucleic acid sequence shown under SEQ ID NO 1 or SEQ ID NO 41, especially preferably a hyaluronan synthase having the nucleic acid sequence shown under SEQ ID NO 3 or SEQ ID NO 63.

The plasmid IC 341-222, which comprises a synthetic nucleic acid molecule coding for a *Paramecium bursaria Chlorella* virus hyaluronan synthase was deposited at the Deutsche Sammiung von Mikroorganismen und Zellkulturen GmbH, Mascheroder Weg 1b, 38124 Brunswick, Germany, on 25, Aug. 2004 under the number DSM16664 according to the Budapest Treaty. The amino acid sequence shown in SEQ ID NO 4 can be derived from the coding region of the nucleic acid sequence integrated into the plasmid IC 341-222 and codes for a *Paramecium bursaria Chlorella* virus hyaluronan synthase.

Accordingly, the present invention also relates to fungal cells according to the invention or fungi according to the invention where the nucleic acid molecule coding for the hyaluronan synthase is characterized in that it codes for a protein whose amino acid sequence can be derived from the coding region of the nucleic acid sequence inserted into plasmid DSM16664.

A large number of techniques are available for (stably) integrating nucleic acids into a fungal cell (overview: Olmedo-Monfil et al., 2004, Methods in Molecular Biology Series 267, 297-314 and Casas-Flores et al., 2004, Methods in Molecular Biology Series 267, 315-326 in "Recombinant Gene Expression", 2nd Edition, 2004, Balbas and Lorenz eds, Humana Press, ISBN: 1-59259-774-2). Examples of methods known to the person skilled in the art include introducing foreign DNA into fungal cells, i.e. nucleic acid sequences which are introduced in addition to the nucleic acid sequences present in the fungal cell in question, with the aid of protoplast electroporation (WO 95 02691; *Agaricus bisporus*;Van de Rhee et al., 1996, Mol Gen Gent 250, 252-258, *Agaricus bisporus*; Noel and Labarere, 1994, Current Genetics 25(5), 432-437, *Agrocybe aegerita*), protoplast transformation with the aid of polyethylene glycol (Ogawa et al., 1998, Appl Microbiol Biotechnol 49, 285-289, *Coprinus cinereus*; Shuren and Wessels, 1994, Curr Genet 26(2), 179-183, *Schizophyllum commune*), protoplast transformation with the aid of polyethylene glycol with the addition of restriction enzymes (REMI=Restriction enzyme-mediated DNA integration, Sato et al., 1998, Biosci. Biotechnol. Biochem. 62(12), 2346-2350, *Lentinus eodes*), protoplast transformation with the aid of polyethylene glycol with the addition of calcium chloride (Yanai et al., 1996, Biosci. Biotechnol. Biochem. 60(3), 472-475, *Pleurotus ostreatus*; Honda et al., 2000, Curr Genet 37, 209.212, *Pleurotus ostreatus*) and protoplast transformation, with the DNA being integrated into the fungal genome by means of homologous recombination (van de Rhee et al., 1996, Curr Genet 30, 166-173, *Agaricus bisporus*). It was also possible to successfully transform fungi with the aid of *Agrobacterium*-mediated gene transfer (Godio et al., 2004 Curr Genet 46, 287-294, *Hypholoma sublateritium*; Mikosch et al., 2001, Curr Genet 39, 35-39, *Agaricus bisporus*; Chen et al., 2000, Applied and Environmental Microbiology 66(10), 4510-4513; US 2002 0016982; WO 02 00896, *Agaricus bisporus*, WO 98 45455; U.S. Pat. No. 6,436,643, *Agaricus bisporus, Pleurotus ostreatus*; Hanif et al., 2002, Curr Genet 41(3), 183-188 *Suillus bovinus*).

Fungal cells according to the invention and fungi according to the invention having a nucleic acid molecule coding for a hyaluronan synthase stably integrated into their genome can be identified inter alia by the fact that they have at least one copy of a nucleic acid molecule coding for a hyaluronan synthase stably integrated into their genome. This can be checked, for example, by a southern blot analysis.

Furthermore, the fungal cells according to the invention and the fungi according to the invention preferably have at least one of the following distinguishing features: the fungal cells according to the invention or fungi according to the invention comprise transcripts of the nucleic acid molecules stably integrated into the genome and coding for a hyaluronan synthase. These can be identified, for example, by northern blot analysis or by RT-PCR (Reverse Transcription Polymerase Chain Reaction). Preferably, the fungal cells according to the invention and the fungi according to the invention comprise a protein which is encoded by nucleic acid molecules stably integrated into the genome coding for a hyaluronan synthase. This can be checked, for example, by immunological methods, in particular by a western blot analysis.

The fact that fungal cells according to the invention or fungi according to the invention comprise an active hyaluronan synthase can preferably be detected by detecting the activity of a hyaluronan synthase in reconstituted membranes which are prepared from membrane fractions isolated from fungal cells according to the invention or fungi according to the invention. A method suitable for detecting the activity of a hyaluronan synthase is described in DeAngelis and Achyuthan (1996, J Biol. Chem. 271(39), 23657-23660).

Methods for preparing antibodies which react specifically with a certain protein, i.e. which bind specifically to said protein, are known to the person skilled in the art (see, for example, Lottspeich and Zorbas (Eds.), 1998, Bioanalytik [bioanalysis], Spektrum akad. Verlag, Heidelberg, Berlin, ISBN 3-8274-0041-4). Some companies (for example Eurogentec, Belgium) offer the preparation of such antibodies as a service. Antibodies which specifically recognize hyaluronan synthases are described, for example, in Jacobson et al. (2000, Biochem J. 348, 29-35).

Fungal cells according to the invention or fungi according to the invention which synthesize hyaluronan can be identified by isolating the hyaluronan that is synthesized by them and proving its structure.

Since fungus tissue has the advantage that it does not contain hyaluronidases, a simple and rapid isolation method can be used for confirming the presence of hyaluronan in fungal cells according to the invention or fungi according to the invention. To this end, water is added to the fungus tissue to be examined and the fungus tissue is then comminuted mechanically (with the aid of, for example, a bead mill, a Warring blender, etc.). If required, more water may then be added to the suspension, and cell debris and water-insoluble components are then removed by centrifugation. The presence of hyaluronan in the supernatant obtained after centrifugation can then be demonstrated using, for example, a protein which binds specifically to hyaluronan. A method for detecting hyaluronan with the aid of a protein that binds specifically to hyaluronan is described, for example, in U.S. Pat. No. 5,019,498. Test kits (for example the hyaluronic acid (HA) test kit from Corgenix, Inc., Colorado, USA, Prod. No. 029-001) for carrying out the method described in U.S. Pat. No. 5,019,498 are commercially available (for example the hyaluronic acid (HA) test kit from Corgenix, Inc., Colorado, USA, Prod. No. 029-001; see also General Methods item 6.). In parallel, it is possible to initially digest an aliquot of the centrifugation supernatant obtained with a hyaluronidase and then to confirm the presence of hyaluronan with the aid of a protein which specifically binds to hyaluronan, as described above. By the action of the hyaluronidase in the parallel batch, the hyaluronan present therein is degraded, so that after complete digestion it is no longer possible to detect significant amounts of hyaluronan.

The presence of hyaluronan in the centrifugation supernatant can furthermore also be confirmed using other analysis methods, such as, for example, IR, NMR or mass spectroscopy.

The present invention furthermore provides fungal cells according to the invention or fungi according to the invention characterized in that the nucleic acid molecule stably integrated into the genome of the fungal cell or the fungus and coding for a hyaluronan synthase is linked to regulatory elements initiating the transcription in fungal cells (promoters). In a preferred embodiment, the promoters are tissue-specific promoters, particularly preferably promoters initiating transcription specifically in fruiting bodies.

For the expression of nucleic acid molecules according to the invention coding for a hyaluronan synthase, these are preferably linked to regulatory DNA sequences which ensure transcription in fungal cells. These include in particular promoters. Suitable for expression are, in general, all promoters active in fungal cells.

The promoter may be chosen such that the expression takes place constitutively or only in a certain tissue, at a certain point in time in the development of the fungus or at a point in time determined by external factors. The promoter may be homologous or heterologous, both with respect to the fungus and with respect to the nucleic acid molecule coding for a hyaluronan synthase.

Examples of promoters suitable for initiating transcription in fungal cells are the promoter of the glyceraldehyde 3-phosphate dehydrogenase gene from *Agaricus bisporus* (Van de Rhee et al., 1996, Mol Gen Genet 250, 252-258; Chen et al., 2000; Applied and Environmental Microbiology 66(10), 4510-4513; US 2002 0016982) and from *Lentinus edodes* (Hirano et al., 2000, Mol Gen Genet 263, 1047-1052), the promoter of the priA gene *Lentinus edodes* (Yanai et al., 1996, Biosci. Biotech. Biochem 60(3), 472-475; Kajiwara et al., 1992, Gene 114(2), 173-178), or the promoter of the *Lentinus edodes* ras gene (Yanai et al., 1996, Biosci. Biotech. Biochem 60(3), 472-475). The cauliflower mosaic virus 35S promoter which is frequently used for expression of foreign nucleic acids in plants has also been shown to initiate transcription in fungal cells (Sun et al., 2002, Molecular Biotechnology 20(3), 239-244). An overview over further promoters which mediate initiation of transcription in fungal cells is described in Burns et al. (2005, Fungal Gentics and Biology, in Press, prepublished online at www.sciencedirect.com, 05, Jan. 2005, doi:10.1016/j.fgb.2004.11.005). An example of a promoter inducible by external influences in fungi is the promoter of the *Phanerochaete chrysosporium* manganese peroxidase 1 (mnp 1) gene (Ma et al., Applied and Environmental Microbiology 67(2), 948-955; Godfrey et al., 1990, Gene 93(1), 119-124).

Examples of fruiting body-specific promoters are, for example, promoters of the Hydrophobin A (hypA), Hydrophobin B (hypB) and Hydrophobin C (hypC) genes from *Agaradicus bisporus* (De Groot et al., 1999, Microbiology 145, 1105-1113), of the *Flammulina velutipes* hydrophobin gene (fvh1) promoter (Ando et al., 2001, Curr Genet 39(3), 190-197), the promoters of the *Schizophyllum commune* hydrophobin genes Sc1 and Sc4 (Schuren and Wessels, 1990, Gene 90(2), 199-205), the promoters of the *Pleurotus ostreatus* hydrophobin genes fbh1 and poh1 (Penas et al., 2004, Mycologica 96(1), 75-82), the promoters of the *Agaricus bisporus* abst1 gene (also referred to as mag1 gene) (WO 04 039985, EMBL Acc. No.: AJ299400.1) or the promoter of the *Agaricus bisporus rafe* gene (WO 04 039985, EMBL Acc. No.: AJ853495.1). Other genes having fruiting body-specific promoters and possibilities of identifying and isolating said genes are described, for example, in De Groot et al. (1997, Microbiology 143, 1993-2001) or Hirano et al. (2004, Biosci. Biotechnol. Biochem. 68, 468-472.

In the context of the present invention, the term "tissue specific" is to be understood as meaning the restriction of a feature (for example initiation of transcription) predominantly to a certain tissue. More specifically, the following tissues can be distinguished in fungi of the division Basidiomycota: mycelium and fruiting body, it being possible for the mycelium to be divided further into a haploid and a dikaryotic mycelium and the fruiting body to be divided further into a stipe, a pireus, lamellae and basidia.

It is furthermore possible for a termination sequence to be present, which serves to add a poly-A tail to the transcript.

In the context of the present invention, the term "termination sequence" is to be understood as meaning nucleic acid sequences which have one or more recognition sequence(s) for the polyadenylation of an RNA transcript (polyadenylation signal) and/or one or more nucleic acid sequence(s), which have the function of a transcription blocker (pause signal).

It is thought that the polyadenylation signal has a function in stabilizing the transcripts. Furthermore, polyadenylation signals serve to prevent transcripts from becoming too long, i.e. to prevent transcripts of a first gene from being produced, which additionally contain sequences of a second gene (e.g. promoter sequences) (Eggermont and Proudfoot, 1993, EMBO J. 12(5), 2539-2548). Elements of this kind have been described in the literature (see, for example, Schuren and Wessels, 1990, Gene 90, 199-205; Penas et al., 2004, Mycologica 96(1), 75-82; Ando et al., 2001, Curr Genet 39(2), 190-197; Sirand-Pugnet et al., 2003, Curr Genet 44, 124-131; Sirand-Pugnet and Labarère, 2002, Curr Genet 41, 31-42; Yanai et al., 1996, Biosci. Biotech. Biochem. 60(3), 472475; Godio et al., 2004, Curr Genet 46, 287-294; Hirano et al., 2000, Mol Gen Genet 263, 1047-1052; Chen et al., 2000, Applied and Environmental Microbiology 66(10), 4510-4513).

The termination blocker is ascribed the function of efficient usage of polyadenylation signals, i.e. the presence of a transcription blocker results in a first, weaker polyadenylation signal being used, if additionally a second, stronger polyadenylation signal is present downstream of the transcription blocker (Enriquez-Harris et al., 1991, EMBO J. 10(7), 1833-1842).

In order to stabilize the transcribed RNA, it may be necessary for the foreign nucleic acid molecule to be transcribed to have intron sequences (Lugones et al., 1999, Molecular Microbiology 32(4), 681-689; Scholtmeijer et al., 2001, Applied and Environmental Microbiology 67(1), 481-483; Ma et al., Applied and Environmental Microbiology 67(2), 948-955, Burns et al. (2005, Fungal Gentics and Biology, in Press, prepublished online at www.sciencedirect.com, 5, Jan. 2005, doi:10.1016/j.fgb.2004.11.005). It is therefore also possible for intron sequences to be located between the promoter and the coding region and/or the termination sequence and the coding region and/or within the coding region of the foreign nucleic acid molecule. It is possible here for a single intron sequence or a plurality of intron sequences to be present. Preference is given to using introns of corresponding naturally occurring fungal genes.

The present invention further relates to fungal cells according to the invention or fungi according to the invention, wherein the nucleic acid molecule stably integrated into the genome of said fungal cell or of said fungus and coding for a hyaluronan synthase comprises intron sequences. Preference is given here to intron sequences which naturally occur in genes of fungal cells.

Fungal cells may be transformed and/or propagated by methods known to the person skilled in the art.

The present invention therefore further relates to fungal cells derived from a fungal cell according to the invention or a fungus according to the invention, comprising the nucleic acid molecule coding for a hyaluronan synthase, which their mother cell from which they derive comprises.

It is known to the person skilled in the art that fungi go through various developmental phases during their life cycle. Fungi of the systematic division Basidiomycota usually have the morphologically distinguishable tissues of a mycelium and a fruiting body. The mycelium which is composed of hyphae may exist in different genetic variants (haploid or dikaryotic). The dikaryotic life phase normally emerges from the fusion of haploid mycelial cells genetically different with respect to the mating factor (somatogamy). Both the haploid mycelium and the mycelium present in the dikaryotic form are able to grow in an unlimited fashion, i.e. they are able to propagate vegetatively. The fruiting body formed by the dikaryotic mycelium mostly consists of dikaryotic cells. In the basidia which are specialized cells of the fruiting body, normally a fusion of the relevant nuclei (karyogamy) takes place, followed by a meiosis (sexual propagation). The haploid nuclei produced therefrom constitute the genome of the subsequently basidiospores which, after germination on a suitable substrate, again form a haploid mycelium. Deviations from this fundamental life cycle are known. Thus, for example, the basidiospores of all cultured *Agaricus bisporus* representatives usually contain in each case two haploid nuclei which subsequently germinate to give hyphae which immediately form a dikaryotic mycelium. In the presence of dikaryotic mycelia it is possible for fruiting bodies to be formed directly, without prior fusion with a second mycelium. However, in rare cases it is also possible for mononuclear *Agaricus bisporus* basidiospores to be produced. It is moreover often the case with *Agaricus bisporus* representatives that the cells forming the mycelium or the fruiting body are polynuclear, i.e. they have more than two nuclei (Kothe, 2001, Appl Microbiol Biotechnol 56, 602-612).

As mentioned above, fungal cells according to the invention may be regenerated to give fungi.

The present invention therefore relates to fungi comprising fungal cells according to the invention.

In the context of the present invention, the term "fungus" is understood as meaning any manifestations of the various developmental phases of a fungus in question. Said manifestations may be mycelia having haploid, dikaryotic or polynuclear fungal cells and/or fruiting bodies having dikaryotic or polynuclear fungal cells and/or basidiospores.

The present invention therefore also relates to fungal mycelia having haploid, dikaryotic or polynuclear fungal cells according to the invention and/or fruiting bodies having dikaryotic or polynuclear fungal cells according to the invention.

Fungal cells according to the invention or fungi according to the invention are preferably fungal cells or fungi of the systematic class Basidiomycetes (toadstools), preferably fungi of the systematic subclass Hymenomycotidae (pileate fungi, also referred to as Agaricomycotidae according to a more recent nomenclature), particularly preferably fungi of the systematic order Agaricales (gill-bearing mushrooms), especially preferably fungi of the systematic family Agaricaceae (mushrooms). In a specially preferred embodiment, the fungal cells according to the invention or fungi according to the invention are fungal cells or fungi of the genus *Agaricus*, in particular especially preferably fungal cells or fungi of the species *Agaricus bisporus*. The systematics of the fungi, used in connection with the present invention, is based on more recent knowledge and follows Ainsworth and Bisby's Dictionary of the Fungi (9th Edition, Utrecht NL, 2001, ISBN 0851 99377X). As mentioned above, fungi may be propagated both sexually and vegetatively, using methods known to the person skilled in the art.

The present invention therefore also relates to propagation material of a fungus according to the invention, characterized in that it comprises the nucleic acid molecule coding for a hyaluronan synthase, which the fungus according to the invention comprises.

Here, the term "propagation material" encompasses those components of the fungus which are suitable for producing progeny in a vegetative or sexual manner. Suitable for vegetative propagation are fungal mycelia which have haploid, dikaryotic or polynuclear fungal cells according to the invention or cells of fruiting bodies which have dikaryotic or polynuclear fungal cells according to the invention. Sexual propagation material relates to spores (Basidio spores) which have one or more nuclei.

The present invention also relates to processable or consumable parts of fungi according to the invention comprising fungal cells according to the invention and/or comprising hyaluronan.

In the context of the present invention, the term "processable parts" is to be understood as meaning fungal tissues used for preparing food or feed, which are used as raw material source for industrial processes, as raw material source for preparing pharmaceutical products or as raw material source for preparing cosmetic products. Preferred processable parts are fruiting bodies of fungi according to the invention.

In the context of the present invention, the term "consumable parts" is to be understood as meaning fungal tissues which serve as food for humans or are used as animal feed. Preferred consumable parts are fruiting bodies of fungi according to the invention.

The present invention preferably relates to propagation material, processable or consumable parts of fungi comprising hyaluronan. Particular preference is given to propagation material, processable or consumable parts of fungi which synthesize hyaluronan.

A further advantage of the present invention consists in the fact that processable parts or consumable parts of fungi according to the invention comprise hyaluronan. Accordingly, these are not only suitable as raw materials from which it is possible to isolate hyaluronan, but they can also be used directly as food/feed or for the preparation of food/feed having a prophylactic or therapeutic character (for example for the prophylaxis of osteoarthritis, U.S. Pat. No. 6,607,745). Thus, for example, it is no longer necessary to add hyaluronan prepared by fermentation or isolated from animal tissues as so-called nutraceuticals when employing fungi according to the invention or parts of fungi according to the invention for preparing nutraceuticals or using them directly as food/feed. By virtue of the high water-binding capacity of hyaluronan, processable parts or consumable parts of fungi according to the invention furthermore have the advantage that fewer thickeners have to be used when preparing solidified food/feed. Thus, for the manufacture of dried "convenience foods", such as, for example, packet soups, the use of processable parts or consumable parts, according to the invention, of fungi according to the invention leads to less thickening agents (e.g. starch) needing to be added. This leads, for example, to lower costs in the manufacture of such products.

The present invention furthermore provides a method for preparing a fungus which synthesizes hyaluronan, wherein
a) a nucleic acid molecule coding for a hyaluronan synthase is integrated into the genome of a fungal cell
b) a fungus is regenerated from fungal cells of step a); and
c) further fungi are, if appropriate, generated with the aid of the fungi of step b).

The regeneration of the fungi according to step b) can be carried out by methods known to the person skilled in the art (described, for example, in "Plant Cell Culture Protocols", 1999, edt. by R. D. Hall, Humana Press, ISBN 0-89603-549-2).

The generation of further fungi according to step c) of the process according to the invention for preparing a fungus can be carried out, for example, by vegetative propagation or by sexual propagation. Here, sexual propagation preferably takes place in a controlled manner, i.e. selected fungi having certain properties are crossbred with one another and propagated. Selection is carried out in a manner such that the further fungi generated according to step c) have, integrated into the genome of the fungus, the nucleic acid molecule coding for a hyaluronan synthase, and/or they synthesize hyaluronan.

In a preferred embodiment of methods according to the invention for preparing a fungus, in an additional process step b)-1, which follows after process step b), the selected fungi comprise, stably integrated into their genome, a nucleic acid molecule coding for a hyaluronan synthase.

In a further preferred embodiment, the methods according to the invention for preparing a fungus have a process step, following after process step b) or b)-1, in which hyaluronan-synthesizing fungi are identified.

In further embodiments, the present invention relates to methods according to the invention for preparing a fungus where the nucleic acid molecule coding for a hyaluronan synthase in step a) is selected from the group consisting of:
a) nucleic acid molecules, characterized in that they code for a hyaluronan synthase Class I,
b) nucleic acid molecules, characterized in that they code for a vertebrate hyaluronan synthase or a viral hyaluronan synthase,
c) nucleic acid molecules, characterized in that they code for a hyaluronan synthase from amphibians or a hyaluronan synthase of a virus which infects algae,
d) nucleic acid molecules, characterized in that they code for a hyaluronan synthase of a *Chlorella*-infecting virus or a hyaluronan synthase from a frog,
e) nucleic acid molecules, characterized in that they code for a hyaluronan synthase of a *Paramecium bursaria Chlorella* virus 1 or a hyaluronan synthase 1 from *Xenopus laevis*,
f) nucleic acid molecules, characterized in that the codons of the nucleic acid molecule coding for a hyaluronan synthase are modified compared to the codons of the nucleic acid molecule coding for the hyaluronan synthase of the parent organism of the hyaluronan synthase,
g) nucleic acid molecules, characterized in that the codons of the hyaluronan synthase are modified such that they are adapted to the frequency of the use of the codons of the fungal cell into whose genome they are or will be integrated,
h) nucleic acid molecules, characterized in that they code for a hyaluronan synthase having the amino acid sequence shown in SEQ ID NO 2, SEQ ID NO 4, SEQ ID NO 6, SEQ ID N08, SEQ ID NO 10, SEQ ID NO 12, SEQ ID NO 14, SEQ ID NO 16, SEQ ID NO 18, SEQ ID NO 20, SEQ ID NO 22, SEQ ID NO 24, SEQ ID NO 26, SEQ ID NO 28, SEQ ID NO 30, SEQ ID NO 32, SEQ ID NO 34, SEQ ID NO 36, SEQ ID NO 38, SEQ ID NO 40, SEQ ID NO 42, SEQ ID NO 44, SEQ ID NO 46, SEQ ID NO 48, SEQ ID NO 50, SEQ ID NO 52, SEQ ID NO 54, SEQ ID NO 56, SEQ ID NO 58, SEQ ID NO 60, SEQ ID NO 62 or SEQ ID NO 64,
i) nucleic acid molecules, characterized in that they code for a protein whose amino acid sequence can be derived from the coding region of the nucleic acid sequence inserted into plasmid DSM16664,
j) nucleic acid molecules comprising a nucleic acid sequence shown in SEQ ID NO 1, SEQ ID NO 3, SEQ ID NO 5, SEQ ID NO 7, SEQ ID NO 9, SEQ ID NO 11, SEQ ID NO 13, SEQ ID NO 15, SEQ ID NO 17, SEQ ID NO 19, SEQ ID NO 21, SEQ ID NO 23, SEQ ID NO 25, SEQ ID NO 27, SEQ ID NO 29, SEQ ID NO 31, SEQ ID NO 33, SEQ ID NO 35, SEQ ID NO 37, SEQ ID NO 39, SEQ ID NO 41, SEQ ID NO 43, SEQ ID NO 45, SEQ ID NO 47, SEQ ID NO 49, SEQ ID NO 51, SEQ ID NO 53, SEQ ID NO 55, SEQ ID NO 57, SEQ ID NO 59, SEQ ID NO 61 or SEQ ID NO 63, k) nucleic acid molecules comprising the nucleic acid sequence inserted into plasmid DSM16664, l) nucleic acid molecules, coding for a hyaluronan synthase, where the nucleic acid sequences coding for hyaluronan synthase are linked to regulatory elements (promoters) which initiate the transcription in fungal cells or m) nucleic acid molecules according to j), where the promoters are tissue-specific promoters, particularly preferably promoters which initiate the transcription specifically in fruiting bodies of fungi.

In a further preferred embodiment, methods according to the invention for preparing a fungus, serve for preparing a fungus according to the invention.

The present invention also provides fungi obtainable by methods according to the invention for preparing a fungus.

The present invention further provides methods for preparing hyaluronan comprising a step where hyaluronan is extracted from fungal cells according to the invention, from fungi according to the invention, from propagation material according to the invention, from consumable fungus parts according to the invention, from processable fungus parts or from fungi obtainable by a method according to the invention. Preferably, such a method also comprises the step where the cultivated fungal cells according to the invention, the fungi according to the invention, the propagation material according to the invention, the consumable fungus parts according to the invention, the processable fungus parts according to the invention are harvested prior to extraction of the hyaluronan, and particularly preferably furthermore the step of the cultivation of fungal cells according to the invention or fungi according to the invention prior to harvesting.

In contrast to bacterial or animal tissues, fungus tissues have no hyaluronidases and do not contain any hyaladherins. Accordingly, as already described above, extraction of hyaluronan from fungus tissues is possible with the aid of relatively simple methods. If required, the aqueous extracts, described above, of fungal cells or tissues containing hyaluronan can be purified further using methods known to the person skilled in the art, such as, for example, repeated precipitation with ethanol.

The present invention also provides the use of fungal cells according to the invention, fungi according to the invention, propagation material according to the invention, processable fungus parts according to the invention, consumable fungus parts according to the invention or fungi obtainable by a method according to the invention for preparing hyaluronan.

The present invention furthermore provides compositions comprising components of fungal cells according to the invention, fungi according to the invention, propagation material according to the invention, processable fungus parts according to the invention, consumable fungus parts according to the invention or fungi obtainable by a method according to the invention. The compositions are preferably food, food supplements or feed, pharmaceutical or cosmetic products.

As already mentioned above, it is possible to use fungus parts according to the invention, fungi according to the invention, propagation material according to the invention, harvestable fungus parts according to the invention, processable fungus parts according to the invention, consumable fungus parts according to the invention or fungi obtainable by a method according to the invention to prepare food or feed. However, use as raw materials for industrial applications is also possible, without hyaluronan having to be isolated. Thus, for example, fungi according to the invention or parts of fungi according to the invention can be applied to areas under agricultural cultivation to achieve increased water binding of the soil. Furthermore, fungi according to the invention or fungal cells according to the invention can be used for preparing drying agents (for example for use when shipping moisture-sensitive items) or as absorbers of liquids (for example in nappies or for absorbing spilled aqueous liquids). For such applications, it is possible to use entire fungi according to the invention, parts of fungi according to the invention or comminuted (for example ground) fungi according to the invention or fungus parts according to the invention, as required.

The present invention also provides methods for preparing a composition according to the invention, where fungal cells according to the invention, fungi according to the invention, propagation material according to the invention, processable fungus parts according to the invention, consumable fungus parts according to the invention or fungi obtainable by a method according to the invention are used. The methods for preparing a composition according to the invention are preferably methods for preparing food or feed, methods for preparing a pharmaceutical product or methods for preparing a cosmetic product.

Methods for preparing food or feed are known to the person skilled in the art. Methods for using fungi or fungus parts in industrial areas are also known to the person skilled in the art. Some of the advantages resulting from using subject-matters according to the invention for preparing food/feed or for use in industrial areas have already been described above.

The present invention also relates to the use of fungal cells according to the invention, fungi according to the invention, propagation material according to the invention, processable fungus parts according to the invention, consumable fungus parts according to the invention or fungi obtainable by a method according to the invention for preparing a fungus for preparing a composition according to the invention. Preference is given to the use of fungal cells according to the invention, fungi according to the invention, propagation material according to the invention, processable fungus parts according to the invention, consumable fungus parts according to the invention or of fungi obtainable by a method according to the invention for preparing a fungus according to the invention for preparing food or feed, for preparing a pharmaceutic or for preparing a cosmetic product.

It is another object of the present invention to provide means, such as, for example, DNA molecules, for generating fungal cells according to the invention and fungi according to the invention.

Accordingly, the present invention furthermore provides recombinant nucleic acid molecules comprising a nucleic acid sequence coding for a hyaluronan synthase and a nucleic acid sequence which initiates transcription (promoter) in a fungal cell of the systematic division Basidiomycota.

In the context of the present invention, the term "recombinant nucleic acid molecule" is to be understood as meaning a nucleic acid molecule which, in addition to nucleic acid molecules coding for a hyaluronan synthase, contains additional sequences which are not naturally present in a combination as present in the recombinant nucleic acids according to the invention. Here, the additional sequences mentioned may be any sequences; preferably, they are sequences of different functional elements (promoters, termination sequences consisting of polyadenylation sequences and/or transcription blockers, intron sequences, enhancers), particularly preferably regulatory sequences (promoters) active in fungus cells and especially preferably tissue-specific regulatory sequences which are active in fruiting body tissue of fungi.

Methods for generating recombinant nucleic acid molecules according to the invention are known to the person skilled in the art and include genetic engineering methods, such as, for example, linking of nucleic acid molecules by ligation, genetic recombination or the de novo synthesis of nucleic acid molecules (see, for example, Sambrook et al., Molecular Cloning, A Laboratory Manual, 3rd edition (2001) Cold Spring Harbour Laboratory Press, Cold Spring Harbour, N.Y. ISBN: 0879695773, Ausubel et al., Short Protocols in Molecular Biology, John Wiley & Sons; 5th edition (2002), ISBN: 0471250929).

In a preferred embodiment, the recombinant nucleic acid molecule comprises a fruiting body-specific promoter and/or at least one intron sequence.

In a further preferred embodiment, recombinant nucleic acid molecules according to the invention also comprise termination sequences. The termination sequences here can comprise nucleic acid sequences which have one of more recognition sequence(s) for the polyadenylation of an RNA transcript (polyadenylation signal) and/or one or more nucleic acid sequence(s) which have the function of a transcription blocker (pause signal).

A further embodiment of inventive recombinant nucleic acid molecules of the present invention are vectors, in particular plasmids, cosmids, virus genomes, bacteriophage genomes and other vectors commonly used in genetic engineering which contain the nucleic acid molecules according to the invention. These are preferably vectors, plasmids, cosmids or virus genomes suitable for transforming fungal cells. The transformation of fungal cells or fungi with the aid of recombinant nucleic acid molecules according to the invention especially preferably results in the stable integration of a hyaluronan synthase-encoding nucleic acid sequence into the genome of the fungal cell and the fungus, respectively.

Recombinant nucleic acid molecules according to the invention may also contain "selection markers" which can be used in assisting the selection of fungal cells or fungi having the recombinant nucleic acid molecule. Selection markers for transformation of fungal cells are known to the person skilled in the art. They may be "auxotrophic" selection markers which ensure growth of the transformed fungal cell or of the fungus on a defined medium (Burns et al. (2005, Fungal Gentics and Biology, in Press, prepublished online at www.sciencedirect.com, 5, Jan. 2005, doi:10.1016/j.fgb.2004.11.005; Ogawa et al., 1998, Appl Microbiol Biotechnol 49, 285-289; Noel and Labarere, 1994, Curr Genet 25, 432-437), selection markers which impart resistance to an antibiotic (Schuren and Wessels, 1994, Curr Genet 26, 179-183; Hanif et al., 2002, Curr Genet 41, 183.188; Chen et al., 2000, Applied and Environmental Microbiology 66(10), 4510-4513; Sato et al., 1998, Biosci. Biotechnol. Biochem. 62(12), 2346-2350), selection markers which impart resistance to a herbicide (Yanai et al., 1996, Biosci. Biotechnol. Biochem. 60(3), 472-475; Sun et al., Plant Molecular Biology Reporter 19, 383a-383j) or selection markers which impart resistance to a fungicide (Honda et al., 2000, Curr Genet 37, 209-212). Another use is that of "marker proteins" such as, for example, fluorescent proteins (Sun et al., Plant Molecular Biology Reporter 19, 383a-383j; Burns et al. (2005, Fungal Gentics and Biology, in Press, prepublished online at www.sciencedirect.com, 5, Jan. 2005, doi:10.1016/j.fgb.2004.11.005; MA et al., 2001, Applied and Environmental Microbiology 67(2), 948-955; Lugones et al., Molecular Biology 32(4), 681-689) or beta-glucoronidase (Sun et al., 2002, Molecular Biotechnology 20, 239-244; Sun et al., Plant Molecular Biology Reporter 19, 383a-383j; Yanai et al., 1996, Biosci. Biotechnol. Biochem. 60(3), 472-475). The sequence coding for the selection marker may also contain modifications so as to achieve improved expression (transcription and/or translation) in the fungal cell in question (Scholtmeijer et al., Applied and Environmental Microbiology 0.67(1), 481-483; Burns et al. (2005, Fungal Gentics and Biology, in Press, prepublished online at www.sciencedirect.com, 5, Jan. 2005, doi:10.1016/j.fgb.2004.11.005; MA et al., 2001, Applied and Environmental Microbiology 67(2), 948-955; Lugones et al., Molecular Biology 32(4), 681-689).

In further embodiments, the present invention relates to recombinant nucleic acid molecules according to the invention where the nucleic acid sequence coding for a hyaluronan synthase is selected from the group consisting of:

a) nucleic acid molecules, characterized in that they code for a hyaluronan synthase Class I, b) nucleic acid molecules, characterized in that they code for a vertebrate hyaluronan synthase or a viral hyaluronan synthase, c) nucleic acid molecules, characterized in that they code for a hyaluronan synthase from amphibians or a hyaluronan synthase of a virus which infects algae, d) nucleic acid molecules, characterized in that they code for a hyaluronan synthase of a Chlorella-infecting virus or a hyaluronan synthase from a frog, e) nucleic acid molecules, characterized in that they code for a hyaluronan synthase of a *Paramecium bursaria Chlorella* virus 1 or a hyaluronan synthase from *Xenopus laevis*, f) nucleic acid molecules, characterized in that the codons of the nucleic acid molecule coding for a hyaluronan synthase are modified compared to the codons of the nucleic acid molecule coding for the hyaluronan synthase of the parent organism of the hyaluronan synthase, g) nucleic acid molecules, characterized in that the codons of the hyaluronan synthase are modified such that they are adapted to the frequency of the use of the codons of the fungal cell into whose genome they are or will be integrated, h) nucleic acid molecules, characterized in that they code for a hyaluronan synthase having the amino acid sequence shown in SEQ ID NO 2, SEQ ID NO 4, SEQ ID NO 6, SEQ ID NO 8, SEQ ID NO 10, SEQ ID NO 12, SEQ ID NO 14, SEQ ID NO 16, SEQ ID NO 18, SEQ ID NO 20, SEQ ID NO 22, SEQ ID NO 24, SEQ ID NO 26, SEQ ID NO 28, SEQ ID NO 30, SEQ ID NO 32, SEQ ID NO 34, SEQ ID NO 36, SEQ ID NO 38, SEQ ID NO 40, SEQ ID NO 42, SEQ ID NO 44, SEQ ID NO 46, SEQ ID NO 48, SEQ ID NO 5, SEQ ID NO 52, SEQ ID NO 54, SEQ ID NO 56, SEQ ID NO 58, SEQ ID NO 60, SEQ ID NO 62 or SEQ ID NO 64, i) nucleic acid molecules, characterized in that they code for a protein whose amino acid sequence can be derived from the coding region of the nucleic acid sequence inserted into plasmid DSM16664, j) nucleic acid molecules comprising a nucleic acid sequence shown in SEQ ID NO 1, SEQ ID NO 3, SEQ ID NO 5, SEQ ID NO 7, SEQ ID NO 9, SEQ ID NO 11, SEQ ID NO 13, SEQ ID NO 15, SEQ ID NO 17, SEQ ID NO 19, SEQ ID NO 21, SEQ ID NO 23, SEQ ID NO 25, SEQ ID NO 27, SEQ ID NO 29, SEQ ID NO 31, SEQ ID NO 33, SEQ ID NO 35, SEQ ID NO 37, SEQ ID NO 39, SEQ ID NO 41, SEQ ID NO 43, SEQ ID NO 45, SEQ ID NO 47, SEQ ID NO 49, SEQ ID NO 51, SEQ ID NO 53, SEQ ID NO 55, SEQ ID NO 57, SEQ ID NO 59, SEQ ID NO 61 or SEQ ID NO 63, or k) nucleic acid molecules comprising the nucleic acid sequence inserted into plasmid DSM16664.

The present invention also provides fungal cells or fungi containing recombinant nucleic acid molecules according to the invention.

The present invention also relates to the use of recombinant nucleic acids according to the invention for preparing a fungal cell according to the invention or a fungus according to the invention.

The present invention furthermore relates to the use of recombinant nucleic acids according to the invention for carrying out methods according to the invention for preparing a fungus.

Description of the Sequences

SEQ ID NO 1: Nucleic acid sequence, coding for a hyaluronan synthase of *Paramecium bursaria Chlorella* virus 1.

SEQ ID NO 2: Amino acid sequence of a hyaluronan synthase of *Paramecium bursaria Chlorella* virus 1. The amino acid sequence shown can be derived from SEQ ID NO 1.

SEQ ID NO 3: Synthetic nucleic acid sequence, coding for a hyaluronan synthase of *Paramecium bursaria Chlorella* virus 1.

SEQ ID NO 4: Amino acid sequence of a hyaluronan synthase of *Paramecium bursaria Chlorella* virus 1. The amino acid sequence shown can be derived from SEQ ID NO 3.

SEQ ID NO 5: Nucleic acid sequence, coding for a hyaluronan synthase 3 from *Homo sapiens*.

SEQ ID NO 6: Amino acid sequence of a hyaluronan synthase 3 from *Homo sapiens*. The amino acid sequence shown can be derived from SEQ ID NO 5.

SEQ ID NO 7: Synthetic nucleic acid sequence, coding for a hyaluronan synthase 3 from *Homo sapiens*.

SEQ ID NO 8: Amino acid sequence of a hyaluronan synthase 3 from *Homo sapiens*. The amino acid sequence shown can be derived from SEQ ID NO 7.

SEQ ID NO 9: Nucleic acid sequence, coding for a hyaluronan synthase 1 from *Homo sapiens*.

SEQ ID NO 10: Amino acid sequence of a hyaluronan synthase 1 from *Homo sapiens*. The amino acid sequence shown can be derived from SEQ ID NO 9.

SEQ ID NO 11: Nucleic acid sequence, coding for a hyaluronan synthase 2 from *Homo sapiens*.

SEQ ID NO 12: Amino acid sequence of a hyaluronan synthase 2 from *Homo sapiens*. The amino acid sequence shown can be derived from SEQ ID NO 11.

SEQ ID NO 13: Nucleic acid sequence, coding for a hyaluronan synthase 1 from *Papio anubis*.

SEQ ID NO 14: Amino acid sequence of a hyaluronan synthase 1 from *Papio anubis*. The amino acid sequence shown can be derived from SEQ ID NO 13.

SEQ ID NO 15: Nucleic acid sequence, coding for a hyaluronan synthase 1 from *Mus musculus*.

SEQ ID NO 16: Amino acid sequence of a hyaluronan synthase 1 from *Mus musculus*. The amino acid sequence shown can be derived from SEQ ID NO 13.

SEQ ID NO 17: Nucleic acid sequence, coding for a hyaluronan synthase 2 from *Mus musculus*.

SEQ ID NO 18: Amino acid sequence of a hyaluronan synthase 2 from *Mus musculus*. The amino acid sequence shown can be derived from SEQ ID NO 17.

SEQ ID NO 19: Nucleic acid sequence, coding for a hyaluronan synthase 3 from *Mus musculus*.

SEQ ID NO 20: Amino acid sequence of a hyaluronan synthase 3 from *Mus musculus*. The amino acid sequence shown can be derived from SEQ ID NO 19.

SEQ ID NO 21: Nucleic acid sequence, coding for a hyaluronan synthase 1 from *Rattus norvegicus*.

SEQ ID NO 22: Amino acid sequence of a hyaluronan synthase 1 from *Rattus norvegicus*. The amino acid sequence shown can be derived from SEQ ID NO 21.

SEQ ID NO 23: Nucleic acid sequence, coding for a hyaluronan synthase 2 from *Rattus norvegicus*.

SEQ ID NO 24: Amino acid sequence of a hyaluronan synthase 2 from *Rattus norvegicus*. The amino acid sequence shown can be derived from SEQ ID NO 23.

SEQ ID NO 25: Nucleic acid sequence, coding for a hyaluronan synthase 3 from *Rattus norvegicus*.

SEQ ID NO 26: Amino acid sequence of a hyaluronan synthase 3 from *Rattus norvegicus*. The amino acid sequence shown can be derived from SEQ ID NO 25.

SEQ ID NO 27: Nucleic acid sequence, coding for a hyaluronan synthase 2 from *Oryctolagus cuniculus*.

SEQ ID NO 28: Amino acid sequence of a hyaluronan synthase 2 from *Oryctolagus cuniculus*. The amino acid sequence shown can be derived from SEQ ID NO 27.

SEQ ID NO 29: Nucleic acid sequence, coding for a hyaluronan synthase 3 from *Oryctolagus cuniculus*.

SEQ ID NO 30: Amino acid sequence of a hyaluronan synthase 3 from *Oryctolagus cuniculus*. The amino acid sequence shown can be derived from SEQ ID NO 29.

SEQ ID NO 31: Nucleic acid sequence, coding for a hyaluronan synthase 2 from *Equus caballus*.

SEQ ID NO 32: Amino acid sequence of a hyaluronan synthase 2 from *Equus caballus*. The amino acid sequence shown can be derived from SEQ ID NO 31.

SEQ ID NO 33: Nucleic acid sequence, coding for a hyaluronan synthase 2 from *Sus scrofa*.

SEQ ID NO 34: Amino acid sequence of a hyaluronan synthase 2 from *Sus scrofa*. The amino acid sequence shown can be derived from SEQ ID NO 33.

SEQ ID NO 35: Nucleic acid sequence, coding for a hyaluronan synthase 3 from *Sus scrofa*.

SEQ ID NO 36: Amino acid sequence of a hyaluronan synthase 3 from *Sus scrofa*. The amino acid sequence shown can be derived from SEQ ID NO 35.

SEQ ID NO 37: Nucleic acid sequence, coding for a hyaluronan synthase 2 from *Bos taurus*.

SEQ ID NO 38: Amino acid sequence of a hyaluronan synthase 2 from *Bos taurus*. The amino acid sequence shown can be derived from SEQ ID NO 37.

SEQ ID NO 39: Nucleic acid sequence, coding for a hyaluronan synthase 2 from *Gallus gallus*.

SEQ ID NO 40: Amino acid sequence of a hyaluronan synthase 2 from *Gallus gallus*. The amino acid sequence shown can be derived from SEQ ID NO 39.

SEQ ID NO 41: Nucleic acid sequence, coding for a hyaluronan synthase 1 from *Xenopus laevis*.

SEQ ID NO 42: Amino acid sequence of a hyaluronan synthase 1 from *Xenopus laevis*. The amino acid sequence shown can be derived from SEQ ID NO 41.

SEQ ID NO 43: Nucleic acid sequence, coding for a hyaluronan synthase 2 from *Xenopus laevis*.

SEQ ID NO 44: Amino acid sequence of a hyaluronan synthase 2 from *Xenopus laevis*. The amino acid sequence shown can be derived from SEQ ID NO 43.

SEQ ID NO 45: Nucleic acid sequence, coding for a hyaluronan synthase 3 from *Xenopus laevis*.

SEQ ID NO 46: Amino acid sequence of a hyaluronan synthase 3 from *Xenopus laevis*. The amino acid sequence shown can be derived from SEQ ID NO 45.

SEQ ID NO 47: Nucleic acid sequence, coding for a hyaluronan synthase 2 from *Danio rerio*.

SEQ ID NO 48: Amino acid sequence of a hyaluronan synthase 2 from *Danio rerio*. The amino acid sequence shown can be derived from SEQ ID NO 47.
SEQ ID NO 49: Genomic nucleic acid sequence, coding for a hyaluronan synthase 3 from *Danio rerio*.
SEQ ID NO 50: Amino acid sequence of a hyaluronan synthase 3 from *Danio rerio*. The amino acid sequence shown can be derived from SEQ ID NO 49.
SEQ ID NO 51: Nucleic acid sequence, coding for a hyaluronan synthase from *Pasteurella multocida*.
SEQ ID NO 52: Amino acid sequence of a hyaluronan synthase from *Pasteurella multocida*. The amino acid sequence shown can be derived from SEQ ID NO 51.
SEQ ID NO 53: Nucleic acid sequence, coding for a hyaluronan synthase from *Streptococcus pyogenes*.
SEQ ID NO 54: Amino acid sequence of a hyaluronan synthase from *Streptococcus pyogenes*. The amino acid sequence shown can be derived from SEQ ID NO 53.
SEQ ID NO 55: Nucleic acid sequence, coding for a hyaluronan synthase from *Streptococcus equi*.
SEQ ID NO 56: Amino acid sequence of a hyaluronan synthase from *Streptococcus equi*. The amino acid sequence shown can be derived from SEQ ID NO 55.
SEQ ID NO 57: Nucleic acid sequence, coding for a hyaluronan synthase from *Streptococcus uberis*.
SEQ ID NO 58: Amino acid sequence of a hyaluronan synthase from *Streptococcus uberis*. The amino acid sequence shown can be derived from SEQ ID NO 57.
SEQ ID NO 59: Nucleic acid sequence, coding for a hyaluronan synthase from *Streptococcus equisimilis*.
SEQ ID NO 60: Amino acid sequence of a hyaluronan synthase from *Streptococcus equisimilis*. The amino acid sequence shown can be derived from SEQ ID NO 59.
SEQ ID NO 61: Nucleic acid sequence, coding for a hyaluronan synthase from *Sulfolobus tokodaii* strain 7.
SEQ ID NO 62: Amino acid sequence of a hyaluronan synthase from *Sulfolobus tokodaii* strain 7. The amino acid sequence shown can be derived from SEQ ID NO 61.
SEQ ID NO 63: Synthetic nucleic acid sequence, coding for a hyaluronan synthase 1 from *Xenopus laevis*.
SEQ ID NO 64: Amino acid sequence of a hyaluronan synthase 1 from *Xenopus laevis*. The amino acid sequence shown can be derived from SEQ ID NO 3.
SEQ ID NO 65: Synthetically produced nucleic acid sequence, comprising the functional elements gpd-promoter (bp 16-269), polylinker (Pac I, Kpn I, Spe I, BamH I; bp 271-296), intron (bp 298-352), mnp polyadenylation signal I (bp356491), polyadenylation signal 11 (bp 492-540, transcription blocker (pause, bp 541-632), which are described in Example 2.

GENERAL METHODS

Figure 1:
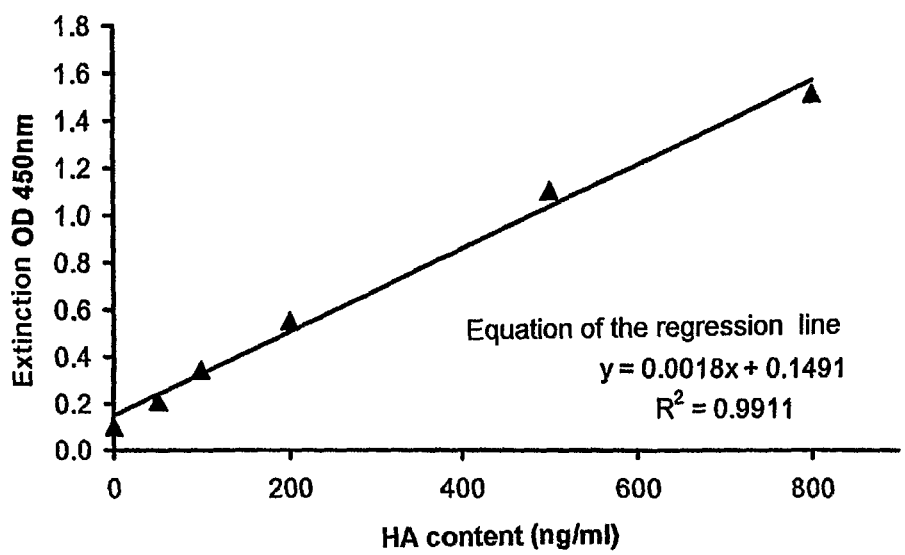
FIG. 1: shows a calibration line and the associated equation of the regression line used for calculating the hyaluronan content in fungus tissue. The calibration line was drawn using the commercial test kit (hyaluronic acid (HA) test kit from Corgenix, Inc., Colorado, USA, Prod. No. 029-001) and the standard solutions contained therein.

Methods which can be used in connection with the present invention are described below. These methods are specific embodiments; however, the present invention is not limited to these methods. It is known to the person skilled in the art that the invention can be carried out in the same manner by modifying the methods described and/or by replacing individual methods or parts of methods by alternative methods or alternative parts of methods.

1. Transformation of Fungi

Fungi (*Agaricus bisporus*) were transformed with the aid of *Agrobacterium*, as described in Chen et al. (2000, Applied and Environmental Microbiology 66(10), 4510-4513).

2. Cultivation of Fungi

Vegetative mycelium of *Agaricus bisporus* was cultivated on sterile PDY agar at 24° C. (Romaine and Schlagnhaufer, 1992, Appl. Environ. Microbiol. 58(9), 3060-3066).

*Agaricus bisporus* fruiting bodies were produced on sterile compost according to the method described in Romaine and Schlagnhaufer (1992, Appl. Environ. Microbiol. 58(9), 3060-3066).

3. Isolation of Hyaluronan from Fungus Tissue

To detect the presence of hyaluronan and to determine the hyaluronan content in fungus tissue, fungus material was worked up as follows: 200 µl of water (demineralized, conductivity ≥18 MΩ) were added to about 0.3 g of tissue of mycelium or fruiting body, and the mixture was comminuted in a laboratory oscillating ball mill (MM200, from Retsch, Germany) (30 sec at 30 Hz). A further 800 µl of water (demineralized, conductivity ≥18 MΩ) was then added, and the mixture was mixed well (using, for example, a Vortex mixer). Cell debris and insoluble components were separated from the supernatant by centrifuging at 16 000×g for 5 minutes.

4. Detection of Hyaluronan and Determination of the Hyaluronan Content

Hyaluronan is detected using a commercial test (hyaluronic acid (HA) test kit from Corgenix, Inc., Colorado, USA, Prod. No. 029-001) according to the instructions of the manufacturer which are herewith incorporated as subject-matter into the description by way of reference. The test principle is based on the availability of a protein which binds specifically to hyaluronan (HABP) and is carried out similarly to an ELISA, where a colour reaction indicates the hyaluronan content in the sample examined. Accordingly, for the quantitative determination of hyaluronan, the samples to be measured should be employed in a concentration such that it is within the stated limits (for example: dilution of the sample in question or use of less water for extracting hyaluronan from fungus tissue, depending on whether a limit was exceeded or not reached).

In parallel batches, aliquots of the samples to be determined are initially subjected to hyaluronidase digestion and then measured using the commercial test (hyaluronic acid (HA) test kit from Corgenix, Inc., Colorado, USA, Prod. No. 5 029-001). Hyaluronidase digestion is carried out using 400 µl of fungal extract in hyaluronidase buffer (0.1 M potassium phosphate buffer, pH 5.3; 150 mm NaCl) by adding 5 µg (~3 units) of hyaluronidase (hyaluronidase type III from Sigma, Prod. No. H 2251) and incubating at 37° C. for 30 min.

All samples are then used in each case for determining the hyaluronan content.

5. Detection of Hyaluronan by NMR Spectroscopy

Analysis by NMR spectroscopy can be carried out using a DRX 700 spectrometer at 700 MHz (Bruker Biospin GMBH D-76287 Rheinstetten/Karlsruhe, Germany). The spectrometer was fitted with a TXI sample head and provided with an SGI workstation, and the Bruker Biospin software XWIN-NMR version 3.5 was used for evaluation. About 0.5 mg to 2 mg of the sample were dissolved in 550 ul of $D_2O$. The $^1$H-NMR spectra are measured using 1024 to 12 000 scans, with a relaxation time of 1 s. The $^1$H-NMR spectra are referenced to the water signal at 4.7 ppm.

6. Molecular Weight Analyses of Hyaluronan a) Agarose Gel Electrophoresis

To characterize the size of the hyaluronan isolated from fungi, an agarose gel electrophoresis-based system described by Lee and Cowman (1994, Anal. Biochem. 219, 278-287) or Armstrong and Bell (2002, Anal. Biochem. 308, 255-264) is used. To this end, hyaluronan-containing samples are applied to a 0.7% TAE (40 mM Tris, 5 mM sodium acetate, 0.8 mM EDTA, pH 7.9) agarose gel and separated in 1×TAE buffer at 50 V over a period of 3 hours. The agarose gel is then stained overnight using 0.005% Stains-all (3,3'-diethyl-9-methyl-4,5,4',5'-dibenzothiacarbocyanine, Fluka, Prod. No. 85663) in 50% ethanol and 50% 1×TAE buffer, and the gel is then decolorized in water and scanned.

b) Gel Permeation Chromatography (GPC)

At a concentration of 1 mg/ml$^{-1}$, the samples are dissolved in GPC mobile phase (0.2 M $NaNO_3$). To this end, the samples are initially stirred on a magnetic stirrer for 1 hour and then allowed to stand at room temperature for 20 hours for equilibration. Prior to the measurement, the samples are filtered through a 5 μm membrane filter. The samples are then analysed by GPC, where the refractive index, light scattering and the viscosity of the eluate are determined. The following instruments and materials are used:

GPC Conditions:

Instruments: Gel Chromatograph PL120 from Polymer Laboratories, Midas Autosampler from Spark,
DAWN-EOS light scattering detector from Wyatt Technology Santa Barbara with $\lambda_0$=690 nm and 16 detectors at an angle range from 14.90 to 162.9°,
K5 flow cell,
Viscosity/refractive index combination detector ρ-1002 (WEG Dr. Bures GmbH & Co KG).

Columns: SUPREMA Gel from PSS, Mainz, Germany
Precolumn and three columns with the separation ranges 300 to $10^4$; 5·$10^4$ to 2·$10^6$ and $10^6$ to $10^8$ were series-connected.

Elution: Mobile phase 0.2 M $NaNO_3$, flow rate 0.8 ml/minute, temperature 30° C., injection volume 500 μl Evaluation:

Using the data obtained, the values given in the examples are calculated. The light scattering data can be evaluated using the software ASTRA Software 4.90.08. The viscosity measurements are able to be evaluated using PSS Win GPC 6.

EXAMPLES

1. Information Regarding Vectors and Plasmids

Preparation of the expression vector IC 400-271 Plasmid IC 400-271 is a derivative of the binary vector plasmid pBHg (Chen et al, 2000, Appl. Environ. Microbiol. 66, 4510-4513), which was constructed as follows:

Plasmid pBGh was cut with BamH I restriction endonuclease, the ends were blunted with Klenow polymerase and the fragment obtained was then cut again with Sma I restriction endonuclease. The vector was subsequently re-ligated. This procedure deleted part of the polylinker of the pBGh plasmid, resulting in the IC 400-271 expression vector which is suitable for fungi.

Figure 2:
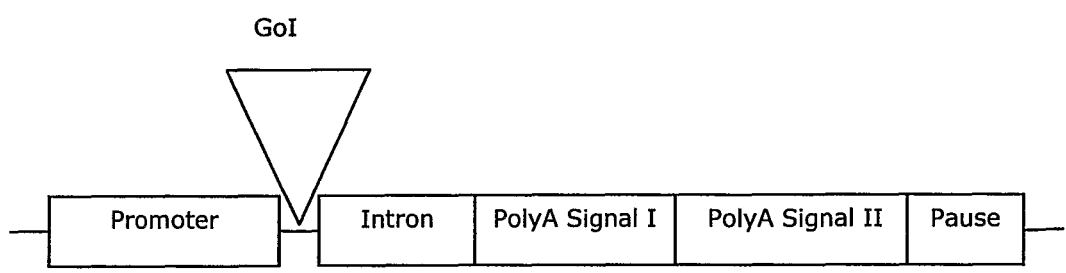
FIG. 2: shows schematically the arrangement of the functional elements of the synthetically prepared sequence comprising a promoter (Promoter), a polylinker having different restriction endonuclease cleavage sites, an intron (Intron) and a termination sequence. A desired nucleic acid sequence (Gol), coding for a protein which is to be expressed, can be inserted in the polylinker. With reference to the present invention nucleic acid sequences coding for hyaluronan synthases have been inserted in the region identified by Gol.

2. Synthesis of the Sequences Coding for a Promoter, a Polylinker, an Intron and a Termination Sequence The nucleic acid sequence comprising the promoter of the protein glyceraldehyde 3-phosphate dehydrogenase (gpd) from *Agaricus bisporus* (Harmsen at al., 1992, Curr. Genet. 22, 447-454), a polylinker with different restriction endonuclease cleavage sites ((Pac I, Kpn I, Spe I, BamH I), an intron with an appropriate donor and acceptor recognition sequence (Ma et al., 2001, Appl. Environ. Microbiol. 67, 948-955) and a termination sequence including a first polyadenylation signal of the manganese peroxidase isoenzyme 1 (mnp1, GenBank Acc: J04621) from *Phanerochaete* chrysosporium (Pribnow et al., 1989, J. Biol. Chem. 264, 5036-5040), a second polyadenylation signal (Levitt et al., Genes & Dev., 1989, 3, 1019-1025) and a transcription blocker (pause signal, Enriquez-Harris et al., EMBO Journal, 1991, 10, 1833-1842) was synthesized by Entelechon GmbH and cloned into the pCR4Topo vector from Invitrogen (product No. K4510-20). The construct is depicted diagrammatically in FIG. 2. The plasmid obtained was referred to as IC 401-271. The synthetic nucleic acid sequence for the elements described is depicted under SEQ ID NO 65.

3. Synthesis of the Nucleic Acid Sequences Coding for an has Protein of *Paramecium bursaria Chlorella* Virus 1

The nucleic acid sequence coding for an HAS (hyaluronan synthase) protein from *Paramecium bursaria Chlorella* virus 1, was synthesized by Medigenomix GmbH (Munich, Germany) and cloned into the vector pCR2.1 from Invitrogen (Prod. No. K2000-01). The plasmid obtained was named IC 323-215. The synthetic nucleic acid sequence coding for the HAS protein from *Paramecium bursaria Chlorella* virus 1 is shown under SEQ ID NO 3. The corresponding nucleic acid sequence originally isolated from *Paramecium bursaria Chlorella* virus 1 is shown under SEQ ID NO 1.

4. Preparation of an Expression Vector Having the Coding Sequence for an HAS Protein from Paramecium Bursaria *Chlorella* Virus 1

The coding sequence of the HAS protein is isolated from plasmid IC 323-215 by means of restriction endonucleases BamHI and PacI and cloned into the BamHI and PacI cleavage sites of IC 401-271. This resulted in the vector IC 402-271. The cassette gpd promoter—HAS protein—intron—termination sequence was then cloned from IC 402-271, using HpaI and SbfI, into the PvuII and SbfI restriction cleavage sites of the IC 400-271 vector. Thus the expression vector IC 403-271 was produced.

5. Synthesis of the Sequences Coding for a *Xenopus laevis* HAS1 (DG42) Protein

The nucleic acid sequence coding for a *Xenopus laevis* xlHAS1 (hyaluronan synthase 1) protein was synthesized by Entelechon GmbH and cloned into the pCR4Topo vector from Invitrogen (product No. K4510-20). The plasmid obtained was referred to as IC 406-271. The synthetic nucleic acid sequence coding for the synthetic *Xenopus laevis* HAS protein is depicted under SEQ ID NO 63. The corresponding nucleic acid sequence originally isolated from *Xenopus laevis* (GenBank M22249) is depicted under SEQ ID NO 41.

6. Transformation of Fungi with Expression Vectors Containing Nucleic Acid Molecules Coding for has Proteins Lamellar tissues from *Agaricus bisporus* fruiting bodies were transformed, in independent transformation procedures, with the IC 403-271 expression vector containing a nucleic acid sequence coding for a *Paramecium bursaria Chlorella* Virus 1 HAS protein and, respectively, with the IC 406-271 expression vector containing a nucleic acid sequence coding for a *Xenopus laevis* HAS-1 protein, according to the method stated under "General Methods", Section 1. The transgenic fungi obtained which had been transformed with plasmid IC 403-271 were referred to as A.b.-cvHAS. The transgenic fungi obtained which had been transformed with plasmid IC 406-271 were referred to as A.b.-xIHAS1.

7. Analysis of Transgenic Fungi

Individual fungi referred to as A.b.-cvHAS and as A.b.-xIHAS1 were cultured as mycelia on PDY agar according to the method described in Section 2 of "General Methods". In each case approx. 0.3 g of mycelial material of the individual fungi was worked up according to the method described under "General Methods", Section 3.

Fruiting bodies of fungi referred to as A.b.-cvHAS and of fungi referred to as A.b.-xIHAS1 were produced on sterile compost according to the method described under "General Methods", Section 2. In each case approx. 0.3 g of fruiting body material of the individual fungi was worked up according to the method described under "General Methods", Section 3. Hyaluronan was determined in the particular fungal extracts by the method described under "General Methods", Section 4. Fungal lines producing hyaluronan were identified.

The invention claimed is:

1. A fungal cell of the systematic order Agaricales systematic class *Basidiomycetes* comprising a foreign nucleic acid molecule coding for a hyaluronan synthase, wherein said fungal cell synthesizes hyaluronan.

2. A fungus comprising the fungal cell of claim 1.

3. A propagation material of a fungus of claim 2, wherein said propagation material comprises said nucleic acid molecule coding for a hyaluronan synthase.

4. A method for preparing a fungus which synthesizes hyaluronan, comprising
   a) transforming a fungal cell of the systematic order Agaricales systematic class *Basidiomycetes* with a nucleic acid molecule coding for a hyaluronan synthase, wherein said nucleic acid is integrated into the genome of said fungal cell; and
   b) regenerating a fungus from the fungal cell of step a).

5. A composition comprising components of the fungal cell of claim 1.

6. The method of claim 4, wherein fungi are generated from the fungi of step b).

7. A composition comprising components of the fungal cell of claim 1.

8. A composition comprising components of the fungus of claim 2.

9. A composition comprising components of the fungi obtainable by the method of claim 4.

10. The fungal cell of claim 1, wherein said fungal cell is of the systematic family Agaricaceae.

11. The method of claim 4, wherein said fungal cell is of the systematic family Agaricaceae.

12. The fungal cell of claim 1, wherein said fungal cell is of the genus *Agaricus*.

13. The method of claim 4, wherein said fungal cell is of the genus *Agaricus*.

14. The fungal cell of claim 1, wherein said fungal cell is of the species *Agaricus bisporus*.

15. The method of claim 4, wherein said fungal cell is of the species *Agaricus bisporus*.

16. The fungal cell of claim 12, wherein the foreign nucleic acid comprises a nucleic acid molecule that encodes the amino acid sequence of SEQ ID NO: 2 or 4.

17. The method of claim 13, wherein the nucleic acid molecule encodes the amino acid sequence of SEQ ID NO: 2 or 4.

18. The fungal cell of claim 14, wherein the foreign nucleic acid comprises a nucleic acid molecule that encodes the amino acid sequence of SEQ ID NO: 2 or 4.

19. The method of claim 15, wherein the nucleic acid molecule encodes the amino acid sequence of SEQ ID NO: 2 or 4.

* * * * *